(12) United States Patent
Wallace et al.

(10) Patent No.: US 11,896,247 B2
(45) Date of Patent: Feb. 13, 2024

(54) INVERTING MECHANICAL THROMBECTOMY APPARATUSES

(71) Applicant: STRYKER CORPORATION, Fremont, CA (US)

(72) Inventors: Michael P. Wallace, Pleasanton, CA (US); E. Skott Greenhalgh, Gladwyne, PA (US); Robert Garabedian, Mountain View, CA (US)

(73) Assignee: STRYKER CORPORATION, Fremont, CA (US)

( * ) Notice: Subject to any disclaimer, the term of this patent is extended or adjusted under 35 U.S.C. 154(b) by 701 days.

(21) Appl. No.: 17/102,360

(22) Filed: Nov. 23, 2020

(65) Prior Publication Data

US 2021/0106346 A1 Apr. 15, 2021

Related U.S. Application Data

(60) Continuation-in-part of application No. 16/790,744, filed on Feb. 14, 2020, now Pat. No. 11,497,514, and a continuation-in-part of application No. 16/707,045, filed on Dec. 9, 2019, and a continuation-in-part of application No. 16/169,334, filed on Oct. 24, 2018,
(Continued)

(51) Int. Cl.
| | |
|---|---|
| *A61B 17/22* | (2006.01) |
| *A61B 17/221* | (2006.01) |
| *A61B 17/00* | (2006.01) |
| *A61B 17/34* | (2006.01) |

(52) U.S. Cl.
CPC ............ *A61B 17/22* (2013.01); *A61B 17/221* (2013.01); *A61B 17/22031* (2013.01); *A61B 2017/00398* (2013.01); *A61B 2017/2215* (2013.01); *A61B 2017/22038* (2013.01); *A61B 2017/22075* (2013.01); *A61B 2017/22079* (2013.01); *A61B 2017/3435* (2013.01)

(58) Field of Classification Search
CPC . A61B 17/22; A61B 17/221; A61B 17/22031; A61B 2017/00398; A61B 2017/22038; A61B 2017/22075; A61B 2017/22079; A61B 2017/2215; A61B 2017/3435
See application file for complete search history.

(56) References Cited

U.S. PATENT DOCUMENTS

| | | | |
|---|---|---|---|
| 3,515,137 A | 6/1970 | Santomieri | |
| 4,222,380 A | 9/1980 | Terayama | |
(Continued)

FOREIGN PATENT DOCUMENTS

| | | |
|---|---|---|
| AU | 2015210338 | 8/2015 |
| CN | 201079423 | 7/2008 |
(Continued)

OTHER PUBLICATIONS

Foreign OA for JP Patent Appln. No. 2019-513286 dated Aug. 3, 2021.
(Continued)

*Primary Examiner* — Phong Son H Dang
(74) *Attorney, Agent, or Firm* — Seager, Tufte & Wickhem, LLP

(57) ABSTRACT

Mechanical thrombectomy apparatuses (devices, systems, etc.) and methods for deploying and/or positioning them within a vessel and/or using them and/or removing a thrombus, e.g., clot, from within a vessel using them.

18 Claims, 67 Drawing Sheets

Related U.S. Application Data now Pat. No. 10,888,343, and a continuation-in-part of application No. 15/794,939, filed on Oct. 26, 2017, now Pat. No. 10,842,513, said application No. 16/790,744 is a continuation of application No. 15/795,097, filed on Oct. 26, 2017, now Pat. No. 10,561,431, said application No. 16/707,045 is a continuation of application No. 15/497,092, filed on Apr. 25, 2017, now Pat. No. 10,512,478, said application No. 16/169,334 is a continuation of application No. PCT/US2017/029345, filed on Apr. 25, 2017, said application No. 15/794,939 is a division of application No. 15/496,786, filed on Apr. 25, 2017, now Pat. No. 10,010,335, said application No. 15/795,097 is a division of application No. 15/496,668, filed on Apr. 25, 2017, now Pat. No. 9,962,178.

(60) Provisional application No. 62/393,460, filed on Sep. 12, 2016, provisional application No. 62/357,677, filed on Jul. 1, 2016, provisional application No. 62/345,152, filed on Jun. 3, 2016, provisional application No. 62/327,024, filed on Apr. 25, 2016.

(56) References Cited

U.S. PATENT DOCUMENTS

| | | |
|---|---|---|
| 4,243,040 A | 1/1981 | Beecher |
| 4,324,262 A | 4/1982 | Hall |
| 4,469,100 A | 9/1984 | Hardwick |
| 4,604,094 A | 8/1986 | Shook |
| 4,646,736 A | 3/1987 | Auth |
| 4,863,440 A | 9/1989 | Chin |
| 4,946,440 A | 8/1990 | Hall |
| 5,011,488 A | 4/1991 | Ginsburg |
| 5,329,923 A | 7/1994 | Lundquist |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,156,055 A | 12/2000 | Ravenscroft |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Brook et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm, III |
| 9,186,487 B2 | 11/2015 | Dubrul et al. |
| 9,358,037 B2 | 1/2016 | Farhangnia et al. |
| 9,259,237 B2 | 2/2016 | Quick et al. |
| 9,351,747 B2 | 5/2016 | Kugler et al. |
| 9,463,035 B1 | 10/2016 | Greenhalgh et al. |
| 9,643,035 B2 | 5/2017 | Mastenbroek |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,130,385 B2 | 11/2018 | Farhangnia et al. |
| 10,271,864 B2 | 4/2019 | Greenhalgh et al. |
| 10,327,883 B2 | 6/2019 | Yachia |
| 2002/0032455 A1 | 3/2002 | Boock et al. |
| 2002/0035373 A1 | 3/2002 | Carlson et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0168068 A1 | 9/2003 | Poole et al. |
| 2003/0176884 A1 | 9/2003 | Berrada et al. |
| 2003/0208224 A1 | 11/2003 | Broome |
| 2004/0098033 A1 | 5/2004 | Leeflang et al. |
| 2004/0199202 A1 | 10/2004 | Dubrul et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0245876 A1 | 11/2005 | Khosravi et al. |
| 2005/0283166 A1 | 12/2005 | Greenhalgh |
| 2005/0283186 A1 | 12/2005 | Berrada et al. |
| 2006/0042786 A1 | 3/2006 | West |
| 2006/0089533 A1 | 4/2006 | Ziegler et al. |
| 2006/0100662 A1 | 5/2006 | Daniel et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0276874 A1 | 12/2006 | Wilson et al. |
| 2006/0293696 A1 | 12/2006 | Fahey et al. |
| 2007/0112374 A1 | 5/2007 | Paul, Jr. et al. |
| 2007/0123798 A1 | 5/2007 | Rahamimov |
| 2007/0149996 A1 | 6/2007 | Coughlin |
| 2007/0213765 A1 | 9/2007 | Adams et al. |
| 2008/0183136 A1 | 7/2008 | Lenker et al. |
| 2009/0076417 A1 | 3/2009 | Jones |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desai |
| 2010/0190156 A1 | 7/2010 | Van Wordragen et al. |
| 2010/0249815 A1 | 9/2010 | Jantzen et al. |
| 2011/0034987 A1 | 2/2011 | Kennedy |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0059309 A1 | 3/2012 | Di Palma et al. |
| 2012/0083824 A1 | 4/2012 | Berrada et al. |
| 2012/0083868 A1 | 4/2012 | Shrivastava |
| 2012/0165859 A1 | 6/2012 | Eckhouse et al. |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0005717 A1 | 1/2014 | Martin et al. |
| 2014/0046133 A1 | 2/2014 | Nakamura et al. |
| 2014/0155980 A1 | 6/2014 | Turjman |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |

(56) References Cited

U.S. PATENT DOCUMENTS

| | | |
|---|---|---|
| 2015/0018859 A1 | 1/2015 | Quick et al. |
| 2015/0018860 A1 | 1/2015 | Quick et al. |
| 2015/0088190 A1 | 3/2015 | Jensen |
| 2015/0112376 A1 | 4/2015 | Molaei et al. |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0351775 A1 | 12/2015 | Fulton, III |
| 2015/0359547 A1 | 12/2015 | Vale et al. |
| 2016/0022293 A1 | 1/2016 | Dubrul et al. |
| 2016/0058458 A1 | 3/2016 | Hansen et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0206371 A1 | 7/2016 | Elgaard et al. |
| 2016/0228134 A1 | 8/2016 | Martin et al. |
| 2016/0242799 A1 | 8/2016 | Bonneau et al. |
| 2016/0256179 A1 | 9/2016 | Walish et al. |
| 2017/0035445 A1 | 2/2017 | Nguyen et al. |
| 2017/0042571 A1 | 2/2017 | Levi |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0112513 A1 | 4/2017 | Marchand et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0348014 A1 | 12/2017 | Wallace et al. |
| 2018/0042624 A1 | 2/2018 | Greenhalgh et al. |
| 2018/0042626 A1 | 2/2018 | Greenhalgh et al. |
| 2018/0049766 A1 | 2/2018 | Nolan et al. |
| 2018/0070968 A1 | 3/2018 | Wallace et al. |
| 2018/0236205 A1 | 8/2018 | Krautkremer et al. |
| 2019/0046219 A1 | 2/2019 | Marchand et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0033614 A1 | 11/2019 | Greenhalgh et al. |
| 2019/0336148 A1 | 11/2019 | Greenhalgh et al. |

FOREIGN PATENT DOCUMENTS

| | | |
|---|---|---|
| CN | 102186427 | 9/2011 |
| CN | 102933161 | 2/2013 |
| CN | 102988096 | 3/2013 |
| CN | 103764049 | 4/2014 |
| CN | 103889347 | 6/2014 |
| CN | 104000635 | 8/2014 |
| CN | 104042304 | 9/2014 |
| CN | 104068910 | 10/2014 |
| CN | 104523320 | 4/2015 |
| CN | 104582608 | 4/2015 |
| CN | 108348319 | 7/2018 |
| CN | 111281482 | 6/2020 |
| EP | 1254634 | 11/2002 |
| GB | 1588072 | 4/1981 |
| GB | 2498349 | 7/2013 |
| JP | 2003-38500 | 2/2003 |
| JP | 2003-135604 | 5/2003 |
| JP | 2016-41275 | 3/2016 |
| WO | WO 00/32118 | 6/2000 |
| WO | WO 0202162 | 1/2002 |
| WO | WO 2005096963 | 10/2005 |
| WO | WO 2008/088371 | 7/2008 |
| WO | WO 2009086482 | 7/2009 |
| WO | WO 2012009675 | 1/2012 |
| WO | WO 2012049652 | 4/2012 |
| WO | WO 2012162437 | 11/2012 |
| WO | WO 2015189354 | 12/2015 |
| WO | WO 2017058280 | 4/2017 |
| WO | WO 2017189535 | 11/2017 |
| WO | WO 2017189550 | 11/2017 |
| WO | WO 2017189591 | 11/2017 |
| WO | WO 2017189615 | 11/2017 |
| WO | WO 2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

Foreign Notice of Reasons of Rejection for JP Patent Appln. No. 2019-513286 dated Jul. 26, 2021 (with English translation).

Foreign Exam Report for EP Patent Appln. No. 19773654.9 dated Aug. 24, 2021.

Foreign OA for JP Patent Appln. No. 2020-093260 dated Apr. 20, 2021.

Non-Final Office Action for U.S. Appl. No. 16/566,393 dated May 11, 2021.

Amendment Response to NFOA for U.S. Appl. No. 16/566,393 dated Aug. 11, 2021.

Non-Final Office Action for U.S. Appl. No. 16/594,259 dated Aug. 31, 2021.

Foreign OA for CN Patent Appln. No. 201880046302.9 dated Aug. 25, 2022 (with English translation).

Foreign OA for JP Patent Appln. No. 2021-125123 dated Aug. 23, 2022.

Non-Final Office Action for U.S. Appl. No. 16/707,045 dated Nov. 14, 2022.

Non-Final Office Action for U.S. Appl. No. 16/594,259 dated Nov. 9, 2022.

Notice of Allowance for U.S. Appl. No. 16/722,880 dated Oct. 5, 2022.

Non-Final Office Action for U.S. Appl. No. 16/790,741 dated Nov. 1, 2022.

Foreign OA for CN Patent Appln. No. 202010148570.0 dated Nov. 1, 2022.

Foreign Search Report for CN Patent Appln. No. 202010148570.0 dated Nov. 1, 2022.

Foreign Response for EP Patent Appln. No. 21211363.3 dated Mar. 17, 2022.

Foreign Exam Report for IN Patent Appln. No. 202147016629 dated Mar. 2, 2022.

Foreign OA for IN Patent Appln. No. 202147016649 dated Mar. 28, 2022.

Non-Final Office Action for U.S. Appl. No. 16/707,045 dated Apr. 11, 2022.

Foreign OA for CN Patent Appln. No. 2017800670344 dated Mar. 21, 2022 with English Translation.

Foreign OA for JP Patent Appln. No. 2021-072088 dated Apr. 5, 2022 with English translation.

Foreign OA for EP Patent Appln. No. 19726855.0 dated May 18, 2022.

Foreign Communication Under Rule 71(3) for EP Patent Appln. No. 18807524.6 dated Jul. 1, 2022.

Foreign Communication Pursuant to Article 94(3) for EP Patent Appln. No. 17772186.7 dated Jun. 17, 2022.

Foreign OA for JP Patent Appln. No. 2019-513286 dated May 10, 2022.

Foreign OA for JP Patent Appln. No. 2019-571360 dated Jun. 9, 2022.

Amendment Response to NFOA for U.S. Appl. No. 16/707,045 dated Jul. 11, 2022.

Extended European Search Report for EP Patent Appln. No. 22162955.3 dated Sep. 5, 2022.

(56) References Cited

OTHER PUBLICATIONS

Foreign Notice of Rejection for JP Patent Appln. No. 2020-093260 dated Aug. 2, 2022.
Final Office Action for U.S. Appl. No. 16/707,045 dated Jul. 22, 2022.
Foreign Response for EP Patent Appln. No. 21192438.6 dated Jul. 18, 2022.
Foreign Response for JP Patent Appln. No. 2021-72088 dated Jul. 4, 2022.
Notice of Rejection for JP Patent Appln. No. 2020-523723 dated Aug. 8, 2022 with English translation.
Notice of Allowance for U.S. Appl. No. 16/790,744 dated Jun. 17, 2022.
Notice of Allowance for U.S. Appl. No. 16/731,649 dated Jul. 20, 2022.
Amendment Response to NFOA for U.S. Appl. No. 16/790,741 dated Nov. 21, 2022.
Amendment Response to NFOA for U.S. Appl. No. 16/594,259 dated Jan. 26, 2023.
Notice of Allowance for U.S. Appl. No. 16/790,741 dated Dec. 21, 2022.
Non-Final Office Action for U.S. Appl. No. 16/169,334 dated Jan. 6, 2023.
Non-Final Office Action for U.S. Appl. No. 17/387,959 dated Jan. 19, 2023.
Foreign OA for CN Patent Appln. No. 201880072826.5 dated Oct. 12, 2022 (with English translation).
Foreign Search Report for CN Patent Appln. No. 201880072826.5 dated Oct. 12, 2022 (with English translation).
Final Office Action for U.S. Appl. No. 16/594,259 dated Mar. 1, 2023.
Notice of Allowance for U.S. Appl. No. 16/183,149 dated Oct. 9, 2020.
Foreign OA for CN Patent Appln. No. 2017800393642 dated Dec. 1, 2020.
Foreign OA for CN Patent Appln. No. 2017800393676 dated Dec. 2, 2020.
Foreign OA for CN Patent Appln. No. 2017800396566 dated Dec. 3, 2020.
Foreign OA for CN Patent Appln. No. 2017800343357 dated Jan. 6, 2021.
Foreign Response for EP Patent Appln. No. 18807524.6 dated Dec. 21, 2020.
PCT International Search Report and Written Opinion for International Appln. No. PCT/US2020/014854, dated Oct. 5, 2020 (13 pages).
PCT International Search Report and Written Opinion for International Appln. No. PCT/US2020/018655, dated Dec. 16, 2020 (22 pages).
PCT International Search Report and Written Opinion for International Appln. No. PCT/US2020/017684, dated Nov. 30, 2020 (19 pages).
Foreign OA for CN Patent Appln. No. 201780067034.4 dated Sep. 3, 2021 (with English translation).
Foreign Search Report for CN Patent Appln. No. 201780067034.4 dated Aug. 30, 2021 (with English translation).
Response to OA for EP Patent Appln. No. 19773654.9 dated Dec. 22, 2021 with Amended Claims and Description.
Extended European Search Report for EP Patent Appln. No. 21192438.6 dated Nov. 23, 2021.
Foreign Notice of Rejection for JP Patent Appln. No. 2020-093260 dated Dec. 21, 2021.
Non-Final Office Action for U.S. Appl. No. 15/496,570, dated Aug. 9, 2017.
PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule 161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.

(56) References Cited

OTHER PUBLICATIONS

Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule 161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule 161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092
Response to Restriction Requirement filed Jun. 11, 2019 for U.S. Appl. No. 15/497,092.
Ex Parte Quayle office action mailed Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action mailed Aug. 2, 2019 for U.S. Appl. No. 15/497,092.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule 161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Amendment Response submitted on Dec. 3, 2019 for U.S. Appl. No. 15/794,939.
PCT International Search Report and Written Opinion for International Patent Appln. No. PCT/US2019/050467, Applicant Stryker Corporation, dated Dec. 18, 2019 (17 pages).
Non Final Office Action dated Dec. 27, 2019 for U.S. Appl. No. 16/594,256.
Final Office Action dated Mar. 2, 2020 for U.S. Appl. No. 15/794,939.
Notice of Allowance for U.S. Appl. No. 15/794,939 dated Mar. 31, 2020.
Amendment Response submitted dated Mar. 27, 2020 for U.S. Appl. No. 16/594,256.
Non-Final Office Action for U.S. Appl. No. 16/096,031 dated May 8, 2020.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/169,334 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.

(56) References Cited

OTHER PUBLICATIONS

Extended European Search Report for EP Patent Appln. No. 20185092.2 dated Sep. 11, 2020.
EP Examination Report for EP Patent Appln. No. 18745794.0 dated Jul. 20, 2020.
Amendment Response to NFOA for U.S. Appl. No. 16/183,149 dated Sep. 25, 2020.
Foreign OA for JP Patent Appln. No. 2019-507078 dated Feb. 3, 2021.
Foreign OA for JP Patent Appln. No. 2019-507075 dated Feb. 1, 2021.
Notice of Allowance for U.S. Appl. No. 16/397,089 dated Feb. 18, 2021.
Foreign OA for JP Patent Appln. No. 2018-562633 dated Mar. 4, 2021.

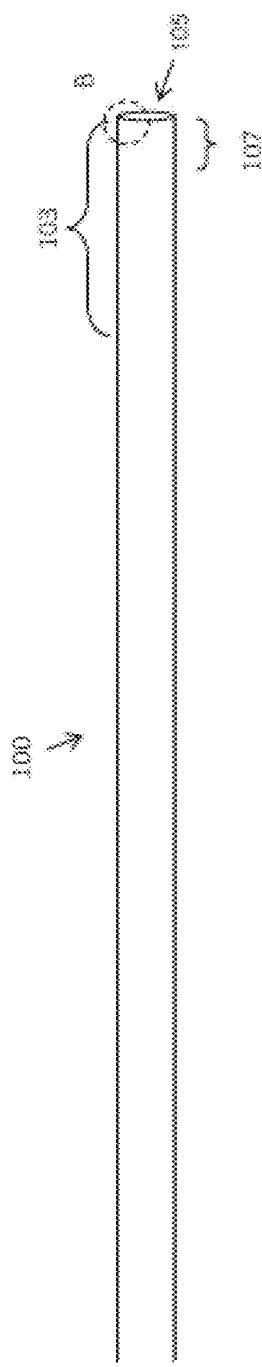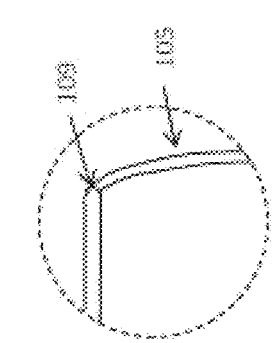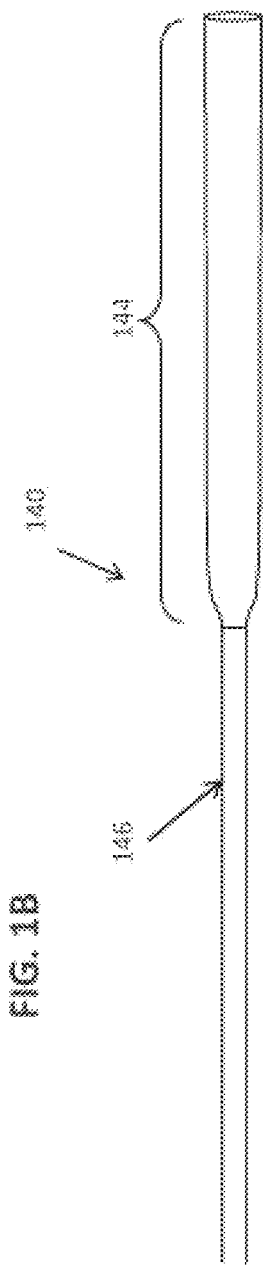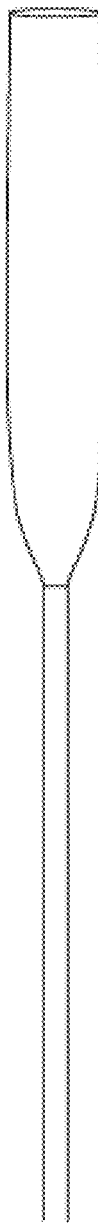
FIG. 1A
FIG. 1B
FIG. 1C
FIG. 1D

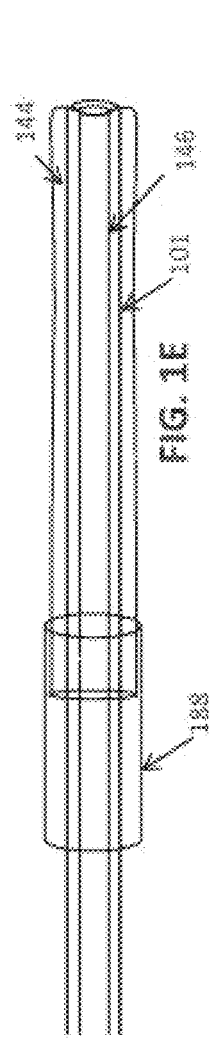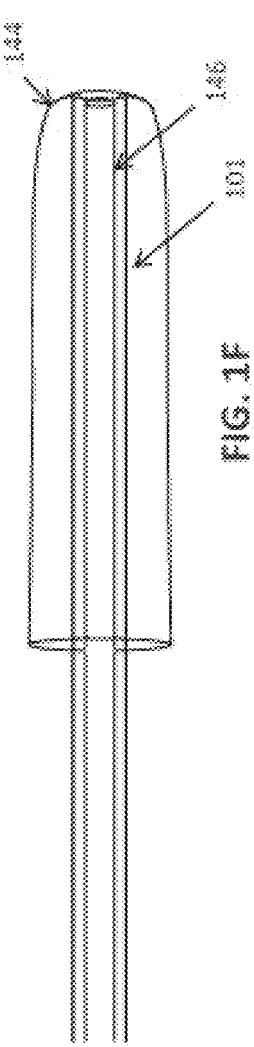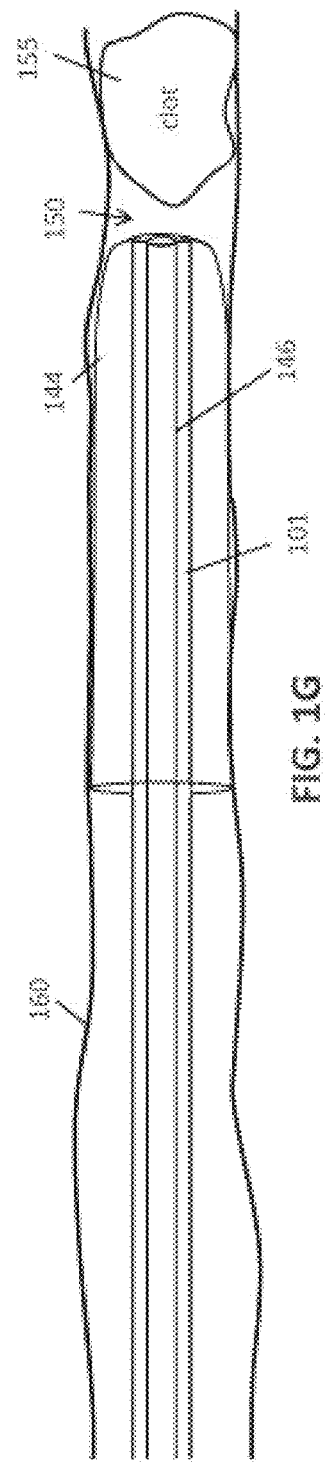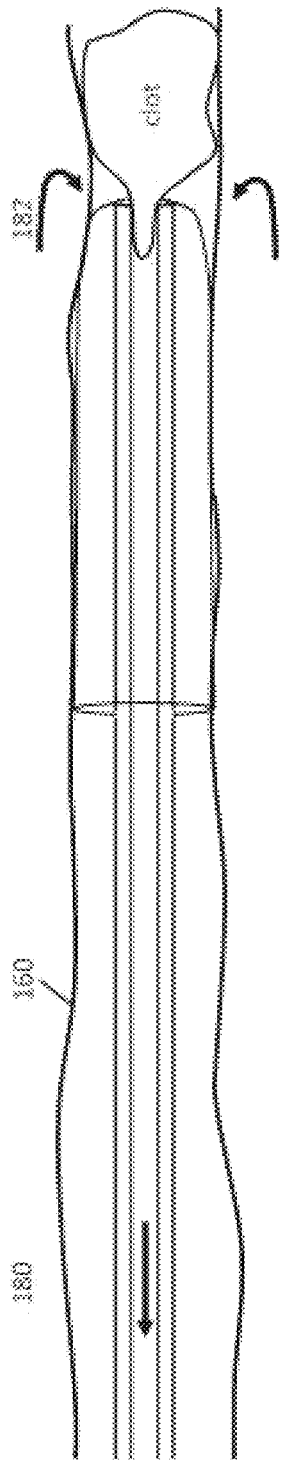

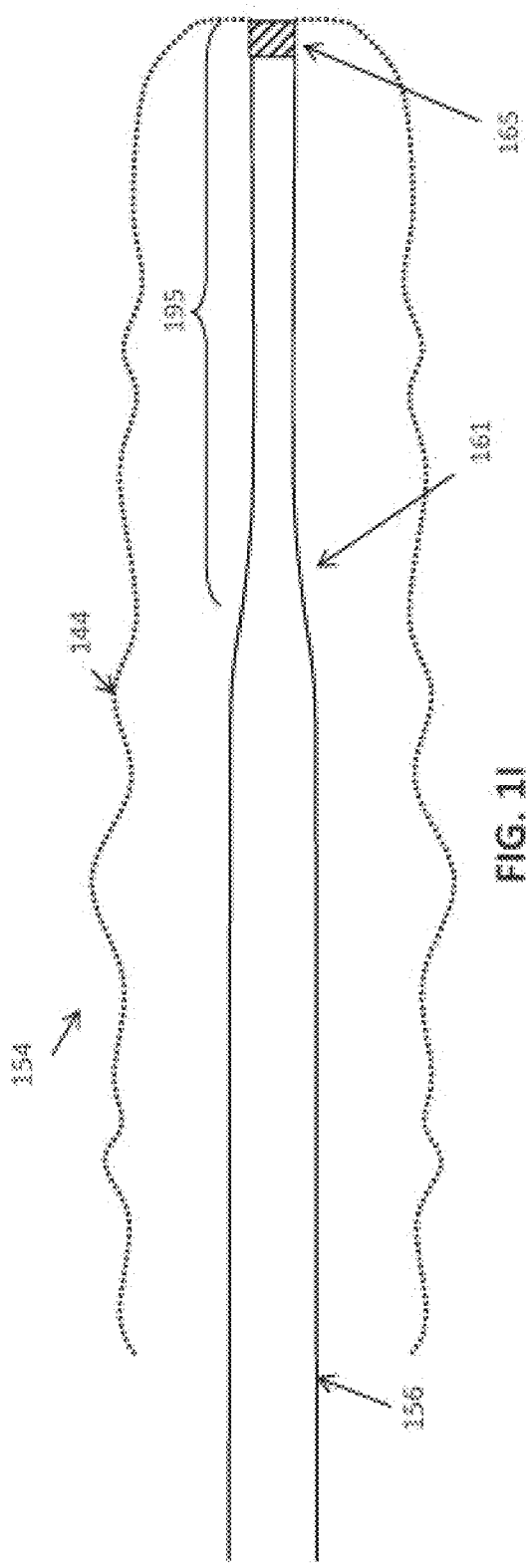
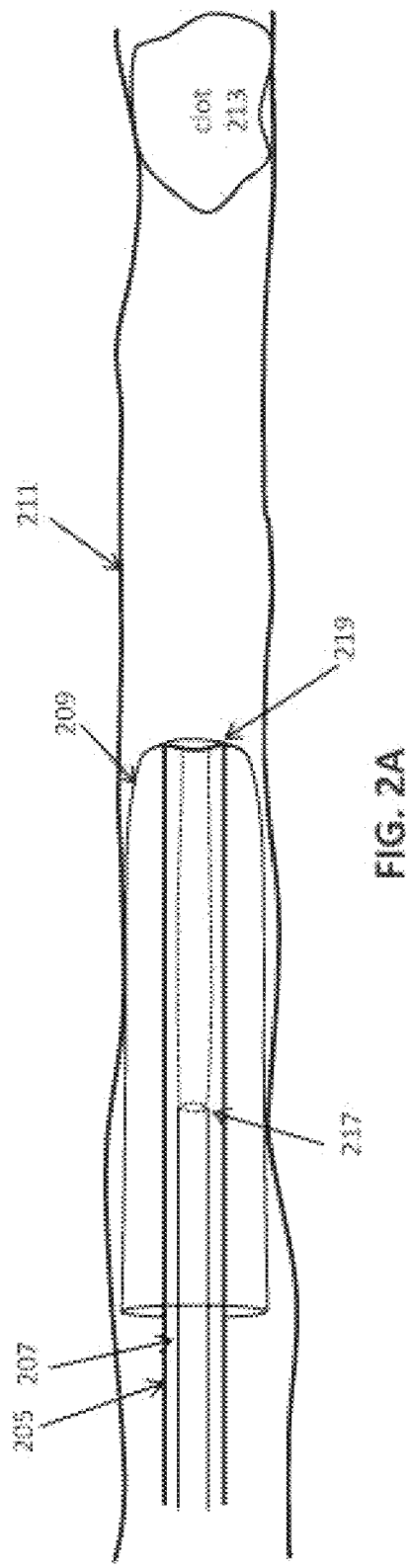

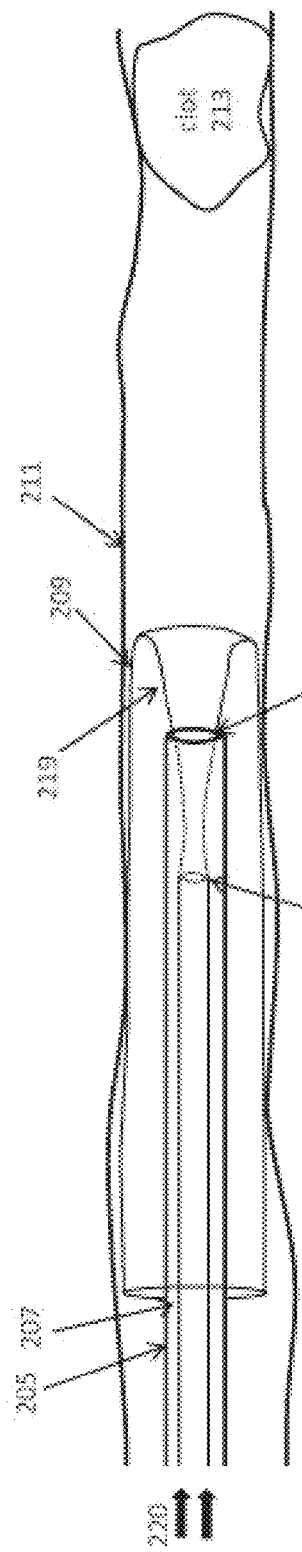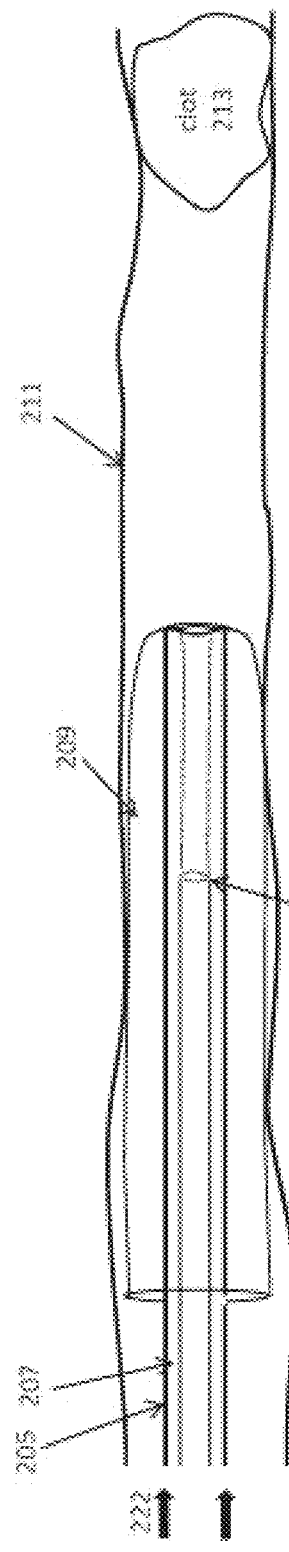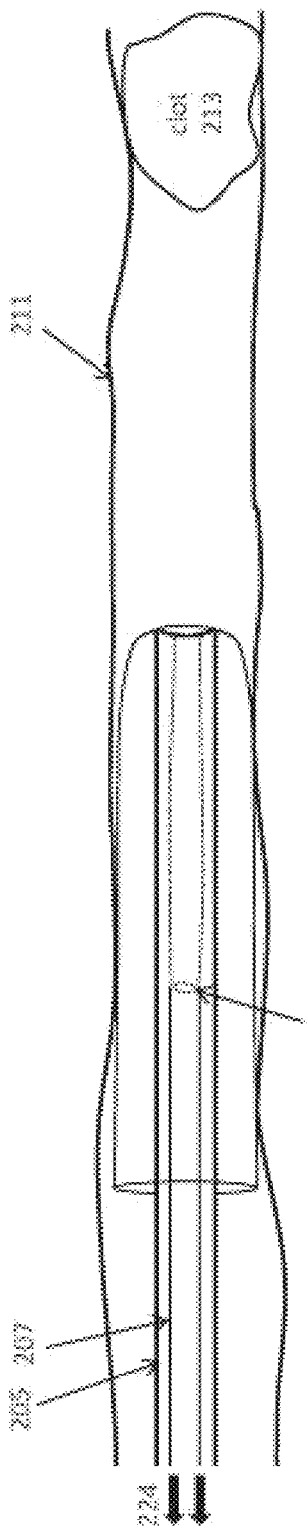

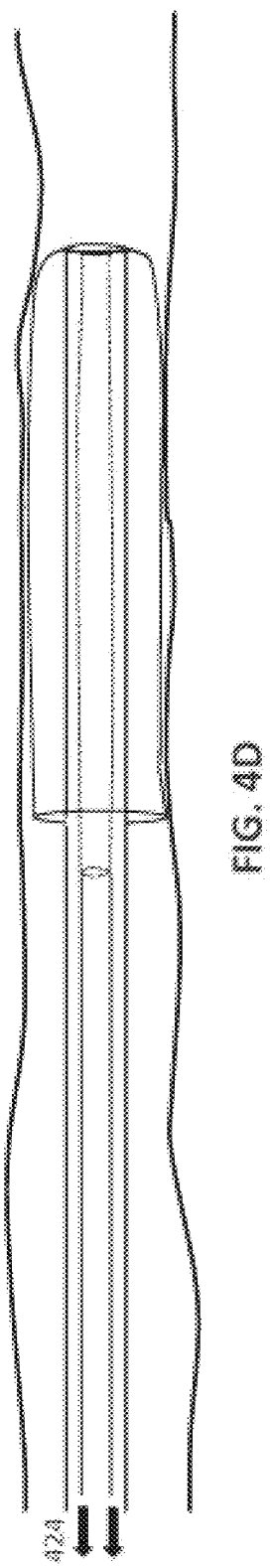

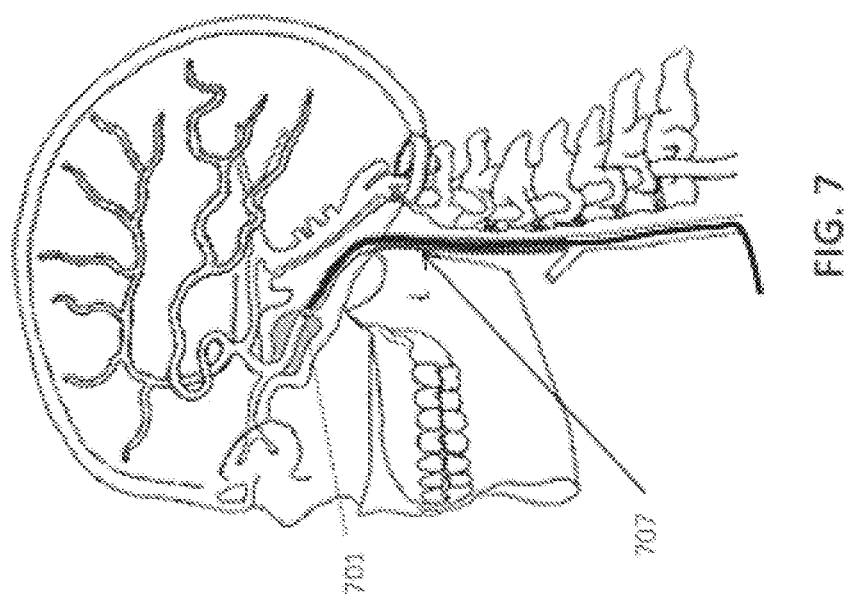

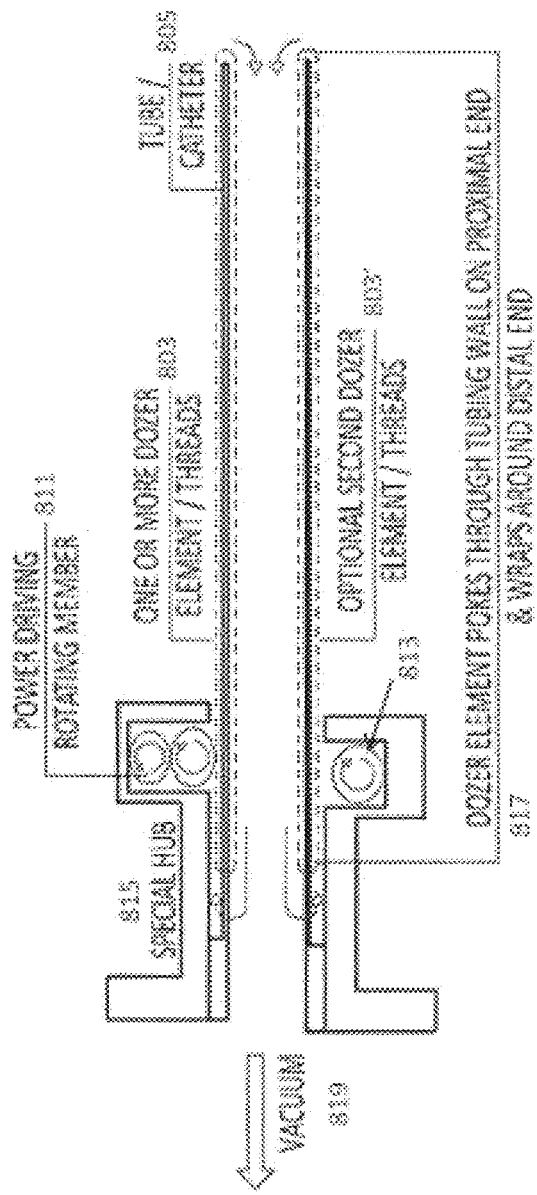
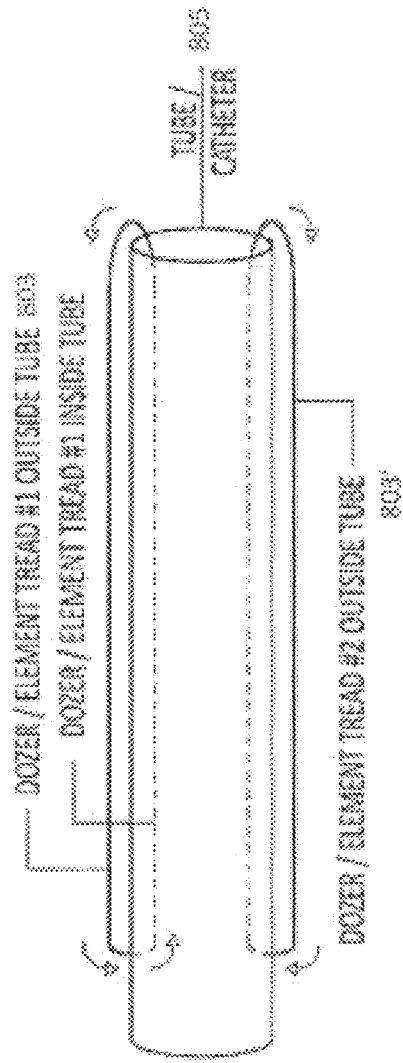
FIG. 8A
FIG. 8B

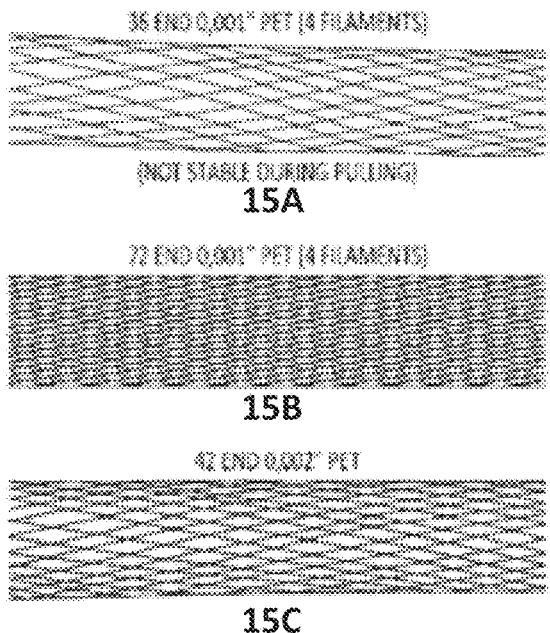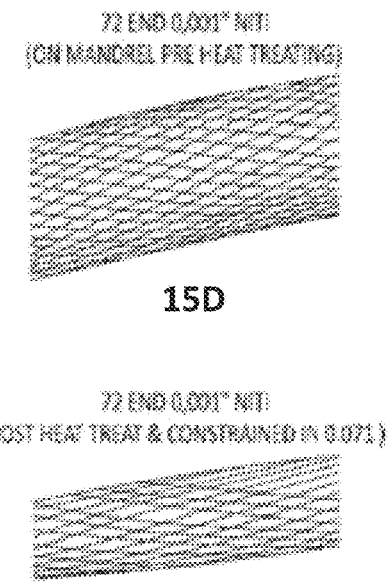
FIGS. 15A-15E
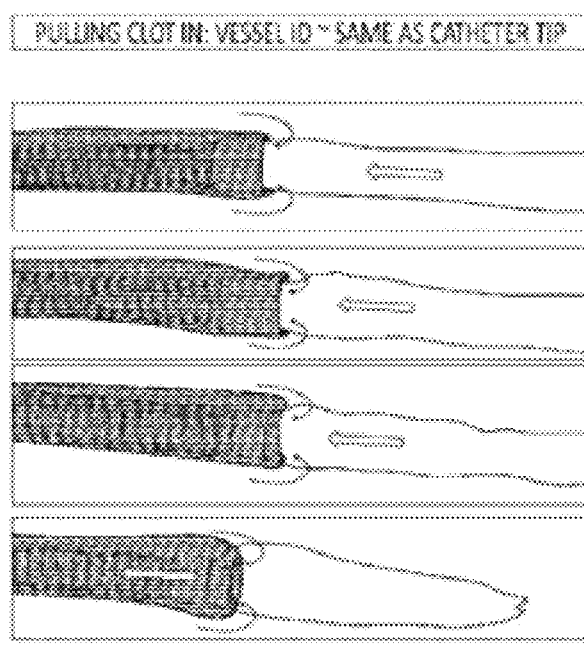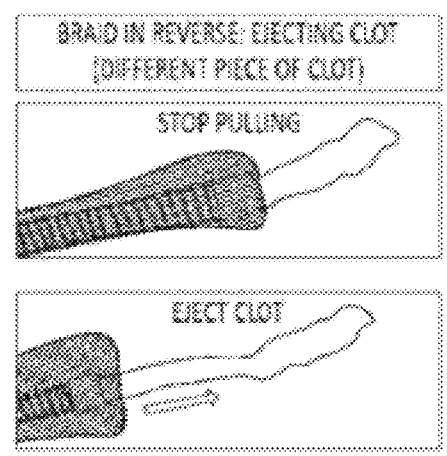
FIGS. 16A-16F

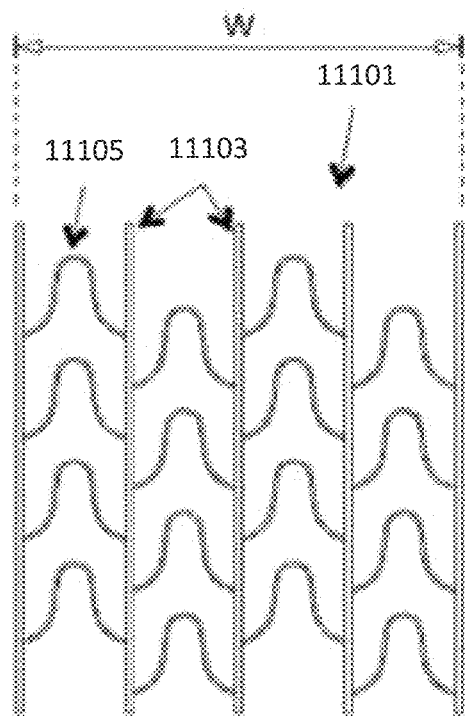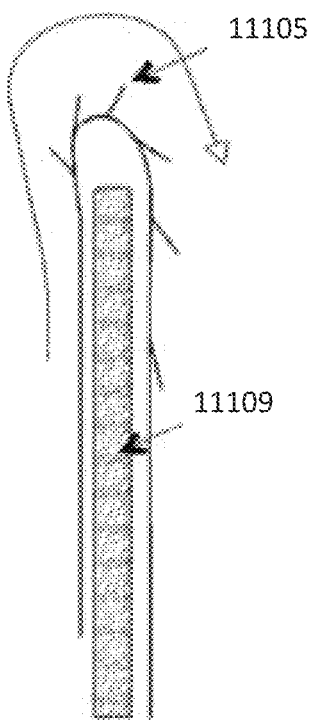
FIG. 21A
FIG. 21B
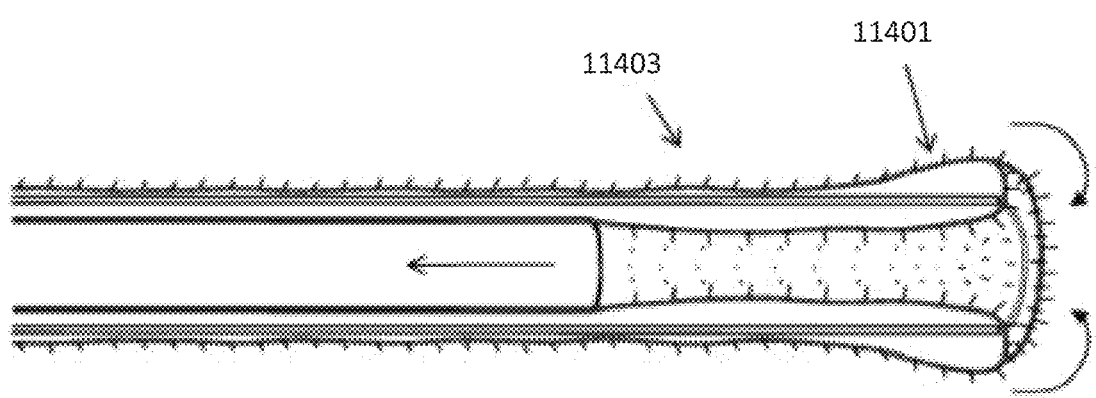
FIG. 22

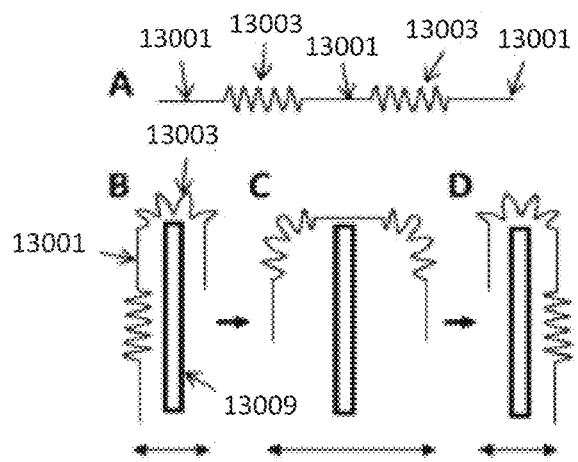
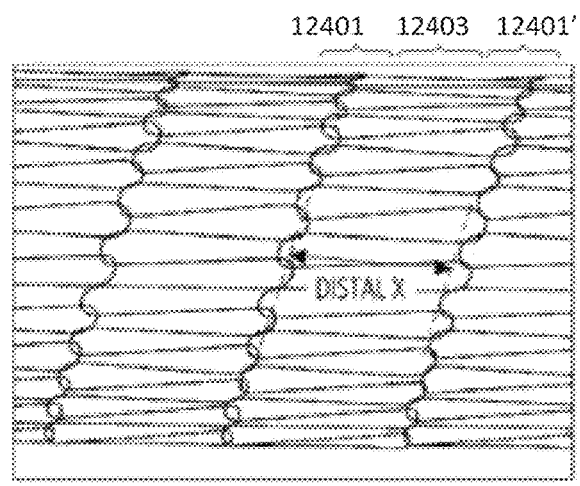
FIG. 38A-38D
FIG. 39A
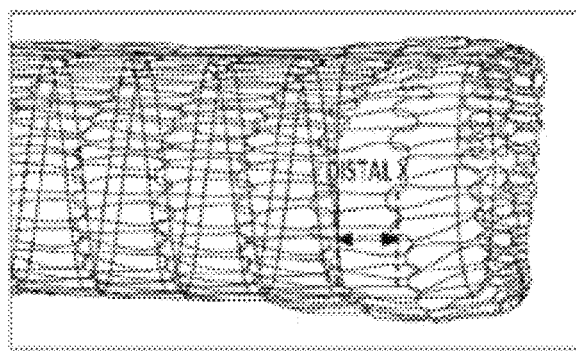
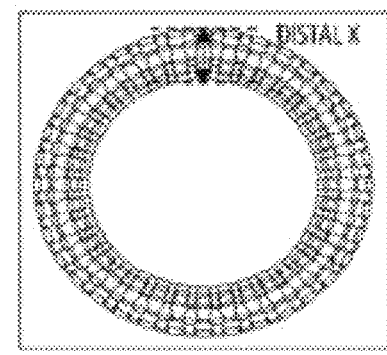
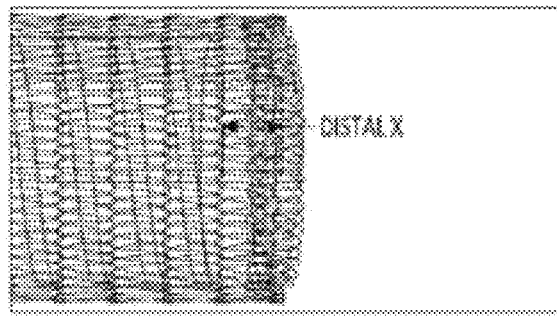
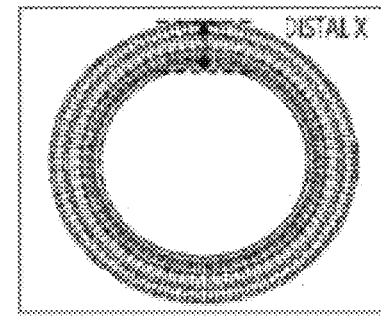
FIG. 39B-39E

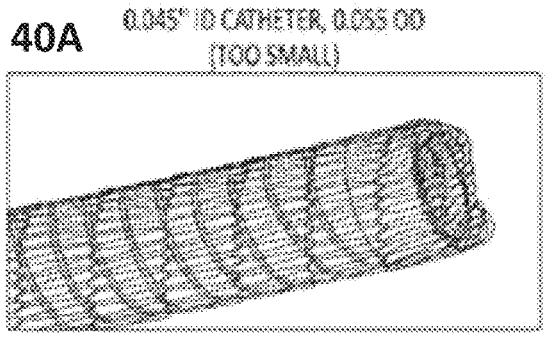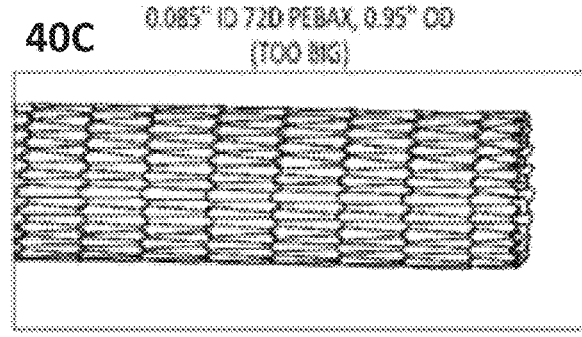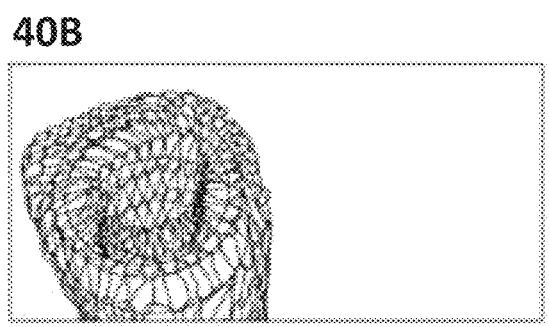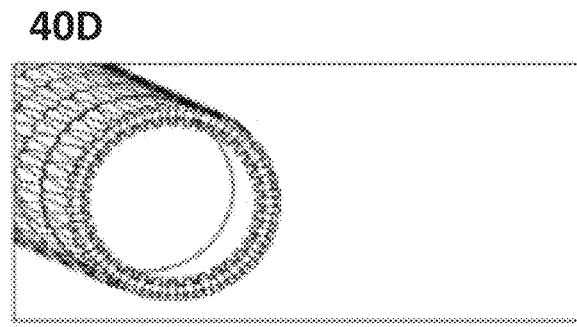
FIGS. 40A-40D
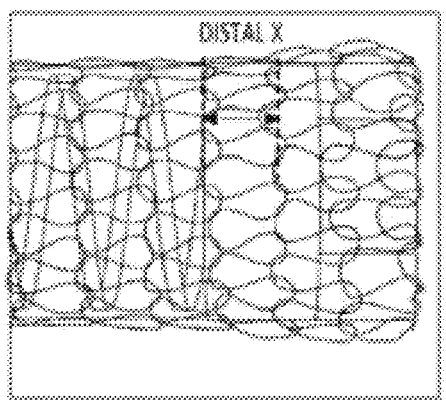
FIG. 41A
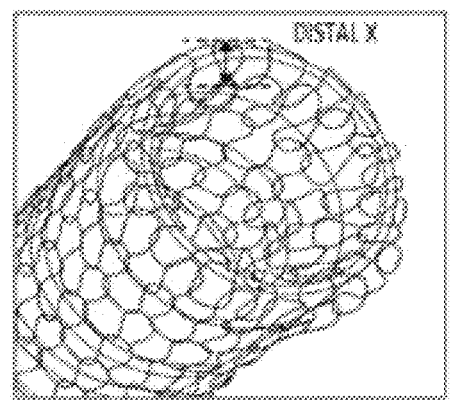
FIG. 41B

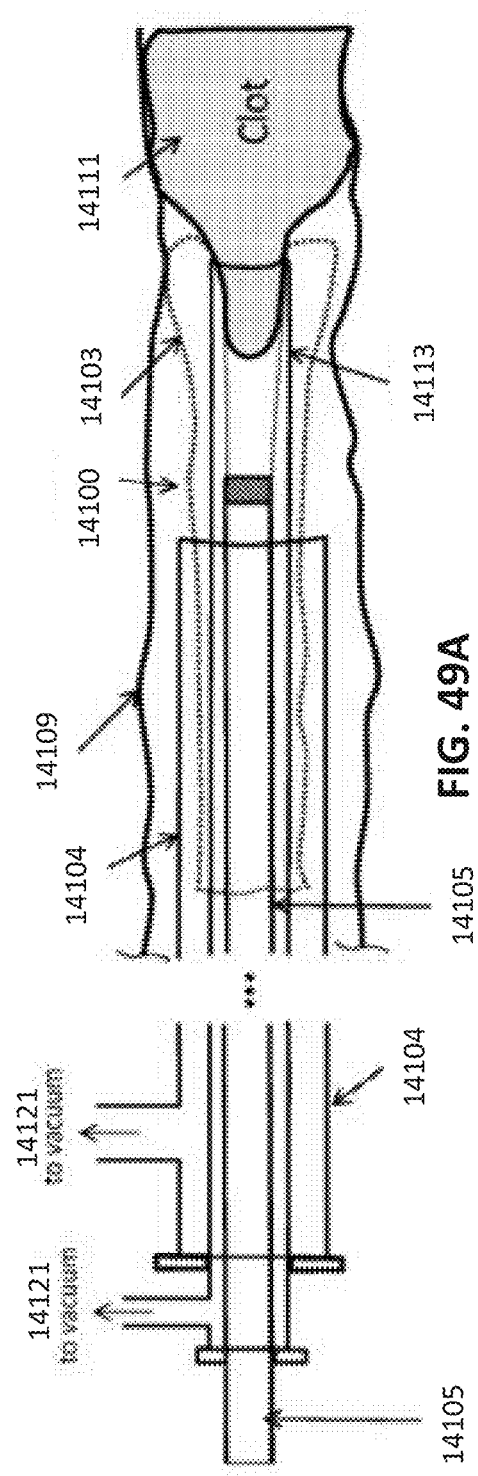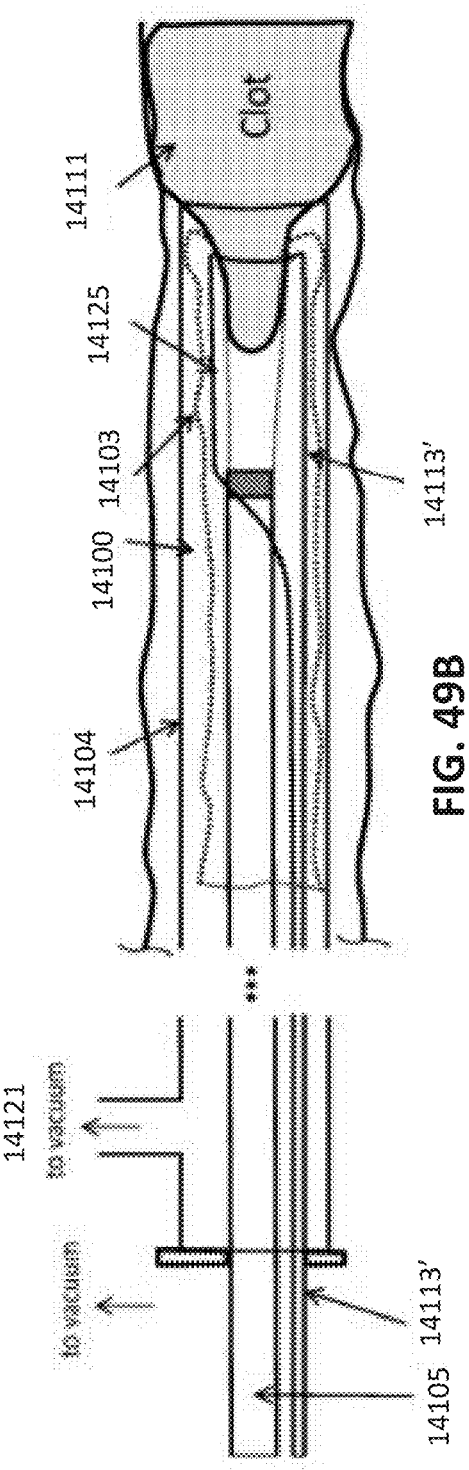

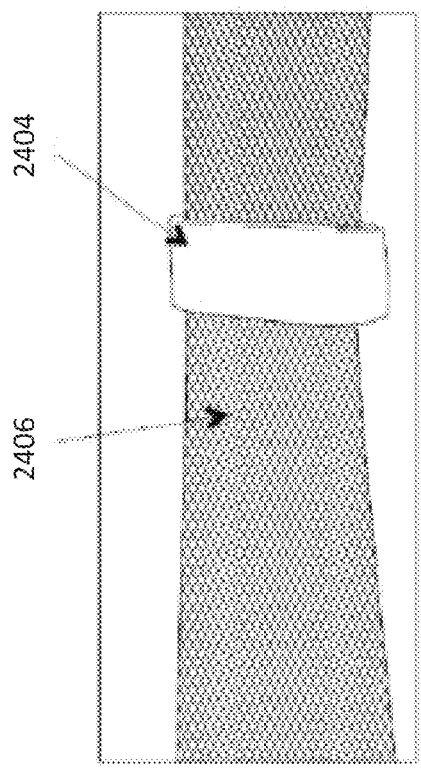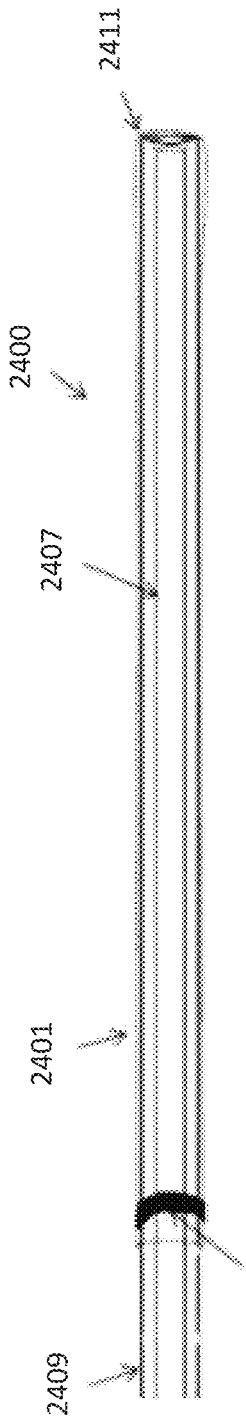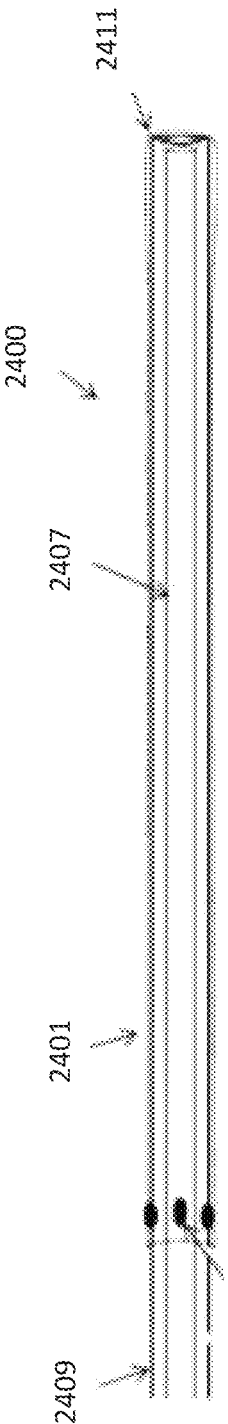
FIG. 55A
FIG. 55B
FIG. 55C

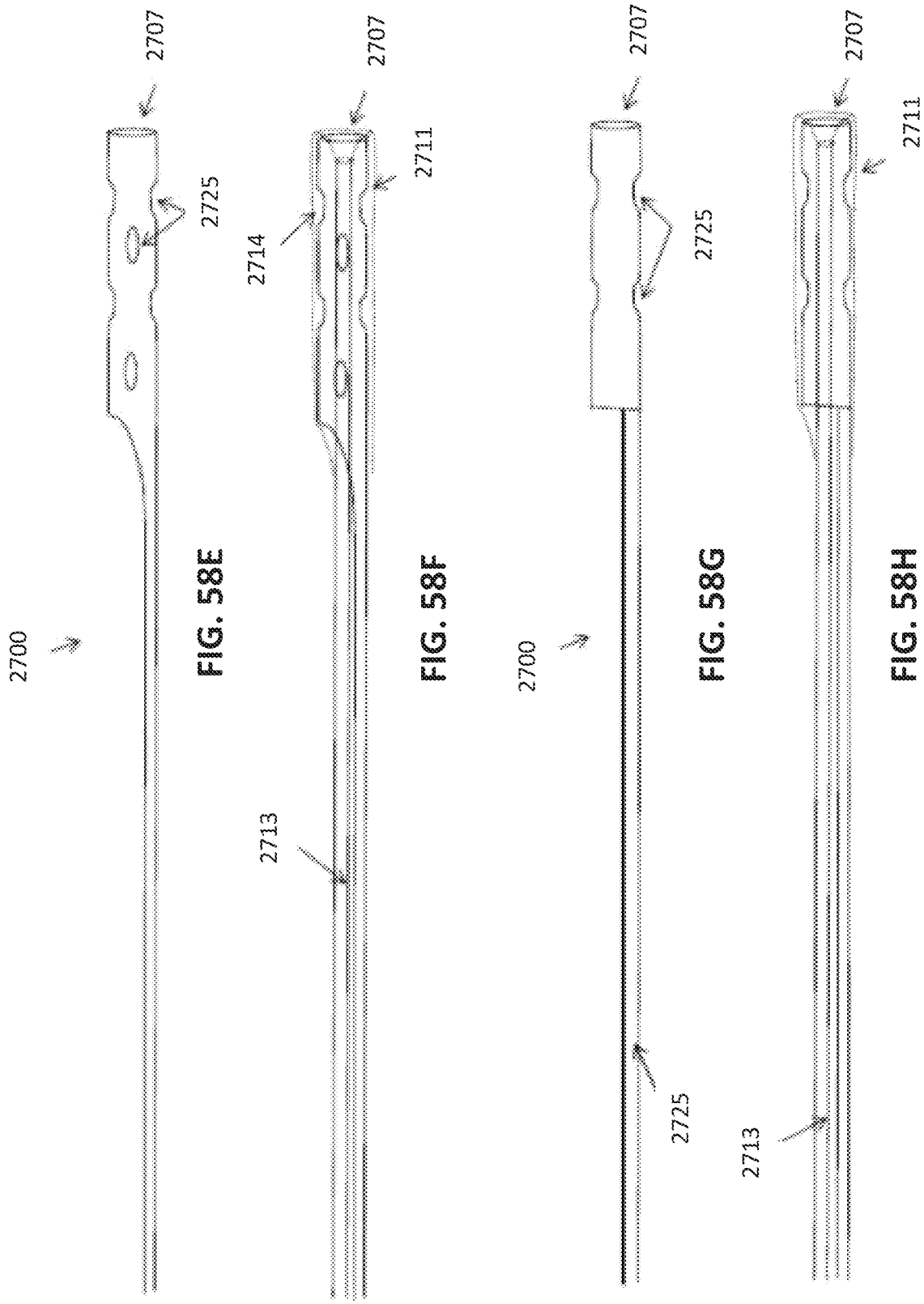

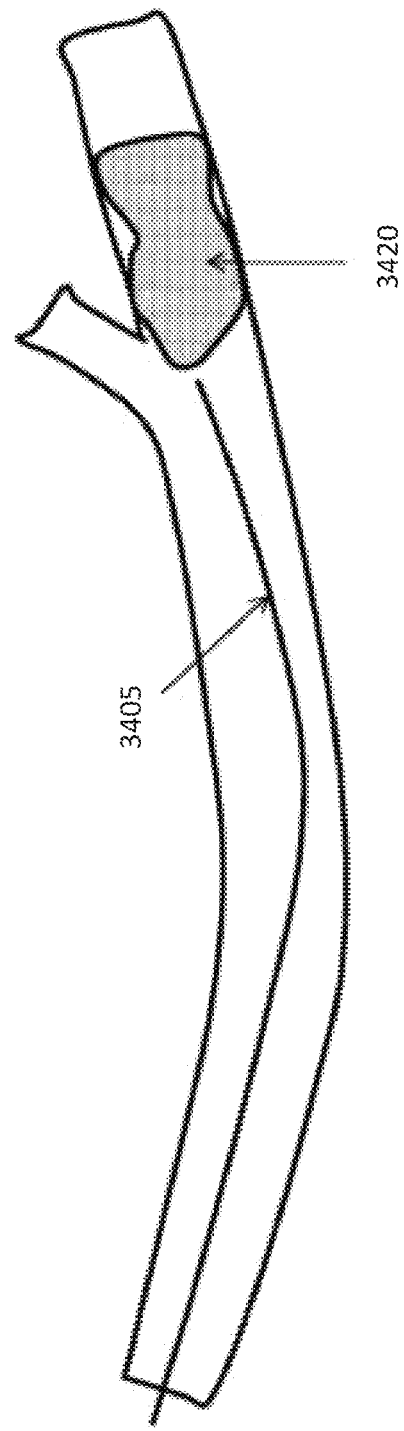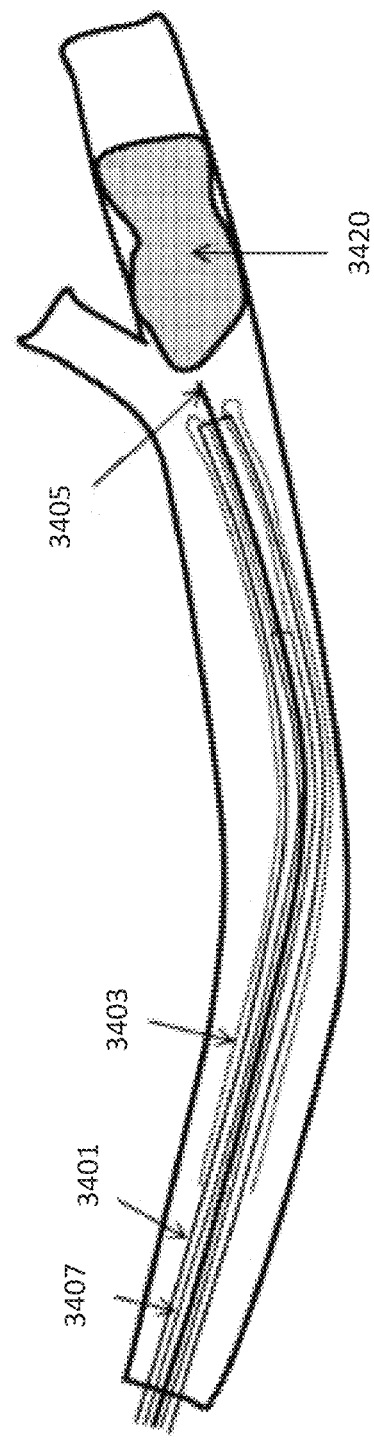
FIG. 64A
FIG. 64B

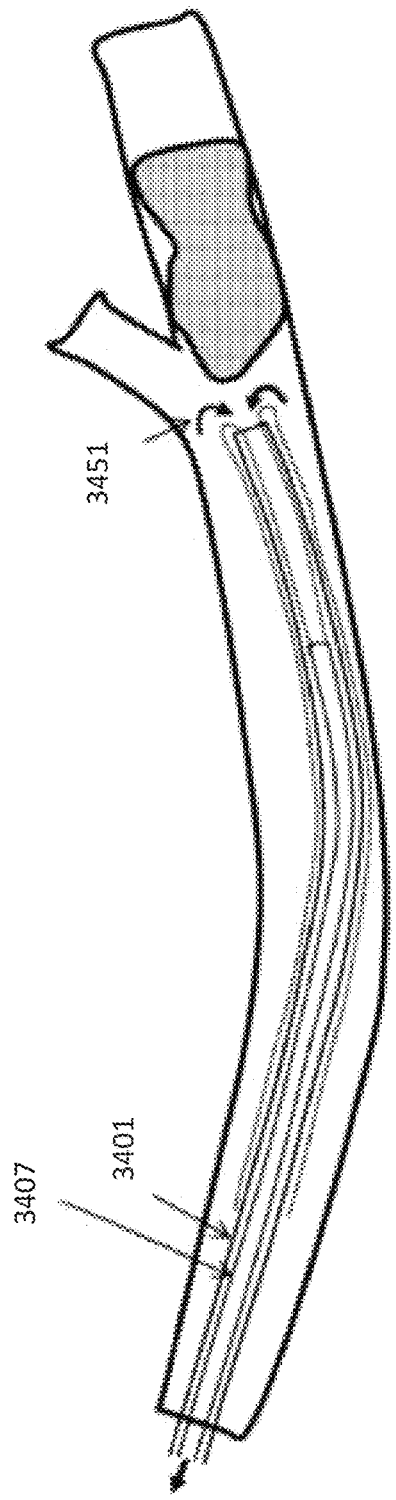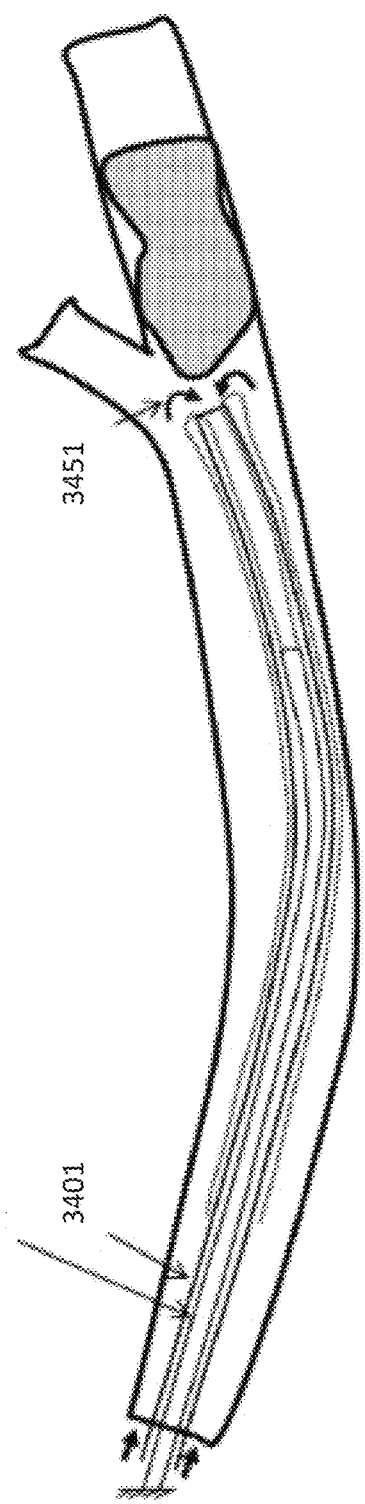
FIG. 64C
FIG. 64D

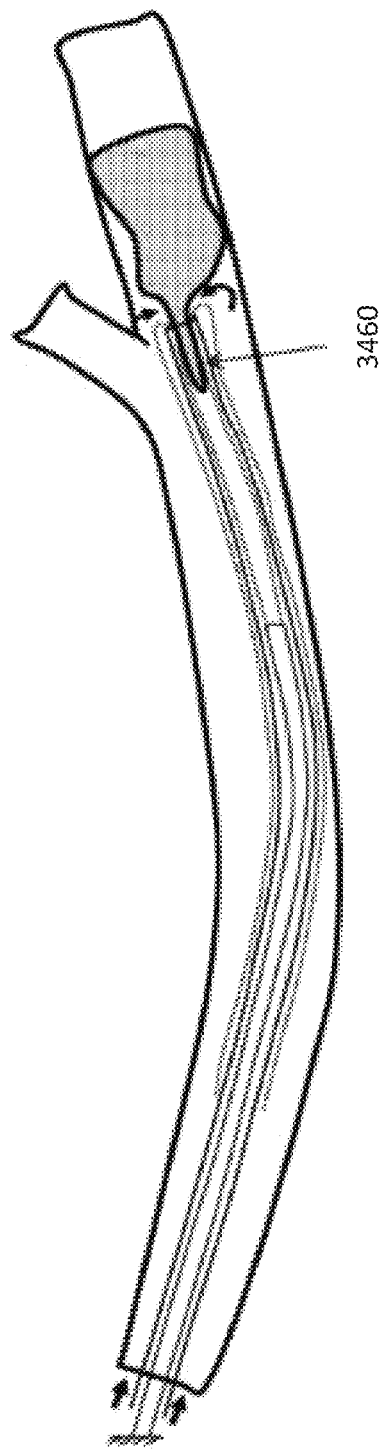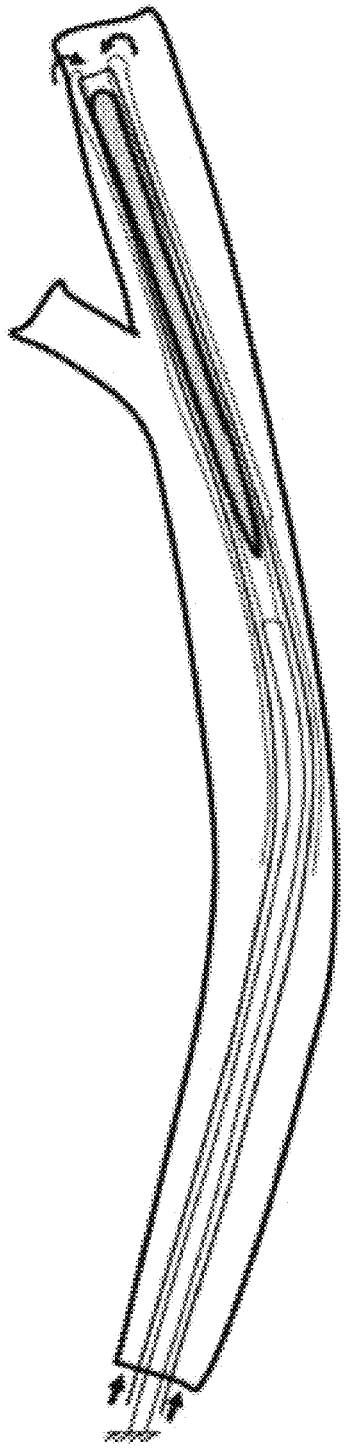
FIG. 64E
FIG. 64F

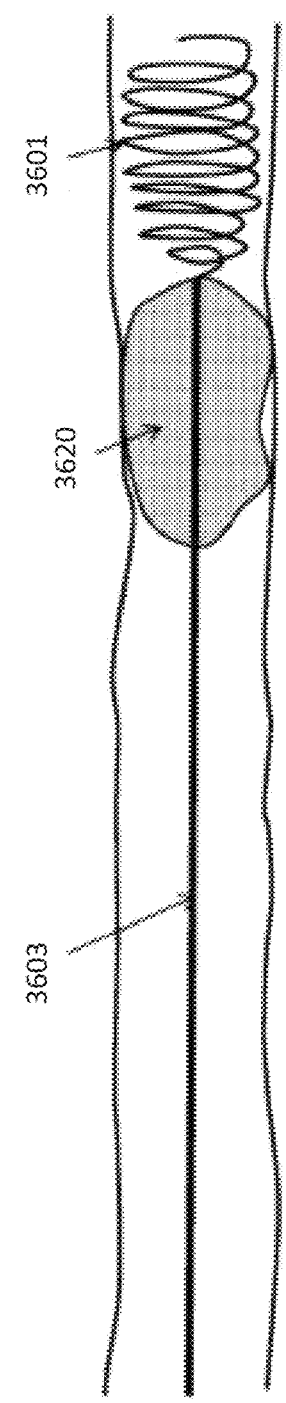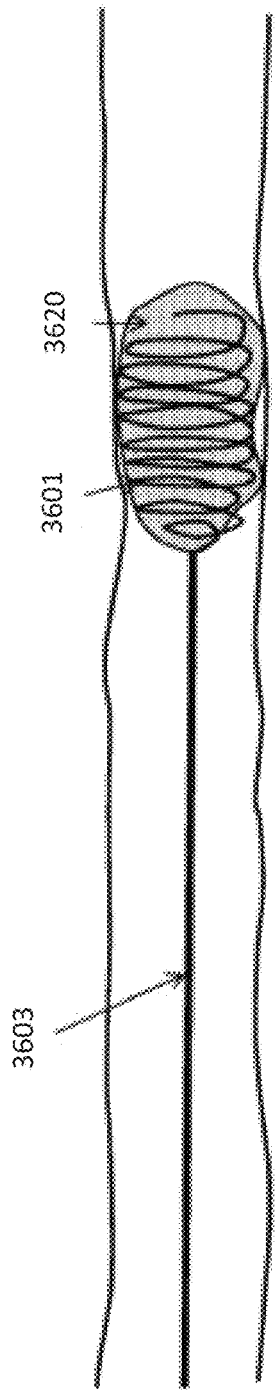

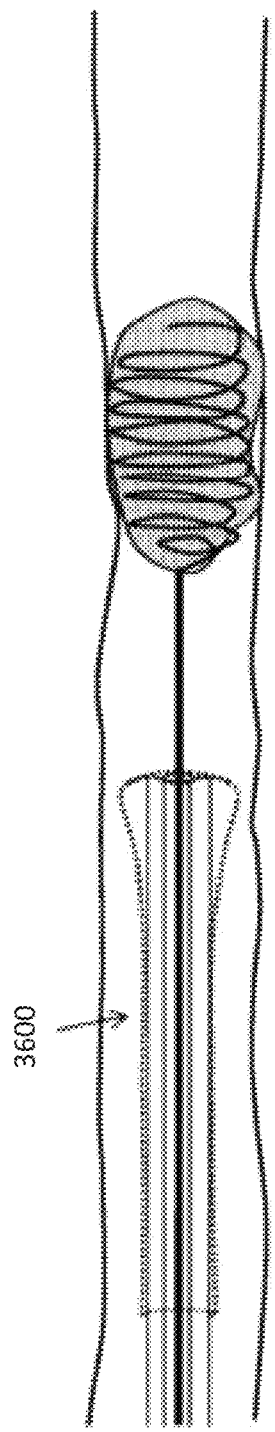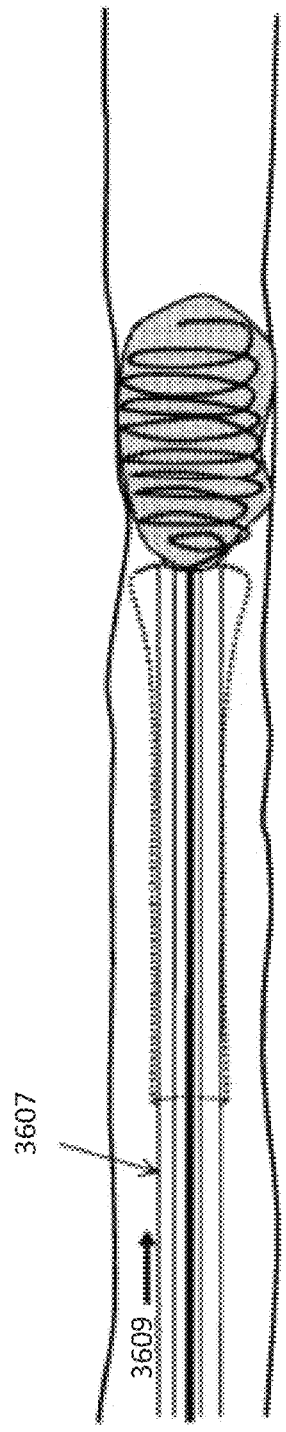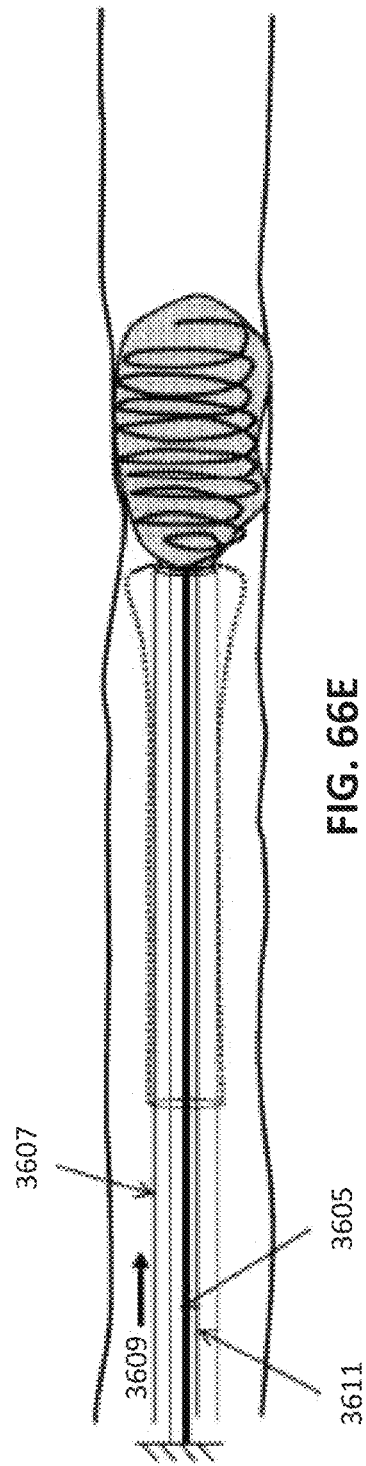

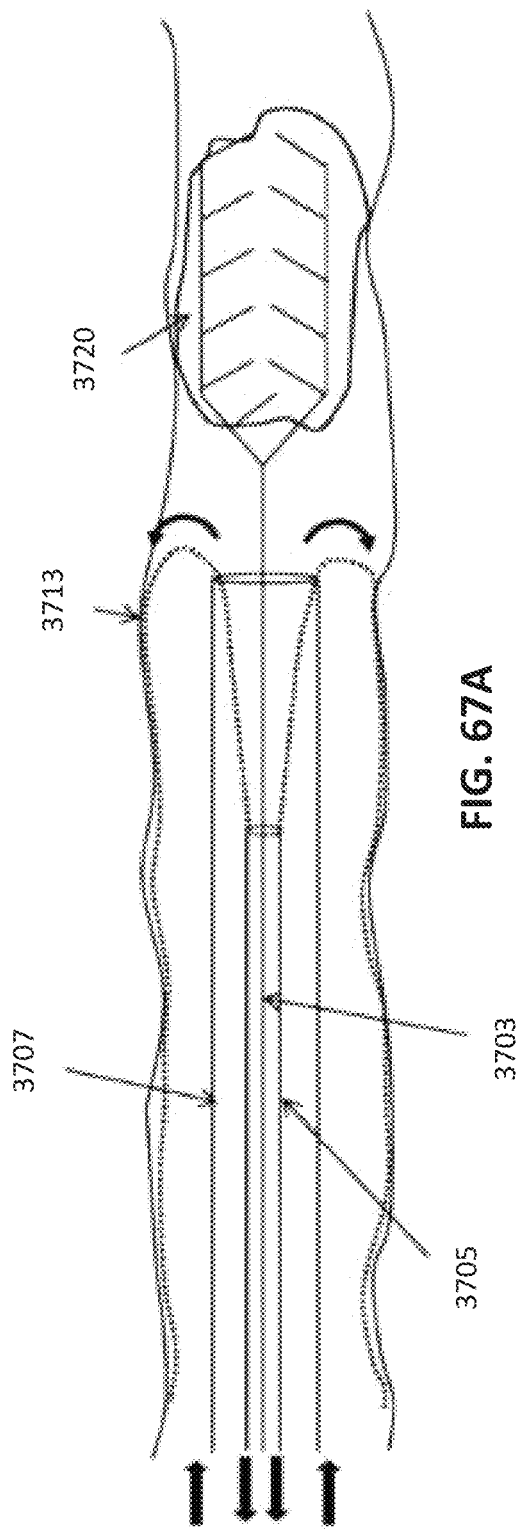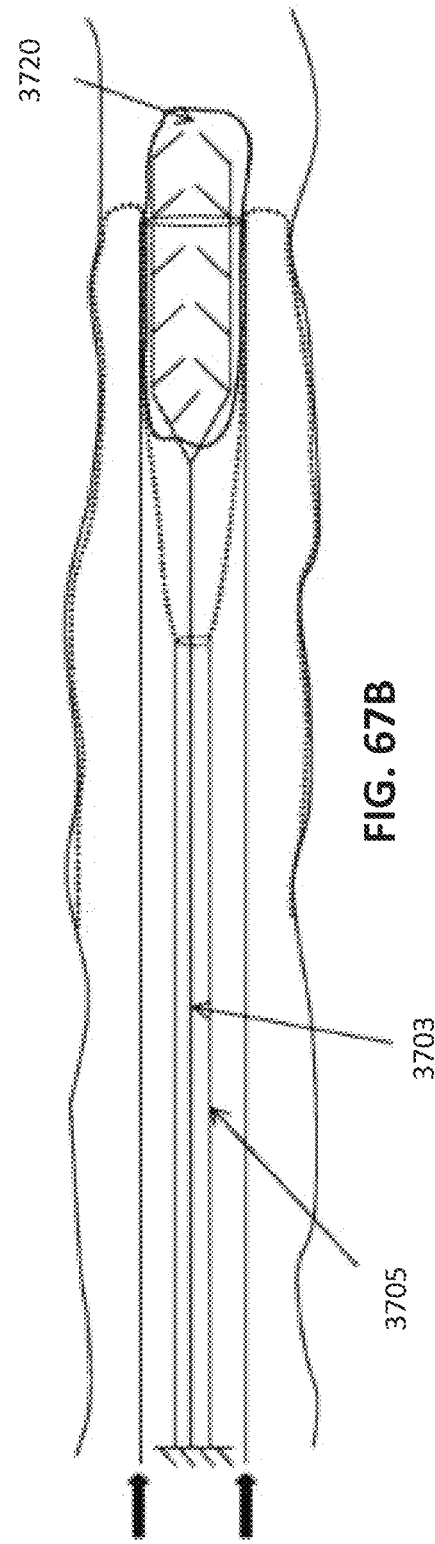

INVERTING MECHANICAL THROMBECTOMY APPARATUSES

CROSS REFERENCE TO RELATED APPLICATIONS

This application is a continuation-in-part of U.S. patent application Ser. No. 15/794,939, filed Oct. 26, 2017, titled "METHODS FOR ADVANCING INVERTING MECHANICAL THROMBECTOMY APPARATUSES IN THE VASCULATURE," now U.S. Pat. No. 10,842,513, which is a divisional of U.S. patent application Ser. No. 15/496,786, filed Apr. 25, 2017, titled "INVERTING MECHANICAL THROMBECTOMY APPARATUSES," which claims priority to U.S. Provisional Patent Application No. 62/327,024, filed on Apr. 25, 2016 and titled "DOZER THROMBECTOMY SYSTEM."

This patent application is also a continuation-in-part of U.S. patent application Ser. No. 16/169,334, filed Oct. 24, 2018, titled "ANTI-JAMMING AND MACERATING THROMBECTOMY APPARATUSES AND METHODS," which is a continuation of PCT Application No. US2017/029345, filed Apr. 25, 2017, which claims priority to U.S. Provisional Patent Application No. 62/327,024, filed on Apr. 25, 2016 and titled "DOZER THROMBECTOMY SYSTEM;" U.S. Provisional Patent Application No. 62/345,152, filed on Jun. 3, 2016, and titled "DOZER THROMBECTOMY SYSTEM 2;" and U.S. Provisional Patent Application No. 62/393,460, filed on Sep. 12, 2016, and titled "DOZER II THROMBECTOMY SYSTEM PROV."

This patent application is also a continuation-in-part of U.S. patent application Ser. No. 16/790,744, filed Feb. 14, 2020, titled "PRE-LOADED INVERTING TRACTOR THROMBECTOMY APPARATUSES AND METHODS," now U.S. Patent Application Publication No. 2020/0178991, which is a continuation of U.S. patent application Ser. No. 15/795,097, filed Oct. 26, 2017, titled "PRE-LOADED INVERTING TRACTOR THROMBECTOMY APPARATUSES AND METHODS," now U.S. Pat. No. 10,561,431, which is a divisional of U.S. patent application Ser. No. 15/496,668, filed Apr. 25, 2017, titled "PRE-LOADED INVERTING TRACTOR THROMBECTOMY APPARATUSES," now U.S. Pat. No. 9,962,178, which claims priority to each of: U.S. Provisional Patent Application No. 62/327,024, filed on Apr. 25, 2016 and titled "DOZER THROMBECTOMY SYSTEM;" U.S. Provisional Patent Application No. 62/345,152, filed on Jun. 3, 2016, and titled "DOZER THROMBECTOMY SYSTEM 2;" and U.S. Provisional Patent Application No. 62/357,677, filed Jul. 1, 2016 and titled "DOZER THROMBECTOMY SYSTEM 3."

This patent application is also a continuation-in-part of U.S. patent application Ser. No. 16/707,045, filed Dec. 9, 2019, titled "CLOT-ENGULFING MECHANICAL THROMBECTOMY APPARATUSES," now U.S. Patent Application Publication No. 2020/0107842, which is a continuation of U.S. patent application Ser. No. 15/497,092, filed Apr. 25, 2017, titled "CLOT-ENGULFING MECHANICAL THROMBECTOMY APPARATUSES," now U.S. Pat. No. 10,512,478, which claims priority to each of: U.S. Provisional Patent Application No. 62/327,024, filed on Apr. 25, 2016 and titled "DOZER THROMBECTOMY SYSTEM;" U.S. Provisional Patent Application No. 62/345,152, filed on Jun. 3, 2016, and titled "DOZER THROMBECTOMY SYSTEM 2;" and U.S. Provisional Patent Application No. 62/357,677, filed Jul. 1, 2016 and titled "DOZER THROMBECTOMY SYSTEM 3."

This patent application is related to U.S. patent application Ser. No. 16/907,153, filed on Jun. 19, 2020, titled "BIOPSY METHODS", which is a continuation of U.S. patent application Ser. No. 16/397,089, filed on Apr. 29, 2019, titled "MECHANICAL THROMBECTOMY APPARATUSES AND METHODS", which is a continuation of U.S. patent application Ser. No. 15/291,015, filed on Oct. 11, 2016, now U.S. Pat. No. 10,271,864, which is a continuation of U.S. patent application Ser. No. 15/043,996, filed Feb. 15, 2016, now U.S. Pat. No. 9,463,035, which claims priority to each of U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical thrombectomy apparatuses and methods. The apparatuses and methods described may also or alternatively herein relate to mechanical removal of objects from within a body. In particular, described herein are mechanical thrombectomy apparatuses and methods. The apparatuses and methods described herein also or alternatively relate to mechanical removal of objects from within a body. The apparatuses described herein also or alternatively relate to mechanical thrombectomy apparatuses and methods for removing a clot, including removing a clot captured by a clot capture device (e.g., a clot engaging member on the distal end of an elongate manipulator) with a rolling tractor that pulls the clot and clot capture device into a catheter.

BACKGROUND

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are apparatuses (devices, systems and kit) and methods of using them that may address the needs and problems discussed above.

SUMMARY OF THE DISCLOSURE

Described herein are mechanical thrombectomy apparatuses (devices, systems, etc.) and methods of using them to remove a thrombus, e.g., clot, including safely and easily removing a clot that is captured in a second clot-grabbing (e.g., thrombectomy) apparatus. The mechanical thrombectomy apparatuses described herein may be inverting tractor thrombectomy apparatuses. An inverting tractor apparatus may include a tractor (tractor region, tractor portion, etc.) comprising a flexible tube of material that inverts as it rolls over itself at a distal end. The tractor may be inverted and/or rolled over the end of a catheter. Thus, the flexible tractor may invert and fold back into itself and may be drawn into a catheter portion in a conveyor-like motion as it rolls around to transition from an outward-facing region of the tractor on an outside of the catheter to an inward-facing region within the lumen of the catheter. The rolling motion may draw a clot and/or clot connected to a clot-grabbing apparatus within a vessel into the catheter, which may also compress and/or macerate the clot. The apparatus, including the clot, and in some variations clot and a clot engaging member engaged with the clot, may then be removed from the body.

Any of these apparatuses may include or may be used as part of a system with, a clot capture device having a clot engaging member (e.g., a "stentriever") at the distal end of an elongate manipulator.

The mechanical thrombectomy apparatuses described herein may include pre-loaded inverting tractor thrombectomy apparatuses (e.g., devices, systems, etc.). Described herein are mechanical thrombectomy apparatuses, including inverting tractor thrombectomy apparatuses that may engulf a clot prior to pulling it (e.g., into the apparatus) and may be used in combination with other systems. Such apparatuses may invert over clot first and may then pull the clot into the catheter. Any of these apparatuses may also incorporate aspiration.

Described herein are mechanical thrombectomy systems that include an elongate inversion support (typically comprising a catheter), a flexible tractor that inverts over the distal end opening of the elongate inversion support, a puller extending proximally to roll and invert the tractor into the distal end opening, and a clot engaging member on the distal end of an elongate manipulator. The puller and tractor are configured to pass the elongate manipulator through a lumen extending continuously through the puller and the tractor. As described above, in operation, this may be used to slide the rolling thrombectomy portion (e.g., the elongate inversion support, a flexible tractor and a puller) over the elongate manipulator of the clot capture device (e.g., clot engaging member on the distal end of an elongate manipulator).

For example, described herein are mechanical thrombectomy systems including: an elongate inversion support comprising a catheter having a distal end and a distal end opening; a tractor comprising a flexible tube that extends distally in an un-inverted configuration within the catheter, inverts over the distal end opening of the catheter and extends proximally in an inverted configuration along the distal end of the catheter, wherein the tractor is configured to invert by rolling over the distal end opening of the catheter when a first end of the tractor is pulled proximally within the catheter; a puller connected to the first end of the tractor extending proximally; a clot engaging member on the distal end of an elongate manipulator; and a lumen extending continuously through the puller and the tractor and configured to pass the expandable elongate manipulator.

In any of these apparatuses (e.g., systems, devices, etc.), the tractor may be sufficiently soft such that without support from the catheter, it collapses radially under an axial compression of less than a small force (e.g., less than 50 g of force, 100 g of force, less than 150 g of force, less than 200 g of force, less than 250 g of force, less than 300 g of force, etc.) when inverting.

Further, in any of these apparatuses, the tractor may be biased to expand to greater than the outer diameter of the catheter in the inverted configuration and is biased to expand to greater than the inner diameter of the catheter in the un-inverted configuration.

The clot engaging member may be expandable. For example, the clot engaging member may be one or more of: a coil, a snare, a basket, or a frame. The elongate manipulator may be a wire, tube (e.g., hypotube), rod, etc.

Any appropriate flexible tractor may be used. For example, the tractor may be one or more of: a braided material, a knitted material, or a woven material. The tractor is typically a tube of material. The tractor may comprise steel, polyester, nylon, expanded Polytetrafluoroethylene (ePTFE), Nitinol, or a fabric.

The catheter of the elongate inversion support may extend the full length of the inversion support, or it may be just at the end of the elongate inversion support. The catheter may be soft (e.g., appropriate for neurovascular use), however the tip may be harder, to resist collapse. For example, the material hardness of catheter decreases over the distal end of the catheter until the distal end opening, wherein the distal end opening has a material hardness that is greater than a material hardness of a region immediately proximal to the distal end, further wherein the distal end opening has a rounded lip profile.

The tractor may be lubricious and/or may comprise one or more coatings from the group of: a lubricious coating, a metal coating, a heparin coating, an adhesive coating, and a drug coating. The tractor may be any appropriate length (e.g., between about is 3 cm to 100 cm long, between about 10 cm to 200 cm long, between about 3 cm to 50 cm long, between about 200 cm to 500 cm long, etc.).

Any of these apparatuses may be configured to controllably deploy the tractor, which may be held compressed and/or against the catheter of the elongate inversion support until being deployed. For example, any of these apparatus may include a releasable attachment between the tractor and an outer surface of the catheter (e.g., a tractor hold), wherein the releasable attachment is configured to release when the tractor is pulled (e.g., proximally by the puller) with a force that is greater than a predetermined force threshold. The deployment force threshold may be between 50 g and 500 g of force (e.g., between 50 g and 400 g of force, between 100 g and 400 g of force, etc.).

Any of these apparatuses may include a sleeve extending over the catheter and tractor. The sleeve may be an outer or intermediate catheter.

A mechanical thrombectomy system for removing a clot from within a vessel may include: an elongate inversion support comprising a catheter having a distal end and a distal end opening; a tractor comprising a flexible tube that extends distally in an un-inverted configuration within the catheter, inverts over the distal end opening of the catheter and extends proximally in an inverted configuration along the distal end of the catheter, wherein the tractor is configured to invert by rolling over the distal end opening of the catheter when a first end of the tractor is pulled proximally within the catheter; a puller extending proximally within the catheter and connected to the first end of the tractor; an expandable clot engaging member on the distal end of an elongate manipulator, wherein the expandable clot engaging member comprises one or more of: a coil, a snare, a basket, or a frame; and a lumen extending continuously through the puller and the tractor and configured to pass the expandable elongate manipulator.

In operation, these systems may be used to withdraw a thrombus (clot) from within a vessel, including peripheral vessels or neurovascular vessels. For example, described herein are methods of removing a clot from within a vessel using a mechanical thrombectomy apparatus. These methods generally include rolling the tractor into the catheter by pulling proximally on the tractor (e.g., by pulling on a puller that extends proximally and is attached to the first end of the tractor within the catheter) to roll the tractor into the catheter. The conveyer-belt like tractor motion, either alone or in conjunction with aspiration applied from the proximal end through the mechanical thrombectomy apparatus (e.g., catheter) and/or an outer catheter within which the mechanical thrombectomy apparatus is passed, may be used to pull a clot into the catheter. Typically when drawing the clot into the apparatus (e.g., into the catheter portion of the apparatus), the clot, or a clot and additional clot engaging member coupled to the clot, may be compressed as it is drawn into the apparatus.

In some cases, the clot may clog or jam in the apparatus. Described herein are methods of removing a clot from within a vessel using a mechanical thrombectomy apparatus, including methods configured to avoid or correct jamming and/or clogging of the apparatus. The method may include: positioning a distal end of the mechanical thrombectomy apparatus adjacent to the clot within a vessel, wherein the mechanical thrombectomy apparatus includes a tractor region that extends along a distal region of a catheter and inverts over a distal end of the catheter so that a first end of the tractor extends proximally within the catheter; pulling the first end of the tractor proximally within the catheter to roll the tractor over the distal end of the catheter so that the tractor inverts over the distal end of the catheter and pull the clot into the catheter with the inverting tractor; withdrawing the catheter proximally away from the tractor and clot when the tractor jams on the distal end of the catheter; pulling the first end of the tractor proximally so that the tractor inverts over the clot within the vessel without rolling over the distal end opening of the catheter; and withdrawing the tractor and clot proximally from the vessel.

Any of the methods described herein may include releasing the tractor from a locked or secured position on the outside of the catheter of the apparatus. Thus, any of these apparatuses used herein may include a tractor hold that releasably secures the tractor to the outside of the catheter. For example, any of the methods described herein may include disengaging a second end of the tractor from a tractor hold that secures the second end of the tractor to an outer surface of the catheter by pulling the tractor proximally with a force greater than a deployment force and expanding the tractor against the vessel wall, wherein the second end of the tractor is disengaged before pulling the first end of the tractor proximally.

Once the clot and/or clot engaging member has been engulfed by the tractor, it may then be withdrawn back into the catheter, without requiring the tractor to invert over the catheter. For example, any of the methods described herein may also or alternatively include pulling proximally on the tractor to draw the tractor and clot into the catheter.

Pulling the first end of the tractor proximally within the catheter to roll the tractor over the distal end of the catheter may comprise advancing the catheter while pulling the first end of the tractor. Alternatively or additionally, pulling the first end of the tractor proximally so that the tractor inverts over the clot may further comprise pulling the catheter proximally with the first end of the tractor. Alternatively or additionally, pulling the first end of the tractor proximally so that the tractor inverts over the clot may comprise pulling a puller at the proximal end of the mechanical thrombectomy apparatus proximally.

Withdrawing the catheter proximally away from the tractor may comprise pulling the catheter proximally a short distance or a substantial distance. For example, the catheter may be pulled proximally only sufficiently far to disengage the jam of the clot (and/or clot engaging member) from the catheter distal end opening. Alternatively or additionally, withdrawing the catheter proximally away from the tractor (the tractor distal-facing end) may include pulling the catheter beyond a second end of the tractor that is outside of the catheter.

Alternatively or additionally, the catheter may be pulled proximally with the first end of the tractor (e.g., the tractor puller) as the tractor is pulled proximally so that the tractor inverts over the clot within the vessel without rolling over the distal end opening of the catheter.

In any of the methods described herein the tractor may be expanded to that all or a portion of the tractor contacts the wall of the vessel. Thus, the tractor may be expanded when released (e.g., from the tractor hold) to contact the wall of the vessel. Any of the tractors described herein may be biased (e.g., heat set, etc.) so that it expands (when over the catheter) to approximately 1× or more (e.g., 1.1×, 1.2×, 1.3×, 1.4×, 1.5×, etc.) the diameter of the vessel. Contact between the vessel wall and the tractor may provide resistance that enhances the ability of the tractor to invert when the first end of the tractor is pulled proximally without inverting over the distal end opening of the catheter. Pulling the first end of the tractor proximally so that the tractor inverts over the clot may comprise pulling the first end of the tractor when the tractor has expanded to contact the vessel wall.

In any of the methods described herein, a guidewire, catheter or the like may be used to position the apparatus near, adjacent to, or on the clot. For example, positioning the distal end of the mechanical thrombectomy apparatus adjacent to the clot may comprise sliding the mechanical thrombectomy apparatus over a guidewire or catheter passing through a lumen in the mechanical thrombectomy apparatus.

A method of removing a clot from within a vessel using a mechanical thrombectomy apparatus may include: positioning a distal end of the mechanical thrombectomy apparatus adjacent to the clot within a vessel, wherein the mechanical thrombectomy apparatus includes a tractor region that extends along a distal region of a catheter and inverts over a distal end of the catheter so that a first end of the tractor extends proximally within the catheter; disengaging a second end of the tractor from a tractor hold that secures the second end of the tractor to an outer surface of the catheter by pulling the tractor proximally with a force greater than a deployment force and expanding the tractor against the vessel wall; pulling the first end of the tractor proximally within the catheter to roll the tractor over the distal end of the catheter so that the tractor inverts over the distal end of the catheter and pull the clot into the catheter with the inverting tractor; withdrawing the catheter proximally away from the tractor and clot when the tractor jams on the distal end of the catheter; pulling the tractor and clot proximally so that the tractor inverts over the clot within the vessel without rolling over the distal end opening of the catheter; pulling proximally on the tractor to draw the tractor and clot into the catheter; and withdrawing the tractor and clot proximally from the vessel.

Also described herein are methods of removing a clot from within a vessel using a mechanical thrombectomy apparatus in which a secondary clot-grabbing device (e.g., generally referred to herein as a clot engaging member), which may be a secondary device or a part of the mechanical thrombectomy apparatuses described herein, is removed with the clot. Any appropriate clot engaging member may be used. In particular, a clot engaging member may include an expandable/compressible clot engaging member that is configured a frame or wire. For example, a clot engagement member may be an expandable coil or plurality of coils, snare, basket, or frame. Any of these clot engagement members may include an elongate manipulator (e.g., an elongate wire, catheter, shaft, member, etc.) attached to the clot engagement member, such as the proximal end of the clot engagement member.

Any of the methods described herein may include tracking over the clot engaging member, including sliding over the elongate member attached to the clot engagement member. The mechanical thrombectomy apparatus may be guided to the clot and/or clot engagement member by sliding distally over an elongate member attached to a clot engagement member that has been previously coupled with a clot.

The clot engagement member may be coupled to the clot by passing into and/or through the clot. For example, the clot engagement member may be passed into the clot where it may engage with the clot material and expanded into the clot. Alternatively or additionally, the clot engagement member may be passed through the clot and expanded distally of the clot so that it may drive the clot proximally when the clot engagement member is pulled proximally, e.g., by pulling proximally on the elongate member coupled to the clot engagement member.

For example a method of removing a clot from within a vessel using a mechanical thrombectomy apparatus may include: engaging the clot with a clot engaging member on the distal end of an elongate manipulator; sliding the mechanical thrombectomy apparatus over the elongate manipulator to position the distal end of the mechanical thrombectomy apparatus adjacent to the clot, wherein the mechanical thrombectomy apparatus includes a tractor region that extends along a distal region of a catheter and inverts over a distal end of the catheter so that a first end of the tractor extends proximally within the catheter; pushing the catheter distally while holding the first end of the tractor within the catheter fixed relatively to the elongate manipulator so that the tractor rolls and inverts over the distal end of the catheter and pulls the clot and the clot engaging member into the catheter with the inverting tractor; and withdrawing the mechanical thrombectomy apparatus, clot and clot engaging member from the vessel.

As mentioned, the clot engaging member may engage with the clot by expanding into the clot and/or beyond the clot. For example, engaging the clot with the clot engaging member on the distal end of the elongate manipulator may comprise expanding the engaging member within the clot. Engaging the clot with the clot engaging member on the distal end of the elongate manipulator may comprise expanding the engaging member on a distal side of the clot. In general, engaging the clot with the clot engaging member on the distal end of the elongate manipulator may comprise expanding the engagement member. For example, the engaging member may comprise an expandable coil(s), snare, basket, or frame.

In any of these methods in which a clot engaging member is used with the rolling mechanical thrombectomy apparatus, the apparatus may be advanced distally over the apparatus to capture the clot and clot engaging member. For example, in any of these methods pulling the first end of the tractor proximally may comprise advancing the catheter distally as the tractor is pulled proximally. Engulfing the clot and/or clot engaging member by advancing distally over the clot and/or clot engaging member may be particularly beneficial compared to methods in which the clot and clot engaging member are drawn proximally to be engulfed.

In any of these apparatuses, pulling the first end of the tractor proximally may comprise pulling a puller proximally wherein the puller is coupled to the first end of the tractor. Alternatively or additionally, pulling the first end of the tractor proximally may comprise pulling the elongate manipulator proximally with the first end of the tractor.

Any of these methods may also include releasing the tractor from the catheter. For example, any of these methods may include disengaging a second end of the tractor from a tractor hold that secures the second end of the tractor to an outer surface of the catheter by pulling the tractor proximally with a force greater than a deployment force and expanding the tractor against the vessel wall.

A method of removing a clot from within a vessel using a mechanical thrombectomy apparatus may include: engaging the clot with a clot engaging member on the distal end of an elongate manipulator; sliding the mechanical thrombectomy apparatus over the elongate manipulator to position the distal end of the mechanical thrombectomy apparatus adjacent to the clot, wherein the mechanical thrombectomy apparatus includes a tractor region that extends along a distal region of a catheter and inverts over a distal end of the catheter so that a first end of the tractor extends proximally within the catheter; sliding the mechanical thrombectomy apparatus over the elongate manipulator to position the distal end of the mechanical thrombectomy apparatus adjacent to the clot, wherein the mechanical thrombectomy apparatus includes a tractor region that extends along a distal region of a catheter and inverts over a distal end of the catheter so that a first end of the tractor extends proximally within the catheter; and withdrawing the mechanical thrombectomy apparatus, clot and clot engaging member proximally from the vessel.

Described herein are mechanical thrombectomy apparatuses (devices, systems, etc.) and methods for using them to remove a thrombus, e.g., clot, from within a vessel. These mechanical thrombectomy apparatuses may be inverting tractor thrombectomy apparatuses. Described herein are mechanical thrombectomy apparatuses (devices, systems, etc.) and methods of using and making them. These apparatuses may be configured to prevent or reduce jamming and enhance grabbing and/or macerating a thrombus, e.g., clot, being removed. Typically, the mechanical thrombectomy apparatuses described herein are inverting tractor thrombectomy apparatuses that includes a tractor (e.g., tractor region, tractor portion, etc.) comprising a flexible tube of material that inverts over itself as it rolls over a distal end opening of an elongate inversion support. The elongate inversion support typically comprises a catheter having a distal end opening into which the tractor inverts. The flexible tractor inverts and rolls back into itself and may be drawn into the elongate inversion support in a conveyor-like motion; the outward-facing region rolls around to become an inward-facing region, e.g., within the lumen of the elongate inversion support. The rolling motion may thus draw a clot or other object within a vessel into the elongate inversion support.

Before these apparatuses can remove a clot from a vessel, however, they must be positioned within the vessel adjacent to the clot to be removed. As described herein, the inverting tractor thrombectomy apparatuses described herein may be accurately positioned either with our without the use of a guidewire or guide sleeve within a vessel by taking advantage of the rolling motion of tractor at the distal end of the apparatus. The arrangement of the tractor, elongate inversion support (e.g. which may be or may include a catheter) and the puller connected to the tractor may be used to easily and accurately position the apparatus adjacent a clot and remove the clot in a manner that may be both easier and more efficient than other methods.

Described herein are methods of advancing an inverting tractor thrombectomy apparatus forward in the vasculature. These systems and methods may use the rolling motion of the tractor to move through the vasculature including over/around clot.

For example, described herein are methods of removing a clot from a vessel using a mechanical thrombectomy apparatus. The mechanical thrombectomy apparatus may include an elongate inversion support (comprising or consisting of a catheter) that extends in a long axis from a proximal end to a distal end, a puller extending distally within the elongate inversion support (e.g. catheter) and a flexible and tubular tractor, wherein the tractor is coupled to a distal end region of the puller and further wherein the tractor is inverted over a distal end opening of the catheter so that the tractor extends proximally over the catheter. Any of these methods may include: advancing the puller distally within the elongate inversion support (e.g., catheter) and within the vessel towards a clot, so that the tractor extends from the puller distally beyond the distal end opening of the catheter, forming a gap between the tractor and the distal end opening of the catheter; advancing the catheter distally over the puller and into the gap; and drawing the clot into the catheter with the tractor by pulling the tractor proximally within the catheter so that the tractor rolls and inverts over the distal end opening of the catheter.

Any of these methods may include repeating the advancing steps one or more times. For example the method may include: advancing the puller distally within the elongate inversion support (e.g., catheter) and within the vessel towards a clot, so that the tractor extends from the puller distally beyond the distal end opening of the catheter, forming a gap between the tractor and the distal end opening of the catheter; advancing the catheter distally over the puller and into the gap; repeating the advance steps until the distal end opening of the catheter is adjacent to the clot; and drawing the clot into the catheter with the tractor by pulling the tractor proximally within the catheter so that the tractor rolls and inverts over the distal end opening of the catheter.

These methods for advancing the apparatus may therefore be described as "inchworm" type advancement, as the tractor is extended from within the catheter to distally extend in the vessel, then the catheter may follow the tractor distally. In any of these methods, the tractor may be 'reset' back into the catheter (as it may otherwise be left deployed out of the catheter along vessel), by pulling it back into the catheter. For example, the tractor may be pulled back into the catheter by pulling proximally on the puller once the catheter distal end opening is positioned against the distal-facing tractor (the region doubling-back or inverting over itself) so that the tractor can roll over the distal end opening. Resetting or repositioning the tractor in this manner may require that the apparatus be configured to prevent jamming (e.g., "anti-jamming"), including one or more of: having a lubricious and/or smooth tip, having a tip region that is more rigid than the more proximal regions of the tip, and/or having a tractor that is biased to have a first relaxed configuration that has an outer diameter that is greater than the inner diameter of the catheter and a second relaxed configuration that has an inner diameter that is greater than the outer diameter of the catheter, where the tractor converts between the first and second configurations by inverting over itself (e.g., over the distal end opening of a catheter). These configurations may prevent the tractor for buckling when pushed out of the distal end opening or when pulled back into the distal end opening of the catheter.

In any of the variations described herein, the repeated steps of inching forward by extending the tractor distally (e.g., pushing the puller coupled to the tractor distally, including distally out of the distal opening of the catheter), then advancing the catheter into the gap formed by the folded-over tractor, e.g., the gap between the distal end opening of the catheter and the tractor, may also include resetting the tractor by pulling the tractor back into the catheter once the distal end of the catheter has been advanced.

In any of these methods, the steps of advancing the tractor distally from the distal-end of the catheter and advancing the catheter behind the tractor (and optionally pulling the tractor back into the catheter by pulling proximally while holding the catheter fixed (or advancing it distally) may be repeated until the apparatus is adjacent to the clot; thereafter the clot can be removed as discussed above, by pulling the puller proximally to draw the tractor into the catheter.

In general, drawing the clot into the catheter may include advancing the catheter distally while pulling the pusher proximally.

In any of the methods described herein, the apparatus may be advanced distally (or retracted proximally) without the use of a guidewire or guide catheter. For example, advancing the puller distally may comprise advancing the puller without using a guidewire extending distal to the puller.

As mentioned, advancing the puller may comprise extending the distal end of the puller out of the distal end opening of the catheter. Alternatively the puller may remain in the catheter when advanced distally.

The tractor may be any appropriate tractor, including a woven, braided, or knitted tractor, or a tractor formed of a solid sheet of material (e.g., that may be cut or perforated). For example, advancing the puller may comprise extending the tractor distally within the vessel, further wherein the tractor comprises a woven flexible and tubular tractor. Advancing the puller may comprise extending the tractor distally within the vessel, further wherein the tractor comprises a knitted tractor.

Any of the methods described herein may include using a puller and tractor having a lumen (e.g., central lumen) through which a guidewire may be advanced. For example, advancing the puller may comprise extending the tractor distally within the vessel, further wherein the puller comprises a central lumen configured to pass a guidewire therethrough.

Further, any of the methods described herein may be performed in any vessel within the body, including peripheral and neurovascular vessels. For example, any of these methods may be performed within an internal carotid artery (e.g., advancing the puller may comprise advancing the puller within an internal carotid artery).

Also described herein are methods of positioning a mechanical thrombectomy apparatus within a vessel and/or removing a clot from a vessel using the mechanical thrombectomy apparatus in which the mechanical thrombectomy apparatus includes a puller within a first catheter that is within a second catheter, wherein the puller and second catheter are connected by a flexible and tubular tractor. For example, the method may comprise: advancing the puller distally through the first catheter and the second catheter and within the vessel towards a clot, so that the flexible and tubular tractor extends from the puller beyond a distal end opening of the first catheter and beyond a distal end opening of the second catheter; advancing the outer catheter distally through the vessel by one or more of: holding the position of the first catheter within the vessel and pulling the puller proximally within the first catheter; or moving the first catheter distally relative to the puller; and drawing the clot into the first catheter with the flexible and tubular tractor by pulling the flexible and tubular tractor proximally within the first catheter so that the flexible and tubular tractor rolls and inverts over the distal end opening of the catheter. Any of these methods may also include repeating the advancing steps until the clot is adjacent to the distal end of the puller.

Drawing the clot into the catheter may further include advancing the first catheter distally while pulling the pusher proximally. Advancing the puller distally may include advancing the puller without using a guidewire extending distal to the puller. Advancing the puller may include extending the flexible and tubular tractor distally within the vessel further wherein the flexible and tubular tractor comprises a woven flexible and tubular tractor. Alternatively, advancing the puller may include extending the flexible and tubular tractor distally within the vessel further wherein the flexible and tubular tractor comprises a knitted flexible and tubular tractor.

As mentioned, advancing the puller may comprise extending the flexible and tubular tractor distally within the vessel further wherein the puller has a central lumen configured to pass a guidewire therethrough.

In any of these methods, drawing the clot into the first catheter may comprise uncoupling the flexible and tubular tractor from the second catheter.

Also described herein are mechanical thrombectomy apparatus for removing a clot from a vessel that include a motorized or motor-driven tractor. For example described herein are apparatuses including: a flexible catheter having a distal end and a distal end opening; a tractor comprising a flexible belt that extends within the catheter, inverts over the distal end opening of the catheter and extends along the outer diameter of the catheter; a power drive at a proximal end of the flexible catheter configured to drive the tractor around the catheter so that it inverts over the distal end opening of the catheter; and a guidewire lumen through the catheter and the tractor configured to pass a guidewire.

The flexible belt may comprise a flexible tube. In some variations, the tractor comprises a plurality of flexible belts that each extend within the catheter, invert over the distal end opening of the catheter and extend along the outer diameter of the catheter.

The power drive may be configured to engage with the flexible belt on an outer surface of the catheter. The power drive may comprise an annular ring surrounding the catheter and the tractor.

Any of these apparatuses may include an outer catheter configured to enclose the flexible catheter and tractor, wherein the flexible catheter and tractor may be inserted through the body within the outer catheter.

Implementation of a rolling tractor that is sufficiently flexible to easily roll at the distal end (e.g., over a catheter) but sufficiently stiff to prevent jamming at the distal end of the elongate inversion support has proven challenging.

The elongate inversion support portion of the apparatus described herein may be or may include (particularly at its distal end) any appropriate catheter, e.g., a flexible tube that can be inserted into a body vessel (e.g., blood vessel) into which the more flexible tractor portion can be withdrawn by pulling against the elongate inversion support. The elongate inversion support may, in some variations, also be referred to as outer catheters (e.g., when the puller for the tractor is referred to as an inner catheter) and/or inversion catheters and/or support catheter, as it may support the inversion of the tractor. The elongate inversion support, including a catheter forming the elongate inversion support, may include a braided or woven portion, a spiral or coiled portion, etc. (e.g., having a braided shaft), may have a single layer or multiple layers, and may be formed of biocompatible materials, including polymers, metals, etc. (e.g., PTFE). Examples of vascular catheters that may form the elongate inversion support include micro catheters.

The mechanical thrombectomy apparatuses described herein include a tractor region and/or elongate inversion support that are configured to prevent jamming, while still able to efficiently "grab" a clot from within a vessel. For example, described herein are mechanical thrombectomy apparatuses that may be configured to grab or grasp and/or macerate a clot as it is mechanically drawn into the apparatus for removal. Although suction may be used in addition to the mechanical grabbing of the clot, in some variations suction is not used.

The tractor regions described herein may include projections that extend from the tractor region, particularly or exclusively as it bends around during inverting (e.g., at the distal end of the device). These projections may remain flat or non-extending when the tractor is held in parallel with the elongate inversion support. Alternatively, the projections may extend at all times. In general, the tractor may be formed of a woven material, knitted material, or laser-cut sheet of material. The knitted and/or woven materials may be fibrous materials (including natural fibers, synthetics fibers, etc.), polymeric materials, or the like. For example, the material (e.g., strands) forming the woven or knitted material may be one or more of: monofilament polymer, multifilament polymer, NiTi filament, NiTi tube with radiopaque metallic center, Cobalt chromium alloy filament, Cobalt chromium alloy tube with radiopaque metallic center, Nylon, Polyester, Polyethylene terephthalate, and Polypropylene. The sheets of material (e.g. a solid sheet of material) formed into the tractor region may be one or more of: polymeric material (e.g., PTFE), silicone materials, polyurethanes, shape memory alloys, stainless steels, etc. The sheets may be extruded, glued, or the like. The sheets may be cut to form pores and/or projections. For example, the sheets may include one or more laser-cut projections. Any of these apparatuses may be coated with a hydrophilic and/or hydrophobic coating, and/or may include pores. The tractor may have a porosity of greater than >60% (greater than 70%, greater than 75%, greater than 80%, greater than 85%, etc., between 60-95, 65-95, 70-95%, etc.).

For example, described herein are clot-grabbing mechanical thrombectomy apparatuses that include a tractor region. The tractor region may include a plurality of clot-grabbing projections extending from one face of the tractor. In some variations, the clot-grabbing projections may be configured so that they move to extend (e.g., out of the plane of the tractor) when the tractor region bends around, e.g., around the distal end of the catheter of the elongate inversion support, to invert.

In general, a mechanical thrombectomy apparatus for removing a clot from a vessel may include: a elongate inversion support comprising a catheter having a distal end and a distal end opening; a tractor comprising a flexible tube extending longitudinally within the catheter and doubling back over the distal end of the catheter to extend along the distal end of the catheter, an inner puller coupled to a distal end of the tractor; and a guidewire lumen extending through the catheter, tractor and the inner puller and configured to pass a guidewire. The proximal end of the tractor may be loose (e.g., may be free to slide over the catheter. The tractor may also be configured so that is it biased to hold itself against outer diameter of the catheter, and simultaneously biased to expand when inverted within the catheter; in this configuration, the inverting distal-facing end of the tractor may be flared outward slightly so that the diameter of the tractor expands slightly near the distal-facing inverting end of the apparatus. This configuration may also maintain the portion of the tractor within the catheter so that it is close to the inner diameter of the catheter; e.g., the inner diameter of the portion of the tractor within the catheter may be greater than 50% of the inner diameter of the catheter, greater than 55% of the inner diameter of the catheter, greater than 60% of the inner diameter of the catheter, greater than 65% of the inner diameter of the catheter, greater than 70% of the inner diameter of the catheter, greater than 75% of the inner diameter of the catheter, etc.

For example, a mechanical thrombectomy apparatus for removing a clot from a vessel may include: an elongate inversion support comprising a catheter having a distal end and a distal end opening; a tractor comprising a flexible tube that extends distally in a first configuration within the catheter, inverts over the distal end opening of the catheter and extends proximally in a second configuration (that is inverted relative to the first configuration) along the distal end of the catheter, wherein the tractor comprises a tubular wall, further wherein the tractor is configured to invert by rolling over the distal end opening of the catheter when a first end of the tractor is pulled proximally within the catheter; and a plurality of projections that extend from a portion of the tractor that is inverted over the distal end opening of the catheter as the tractor rolls over the distal end opening of the catheter, wherein the plurality of projections do not extend from the tractor as it extends proximally in the inverted configuration along the distal end of the catheter.

As mentioned, in general, the mechanical thrombectomy apparatuses described herein may include a clot-grabbing projection. For example, a mechanical thrombectomy apparatus for removing a clot from a vessel may include: an elongate inversion support comprising a catheter having a distal end and a distal end opening; a tractor comprising a flexible tube extending within the catheter and doubling back over the distal end of the catheter to extend along the distal end of the catheter, the flexible tube comprising a tube wall, wherein the tractor is configured to invert over the distal end opening when a first end of the tractor is pulled proximally within the catheter, further wherein the tractor comprises a plurality of projections configured so that the plurality of projections extend out of a plane of the tube wall as the tube wall inverts over the distal end opening, further wherein the plurality of projections remain in the plane of the tube wall as the tube wall extends along the distal end of the catheter; and a guidewire lumen extending through the catheter and the tractor and configured to pass a guidewire.

In particular, the tractor may be a tube of woven ribbons, further wherein the plurality of projections is formed from edges of the ribbons. The ribbons may comprise flattened strips or strands of material having at least one (through typically four) elongate edges. For example, the ribbons may have a rectangular cross-section. In some variations the ribbons may have square or triangular or other cross-sections having one or more edges. Ribbons having edges may be woven, e.g., so that they are arranged in a helical pattern as they extend over the distal end of the elongate inversion support. Thus, the edge(s) of the ribbon may extend outward, out of the plane of the tractor, when the tractor inverts. These extending edges may bend up, forming scooping, cutting and/or grabbing projections over the bending region of the tractor. The ribbons may be formed of any appropriate material, including those discussed above, such as a metallic or polymeric material.

The projections from the tractor regions described herein may be formed by cut-out regions in the tractor material. For example, a sheet or tube of material may be used to form the tractor, such as a tube of steel (e.g., stainless steel), polyester, nylon, expanded Polytetrafluoroethylene (ePTFE), Nitinol, or a fabric, and projections may be formed, e.g., by cutting, from the tube or sheet. For example, the projections may be cut from the tube wall. In some variations the projections may be cut in addition to openings, slits, slots, or gaps (e.g., forming pores). For example, a tractor may have at least one porous section having a pore pattern having a longitudinal separation between pores of less than about 0.005 inches in width. In some variations, the projections may be cut from the tube wall at an angle of less than 90° tangent to the tube wall. For example, each of the plurality of projections may have a width in a direction transverse to the flexible tube and a length in a direction along a long axis of the flexible tube; the ratio of length to width may be between, e.g., 2 and 100 (e.g., 5 and 100, 10 and 100, 5 and 90, 5 and 80, 5 and 70, 5 and 50, 10 and 90, 10 and 80, 10 and 70, 10 and 60, etc.).

The projections may be shaped to grab and/or macerate the clot. For example, all or some of the plurality of projections may have one or more of: a paddle shape, a scoop shape, and spike shape. The projections may extend proud of the plane of the tractor (e.g., at 90° or perpendicular to the tractor surface from which the projection extends, or between about 45-135° from the plane of the tractor surface, etc.). The projections may be sharp (e.g., may have sharp ends). The projections may extend between 0.01 mm to 5 mm from the tractor surface (e.g., between 0.01 mm and 2 mm, between 0.05 mm and 1 mm, etc.). The size of the projections may be scaled to the size of the tractor and/or the size of the vessel into which the apparatus is intended to be inserted into.

In any of the apparatuses described herein, the elongate inversion support (e.g., catheter) may be adapted to enhance rolling of the tractor region (inverting) over the distal end. For example, in any of the apparatuses described herein, the catheter may be configured so that the material hardness of the catheter decreases over the distal end of the catheter until the distal end opening, wherein the distal end opening has a material hardness that is greater than a material hardness of a region immediately proximal to the distal end, further wherein the distal end opening has a rounded lip profile. The catheter distal end may be stiffer because it is thicker (e.g., it may be formed by inverting the distal end of the catheter back over itself, and/or it may be formed of a stiffer material than the adjacent more proximal region (including by including a reinforcing material).

The projections configured to help grab clot may be distributed over the entire length of the tractor, or only over a region of the tractor (e.g., the distal end region, e.g., the distal 5 mm, 7 mm, 10 mm, 15 mm, 20 mm, etc. or less). In some variations, the distribution of projections may be non-uniform distributed, e.g., the tractor may include a non-uniform density of projections along the length of the tractor. The projections may be oriented relative to the tractor so that the projections extend in the distal direction when the tractor is on the outer diameter of the catheter, which may help them grab clot.

The projections may be configured (e.g., by laser cutting the tube forming the tractor) as a plurality of slots or openings through the tractor.

In any of the apparatuses described herein, the tractor may include one or more coatings from the group of: a lubricious coating, a metal coating, a heparin coating, an adhesive coating, and a drug coating. In particular the tractor may include a uniform or non-uniform lubricious (e.g., hydrophilic) coating. Such coatings may assist in making the tractor slide more easily to invert (e.g., over the distal end of the catheter), but may make it particularly hard to grab clot. The projections described herein may address this issue.

Any of the apparatuses described herein may include a releasable attachment between the tractor and an outer surface of the elongate inversion support (e.g., catheter), configured to release when the tractor is pulled with a force that is greater than a predetermined force threshold. This may prevent premature deployment of the apparatus. The releasable attachment may be a breakable (e.g., frangible) region, e.g., of an adhesive, etc. or a releasable tie, etc. The releasable attachment may be formed by regions of different hydrophobicity/hydrophilicity. Any of these apparatuses may be configured so that the force required to deploy the apparatus is greater than a predetermined threshold, e.g., the releasable force threshold may be greater than 50 g, 100 g, 200 g, 300 g, 400 g, 500 g, 600 g, 700 g, 800 g, 900 g, 1000 g, etc. of force (e.g., greater than 200 g of force). In addition, any of these apparatuses may include a cover, an outer elongate inversion support comprising a catheter, sleeve, sheath, etc., holding the proximal end of the tractor against the catheter until it is ready to be deployed. Deployment may mean releasing the end (e.g., the end on the outer surface of the catheter) from a releasable attachment; once deployed, the force required to pull the tractor proximally in the catheter, including drawing the tractor from along the outer diameter of the catheter, inverting the tractor and pulling the tractor into the catheter distal end opening (without a clot or other material in the tractor) may be substantially less than the initial deployment force. For example, the force required to pull the tractor into the catheter proximally may be 1 gram (g) of force or less (or 2 g, 3 g, 4 g, 5 g, 6 g, 7 g, 8 g, 9 g, 10 g, 20 g, 30 g, 40 g, 50 g, etc., of force or less). Alternatively or additionally, any of these apparatuses may include a material between the tractor and the catheter (e.g., a sleeve, coating, etc.) to reduce the amount of force required to invert the catheter over the distal end of the catheter, and/or to prevent jamming of the tractor in the catheter.

As mentioned, any of these apparatuses may include a puller, e.g., an elongate puller coupled to a distal end of the tractor. Any of these apparatuses may include an elongate puller within the catheter coupled to a distal end of the tractor. The elongate puller may comprise a hypotube having an inner lumen that is continuous with the guidewire lumen though the flexible tube.

In general, the tractor may be any appropriate length. For example, the tractor may be between 3 to 100 cm long (e.g., between 3 and 50 cm, between 3 and 40 cm, between 3 and 30 cm, between 3 and 20 cm, between 10 and 100 cm, between 10 and 50 cm, between 20 and 100 cm, between 20 and 50 cm, etc.).

In any of these apparatuses, the apparatus may be configured so that the tractor may be retracted into the catheter by applying less than 300 grams of force (e.g., less than 400 g of force, less than 300 g of force, less than 200 g of force, less than 100 g of force, less than 90 g of force, less 80 g of force, less than 70 g of force, less than 60 g of force, less than 50 g of force, less than 10 g of force, etc.) to a distal end of the flexible tube. For example, as mentioned above, the apparatus may include a hydrophilic coating, a lubricant on the catheter and/or tractor, a sleeve between the tractor and catheter, etc. This force required to retract the tractor into the catheter typically refers to the force required to roll the tractor over the distal end of the tractor; an initial deployment force (e.g., to release the end of the tractor outside of the catheter) may be greater than the force required to retract the catheter (e.g., greater than 100 g of force, 200 g of force, 300 g of force, 400 g of force, 500 g of force, 600 g of force, 700 g of force, 800 g of force, 900 g of force, 1000 g of force, 1500 g of force, 2000 g of force, etc.).

For example, a mechanical thrombectomy apparatus for removing a clot from a vessel may include: an elongate inversion support comprising a catheter having a distal end and a distal end opening; a tractor comprising a flexible tube that extends distally in a first (e.g., "un-inverted") configuration within the catheter, inverts over the distal end opening of the catheter into a second configuration (that is inverted relative to the first configuration) and extends proximally in an inverted configuration along the distal end of the catheter, the flexible tube comprising a plurality of ribbons having a square or rectangular cross-section woven together, wherein the tractor is configured to invert by rolling over the distal end opening of the catheter when a first end of the tractor is pulled proximally within the catheter, wherein a plurality of edges of the plurality of ribbons extend from a portion of the tractor that is inverted over the distal end opening of the catheter as the tractor rolls over the distal end opening of the catheter, further wherein the projecting edges are not extended from the tractor in a portion of the tractor that extends over the distal end of the catheter; and a guidewire lumen extending through the catheter and the tractor and configured to pass a guidewire.

A mechanical thrombectomy apparatus for removing a clot from a vessel may include: an elongate inversion support comprising an elongate inversion support comprising a catheter having a distal end and a distal end opening; a tractor comprising a flexible tube extending within the catheter and doubling back over the distal end of the catheter to extend along the distal end of the catheter, the flexible tube comprising a tube wall formed from a plurality of woven ribbons having a square or rectangular cross-section, wherein the tractor is configured to invert over the distal end opening when a first end of the tractor is pulled proximally within the catheter, further wherein the tractor comprises a plurality of projections configured so that the plurality of projections extend out of a plane of the tube wall as the tube wall inverts over the distal end opening, further wherein the plurality of projections are formed from edges of the ribbons and the projections remain in the plane of the tube wall as the tube wall extends along the distal end of the catheter; and a guidewire lumen extending through the catheter and the tractor and configured to pass a guidewire.

A mechanical thrombectomy apparatus for removing a clot from a vessel may include: an elongate inversion support comprising a catheter having a distal end and a distal end opening; a tractor comprising a flexible tube extending within the catheter and doubling back over the distal end of the catheter, the flexible tube comprising a tube wall, wherein the tractor is configured to invert over the distal end opening when a first end of the tractor is pulled proximally within the catheter, further wherein the tractor comprises a plurality of projections formed in the tube wall and configured so that the plurality of projections extend proud of the tractor when the tractor inverts over the distal end opening and otherwise remain in a plane of the tube wall; wherein each of the plurality of projections have a width in a direction transverse to the flexible tube and a length in a direction along a long axis of the flexible tube, further wherein the ratio of length to width is between 10 and 100; and a guidewire lumen through the catheter and the tractor configured to pass a guidewire.

Any of the apparatuses described herein may be configured so that the tractor is highly soft, and therefore rolls around the distal end of the catheter forming the elongate inversion support easily without jamming and/or requiring a large force to roll the tractor over the distal end opening of the catheter. In particular, tractors having a low axial compression strength, that would, but for the elongate inversion support, typically buckle, have been found to prevent jamming of the elongate inversion support as the tractor inverts. In particular, unsupported tractors (e.g., tractor that are not rolling over a catheter supported annular opening) that are configured to collapse radially under an axial compression of less than about 500 g of force (e.g., less than: about 500 g force, about 400 g force, about 300 g force, about 200 g force, about 150 g force, about 100 g force, about 50 g force, etc.) may be particularly helpful in preventing jamming. For most knitted, woven, and braided tractors, including those described herein, when the tractor is configured to withstand greater that this amount of axial compression force, the tractor may jam, and/or may require excessive force to invert. Thus, in any of the apparatuses and methods described herein, the tractor maybe sufficiently soft such that without support from the catheter, the tractor collapses radially under an axial compression of less than 200 g of force when inverting (and may instead buckle).

Further, in any of the apparatuses described herein, the tractor may be biased to expand to greater than the outer diameter of the catheter in a second configuration (that is inverted relative to the first configuration) where the tractor is extending over the outer diameter of the catheter. The same tractor may be biased to expand to greater than the inner diameter of the catheter of the elongate inversion support in the first (e.g., un-inverted), configuration where the tractor is within the catheter of the elongate inversion support. Thus, in relaxed configuration, prior to assembling with the elongate inversion support, the tractor may be oversized compared to the catheter of the elongate inversion support; the portion of the tractor that extends within the catheter of the elongate inversion support, referred to as "un-inverted," may have an inner diameter that is greater than the inner diameter of the catheter, which may tend to drive the tractor toward the walls of the inner diameter of the catheter without collapsing down into the catheter. Further, the inner diameter of the tractor in the "inverted" configuration, e.g., the configuration of the portion that is doubled back over and along the catheter of the elongate inversion support, may be greater than the outer diameter of the catheter of the elongate inversion support. This arrangement may prevent jamming and an increased resistance between the tractor and the outside of the catheter of the elongate inversion support. The catheter may be biased to expand in both the inverted and un-inverted configurations by, e.g., heat setting. The tractor may be inverted to transition between the first and second configurations by rolling over the distal end of the catheter; the terms "inverted" and "un-inverted" are therefore relative terms.

Also described herein are methods of removing a clot using a mechanical thrombectomy apparatus. For example, a method of removing a clot using a mechanical thrombectomy apparatus may include: positioning a distal end of the mechanical thrombectomy apparatus adjacent to a clot within a vessel, wherein the mechanical thrombectomy apparatus includes a tractor region that extends along a distal region of an elongate inversion support having a catheter and inverts over a distal end of the catheter so that a distal end of the tractor extends proximally within the catheter; pulling the distal end of the tractor proximally within the catheter to invert the tractor over the distal end of the catheter to extend a plurality of projections from the tractor and grab the clot; and drawing the clot into the catheter.

Any of these methods may include macerating the clot with the plurality of projections.

For example, a method of removing a clot using a mechanical thrombectomy apparatus may include: positioning a distal end of the mechanical thrombectomy apparatus adjacent to a clot within a vessel, wherein the mechanical thrombectomy apparatus includes a tractor region that extends along a distal region of a catheter and inverts over a distal end of the catheter so that a first end of the tractor extends proximally within the catheter; pulling the first end of the tractor proximally within the catheter to roll the tractor over the distal end of the catheter so that the tractor inverts over the distal end of the catheter and extends a plurality of projections from the tractor; grabbing the clot with the plurality of projections; and drawing the clot into the catheter.

As mentioned above, the tractor may comprises a plurality of woven ribbons having a square or rectangular cross-section, further wherein pulling the distal end of the tractor proximally within the catheter to invert the tractor over the distal end of the catheter to extend a plurality of projections from the tractor comprises extending a plurality of edges of the woven ribbons from out of a plane of the tractor as the tractor is inverted over the distal end of the catheter to grab the clot with the extended edges.

Alternatively or additionally, the tractor may comprise a plurality of cut-out regions formed in the tractor, further wherein pulling the distal end of the tractor proximally within the catheter to invert the tractor over the distal end of the catheter extends the cut-out regions forming the plurality of projections from the tractor to grab the clot. Any of these methods may include sliding a loose proximal end of the tractor over the catheter as the distal end of the tractor is pulled proximally.

Any of these methods may include using a guidewire. For example, positioning the distal end of the mechanical thrombectomy apparatus may comprise sliding the mechanical thrombectomy apparatus over a guidewire.

Similarly, any of these methods may include releasing a releasable attachment between the tractor and an outer surface of the catheter.

Pulling the distal end of the tractor proximally may comprises maintaining an inner diameter of the tractor within the catheter at greater than 60% of an inner diameter of the catheter to prevent the tractor from locking over the distal end of the catheter.

Also described herein are apparatuses having tractor regions with variable stiffness along the length of the tractor. These apparatuses may invert (roll) at their distal-facing end of the tractor with a ratcheting motion. These apparatuses, and methods of using them, may provide a movement that prevents jamming, and may also help grab clot.

For example, described herein are mechanical thrombectomy apparatuses for removing a clot from a vessel that may include: a catheter having a distal end and a distal end opening; a tractor comprising a flexible tube extending longitudinally within the catheter and doubling back over the distal end of the catheter to extend along the distal end of the catheter, wherein the flexible tube comprises longitudinally alternating regions of higher and lower stiffness, wherein the regions of higher stiffness have a stiffness that is greater than the regions of lower stiffness; an inner puller coupled to a distal end of the tractor; and a guidewire lumen extending through the catheter, tractor and the inner puller and configured to pass a guidewire.

A mechanical thrombectomy apparatus for removing a clot from a vessel may include: a catheter having a distal end and a distal end opening; a tractor comprising a flexible tube extending longitudinally within the catheter and doubling back over the distal end of the catheter to extend along the distal end of the catheter, wherein the flexible tube comprises longitudinally alternating regions of higher and lower stiffness, wherein the regions of higher stiffness have a stiffness that is greater than the regions of lower stiffness, further wherein a diameter of the distal-facing end of the tractor oscillates as the tractor is pulled proximally within the catheter to invert the tractor over the distal end of the catheter; an inner puller coupled to a distal end of the tractor; and a guidewire lumen extending through the catheter, tractor and the inner puller and configured to pass a guidewire.

A mechanical thrombectomy apparatus for removing a clot from a vessel may include: a catheter having a distal end and a distal end opening having a radius; a tractor comprising a flexible tube extending longitudinally within the catheter and doubling back over the distal end of the catheter to extend along the distal end of the catheter, wherein the flexible tube comprises longitudinally alternating regions of higher and lower stiffness helically arranged around the flexible tube, wherein the regions of higher stiffness have a first length and a stiffness that is greater than the regions of lower stiffness, wherein the first length is between about 0.1 and 1.1 times the radius of the catheter; an inner puller coupled to a distal end of the tractor; and a guidewire lumen extending through the catheter, tractor and the inner puller and configured to pass a guidewire.

Thus, the regions of higher stiffness may have a longitudinal length along the flexible tube that is between about 0.05 and 1.2 (e.g. between 0.1 and 1.1 between 0.2 and 1 between 0.3 and 1 between 0.5 and 1, between 0.5 and 1.1, etc.) times the radius of the catheter. The regions of higher and lower stiffness may be helically arranged around the flexible tube. In any of these apparatuses, the ratcheting motion may be seen by an oscillation of the diameter of the distal end-facing end of the tractor as it rolls over the catheter. For example, the diameter of the distal-facing end of the tractor may oscillate as the tractor is pulled proximally within the catheter to invert the tractor over the distal end of the catheter.

As mentioned, the tractor may be formed of a woven and/or knitted material. For example tractor may comprise a knitted material comprising one or more of: steel, polyester, nylon, expanded Polytetrafluoroethylene (ePTFE), and Nitinol. The tractor may comprise a sheet of one or more of: steel, polyester, nylon, expanded Polytetrafluoroethylene (ePTFE), Nitinol, or a fabric. The sheet may comprise a plurality of cut-out regions modifying the stiffness.

Methods of operating any of the apparatuses described herein (including the apparatuses including a ratcheting or see-saw tractors) are also described herein.

As mentioned above, any of the apparatuses described herein may be configured to prevent jamming by pre-biasing the tractor region so that it has an inner diameter in a first configuration within the lumen of the catheter (referred to for convenience herein as the "un-inverted" configuration, relative to the configuration of the portion of the tractor that has rolled over the distal end opening of the catheter) has a greater outer diameter than the inner diameter of the catheter. Further, any of the apparatuses described herein may also have an inner diameter in a second configuration over the catheter (referred to herein as the "inverted" configuration, relative to the first configuration) that is greater than the outer diameter of the catheter.

For example, described herein are mechanical thrombectomy apparatus for removing a clot from a vessel without jamming comprising: an elongate inversion support comprising a catheter having a distal end and a distal end opening; a tractor comprising a flexible tube that extends distally in a first configuration (e.g., an "un-inverted" configuration) within the catheter, inverts over the distal end opening of the catheter and extends proximally in a second (e.g., "inverted") configuration along the distal end of the catheter, wherein the tractor comprises a tubular wall, further wherein the tractor is configured to invert by rolling over the distal end opening of the catheter when a first end of the tractor is pulled proximally within the catheter, wherein the tractor is biased to expand to have an inner diameter that is greater than the outer diameter of the catheter in the inverted configuration and is biased to expand to have an inner diameter that is greater than the inner diameter of the catheter in the un-inverted configuration; and an elongate puller coupled to the first end of the tractor.

A mechanical thrombectomy apparatus for removing a clot from a vessel without jamming may include: an elongate inversion support comprising a catheter having a distal end and a distal end opening; a tractor comprising a flexible tube that extends distally in a first (an "un-inverted") configuration within the catheter, inverts over the distal end opening of the catheter and extends proximally in a second (an "inverted") configuration along the distal end of the catheter, wherein the tractor comprises a tubular wall, further wherein the tractor is configured to invert by rolling over the distal end opening of the catheter when a first end of the tractor is pulled proximally within the catheter, wherein the tractor is biased to expand to greater than the outer diameter of the catheter in the inverted configuration and is biased to expand to greater than the inner diameter of the catheter in the un-inverted configuration; an elongate puller coupled to a first end of the tractor and configured to pull the tractor proximally to invert the tractor over the distal end opening; and a guidewire lumen extending through the elongate inversion support, puller, and tractor that is configured to pass a guidewire. The tractor may be any of the tractors described herein, e.g., a woven tube, a braided tube, a knitted material, etc.

Any of the apparatuses described herein may be used with or may include an outer catheter within which the elongate inversion support extends distally; this outer catheter may be referred to as a sleeve or sheath, or in some variations an "intermediate" catheter, as it may be positioned, e.g., using a guidewire or by itself, first within the vasculature and then the elongate inversion support and tractor may be inserted within it to guide them to the clot to be removed, including after removing the guidewire, or leaving the guidewire in position. Any of these devices may be used with a vacuum to help capture and pull clot. For example, if an outer catheter is used, the outer catheter (within which the elongate inversion support can extend distally) may be proximally coupled to a vacuum source. The elongate inversion support may be configured as described herein to permit drawing the vacuum to the end of the elongate inversion support and/or outer catheter. For example, the elongate inversion support may have a diameter that is leaves sufficient clearance. In particular, the apparatus may be configured so that there is at least about 0.002 inches or greater (e.g., 0.003 inches or greater, 0.004 inches or greater, 0.005 inches or greater, 0.006 inches or greater, etc.) between the outer diameter of the catheter and the inner diameter of the outer catheter. The elongate inversion support may have a catheter with the distal end opening about which the tractor inverts that extends only part ways from the distal end towards the proximal end of the elongate inversion support. For example, the full catheter portion of the elongate inversion support may extend less 0.5 cm or less, 1 cm or less, 2 cm or less, 3 cm or less, 4 cm or less, 5 cm or less, etc. In some variations the elongate inversion support comprises a catheter that is skived at the proximal end. The catheter, and particularly the distal end region of the elongate inversion support, may include one or more openings, slots, holes, windows, cut-out regions, etc. for allowing vacuum to pass from the outer sleeve and preventing choking of the flow of vacuum from the distal end of the apparatus.

As mentioned, in any of the variations described herein, the tractor may be configured to collapse radially under an axial compression of less than 200 g of force. Thus, the tractor may be sufficiently soft and easy to roll (and invert) over the distal end aperture (distal end opening, e.g. of a catheter of the elongate inversion support). Similarly, the elongate inversion support may be configured to withstand buckling of an axial compression of greater than 500 g of force, sufficient to allow pulling of the tractor over the distal end opening (e.g. aperture) of the elongate inversion support without collapsing, kinking or displacing the elongate inversion support. In some variations, and particularly peripheral vascular variations, the elongate inversion support is configured to withstand buckling of an axial compression of greater than 1500 g of force.

Any of the apparatuses described herein may include a tractor having one or more coatings from the group of: a lubricious coating, a metal coating, a heparin coating, an adhesive coating, and a drug coating.

Also described herein are mechanical thrombectomy apparatuses (devices, methods, systems, etc.) that include a distal inverting tube of highly flexible material, referred to herein as a tractor, that is pulled to continuously invert over a distal opening, such as the distal end of a catheter or annulus, in a rolling manner. This rolling can be used, alone or on conjunction with a vacuum or mechanical thrombus (e.g., "clot") grabber, to grab, capture and remove a clot from a vessel. As mentioned, the tractor may be formed of a material having many openings and may therefore be flexible, and loose, and may be biased so as to flare open within the vessel when deployed. Prior to positioning the apparatus for grabbing the clot, it may be particularly desirable to prevent the tractor from deploying (e.g., sliding axially, expanding, etc.) so as to allow accurate tracking within the body as well as to ensure reliable operation of the device. Thus, it may be helpful to pin or hold the tractor, and particularly the end of the tractor that has not been inverted (e.g., within a catheter and/or within the tractor itself) prior to deployment. However, holding or and/or retaining the tractor prior to deployment must be properly balanced. If too much force is required to deploy the tractor, the force may cause the apparatus to kink, collapse, and/or jam. If the tractor can be deployed with too little force may deploy prematurely. Further, since the apparatus is likely to be used in highly tortious vessels of the body, including arteries such as the internal carotid artery, it must be retained in a manner that does not inhibit overall flexibility of the device, or trigger premature release when navigating through the vessels.

In general, an inverting tractor apparatus may include a tractor (e.g., tractor region, tractor portion, etc.) comprising a flexible tube of material that inverts as it rolls over itself at a distal end. The inverting/rolling portion may be performed over an annulus that may be separately maneuvered relative to the tractor; the annual may be part of a catheter (e.g., the distal end of a catheter) or may be attached to a wire or other element having sufficient column strength to prevent the annulus (distal opening) over which the tractor is inverting from being collapsed or pulled proximally as the tractor is rolled.

In operation, the tractor inverts and may roll back into itself. When an outer catheter is used, the tractor may be drawn into the catheter. The annulus about which the tractor inverts at the distal end region of the apparatus is supported by a structure (e.g., rod, hypotube, catheter) that typically is more rigid (has a much larger column strength) than the tractor. Thus, as the tractor rolls, it produces a conveyor-like motion as a formerly outward-facing tractor region rolls around to become an inward-facing region within the lumen of the tractor and/or within the lumen of the catheter. This conveyor or rolling motion may draw a clot (or other object) from a vessel into the catheter.

The mechanical thrombectomy apparatuses described herein include pre-loaded inverting tractor thrombectomy apparatuses (e.g., devices, systems, etc.). These apparatuses may be configured to prevent premature release of the tractor. Any of these apparatuses may include, for example, a tractor hold that prevents the end of the tractor that is "outside" of the inner lumen from sliding axially and inverting until deployment. The tractor hold may include a housing, and particularly a housing extends only a slight distance proximally (therefor preventing increasing the stiffness of the apparatus or otherwise inhibiting maneuverability/tracking). The tractor hold may include hydrophobic and/or hydrophilic surfaces, e.g., coatings, on the outside end region of the tractor and/or the outer portion of a catheter over which the tractor rolls; these hydrophobic/hydrophilic surfaces may be arranged in a pattern. Any of the tractor holds described herein may include a releasable attachment, such as an adhesive, a mechanical attachment such as a clamp or interference region or the like. Any of the tractor holds may include a pair of engaging portions, such as a stop or hold (e.g., a tractor hold or stop element on the catheter) and a lock (e.g., a tractor lock, such as a ring on the end region of the tractor).

As mentioned, any of these apparatuses may include an inverting annuls that may be part of an elongate member having sufficient column strength to resist collapsing or deflecting when the tractor is pulled proximally through the annuls to roll over and invert. The annulus may be the distal end of a catheter, or a portion of a catheter, or it may be a ring or cylindrical region to which an elongate support (e.g., wire, rod, hypotube, or any combination of these, including concentric or sequential arrangements). The annulus is typically a ring-shaped opening (the opening of which may be any shape, including but not limited to round, oval, triangular, square, rectangular, etc.), over which the tractor is inverted, and this annulus is typically connected to an elongate supporting member. The annulus may be integral with the elongate supporting member. The annulus and elongate support member may together be referred to as an elongate inversion support. As mentioned this elongate inversion support may generically be referred to herein as a catheter, which may include a tube, rod, hypotube, wire, shaft, etc. having an annuls or distal end opening over which the tractor is inverted so that the tractor rolls over the distal end opening (annulus) when an end of the tractor that is more radially positioned in the apparatus is pulled proximally. Also described herein are a variety of elongate inversion supports (e.g., catheters), as the shape (e.g., outer diameter) of the inverting support may affect the retention of the tractor prior to deployment.

For example, described herein are mechanical thrombectomy apparatuses for removing a clot from a vessel that include: an elongate inversion support (e.g., a catheter) having a proximal end and a distal end and a distal annulus (e.g., distal end opening); a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter; a puller coupled to first end of the tractor, wherein the puller extends within the catheter to the proximal end of the catheter; and a tractor hold attached to an outer diameter of the catheter proximal to the distal end of the catheter, wherein the tractor hold secures a second end of the tractor that extends over the distal end of the catheter until a force greater than a threshold force is applied by pulling the first of the tractor proximally within the catheter. Any of these apparatuses may include a guidewire lumen extending through the catheter, the puller and the tractor, and configured to pass a guidewire.

In any of these variations, the tractor hold may be a housing. The housing may be a cylinder that is pinned or closed on one (e.g., the proximal) end, leaving an annular opening for the outermost end of the tractor.

The tractor hold may not extend to the proximal end of the catheter. For example, the tractor hold may extend proximally along the catheter for less than 10 cm (e.g. for less than 9 cm less than 8 cm, less than 7 cm, less than 6 cm, less than 5 cm, etc.).

In any of these variations, the tractor hold may compress the tractor against the catheter. Typically, the threshold force for the tractor hold is determined by the force required to deploy the tractor within the lumen, which may depend upon the length of the apparatus, the diameter of the tractor and/or catheter, and the materials of the tractor and elongate inversion support (e.g., catheter). For example, the tractor hold may be configured to hold the second end of the tractor until the threshold force is applied, wherein the threshold force is between 50 g force and 2000 g force (e.g., between 50 g of force and 1700 g of force, between 50 g of force and 1500 g of force, between 40 g of force and 1000 g of force, between 50 g of force and 500 g of force, between 100 g of force and 500 g of force, between 200 g of force and 500 g of force, between 250 g of force and 500 g of force, between 50 g of force and 450 g of force, between 100 g of force and 450 g of force, between 100 g of force and 400 g of force, between 200 g of force and 400 g of force, etc.). The range of force appropriate to the threshold force may be important in proper functioning of the apparatus, particularly when the force is applied by pulling proximally on the puller and/or tractor; too little force for the threshold and the tractor will prematurely deploy; too much force and the apparatus will jam (e.g., by kinking the elongate inversion support).

In any of the variations described herein, the tractor may be biased to collapse and/or expand. For example, the tractor may be biased to collapse over the catheter outer diameter (e.g., the outer diameter of the elongate inversion support, including the distal end of the catheter); such tractors may also be biased to expand after inverting (e.g., within the catheter) over the distal end opening of the elongate inversion support. This arrangement may cause the tractor to form a distal-facing region that flares, trumpet-like, towards a clot distal to the device, which may help in capturing the clot and also may prevent jamming of the tractor. Alternatively or additionally, some or all of the tractor regions may be configured to expand over the outer diameter of the elongate inversion support.

The proximal end of the tractor hold may be attached to the catheter. The tractor hold may be fixed, fused, or integrally formed with the catheter.

In any of these variations, the catheter (elongate inversion support) may include comprises a larger outer diameter region and a smaller outer diameter region that is proximal to the larger outer diameter region; the annulus (distal end opening) may be at the distal end of the elongate inversion support. The tractor hold may secure the tractor at one or more of: over the smaller outer diameter region, and between the larger outer diameter region and the smaller outer diameter region. The outer diameter of the tractor hold may be flush with the larger outer diameter region. The tractor hold may reside in a narrowing (necked) region of the catheter to avoid forming a larger-diameter region. Any of these elongate inversion supports (e.g., catheters) having regions of different diameter may have a gradual (angled) or rapid (e.g., stepped) transition between the larger outer diameter and the smaller outer diameter.

The tractor hold may comprise one or more of: a polyether block amide, a polyolefin, a polyethylene, a polypropylene, a polyethylene terephthalate (PET), and a Polytetrafluoroethylene (PTFE).

The apparatus may include a tractor lock on the second end of the tractor, wherein the tractor lock engages with the tractor hold to secure the tractor lock on a proximal side of the tractor hold until the threshold force is applied by pulling the first of the tractor proximally within the catheter. For example, the tractor lock may be a ring affixed to the end region of the tractor. The tractor lock may be a band configured to slide over the outer diameter of the catheter. The tractor hold may be a projection extending from the outer diameter of the catheter. Either or both the tractor lock and tractor hold may be elastic (e.g., compliant, rubbery, etc.) so that pulling above the threshold deployment force may cause the tractor lock to release from the tractor hold.

For example, described herein are mechanical thrombectomy apparatuses for removing a clot from a vessel, the apparatus comprising: a catheter having a proximal end and a distal end and a distal end opening, wherein the catheter comprises a larger outer diameter region and a smaller outer diameter region that is proximal to the larger outer diameter region; a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter; a puller coupled to first end of the tractor, wherein the puller extends within the catheter to the proximal end of the catheter; and a tractor hold on an outer diameter of the catheter proximal to the distal end of the catheter, wherein the tractor hold secures a second end of the tractor that extends over the distal end of the catheter until a force greater than a threshold force is applied by pulling the first of the tractor proximally within the catheter, further wherein the tractor hold secures the tractor at one or more of: over the smaller outer diameter region, and between the larger outer diameter region and the smaller outer diameter region.

Also described herein are methods of removing a clot using a mechanical thrombectomy apparatus. These methods may include: positioning a distal end of the mechanical thrombectomy apparatus adjacent to a clot within a vessel, wherein the mechanical thrombectomy apparatus includes a tractor region that extends along a distal region of a catheter and inverts over a distal end of the catheter so that a first end of the tractor extends proximally within the catheter; disengaging a second end of the tractor from a tractor hold that secures the second end of the tractor to an outer diameter of the catheter by applying a first force that is greater than a threshold force (threshold deployment force) to the first end of the tractor; pulling the distal end of the tractor proximally within the catheter to roll the tractor over the distal end of the catheter so that the tractor inverts over the distal end of the catheter; and drawing the clot into the catheter with the inverting tractor.

Disengaging the second end of the tractor from the tractor hold may include disengaging the second end of the tractor from a tractor hold that is attached to an outer diameter of the catheter. For example, disengaging the second end of the tractor from the tractor hold may comprise disengaging the second end of the tractor from a tractor hold that extends proximally along the catheter for less than 10 cm.

Disengaging the second end of the tractor from the tractor hold may include disengaging the second end of the tractor from a tractor hold that is open at a distal-facing end; a proximal end of the tractor hold may be attached to the outer diameter of the catheter. Disengaging the second end of the tractor from the tractor hold may include disengaging the second end of the tractor from a tractor hold that secures the second end of the tractor over a smaller outer diameter region of the catheter that is distal to a larger outer diameter region of the catheter.

Disengaging the second end of the tractor from the tractor hold may comprise disengaging the second end of the tractor from a tractor hold that secures the second end of the tractor between a larger outer diameter region of the catheter and a larger outer diameter region of the catheter, wherein the larger diameter outer region is distal to the smaller outer diameter region. Disengaging the second end of the tractor from the tractor hold may comprise disengaging a tractor hold from a tractor lock, wherein the tractor lock is on the second end of the tractor. Disengaging the second end of the tractor from the tractor hold may include compressing either or both the tractor hold and a tractor lock on the second end of the tractor so that the tractor lock moves from a position proximal to the tractor hold to a position that is distal to the tractor hold.

As mentioned, the deployment threshold may be between 0.5 N and 50 N. For example, disengaging the second end of the tractor from the tractor hold may comprise pulling the first end of the tractor with the first force wherein the threshold force is between 1 N and 20 N.

In any of the apparatuses described herein the puller to which the tractor is coupled may be configured to extend from the distal end of the apparatus further than the tractor. In any of these apparatuses, the puller may be a tube (inner catheter, hypotube, etc.), and may be inserted into the clot, or may be used to draw a vacuum, apply an agent (e.g., anticoagulant, etc.) or the like. For example, described herein are mechanical thrombectomy apparatuses for removing a clot from a vessel that include: a catheter having a proximal end and a distal end and a distal end opening; a tractor comprising a flexible tube that extends within the catheter, inverts over the distal end opening of the catheter and extends over the distal end of the catheter, wherein the tractor is configured to invert by rolling over the distal end opening of the catheter when a first end of the tractor is pulled proximally within the catheter; a puller having a proximal end and a distal end, wherein the first end of the tractor is coupled to the puller at a region that is proximal to the distal end, further wherein the puller extends within the catheter to the proximal end of the catheter. Any of these apparatuses may include a guidewire lumen extending through the catheter, the puller and the tractor, and configured to pass a guidewire.

For example, the apparatus may further include a stop between the distal end of the puller and the distal end opening. For example, the apparatus may include a stop on the puller between the distal end of the puller and the first end of the tractor, wherein first end of the tractor is coupled to a sliding ring configured to slide over the puller until it engages the stop. Any of these apparatuses may include a 2 mm or greater distance between the distal end of the puller and the region of the puller to which the first end of the tractor is coupled.

As mentioned, the proximal end of the puller may be configured to couple to a vacuum source. For example, the proximal end of the puller may include a valve, e.g., a Tuohy-Borst valve/rotating hemostasis valve (RHV).

Thus, described herein are mechanical thrombectomy apparatuses (devices, systems, etc.) and methods for positioning them within a vessel and using them to remove a thrombus, e.g., clot, from within a vessel. In particular, described herein are methods of advancing an inverting tractor thrombectomy apparatus having a tractor comprising a flexible tube of material that inverts over itself as it rolls over a distal end opening of an elongate inversion support by extending the tractor region and/or a puller coupled to the tractor distally beyond the end of the catheter. Also described herein are power-driven mechanical thrombectomy apparatuses.

In some examples, these mechanical thrombectomy apparatuses may be configured to prevent or reduce jamming (e.g., "anti-jamming" thrombectomy devices), grab clot, and/or macerate the thrombus, e.g., clot, being removed. These mechanical thrombectomy apparatuses may include a tractor comprising a flexible tube of material that inverts as it rolls over itself while being drawn into a catheter in a conveyor-like motion. In particular, described herein are mechanical thrombectomy apparatuses having tractors selectably extendable projections that may aid in grabbing and/or macerating a clot. Also described herein are seesawing tractors for mechanical thrombectomy apparatuses.

The mechanical thrombectomy apparatuses may include an inverting, rolling conveyor region ("tractor") at the distal end that are configured to grab and remove thrombus material. In particular, described herein are mechanical thrombectomy apparatuses that are adapted to prevent premature deployment of the tractor, e.g., by including a tractor hold (e.g., a housing, a lock, a clamp, etc.) or the like to secure the outer end of the tractor against and/or relative to the elongate inversion support.

In some examples, these mechanical thrombectomy systems may include an elongate catheter configured as an elongate inversion support, a flexible tractor configured to roll and invert over the distal end of the elongate inversion support, and a clot engaging member on the distal end of an elongate manipulator are described herein. These systems may capture a clot using the clot engaging member and draw the clot and clot engaging member and roll the flexible tractor into the catheter to remove the clot and clot engaging member from a vessel.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1H illustrate an example of an apparatus for mechanically removing an object such as a clot form a body region. FIG. 1A shows an example of an elongate inversion support portion of an apparatus, configured as a catheter portion. For example, at least the distal end of the elongate inversion support may be configured as a catheter. FIG. 1B shows an enlarged view of a distal end (opening) of the catheter of the elongate inversion support of FIG. 1A, showing the aperture formed by the distal end opening; FIG. 1C shows an example of a distal tractor region of a flexible tube (tractor tube) extending from a puller (the puller in this example is configured as a catheter. The tractor is shown in a first (e.g., un-inverted) configuration) and may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. 1E. In FIG. 1E, the assembled mechanical thrombectomy apparatus with the elongate inversion support and the flexible tube forming the tractor is shown. The tractor extends through the catheter of the elongate inversion support and doubles back over the distal end opening of the catheter and extends over the outer diameter of the catheter. The outer portion of the tractor (extending along the outer diameter of the catheter) may be held in a collapsed configuration (as shown in FIG. 1E), or it may be expanded, as shown in FIG. 1F. Thus, the tractor may be biased so that in the second configuration (inverted over the distal end of the catheter), the tractor has a 'relaxed' outer diameter that is greater than the outer diameter of the catheter of the elongate inversion support. FIGS. 1G and 1H illustrate the use of the apparatus of FIGS. 1E and 1F to remove a clot by drawing the flexible tube proximally and/or advancing the catheter distally towards the clot so that the expandable first end region inverts as it is drawn into the distal end of the catheter, pulling the clot into the catheter.

FIG. 1I illustrates an alternative variation of a tractor and puller. In FIG. 1I, the tractor is shown attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

FIGS. 2A-2E illustrate a method of positioning a mechanical thrombectomy apparatus within a vessel and/or removing a clot from a vessel using the mechanical thrombectomy apparatus. In FIGS. 2A-2E the apparatus is shown inching distally within the vessel towards the clot using the tractor, so that the clot may be captured and removed by the tractor. In FIGS. 2A-2E the apparatus is advanced distally without the use of a guidewire.

FIGS. 4A-4D illustrate a method of positioning a mechanical thrombectomy apparatus within a vessel and/or removing a clot from a vessel using the mechanical thrombectomy apparatus in which the distal end of the puller, to which one end of the tractor is attached, is extended distally from the catheter.

FIG. 7 illustrates one region (e.g., the internal carotid artery) in which the apparatuses and methods described herein may be used.

FIG. 8A-8B illustrate an example of a mechanical thrombectomy apparatus for removing a clot from a vessel that include a motorized or motor-driven tractor. FIG. 8A shows the apparatus in a side view, schematically illustrating the internal components. FIG. 8B is an example of a catheter and tractor(s) that may be used with an apparatus such as the one shown in FIG. 8A.

In FIG. 10A the mechanical thrombectomy apparatus includes a tractor region that collapses within the inner diameter (lumen) of the catheter portion of the elongate inversion support, jamming so that the tractor region cannot roll, without applying excessive force, or at all, around the open end of the catheter. Similarly, in FIG. 10B, the tractor region is loose, and also jams on the distal open end of the catheter as it inverts.

In FIG. 11A the apparatus is positioned adjacent to the clot. FIG. 11B shows an alternative variation in which a guidewire is used to position the apparatus; the guidewire may remain in place during capture of the clot, or it may be removed. FIG. 11C shows the apparatus capturing the clot by rolling the tractor portion of the apparatus over the end of the catheter of the elongate inversion support as the tractor portion is drawn proximally; the apparatus may be advanced distally within the lumen of the vessel.

In FIG. 12A the tractor portion is configured to include a central guidewire lumen and a hypotube (inner catheter) is used to pull the proximal end of the tractor; in FIG. 12B the tractor is configured to collapse down to a puller wire.

In FIG. 13A the tip is shown with a slightly proximally-offset from the distal end marker band; in FIG. 13B the tip of the catheter has been folded back over itself, increasing both the diameter of the catheter at the distal end and the stiffness of the distal end.

FIG. 14A is an example of a side perspective view and FIG. 14B shows the distal end face of the apparatus.

FIGS. 15A-15E illustrate examples of heat set 0.085" ID PET (FIGS. 15A-15C) tractors and nickel titanium heat-set 0.085" ID tractors.

FIGS. 16A-16D illustrate operation of mechanical thrombectomy apparatus pulling in a clot. FIGS. 16E-16F illustrate reversal of the apparatus of FIGS. 16A-16D, ejecting the clot.

FIGS. 21A and 21B show side and cross-sectional views, respectively, illustrate an example of a tractor having selectively deployable projections that may extend from the inverting region of the tractor to assist in grabbing and/or macerating a clot.

FIG. 22 illustrates an example of an apparatus including a plurality of projections extending from the tractor region that may aid in grabbing and/or macerating a clot.

FIG. 24A shows a top perspective view and FIG. 23B is a side view.

FIG. 28B is an enlarged view of the pattern of FIG. 28A.

FIG. 29B is an enlarged view of the pattern of FIG. 29A.

FIG. 30B is an enlarged view of the pattern of FIG. 30A.

FIG. 31B is an enlarged view of the pattern of FIG. 31A.

FIG. 32B is an enlarged view of the pattern of FIG. 32A.

FIGS. 37A-39B is an example of a catheter design.

FIG. 38A schematically illustrates a portion of a tractor having alternating stiff/less stiff regions. FIGS. 38B-38D illustrate the seesawing motion of a tractor having alternating stiff/less stiff regions.

FIG. 39A is an example of a knitted tractor having alternating more stiff/less stiff regions extending in a corkscrewing/helical pattern along the length of the tractor.

FIGS. 39B-39C show side and end views, respectively of an apparatus having a knitted tractor, similar to that shown in FIG. 39A.

FIGS. 39D and 39E show side and end views, respectively of an apparatus having a knitted tractor.

FIGS. 40A-40B illustrate jamming in an apparatus having a seesawing tractor region that has alternating stiff regions that are too long for the diameter of the catheter over which it is inverting.

FIGS. 40C-40D illustrate jamming in an apparatus having a seesawing tractor region that has alternating stiff regions that are too small for the catheter over which it is inverting.

FIGS. 41A and 41B illustrate another example of an apparatus having a knitted tractor.

FIG. 49A illustrates a method for removing clot using an intermediate catheter (e.g., sleeve) and a vacuum, in which a mechanical thrombectomy apparatus is extended from a distal end of the intermediate catheter to remove a clot.

FIG. 49B illustrates a method for removing clot using an intermediate catheter (e.g., sleeve) and a vacuum, in which a mechanical thrombectomy apparatus removes a clot that has been drawn into the distal end of the intermediate catheter.

FIGS. 55A-55C illustrate examples of mechanical thrombectomy apparatuses including a tractor hold that secures the tractor to the outer diameter of the catheter until release.

FIG. 58A-58L illustrate examples of different elongate inversion supports for mechanical thrombectomy apparatuses. FIGS. 58A-58B illustrate a catheter portion of an elongate inversion support having both different diameters (e.g., a larger-diameter distal catheter connected to a smaller-diameter proximal region extending longitudinally in the proximal-to-distal axis), and a plurality of openings (e.g., cut-out regions, holes, etc.). FIGS. 58C-58D illustrate a catheter of an elongate inversion support having a plurality of opening formed therethrough. FIGS. 58E-58F illustrate another variation of a catheter of an elongate inversion support having a distal catheter region and an elongate support member formed by skive cutting the catheter. FIGS. 58G-58H illustrate another variation of an elongate inversion support having a distal catheter region and an elongate support member extending from the catheter region. FIGS. 58I-58J illustrate another variation of an elongate inversion support having a plurality or openings along the distal-to-proximal length. FIGS. 58K-58L illustrate another variation of an elongate inversion support having a minimal catheter region at the distal end forming a distal end opening that is connected to an elongate support (e.g., wire, tube, bar, rod, etc.).

FIG. 59A shows the elongate inversion support. FIG. 59B shows a variation of the elongate inversion support of FIG. 59A including guide rings for the puller and tractor. FIG. 59C shows the elongate inversion support of FIG. 59B with the tractor and puller attached. FIG. 59D shows a mechanical thrombectomy apparatuses including that shown in FIG. 59C with an additional outer catheter.

As shown in FIGS. 62F and 62G, the clot and tractor may then be drawn proximally out of the vessel, including by drawing proximally into the catheter first.

FIGS. 64A-64G illustrate an example of a rolling mechanical thrombectomy apparatus in which the clot has jammed while rolling the tractor into the distal end opening of the catheter portion of the rolling mechanical thrombectomy apparatus.

FIGS. 65A-65C illustrate examples of clot engaging members coupled to elongate manipulators that may be used with any of the apparatuses described herein.

FIGS. 66A-66H illustrate a method of capturing a clot engaged with a clot engagement member by advancing a rolling mechanical thrombectomy apparatus over the clot and clot engagement member.

FIGS. 67A-67B illustrate a method of capturing a clot engaged with a clot engagement member as described herein.

DETAILED DESCRIPTION

Figure 2E:
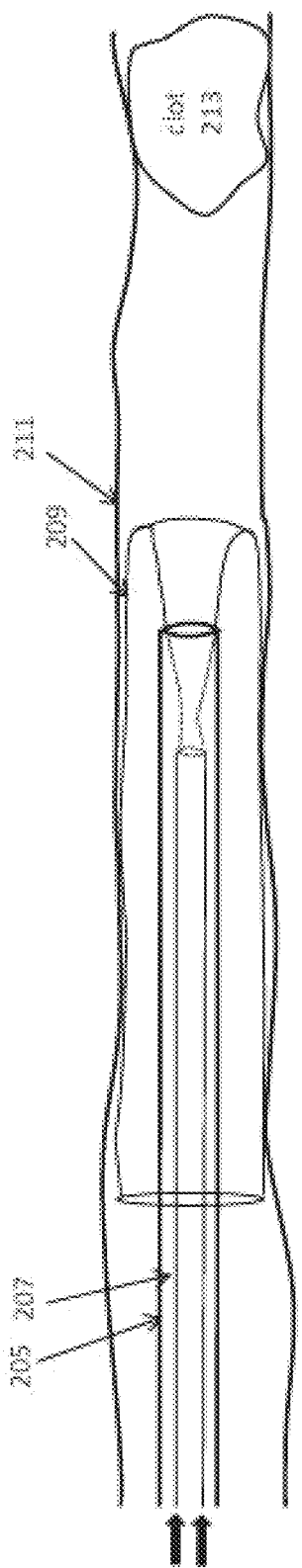
Figure 3A:
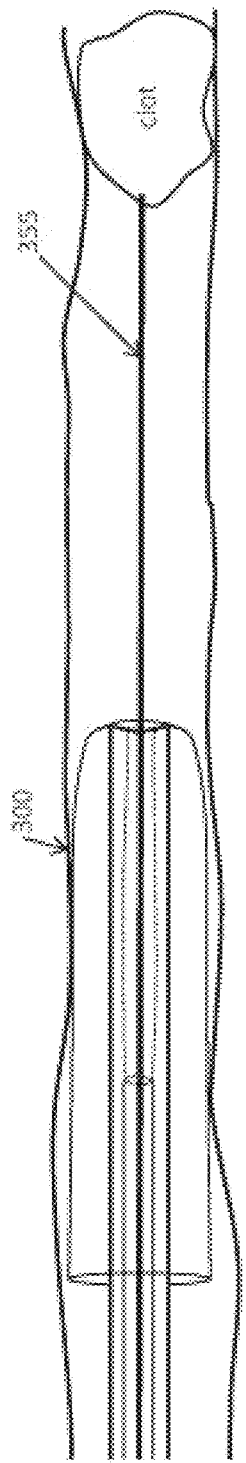
FIGS. 3A-3D illustrate a method of positioning a mechanical thrombectomy apparatus within a vessel and/or removing a clot from a vessel using the mechanical thrombectomy apparatus similar to that shown in FIGS. 2A-2E only using a guidewire.
Figure 3B:
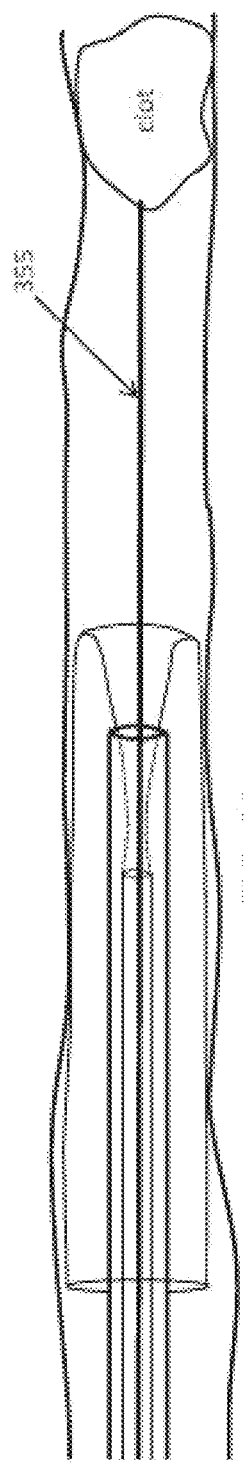
Figure 3C:
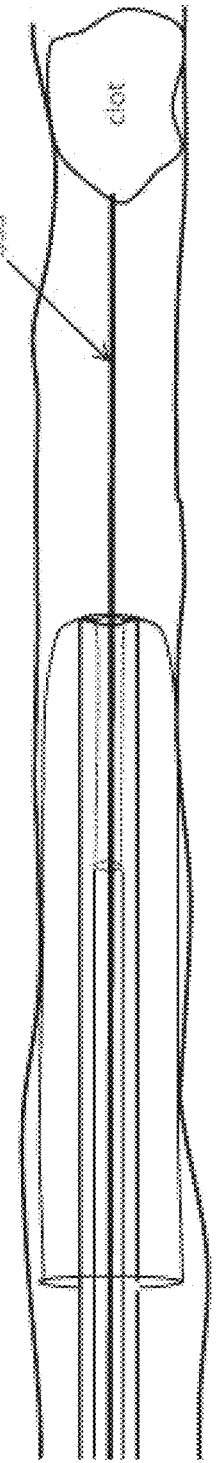
Figure 3D:
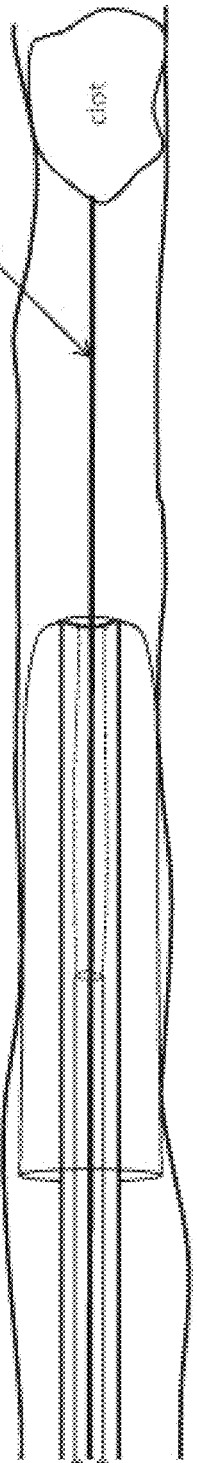

Described herein are mechanical thrombectomy apparatuses, including manually drive and power-driven apparatuses, and methods of using them. In particular, described herein are methods of positioning these apparatuses within a vessel and/or removing clot with them that may include extending the tractor region and/or the puller distally of the distal end of the apparatus to assist in advancing the apparatus distally.

In general, described herein are mechanical thrombectomy apparatuses having an inverting tractor region and an elongate inversion support having a distal annulus over which the tractor rolls and inverts over itself. Any of these apparatuses, and methods of using them, may be configured to prevent premature deployment of the tractor. The elongate inversion support may be a catheter having a distal end opening. The tractor may comprise a flexible tube that may be formed of a sheet having openings, or may be a woven, braided, knitted, etc. material such as a fiber. The tractor may extend longitudinally within the elongate inversion support and may and double back (e.g., invert) over the annulus of the elongate inversion support (e.g., the distal end of a catheter) so that it extends along the midline of the apparatus; when the elongate inversion support is a catheter, the tractor may extend within the catheter lumen. The tractor may connect to an inner puller that is typically coupled to an end of the tractor (which may be referred to as the inner end or the distal end) that can be pulled proximally to pull and invert the tractor over the distal end so that it rolls over the distal end, which may capture a clot. The apparatus may include a guidewire lumen extending through the catheter, tractor and/or tractor puller.

In general, described herein are mechanical thrombectomy apparatuses having an inverting tractor that is configured to prevent jamming and grab a blood clot. These apparatuses may include an elongate inversion support that supports an annulus over which the tractor inverts at the distal end. The tractor may comprise a flexible tube that doubles back over (e.g., inverts) over the distal end of the elongate inverting support (e.g., a catheter) so that it extends into the annuls opening of the elongate inverting support and an inner puller coupled to the inner end of the tractor that the tractor can be pulled proximally to pull and invert the tractor over the annulus at the distal end of the elongate inverting support to roll and capture a clot. The apparatus may include a guidewire lumen extending through the elongate inversion support, and/or tractor puller that is configured to pass a guidewire.

Any of the apparatuses described herein may be adapted to prevent jamming, e.g., by including a coating (e.g., hydrophilic, lubricious coating, etc.) or the like to enhance the sliding and inverting of the tractor over the distal end. Further, any of these apparatuses may include one or more projections that are configured to enhance grabbing and/or maceration of a clot. Grabbing of a clot may be particularly, but not exclusively, helpful when the tractor is lubricious.

Although lubricious tractors may resist jamming and require less force to operate, e.g., inverting over the distal end of the catheter, it may be more difficult to initially grab or grasp clot when the tractor is more lubricious. It may also be particularly helpful to include projections that are retracted along the length of the tractor adjacent to the outer diameter of the elongate inverting support (e.g., catheter), for example, when positioning the apparatus within a vessel, but extend the projections outward from the tractor when rolling and inverting to grab a clot.

In general, a mechanical thrombectomy apparatus for removing a clot from a vessel may be a system, assembly or device including an elongate inversion support having a distal end and a distal annulus, and a flexible tractor assembly at least partially inverted and configured to roll and invert over the distal annulus of the elongate inverting support.

In many of the examples described herein, the elongate inversion support is a catheter (or a portion of a catheter at the distal end) and the annulus is formed by the distal end opening of the catheter; the tractor extends within the catheter and doubles back over the distal end of the catheter to extend over the outer diameter of the catheter at the distal end of the catheter, although it may extend proximal for any appropriate distance (including between 1-30 cm, between 2-20 cm, greater than 1 cm, 2 cm, 3 cm, 4 cm, 5 cm, 6 cm, 7 cm, 8 cm, 9 cm, 10 cm, 11 cm, 12 cm, 15 cm, 20 cm, etc.). The end of the tractor within the catheter may be coupled to a puller or pusher (e.g., at a proximate puller or proximate pusher region connected to the distal or inner end of the tractor). The tubular tractor may include an elongate lumen that is configured to allow passage of a guidewire. The tubular tractor may also be configured to slide along the long axis within the catheter lumen and invert over the distal end opening of the catheter when the proximal end region is pulled proximally. The tractor may be referred to herein as a tractor assembly, tractor portion, tractor tube, or simply a tractor, and is typically positioned and longitudinally slideable within the catheter, and arranged so a portion of the tractor (sometimes referred to as the "distal tractor region" or "distal-facing" tractor region) doubles back over itself.

In any of the apparatuses described herein, in which the tractor is at least partially inverted over the distal end of the catheter so that the tractor extends on the outer surface of the catheter, the tractor may be releasably coupled to the outer diameter of the catheter to allow the apparatus to be inserted through a body, including through tortious vessels in the body, prior to being deployed to remove a clot or other element from the vessel. The tractor may be a braided, woven or knit material tube of material that is inverted over the distal end of the catheter; alternatively the tractor may be formed of a sheet of material that include openings therethrough.

Any of the apparatuses described herein may be adapted to prevent premature deployment of the tractor, e.g., by including a tractor hold (e.g., a housing, a lock, a clamp, etc.) or the like to secure the outer end of the tractor against and/or relative to the elongate inversion support. For example, a tractor hold may secure the outer end of the tractor against a catheter into which the tractor inverts when pulled proximally by the puller.

For example, FIG. 1A shows one variation of a catheter that may form part of the apparatuses described herein. In this example, the catheter 100 includes a distal end region 103 that includes a distal end 105. The distal end region may have an increasing softness (measured by durometer, e.g., shore durometer) except that the very distal tip (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

For example, FIG. 1A shows one variation of a catheter of an elongate inversion support that may form part of the apparatuses described herein. In this example, the elongate inversion support includes a catheter 100 having a distal end region 103 that includes a distal end opening 105. The distal end region may have an increasing softness (measured by durometer, e.g., shore durometer) except that the very distalmost end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include a elongate inversion support that is not a full-length catheter, but may include a portion of a catheter, typically at the distal end, connected to a rod, wire, hypotube, or the like (as will be described in greater detail below in reference to FIGS. 42A-43D) or may be skived. Thus, any of the apparatuses and methods described herein may be adapted for use with an elongate inversion support that is not limited to catheters, including elongate inversion supports that include a portion of a catheter, or that include a ring or other structure forming the annulus at the distal end. In FIG. 1A the catheter 100 of the elongate inversion support may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end)

may be curved or radiused 109 as shown in FIG. 1B, particularly on the outer surface (e.g., the transition from outer diameter to inner diameter).

FIG. 1C shows an example of a flexible tractor 144 coupled to a puller 146. In this example to form a pullable tractor assembly 140, the tractor is shown integrated with the puller, forming the assembly. In FIG. 1C, the tractor is a tube of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less expandable (or non-expandable) structure (tube, puller, etc.). In the example shown in FIG. 1C, the tractor 144 is configured, e.g., by shape-setting (heat setting, etc.), to expand in the relaxed first configuration to a radial diameter that is between 1.1 and 10 times the diameter of the inner diameter of the catheter of the elongate inversion support when unconstrained, as shown in FIG. 1D. In FIG. 1D, the tractor of FIG. 1C is shown in an expanded, relaxed, configuration. Thus the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor 144 and a less expandable (or non-expandable) proximal portion comprising the puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

In FIG. 1E, the flexible tractor of FIG. 1C is shown with the tractor doubled back over itself an over the distal end of the catheter of the elongate inversion support 101. The distal end region is collapsed down, e.g., onto the puller and the elongate inversion support, and may be held collapsed. In this example a tractor hold 188 may be used to hold the tractor collapsed down onto the outer diameter of the elongate inversion support. However, in an unconstrained or deployed configuration, as shown in FIG. 1F, the tractor in this second configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration in the first configuration (as shown in FIG. 1C) that is greater than the inner diameter (ID) of the catheter of the elongate inversion support portion of the apparatus and the relaxed expanded configuration of the second configuration (shown in FIG. 1F) inverted over the catheter has an OD that is greater than the OD of the catheter. The tractor is expandable and may be coupled to the puller. In some variations the flexible tractor and the puller may comprise the same material, but the tractor may be more flexible and/or expandable or may be connected to a push/pull wire or catheter.

FIGS. 1G and 1H illustrate the removal of a clot using an apparatus such as the apparatus assembled from the components of FIGS. 1A and 1E. In this example the apparatus is configured as a thrombectomy apparatus including a catheter of an elongate inversion support 101 and a flexible tractor that extends over the distal end region of the catheter and doubles-over itself at the distal end of the catheter to invert so that the external tractor end region is continuous with an inner less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. FIG. 1I illustrates another example of a tractor assembly 154 including a tractor 144 that is coupled to a puller 156. The puller in this example is tapered (having tapering region 161) and may therefore have a different flexibility of the distal end region than the proximal end region. For example the proximal end region may be less flexible than the narrower-diameter distal end region 195 to which the tractor is coupled. The assembly includes a radiopaque marker 165. The tractor may be attached to the puller by any appropriate means. For example, the tractor may be crimped, glued, fused, or otherwise attached to the puller, typically permanently.

In general the mechanical thrombectomy apparatuses described herein may be highly flexible, both before actuating and during operation. For example, the flexible tractor may not increase the stiffness/flexibility of the catheter of the elongate inversion support, and particularly the distal end region of the catheter too much, to avoid impacting maneuverability, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

A mechanical thrombectomy apparatus may be advanced distally within a vessel and may grab and engulf a clot that is located distally by using the tractor to extend distally ahead of the apparatus, and in some cases pull (e.g., against the vessel walls) to guide or draw the catheter distally forward. This method of advancement may be referred to as "inchworm" or 'worm-like' motion within the vessel. For example, FIGS. 2A-2E illustrate a first method of advancing a mechanical thrombectomy apparatus and/or removing a clot from a vessel using the mechanical thrombectomy apparatus. In this example, the apparatus includes a catheter 205 extending proximally to distally, a puller 207 (shown as a thin tube or hypotube, though it may be a wire or rod, as mentioned above), extending distally within the catheter and a flexible and tubular tractor 209. The tractor is coupled to a distal end region of the puller 217 and the tractor is inverted over a distal end opening of the catheter 219 so that the tractor extends proximally over the outside (outer diameter) of the catheter. In operation, the apparatus may be advanced distally (e.g., towards a clot 213) in a vessel 211, as shown in FIGS. 2B-2D. In FIG. 2B, the puller is pushed distally 220 (shown by arrows on the left) to advanced distally within the catheter and within the vessel towards a clot, so that the tractor extends from the puller distally beyond the distal end opening of the catheter 218, forming a gap 219 between the tractor and the distal end opening of the catheter. This gap is an annular, distal-facing cavity (e.g. pouch) formed in the tractor, and into which the distal end opening of the catheter may be advanced, as shown in FIG. 2C. In FIG. 2C, the catheter is advanced distally over the puller and into the gap. Following this step, the tractor is extended further outside of the catheter, and is in contact with the walls of the vessel 211, through it does not have to be. The outer diameter of the expanded tractor maybe narrower than the vessel inner diameter (ID) or it may be greater than then ID of the vessel (and may therefore touch against them.

When advancing the catheter distally 222 (shown in arrows on left) and into the gap, the puller may be held in position relative to the catheter. In variations in which the tractor contacts the outer diameter of the vessel, this contact may hold the tractor in place against the vessel wall.

The steps of FIGS. 2B and 2C may be repeated multiple times to continue to advance the apparatus distally, however, in some variations it may be beneficial to retract or reset the tractor back into the catheter, e.g., by withdrawing the puller proximally to pull the tractor back into the catheter. This is illustrated in FIG. 2D. In this example, the puller 207 is withdrawn proximally 224 (arrows on left), so that the tractor coupled to the puller 217 is pulled back into the catheter after inverting over the distal end opening of the catheter. It may be beneficial to perform this step after the catheter has been extended distally fully, e.g., until it pushes distally against the back of the inverting (bent over) region, as shown in FIG. 2D. One the tractor has been sufficiently retracted, the steps shown in FIGS. 2B-2C may be repeated, as shown in FIG. 2E, until the distal end opening of the catheter is adjacent to the clot. After positioning next to the clot (and in some cases adjacent to it), vacuum may be applied to pull the clot into contact with the apparatus, and/or the device may be advanced by pushing the catheter distally while pulling the puller proximally to roll and invert the tractor into the catheter (see, e.g., FIG. 1H).

The method of advancing the apparatus described in FIGS. 2A-2E above may be particularly helpful in advancing the apparatus within a vessel even without the use of a guidewire or equivalent (e.g., guide catheter). However this method may also be used with a guidewire, as illustrated in FIGS. 3A-3D. In this example, the apparatus 300 is otherwise the same as shown in FIGS. 2A-2E but may include or be used with a guidewire 355. In general, the same steps may be performed as discussed above. Alternatively, before or after a cycle of inching forward as describe in FIGS. 2A-2E, the apparatus may be slid distally along the guidewire toward the clot. Thus, in some variations, this method may be used to help navigate the apparatus within congested or tortious regions where advancing by sliding may not be as effective.

Another method of advancing an apparatus distally using the tractor is illustrated in FIGS. 4A-4D. This method is also similar to that shown in FIGS. 2A-2E and 3A-3C above, but may extend the tractor portion even further distally using the pusher, so that the pusher extends past the distal end of the apparatus, out of the catheter. In contrast, in FIGS. 2A-2E, the pusher remains substantially within the catheter, thus smaller 'steps' may be taken by the device.

Figure 4A:
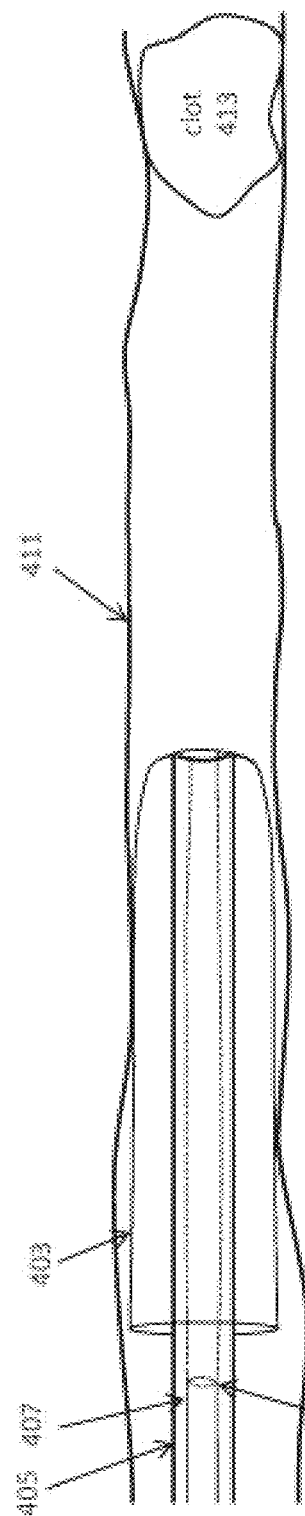
Figure 4B:
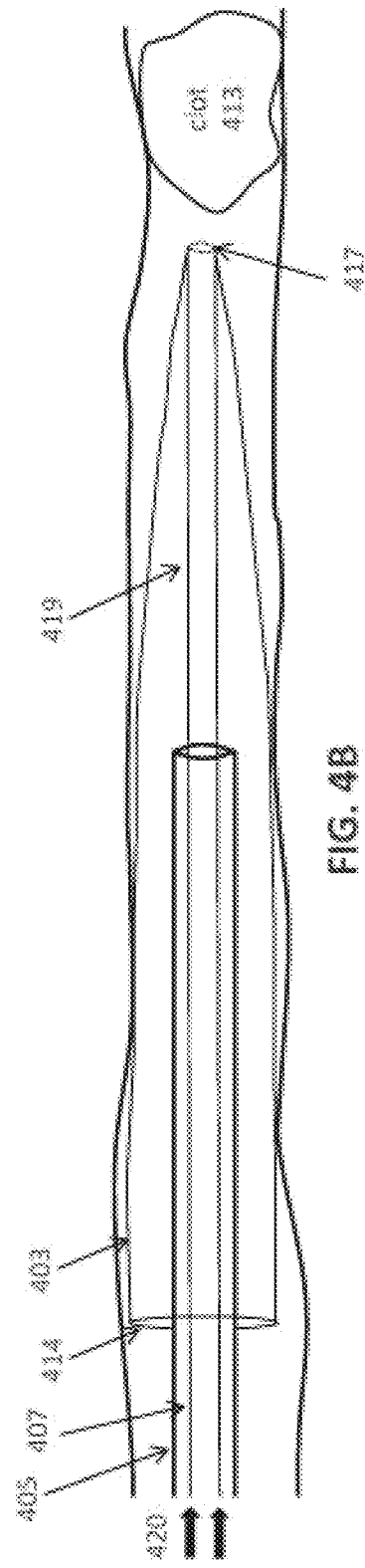
Figure 4C:
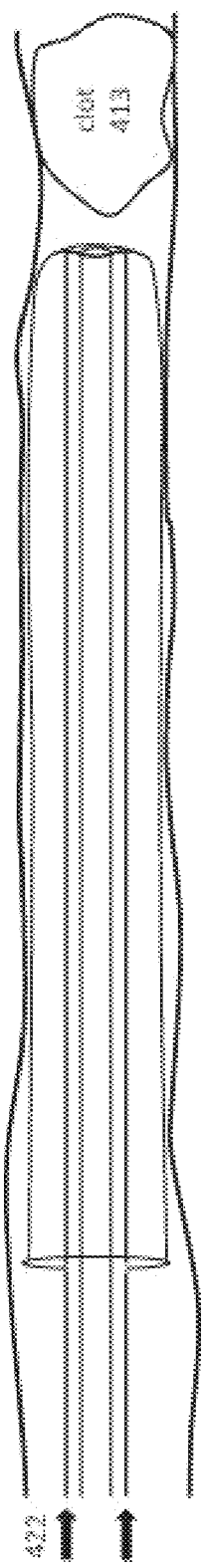

In FIG. 4A, the apparatus is similar to that discussed above, including a puller 407 that is connected at a distal end region 417 to a tractor 403. The tractor is inverted over the distal end opening of a catheter 405. The apparatus may be advanced within a vessel 411 towards a clot 413, as shown in FIG. 4B, by advancing the inner puller 407 distally 420 so that the puller distal end (and attached tractor) extends distally from the catheter distal end opening. The tractor may tent, forming a gap 419 or pouch between the distal end of the catheter and the distal face of the tractor (distal-facing end). In this example, the gap 419 is formed between the distal end of the catheter and the end of the puller. Thereafter, as shown in FIG. 4C, the catheter may be advanced distally 422 within the gap of the tractor. In both this example and the example shown in FIGS. 2A-2E, the puller and tractor may be advanced distal of the catheter distally while the outer portion of the tractor remains over the catheter, e.g. the second end of the tractor 414 that is shown extended over the outer diameter of the catheter remain proximal to the distal end of the catheter. Once positioned near the clot 413, the tractor may be rolled into the catheter by pulling proximally on the puller and (optionally) advancing the apparatus distally by pushing the catheter distally.

If the distal end of the apparatus (e.g., the distal-facing, inverting tractor) is not adjacent to the clot 413, the steps above can be repeated, either with or without retracting the tractor into the catheter (e.g., by pulling proximally on the puller). FIG. 4D illustrates an example of retracting the tractor into the catheter by pulling proximally on the puller 424.

Figure 5A:
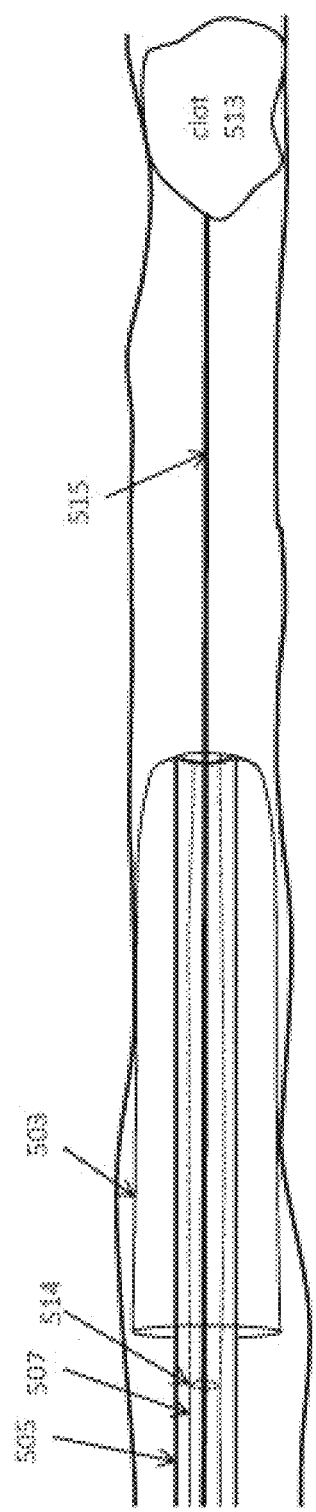
FIGS. 5A-5C illustrate a method of positioning a mechanical thrombectomy apparatus within a vessel and/or removing a clot from a vessel using the mechanical thrombectomy apparatus similar to that shown in FIGS. 4A-4D but include the use of a guidewire.
Figure 5B:
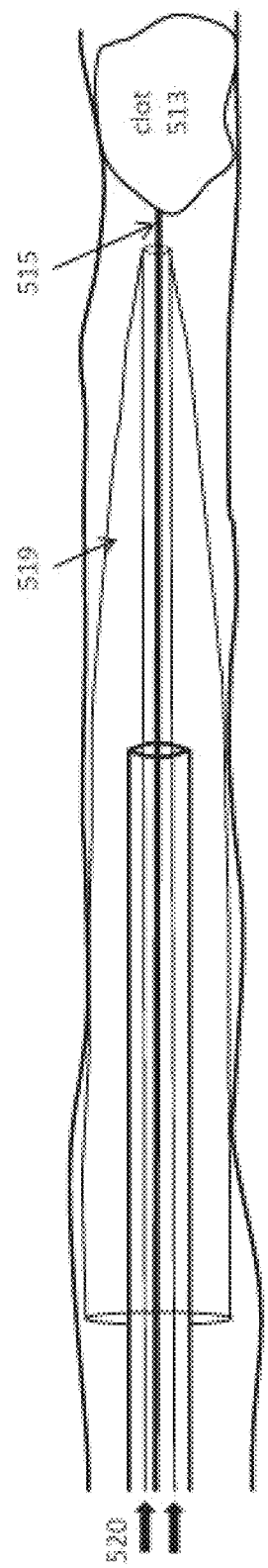
Figure 5C:
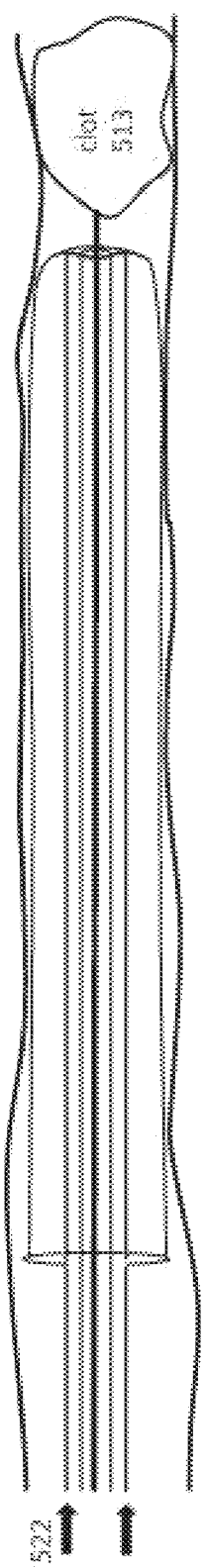

FIGS. 5A-5C illustrate the method of FIGS. 4A-4C with a guidewire 515. The apparatus may be the same (e.g., may include a puller 507 coupled at a distal end 517 to a flexible tractor 503 that is inverted over the distal end opening of a catheter 505 and extending along the outer surface of the catheter). The steps may be the same as discussed above, including advancing the tractor and puller distally by pushing the puller distally 520 towards a clot 513, as shown in FIG. 5B. The catheter may then be advanced (by sliding over the guidewire) as shown in FIG. 5C into the gap or pouch formed by the tractor 519. Once positioned near the clot 513, the tractor may be rolled into the catheter by pulling proximally on the puller and (optionally) advancing the apparatus distally by pushing the catheter distally.

Figure 6A:
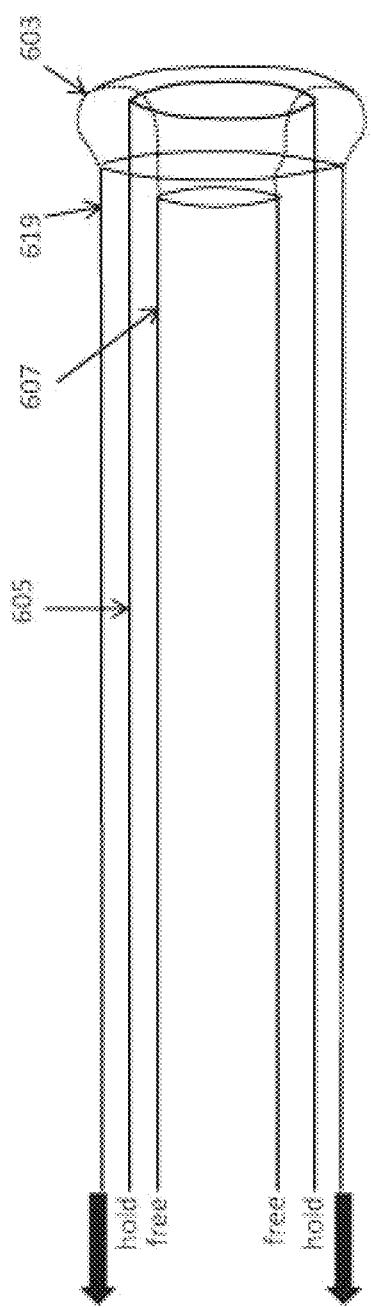
FIGS. 6A-6B illustrates another method of positioning a mechanical thrombectomy apparatus within a vessel and/or removing a clot from a vessel using the mechanical thrombectomy apparatus, in which the apparatus include a tractor that is connected (attached) to both the pusher and an outer catheter or element.
Figure 6B:
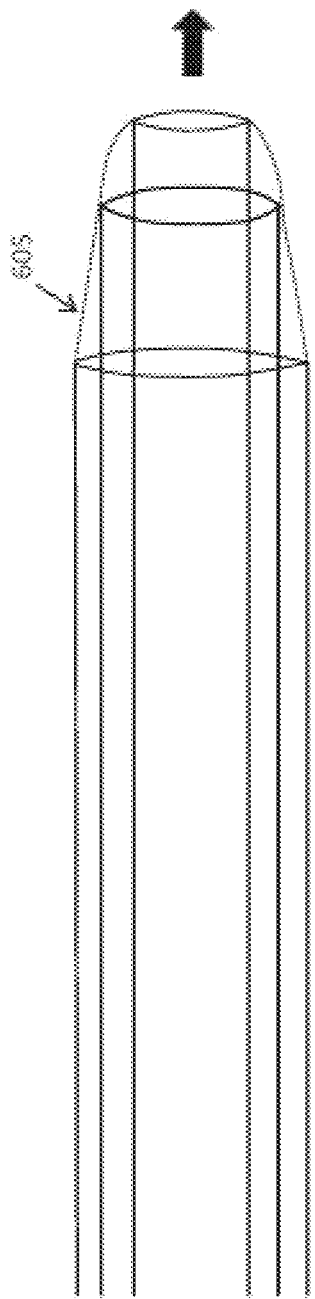

FIGS. 6A-6B illustrate another method for advancing an apparatus distally, in which both ends of the tractor 603 are coupled to axially movable elements. For example, in FIG. 6A the first end of the tractor 603 is coupled to a puller 607 within the catheter 605. In addition, the second end of the tractor is shown coupled to an outer axially movable member (second or outer catheter 619). This tri-axial system may be used to inchworm the apparatus distally by alternately holding and pulling on the various pullers and catheters. For example, in FIG. 6A, the tip of the apparatus may be advanced distally toward a clot by holding the catheter fixed, allowing the puller to float (e.g., not constraining it) and pulling the outer catheter proximally 640. As a result, the outer portion of the flexible tractor may be pulled proximally, pulling the puller and opposite end of the tractor distally, as shown in FIG. 6B. Thereafter, the puller may be held in place, the outer catheter may be free to move axially, and the catheter may be advanced distally into the gap formed by the tractor, which may drive the tractor distally (e.g., back to the configuration shown in FIG. 6A) and pull the outer catheter distally. These steps may be repeated as necessary. In some variations the outer catheter may be removably attached to the tractor, and the tractor may be pulled proximally to separate from the outer catheter.

A guidewire may also be used with this method. In this example, tip advancement of the apparatus may take advantage of the outer (e.g., guide) catheter stiffness (e.g., bending and column stiffness) to aid in catheter tip advancement. This may be particularly helpful in neurovascular regions, such as shown in FIG. 7.

FIG. 7 illustrate the uses of the methods described herein to advance the apparatus 701 within a neurovascular structure such as the internal carotid segment in the head. For example, the distal tip of the apparatus may be positioned at the distal tip of the internal carotid segment; once positioned, an advancement method such as one of those described herein may be used drive the apparatus distally forward towards the clot. Such a method may create a pushing force forward from the internal carotid artery without sacrificing the trackability of the apparatus or the small outer diameter of the apparatus.

The apparatuses described herein may also be used to advance other apparatuses (including catheters and tubes). For example, any of these apparatuses and methods may be used in reverse (e.g. pulling proximally on an outer portion of the catheter) to pull an apparatus within the lumen of the tractor distally for delivery at an internal vessel site.

Thus, to advance a tool (e.g., a tube, etc.) into the patient, a tractor inserted into the body (which may be advanced as descried herein, even for use without performing a thrombectomy or in addition to a thrombectomy) may be pulled from the outside of the catheter proximally (e.g., with an overtube or pull wire) to invert the tractor in the opposite direction from out of the catheter. As the tractor on the OD of the catheter is pulled proximally, it may advance a tool (e.g., tube) inside the apparatus to the target location in the patient. This mechanism could be used in a variety of applications including; passing mature clot or vessel lesion, placing an intubation system (e.g., in a throat), providing rectal or vaginal access, performing NOTES surgery, inserting a tool such as a trocar, inserting a scope into a body region (e.g., gastrointestinal region, colon, blood vessel lumen, etc.), inserting a robotic tool, crossing a calcified vessel, etc. Other applications of the apparatuses and methods of removing and/or placing material using the apparatuses described herein may include removal of tissue, such as gall bladder removal and removal of fat (liposuction). For example a cutting or ablative tool may be passed down the middle of the apparatus, through the catheter, the puller and the tractor, and extended from the distal end, where it may be used to cut tissue that may then be pulled out of the body using the tractor by pulling the tractor proximally within the catheter. Note that this method may be used to remove both the tool and/or the cut tissue. Thus, despite referring to these apparatuses as mechanical thrombectomy apparatuses herein, any of these devices may be adapted for uses not limited to thrombectomy and may alternatively be referred to as mechanical tractor apparatuses.

Also described herein are powered mechanical thrombectomy apparatuses in which the tractor may be driven by a driver such as an electrical motor. For example, FIG. 8A illustrates an example of a power-driven tractor in a mechanical thrombectomy apparatus. The apparatus may drive the tractor continuously in a loop; thus the tractor may be configured as a closed loop, belt or toroid of material that extends around a catheter. The power drive may run the apparatus in either the forward or reverse directions. In FIG. 8A, the tractor comprises a plurality of belts 803 that extend around and through the catheter 805. A drive motor 811 drives rotation of the belts. In FIG. 8A the drive motor drives a ring 813 that can therefor drive multiple belts forming the tractor or in some variations, a single torus that passes over the supporting catheter. The catheter may include holes or openings 817 into which the belts forming the tractor may reside. The belts extend along the length of the catheter 805. In this example, a hub 815 holds the proximal end of the catheter and holds the belts against the drive motor and/or drive ring that is driven by the drive motor and may also connect to a vacuum 819.

FIG. 8B shows an enlarged view of a catheter and tractor that may be used with the apparatus shown in FIG. 8A. FIG. 8B shows the catheter 805 including a plurality of belts 803, 803' forming the tractor. The belts pass through an opening in the catheter at the proximal end, but roll over the distal end of the catheter, and extend along the outer and inner longitudinal axis.

Figure 9A:
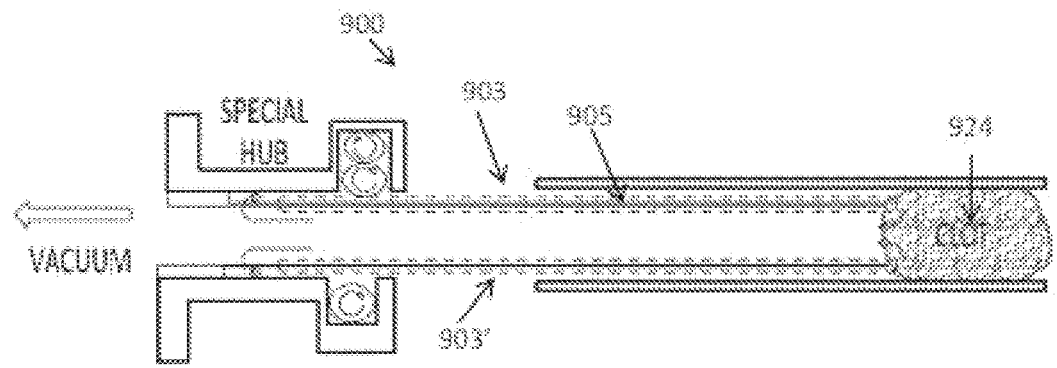
FIGS. 9A-9B illustrate a method of operating a mechanical thrombectomy apparatus for removing a clot from a vessel that include a motorized or motor-driven tractor, such as the one shown in FIGS. 8A-8B.
Figure 9B:
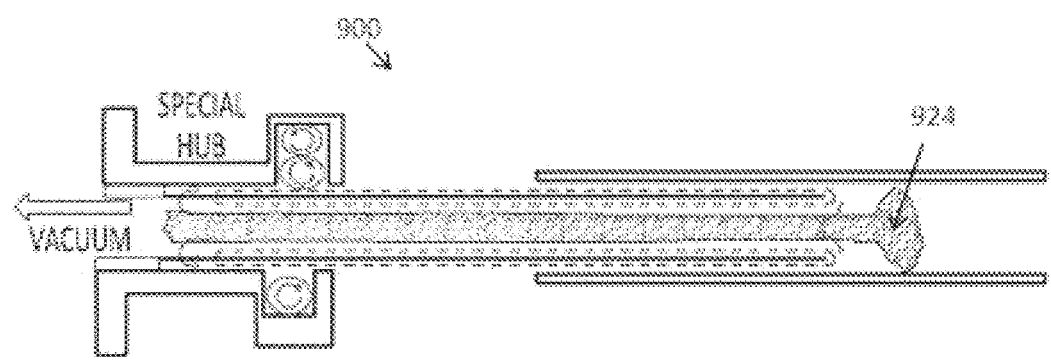

FIGS. 9A-9B illustrates an example of operation of a power driven mechanical thrombectomy apparatus configured to grab a clot. In FIG. 9A, the apparatus 900 is similar to that shown in FIG. 8A, above, including a plurality of belts 903, 903' forming the tractor, and an internal catheter 905; the bests rotate down the length of the catheter. Note that the catheter may be rigid or flexible. The catheter may include channels, and/or notches or other guide along its length for guiding and/or enclosing the belts at various portions. In FIG. 9A, the apparatus is positioned adjacent to a clot 924. The clot may initially be grabbed using aspiration (e.g., vacuum). In FIG. 9B, the apparatus is shown after grabbing the clot, and compressing it within the catheter.

Note that the power-driven mechanical thrombectomy apparatuses shown in FIGS. 9A and 9B do not include a puller, as the motor may act like a puller. In some variations a separate puller may be used.

Figure 9C:
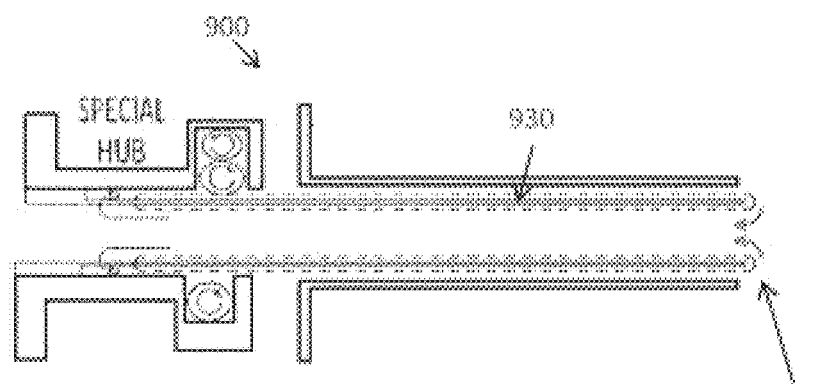
FIG. 9C illustrates a motorized or motor-driven (e.g., "power driven) continuous tractor that is loaded into a larger catheter (e.g., an intermediate catheter).

As mentioned above, any of the apparatuses described herein may be used with an additional outer catheter, including the powered apparatuses described herein. For example, FIG. 9C illustrates an example of a powered apparatus 900 used with an intermediate catheter having a larger OD than the powered mechanical thrombectomy apparatus. In this example, the length of the apparatus is slightly greater or almost equal to the length of the intermediate catheter 930, so that just the distal end region of the apparatus, including the inverting tractor (belts) is accessible and/or sticks out 933 of the intermediate catheter. Alternatively, the apparatus may be retracted into the outer (intermediate) catheter slightly or may extend substantially from the end of the outer catheter.

Figure 10A:
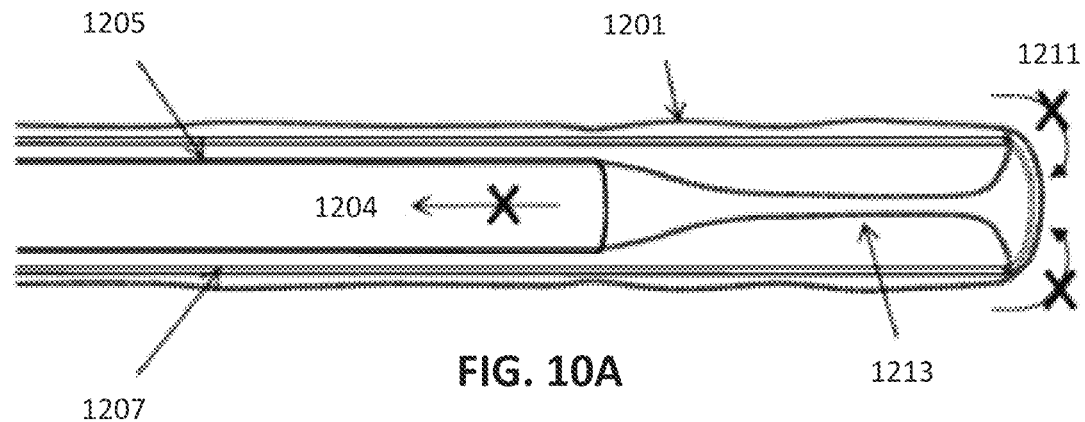
FIGS. 10A and 10B illustrate jamming of a mechanical thrombectomy apparatus.
Figure 10B:
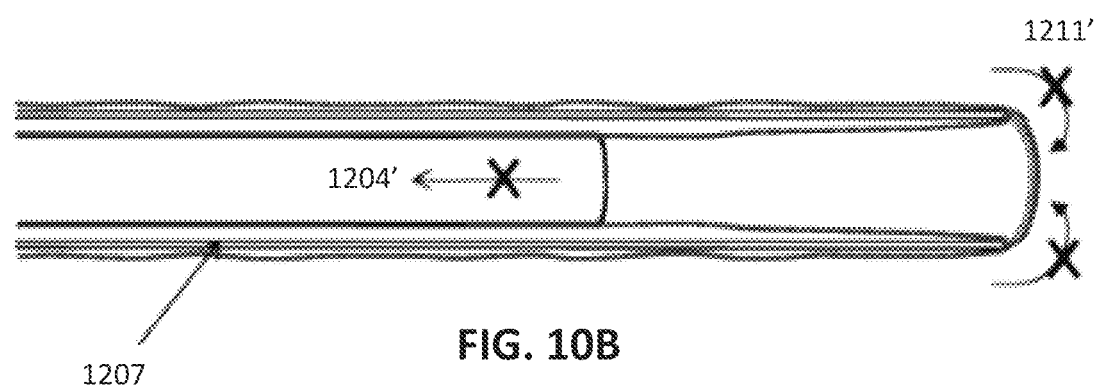

Jamming may occur if the tractor cannot easily invert over the distal end of the catheter, as shown in FIGS. 10A and 10B. In FIG. 10A, pulling the tractor 1201 proximally from within the catheter 1207 of the elongate inversion support, e.g., by pulling 1204 on the inner puller catheter 1205, would normally cause the tractor to roll 1211 over the distal end of the catheter tip. If the force required to pull the tractor so that it inverts and rolls into the catheter is too great, such as 200 g of force (e.g., greater than 10 g force, greater than 20 g force, greater than 30 g force, greater than 40 g force, greater than 50 g force, greater than 60 g force, greater than 70 g force, greater than 80 g force, greater than 90 g force, greater than 100 g force, etc.), exclusive of any initial deployment force to release the tractor, described herein, then the device is jammed. Typically the tractor may be pulled and inverted over the distal end opening with significantly less force that this jamming force. Jamming may lead to collapse of the elongate inversion support, and device failure. Jamming may occur when, for example, the tractor gets caught on the distal end opening of the catheter of the elongate inversion support. In FIG. 10A, one failure mode leading to jamming results when the portion of the tractor within the catheter 1213 collapses inward, as shown. The inventors have found that it is desirable, and may prevent jamming, if the portion of the tractor within the catheter collapses only so that it has a diameter (e.g., inner diameter) of 40% or more of the inner diameter of the catheter (e.g., 45% or more, 50% or more, 55% or more, 60% or more, 65% or more, 70% or more, 75% or more, etc. of the inner diameter of the catheter).

Similarly, FIG. 10B illustrates another example of an apparatus in which jamming has occurred, as indicate by the "X" through the arrows showing the proximal movement of the tractor within the catheter 1204' and rolling 1211' of the distal-facing inverting portion of the tractor. In FIG. 10B, the tractor bends sharply around the distal end of the catheter. This sharp bend may result in jamming over the distal end of the catheter, as shown.

Figure 10C:
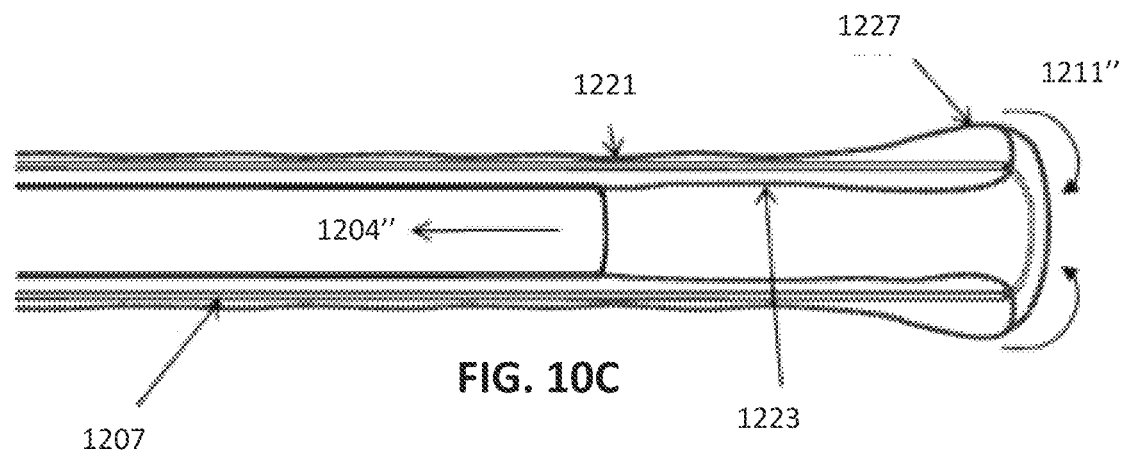
FIG. 10C illustrates an example of an anti jamming configuration, in which the distal-facing, inverting portion of the tractor is flared outwards at an angle, so that the portion of the tractor on either side of the catheter end approaches at an angle of less than 45 degrees relative to a length of the tractor (e.g., 0.5 mm, 1 mm, 2 mm) on either side of the opening. In this example, the portion of the tractor that is around the outer diameter is biased to contract down onto the outer diameter of the catheter, and after inverting the bias is to expand outward slightly, resulting in the trumpet-shaped inverting region. Even in this configuration, the tractor may be set (e.g., biased) so that the outer diameter of the first configuration (within the catheter of the elongate inversion support) has a greater outer diameter than the inner diameter of the catheter in the relaxed state (e.g., when not compressed and constrained in the catheter inner diameter), and the outer diameter of the tractor in the second configuration (inverted over the outer diameter of the catheter of the elongate inversion support) is greater than the outer diameter of the catheter. In some variations the unconstrained first configuration has a greater OD than the unconstrained OD of the second configuration. Alternatively, the unconstrained OD of the first configuration may be less than the OD of the unconstrained OD of the second configuration.
Figure 11A:
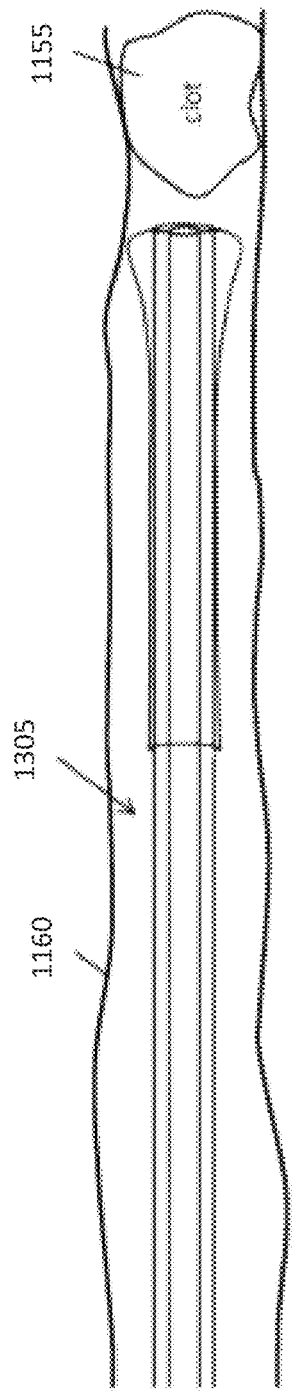
FIGS. 11A-11C illustrate the operation of a mechanical thrombectomy apparatus having a tractor region such as that shown in FIG. 10C capturing a clot.
Figure 11B:
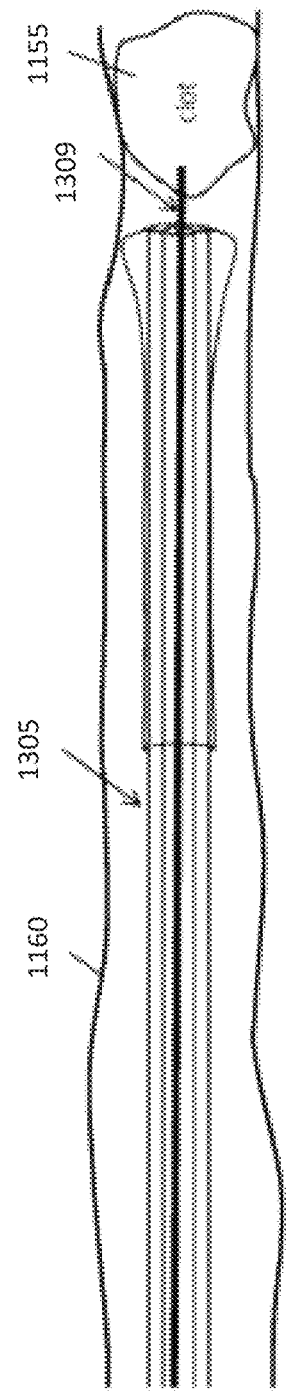
Figure 11C:
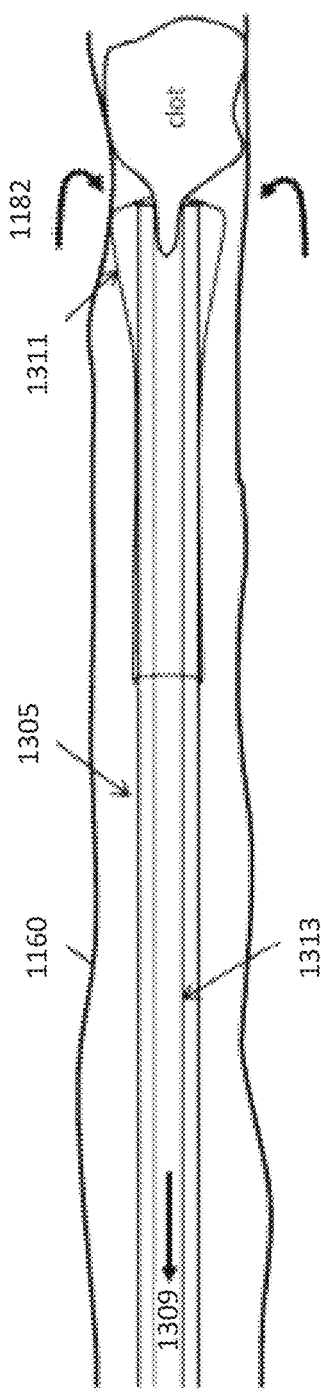

Various features that may be used alone or in any combination to prevent jamming of the tractor on the catheter are described herein. For example, in FIG. 10C, a the tractor may be biased so that the portion of the tractor within the catheter in the first configuration 1223 (e.g., extending from the puller in an un-inverted configuration in FIG. 10C) would have a relaxed outer diameter (OD) that is approximately equal to or greater than the ID of the catheter (e.g., the relaxed OD of the tractor is between 0.8× to 3× the ID of the catheter), and the OD of the tractor in a second configuration (inverted relative to the first configuration) 1221 is typically greater than or approximately equal to the OD of the catheter (e.g., the relaxed OD of the tractor in the second configuration is between about 0.9× and 5× the OD of the catheter, e.g., >1× the OD of the catheter, etc.). It should be noted that the tractor may be configured so that the relaxed OD of the first configuration of the tractor is greater than the relaxed OD of the tractor in the second (inverted) configuration, or vice versa. This combination of biasing may result in a distal-facing inverting region that is slightly trumpet-shaped 1227, as shown. This trumpet shape may result in an angle of approach between the surface of the tractor and the open end of the catheter that is more close to perpendicular relative to the open end, as can be seen by comparing FIG. 10C with FIGS. 10A and 10B. The outwardly flaring distal-facing tractor region may therefore prevent jamming. FIGS. 11A-11C illustrate the operation of an apparatus including a tractor region that flares outward at the distal-facing rolling/inverting region as it rolls over the distal end of the catheter. In FIG. 11A, the apparatus 305 is driven down the vessel 1160 into proximity with the clot 1155. A guidewire 1309 may be used to aid in positioning, as shown in the alternative view of FIG. 10B. For example, a guidewire may be first guided to the clot, and the apparatus may then be slid over the guidewire to position adjacent to the clot. The guidewire may be left in place or removed before actuating the apparatus as shown in FIG. 11C to remove the clot. In FIG. 11C, the apparatus is actuated by drawing proximally 1309 on the inner portion of the tractor 1311 so that it rolls and inverts 1182 over the distal end of the catheter, as shown. The inverting tractor grabs and pulls the clot into the catheter, compressing and/or distorting it as it pulls it inside. The apparatus may be advanced distally as the tractor is pulled proximally. In some variations the tractor may be expanded longitudinally (distally-proxi-
mally) within the catheter as it is drawn proximally within the catheter, because it may be a woven, knitted or elastic material. This may allow the clot to be drawn in quickly and may secure it within the catheter.

The tractors may be woven, braided and/or knitted materials. For woven and braided materials, which may include a plurality of fibers that are woven or braided to form the inverting tube, these structures may be tuned to prevent jamming and/or to reduce the force necessary to pull the tractor and invert over the catheter tip. For example, the mechanical atherectomy apparatus may include a braid-type tractor that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., tractor); including a radiused wall on the catheter; and/or increasing the stiffness of the distal tip region relative to adjacent proximal regions.

As mentioned, the tractor (e.g., braided, woven, knitted, etc.) may be configured to collapse down into the inner diameter (ID) of the catheter as little as possible. For example the tractor may collapse to an ID that is greater than, equal to, or within 90%, 85%, 75%, 70%, 65%, 60%, or 50% of the catheter inner diameter (ID)/Catheter Tip OD, since, when the tractor is being pulled around catheter tip it may create axial tension on the tractor (e.g., braid, knit, etc.) that can inadvertently cause the tractor to jam on the catheter tip. When tractor is pulled around catheter tip, the tractor is being pulled in the axial orientation creating axial tension on tractor structure as the tractor is being pulled through the catheter ID. By having the tractor elements jam at an ID greater than or equal to 90%, 85%, 75%, 70%, 65%, 60%, or 50% of the catheter ID (or in some variations, OD), when being axially tensioned, the tractor is less likely to grab/synch down onto the catheter tip, helping the braid roll around the catheter tip with less axial force applied by the user. If less axial force is required by the user to pull the tractor structure around the tip then the catheter tip is less likely to buckle or deflect when retracting the tractor. It may be advantageous to minimize the chance the catheter tip will buckle. The tractor can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the tractor over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations described herein, the catheter and/or a surface of the tractor may be coated to enhance rolling over the distal end region of the catheter. It may be helpful to have a hydrophilic coating on the distal aspect of the catheter OD or the ID of the tractor so the tractor can more easily side over the catheters distal end and around the tip of the catheter when pulled through the inside of the catheter.

The radius wall of the catheter tip may be chosen/set to within a range that allows sliding. For example, it may be helpful for the tip of the catheter to have the largest radius possible but at least 0.0025" radius wall on the catheter, ideally approximately 0.005" radius wall.

The stiffness of the distal of the catheter may be sufficiently stiff to prevent collapse as the tractor is pulled; it may also be lubricious (e.g., by a coating or material property). The distal most section of the catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

As will be described in greater detail below, it may be helpful or desirable to have pores in the tractor. A lack of gaps or small pore size may limit the ability of the braid to grab clot. Alternatively or additionally, it may be desirable to form a braid structure with texture. One example is to braid 2 or more different diameter braid ends into the same structure: the difference in braid end diameters will help form a texture to the braid structures outer surface, aiding the grabbing of the clot when rolling the braid-dozer around the catheter tip.

As an alternative (or in addition) the tractor may be configured to lock so it does not compress in diameter during axial load by adding a coating, laminate or adhesive to the braid at a desired diameter. Adding a thin coating, laminate or adhesive can inhibit the braid elements from sliding with respect to each other, thereby locking the braid to a specific diameter. The coating can be applied while leaving the majority of the pores and pore area substantially open. Examples of thin coatings include urethanes and silicones with and without hydrophilic coatings and hydrophilic coatings with no tie layer.

Reducing the sliding friction of tractor to outer catheter wall, improving tractor to tip rolling, and/or enhancing tractor to inner catheter sliding may also be achieved by including a sliding skin or sleeve. For example, a thin (e.g., ultrathin) sleeve may be used. The sleeve would be made from low friction polymer (PET, PE, PP, PTFE, ePTFE, PEBAX, urethanes) by braiding, knitting, weaving, extrusion, melt blown, melt spinning, etc. The sleeve could be made from laser slotted tubing, chemical etching, micro machining. The sleeve could be also coated with a lubricious coating such as a hydrophilic coating. Lubricious coatings can be located on the outside and/or inside surfaces. The sleeve may be placed between the dozer element and the catheter wall and attached to the puller element. The sleeve may be less than 0.002" thick, ideally, less than 0.001" wall thickness. The sleeve may decouple the tractor clot grabbing system from the catheter wall, tip rolling and inner catheter dragging friction. The sleeve could be totally free from the tractor, connected to the tractor in discrete locations or connected fully to the tractor. This may allow the tractor to be designed to grab clot (larger wires: 0.001" to 0.002" for neuro, and 0.002" to 0.007" for other applications) and the skin to minimized in thickness and structure to reduce friction and skin bending stiffness.

Figure 12A:
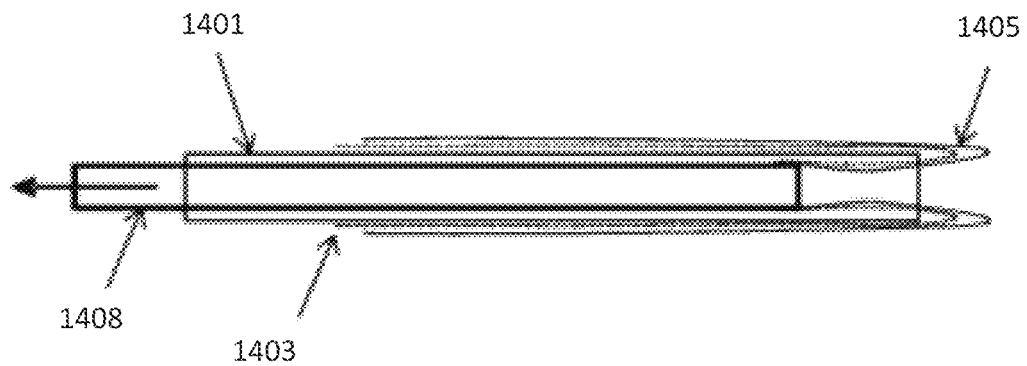
FIGS. 12A and 12B illustrate another example of a mechanical thrombectomy apparatus having a tractor in which an anti-jamming sleeve portion is included between the catheter outer diameter and the tractor.
Figure 12B:
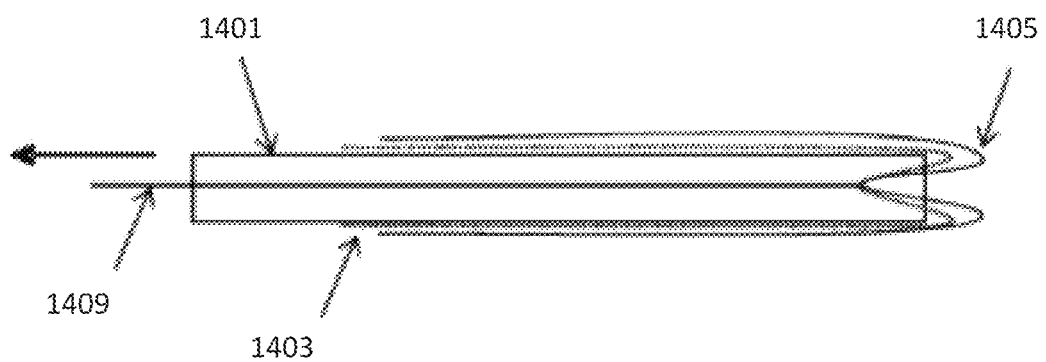

FIG. 12A shows one example of a sleeve that may be used. In this example, the sleeve 1403, such as those described above, may be positioned between the catheter 1401 outer diameter and the tractor 1405. The sleeve (or "skin") may be inverted with the tractor, or it may be held on the outer diameter and the tractor moved over it. FIG. 12B is another example in which the tractor is pulled by a pull wire 1409; in FIG. 12A the tractor is pulled by a puller catheter 1408 within the outer device catheter 1401.

In some variations, the tractor region may be formed of with a mixed or hybrid structure, combining one or more of interwoven or knitted braid polymer filaments with metallic filaments. The mixed structure (hybrid structure) may leverage both metallic elements interwoven with low friction polymer elements. The metallic filaments may create stiffness elements that may grip/grab a clot. The polymer filaments may aid in grabbing clot but may provide surface friction reduction to the outer catheter wall, the catheter tip and the inner catheter wall once around the tip.

Any of the apparatuses described herein may include a tractor having a hydrophilic/lubricous coating on the inside surface, e.g., for braided/knitted tractors, on the inside surface (contacting the outer and inner diameter of the catheter) of the braid/knit, which is in contact with the outside of the catheter. Examples of lubricous coatings include hydrophilic coatings (e.g., hydrogels) and hydrophobic coatings (e.g., fluorine coating such as PTFE & FEP, parylene, silicone, siloxane (silicone additive) added to various polymers including PEBAX to make any material more lubricious, Polyethylene, polypropylene, FEP)

Figure 13A:
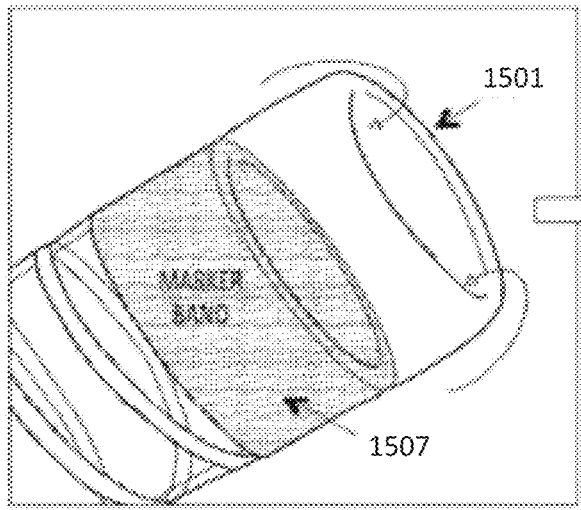
FIGS. 13A-13B illustrate formation of catheter tip having a stiffer distal end adapted to prevent jamming and/or collapse of the catheter distal opening when inverting a tractor over the distal end.
Figure 13B:
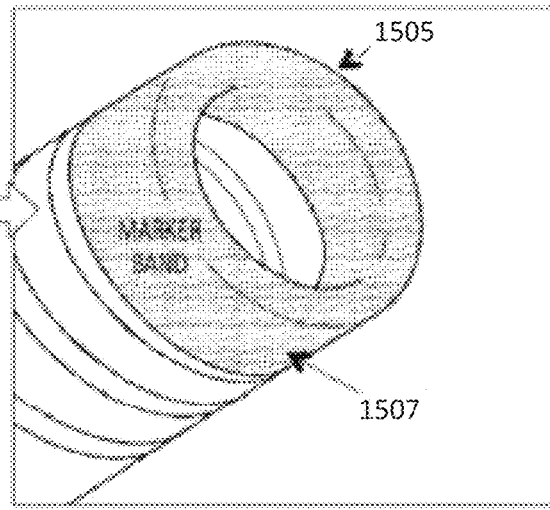

As mentioned above, any of these apparatuses may include a distal tip that is less rigid (e.g., 'softer') than the more proximal regions of the distal tip. This may be achieved by having a structural supporting member reinforcing the distal tip, or by modifying the material forming the distal tip. In some variations, the distal tip of the catheter may be stiffened (made more rigid) by inverting over the catheter end. See, e.g., FIGS. 13A-13B showing an inverted soft tip of a catheter. In this example, a 72-end PET braid was used to invert the tip 1501 of the 0.071 catheter back over itself 1505 as shown in FIG. 13B. Inverting the distal section of the catheter tip, which may include a hydrophilic coating, inside of the catheter and (in this example, though not a necessity) a radiopaque marker band 1507. This may crease a larger radius tip which is relatively stiffer than the tip and has a hydrophilic coating around the outer diameter and inner diameter all the way on the last 2-5 mm of the catheter. Optionally, the catheter may be delivered with a tip similar to that show in FIG. 13A, but when the tractor is pulled initially into the catheter, the distal end of the catheter may invert to form the tip as shown in FIG. 13B.

Figure 14A:
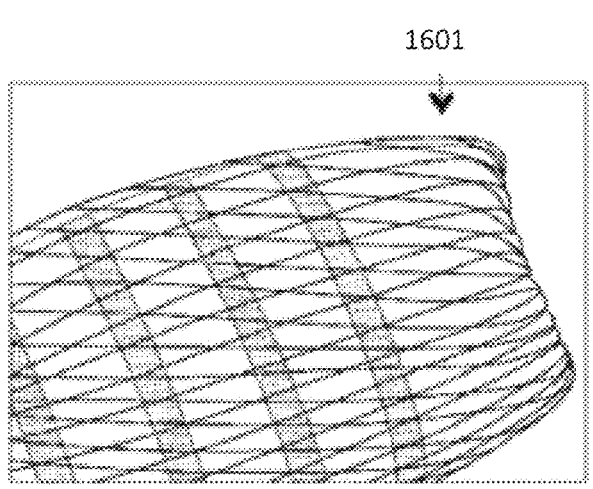
FIGS. 14A-14B is an example of a distal tip or end region of a catheter such as that shown in FIG. 13B, over which a tractor is inverting.
Figure 14B:
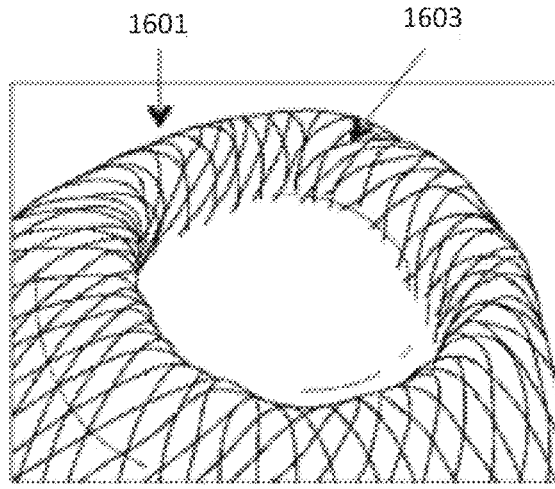

FIGS. 14A and 14B show another example of an inverted soft-tip catheter over which a tractor 1601 (in this example, a PET braid having 72 ends and a 4×0.0008" material). The tractor in FIG. 14A is rolled over the hydrophilic coated tip 1603 showing a large collapsed radius (e.g., it does not collapse down on itself). The coating of hydrophilic material enhanced the rolling of the material over the catheter. The catheter was loaded with the tractor having a small (2 mm) ID tube, which is very close to the catheter OD. In this example, 23 cm of tractor was pulled easily into the catheter having a rolled tip as shown in FIG. 13B. In this example, the tip did not collapse, however other tractor materials (e.g., metallic, such as Nitinol materials) may collapse the tip, even when inverted as shown.

FIGS. 15A-15F illustrate examples of braided tractors that may be used. In these examples, FIGS. 15A-15C show PET braids that are heat-set to 0.085" IDs (at 395° F. for 10 min). For example, FIG. 15A is a 0.001 inch PET, having 36 ends and a 77° braid angle at 9 mm, and 0.008 OD filaments. This example was highly porous but was the least stable of all of the examples shown in FIGS. 15A-15F. FIG. 15B is a 72-end 0.001 polyester strand braid of 8 mm, 90° braid angle, with 4 filaments in each strand. FIG. 15C is a 48-end braid tractor of 0.002" polyester, 90° angle over 9 mm mandrel. The braid shown in FIG. 15A collapses 50% of the diameter, while the braided tractor shown in FIG. 15B collapsed less than 5% of the diameter, and the braided tractor of FIG. 15C collapsed less than 25% of the diameter.

FIGS. 15D and 15E show Nitinol braided tractors heat-set to 0.085" ID (at 510° C. for 8 min). These braided tractors were constrained to 0.070 inches to show the pore size when pulling into a 0.071 catheter. Other examples of braided tractors had between 96 or 144 ends of 0.0005"-0.0015" PET mono or 0.0005"-0.001" filaments with a <35° braid angle.

FIGS. 16A-16D illustrate the operation of a 72-end 0.001" NiTi tractor capturing clot in a model vessel. In this example showing pulling the clot into the catheter, the ID of the vessel is nearly the same as the OD of the catheter tip. Drawing the tractor into the vessel shows that the tractor region does not collapse down with inverted into the vessel, preventing locking of the end, and leaving space for drawing the clot, as shown. FIGS. 16E and 16F illustrate reversing the rolling movement of the device to eject the clot from the apparatus.

Figures 17A, 17B, 17C, 17D, 17E, 17F, 17G:
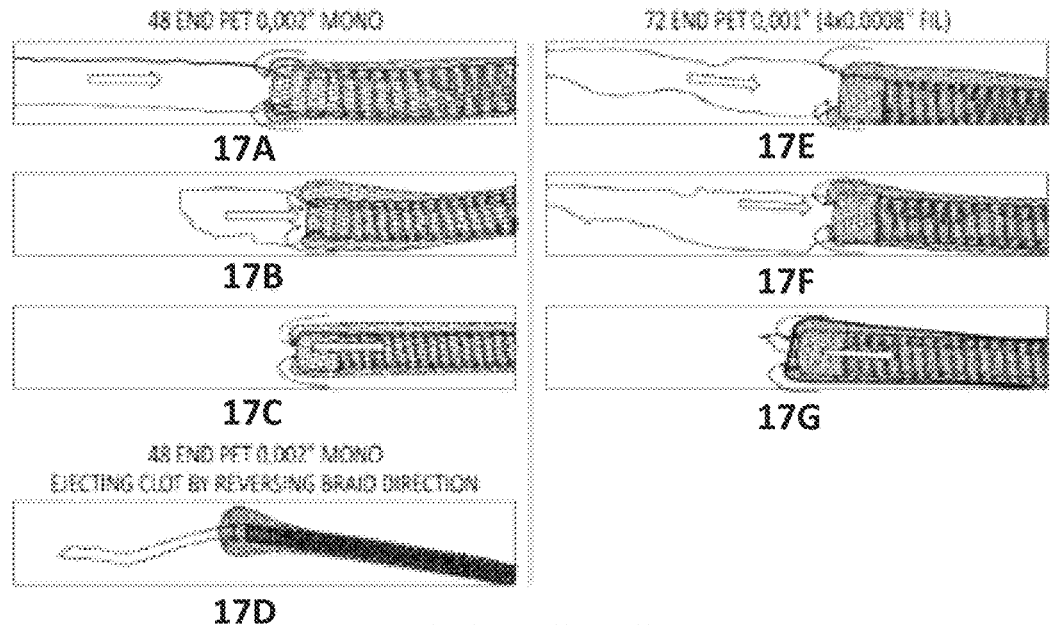
FIGS. 17A-17C illustrate operation of an apparatus having a 48-end PET (0.002" monofilament) tractor.
FIG. 17D illustrates reversing the apparatus of FIGS. 9A-9C.
FIGS. 17E-17G illustrate operation of an apparatus having a 72-end PET (0.002" 4×0.0008" filament) tractor drawing in a clot.

Similarly, FIGS. 17A-17C illustrate using a 48-end 0.002" PET monofilament braided tractor capturing a clot in a vessel. FIG. 17D shows reversing of the same apparatus to eject the clot. FIGS. 17E-17G show another example of a braided tractor, comprising a 72-end 0.001" PET (4×0.0008" fil) material drawing clot into the device by rolling the tractor region into the catheter, as shown.

Figures 18A, 18B, 18C, 18D, 18E:
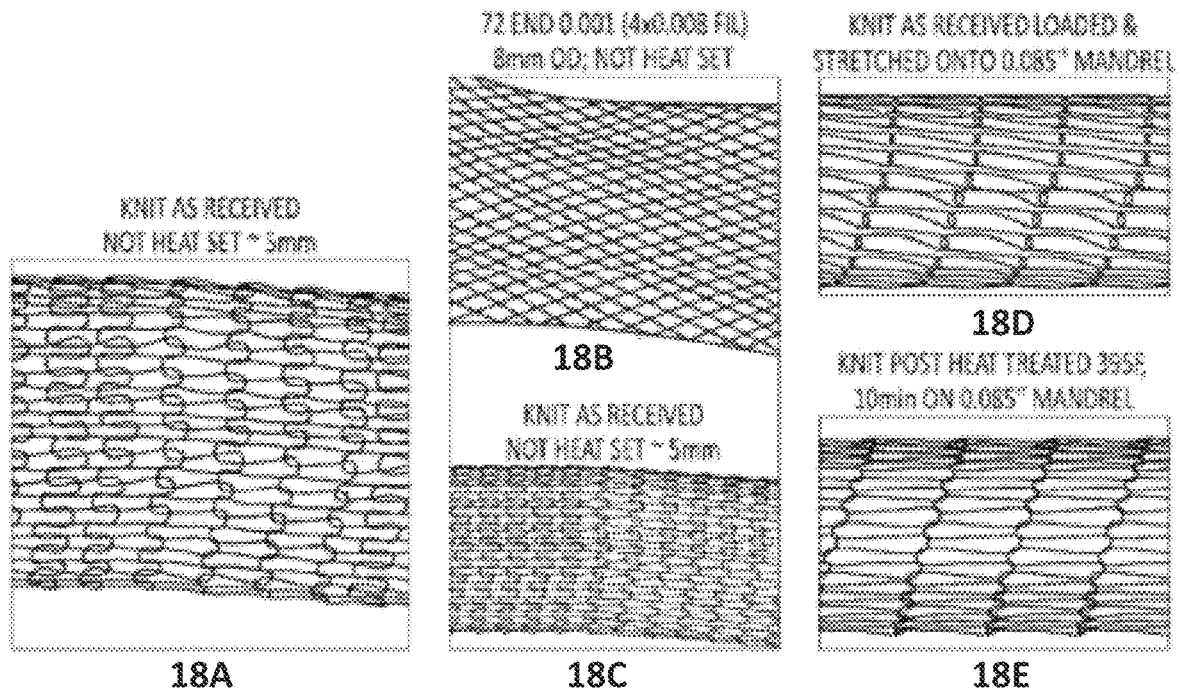
FIGS. 18A-18E illustrate examples of knitted tractors.

As discussed above, tractors may also be formed of a knitted material. A knitted material typically includes materials in which the same filament (or a series of filaments connected in tandem) is knitted to itself to form the tractor. It may be particularly advantageous to use a knit to form a tractor as described herein. For example, FIGS. 17A-17F illustrate an example of a 0.002" knitted tractor 26 needle (SN5923) material, which is a circular weft knit of 0.002" PET monofilament 26 needle head Greige (from Secant Medical). In FIGS. 18A-18C, the knit material is not heat set; the tractor regions shown in FIG. 18E is heat set, knot post-heat treated (at 395° F., 10 min on 0.085" mandrel).

Any of the apparatuses described herein may include a tractor region that is configured to grab a clot. In particular, described herein are apparatuses that may include a tractor region that has a plurality of projections extending from the tractor, particularly when the tractor rolls around the distal end of the catheter and inverts; these projections may help grab and/or macerate the clot.

For example, described herein are apparatuses including a plurality of projections that are formed as part of the tractor region. For example, any of these apparatuses may be configured to include projections that are formed by cutting (e.g., laser cutting) or forming from the tractor. Cutting and may be used to form projections or protrusions from a tube of material (or a sheet formed into a tube during processing) such as a sheet or tube of NiTi, thin-film NiTi, cobalt chromium, stainless steel, etc. Projections may be formed from a laser cut NiTi hypotube, a NiTi laser cut sheet, or the like. Projections may also be formed on any of these devices by welding. For example, projections may be formed by welding to a thin-film NiTi tube or sheet. The cut or formed tractor regions may be configured to have virtually any pattern or shape. For example a tractor region having projections that extend from an inverting/rolling tractor region may be formed of a metallic or polymeric material that can include any cut or shaped pattern so that the pattern lays flat (e.g., in the plane of the tractor) on outside of catheter and extend from the tractor (e.g., out of the plane of the tractor) as it rolls around the catheter. The projections may comprise portions of the tractor region pattern that extend and may grab and/or cut, e.g., macerate, the clot as they stick into the clot. These same regions of the tractor may then lie relatively flat against the ID of the catheter when fully inverted and pulled into the catheter.

In general, cut may be made in the tubes or sheets (e.g., sheets to be formed into tubes) in order to enhance flexibility, porosity and/or to add projections that may extend from the tractor as it is rolled over the distal end opening of a flexible tube (e.g., catheter). A tractor may therefore be formed into any appropriate pattern, so long as it is sufficiently flexible.

For example, FIGS. 19A-19D illustrate examples of patterns that may be used for a flexible tractor region. These two dimensional (2D) patterns (e.g., textured surfaces) may provide flexibility of the tractor region in rolling and inverting over the catheter distal end; in some variations, such patterns may help grab a clot when the tractor is rolled and pulled into catheter. These patterns or textures could be formed by laser cutting, molding of plastics or thin film metal (e.g., NiTi Technology), stamping, etching, or the like. The patterns shown in FIGS. 19A-19D generally form closed-cell shapes having angled arms forming the cell walls. The angles may allow deformation in one or more directions. The pattern may mimic the patterns of woven, braided and/or knitted materials, or may be different.

In any of the apparatuses described herein, the tractor region may also include surface micropatterns that may be added or formed onto the tractor. These micropatterns may help with grabbing a clot. For example, FIGS. 20A-20I illustrate micropatterns protrusions, projections, knobs, bumps, spikes, etc. that may extend from the surface of the tractor. In some variations, e.g., in FIGS. 20A-20C, 20E and 20F, the micropatterns may extend from the tractor region at all times, not just when rolling over the end of the catheter. Another example of an apparatus including a tractor having projections that extend from the tractor including the portion of the tractor that is over the catheter is shown in the apparatus of FIG. 22. In FIG. 22, the tractor 11401 includes a plurality of projections 11403 that extend from the tractor at all times, including the portion of the tractor that is rolling over the distal end opening of the catheter (the distal-facing tractor portion) as well as the portion that is over the outer diameter of the catheter, and within the inner diameter of the catheter. Other variations (e.g., FIG. 20D-20I, FIGS. 21A-21B, and 24A-24B) may project only from the portion of the tractor that is rolling over the distal end opening of the catheter.

Figure 19A:
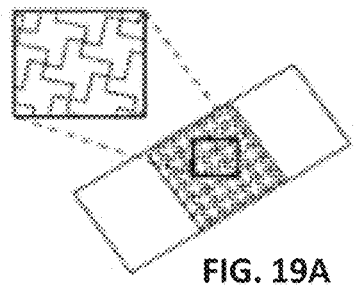
FIGS. 19A-19D illustrate patterns that may be used to form a tractor for a mechanical thrombectomy apparatus.
Figure 19B:
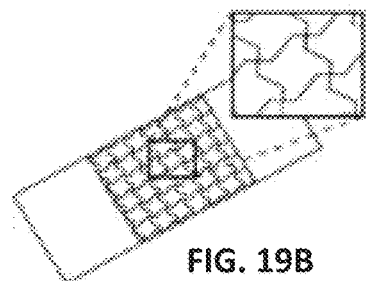
Figure 19C:
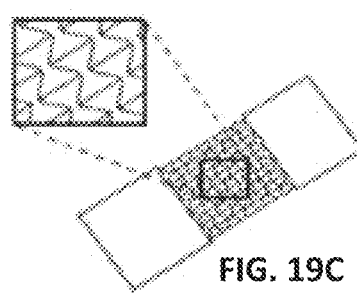
Figure 19D:
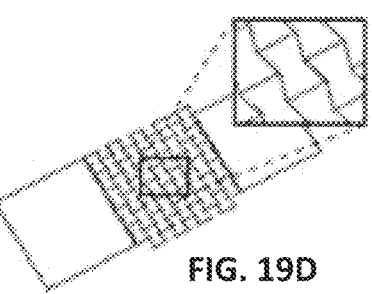
Figure 20A:
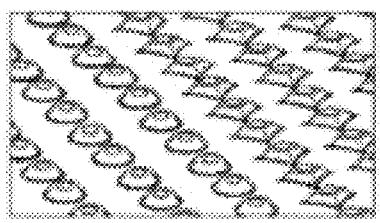
FIGS. 20A-20I show examples of microstructures that may be included in any of the mechanical thrombectomy apparatuses described herein.
Figure 20B:
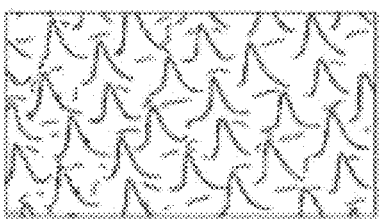
Figure 20C:
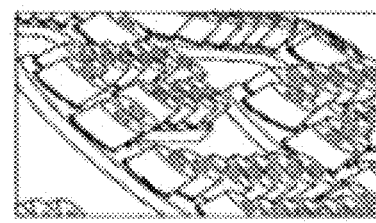
Figure 20D:
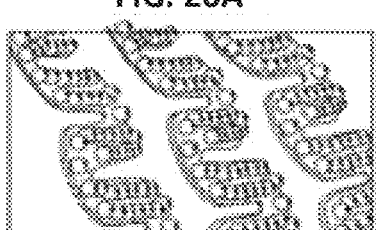
Figure 20E:
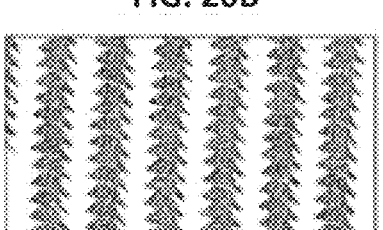
Figure 20F:
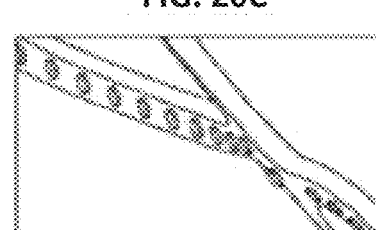
Figure 20G:
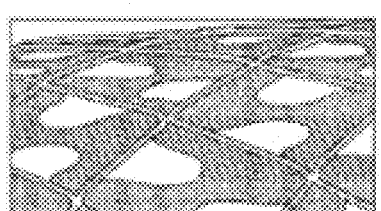
Figure 20H:
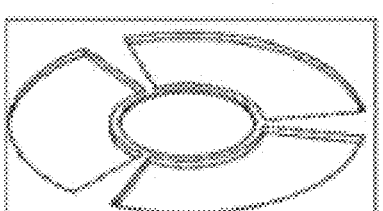
Figure 20I:

For example, FIGS. 21A and 21B illustrate an example of a tractor region having a plurality of projections that extend from the portion of the surface of the tractor only when that portion of the tractor is inverting and rolling. FIG. 21B illustrates the extension of the projections 11105 from the tractor as the tractor is rolling over the distal catheter opening 11109 to invert. In this example, the tractor is a tubular structure 11101 having longitudinally arranged lengths of tractor material 11103 forming a backbone. Spanning between these flat, elongate regions 11103 are regions that extend between adjacent elongate regions first distally in the long axis, then back proximally. As the tractor rolls over the end of the catheter opening, e.g., as shown in cross-section in FIG. 21B, the loops of material 11105 extend out of the tractor (out of the plane of the tractor that is defined by the long axis of the tractor), and form projections 11105 that, as the tractor rolls over itself (inverting), extend outward, as shown in FIG. 19B. These projections may help grab a clot.

Projections formed in the tractor may be formed by cutting (e.g., laser cutting, press cutting, etc.), etching, etc., or they may be woven, braided or knitted into the tractor. For example when the tractor is formed of tube or sheet of material, the projections may be formed from the plane of the tractor material by removing material to leave a projection that may extend up and out of the material. When the tractor is not bending (e.g., inverting), the projections may have a low profile that does not substantially impact tracking of the tractor region when positioning the apparatus, e.g., moving it through a vessel in a patient's anatomy, while still enabling and enhancing rolling around the tip of the catheter. A projection that may help grab a clot may extend distally (e.g., towards the distal tip of the catheter when positioned on the outer catheter surface), so that as the tractor is rolled into the catheter, they extend distally (e.g., shown in FIG. 19B). Thus, the projections may create a grabbing effect. In some variations the projections may also cut into the clot and may macerate it. The projections may also help with catheter removal.

Figure 23A:
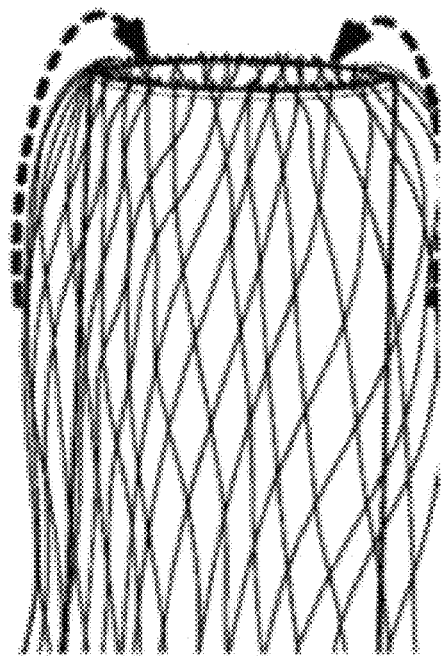
FIG. 23A shows an example of a distal end of a mechanical thrombectomy apparatus having a tractor formed from a plurality of filaments having a round cross-sectional profile; the tractor of FIG. 23A does not include any projections extending therefrom.
Figure 23B:
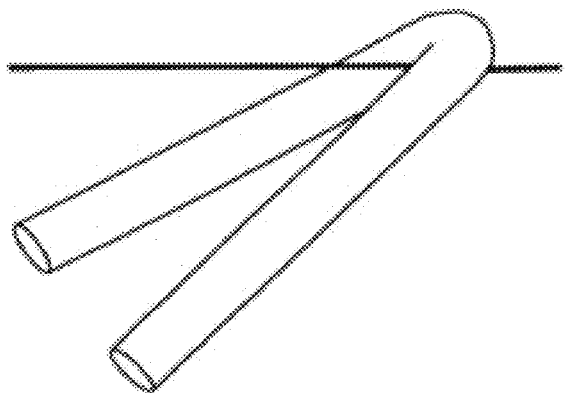
FIG. 23B illustrates the outer profile of a filament of the device of FIG. 23A as it inverts over a distal catheter opening of the elongate inversion support.
Figure 23C:
FIG. 23C illustrates the rounded profile of the filaments forming the tractor of FIG. 23A.

In some variations the tractor is a woven, braided or knitted tractor that may be formed of one or more strands that have one or more (e.g., 2, 3, 4, etc.) edges that may project from the plane of the tractor as it rolls over the distal end of the catheter. When the strand(s) forming the tractor have a rounded profile (see, e.g. FIG. 23C), as the tractor inverts over the catheter, the face of the inverting distal-facing tractor region remains smooth, as shown in FIG. 23A. FIG. 23B shows a single strand inverting over the distal end opening of a catheter.

Figure 23D:
FIG. 23D is a section through a rectangular filament (e.g., ribbon filament) having four edges.
Figure 23E:
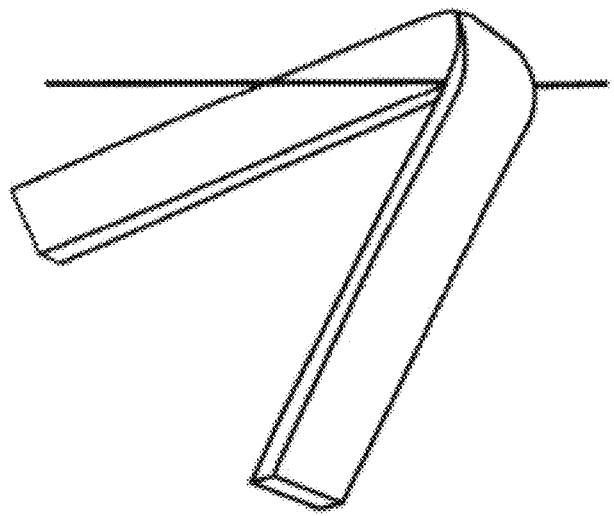
FIG. 23E illustrates the projection of a ribbon filament as it inverts over a catheter filament; because it approaches from an angle relative to the catheter opening (and because it is constrained by the adjacent filaments) the edge of the ribbon forming the inverting region may project up and out of the plane of the tractor.

If the strand forming the braided or woven tractor region is instead formed of a material having an edge (e.g., a ribbon, such as a ribbon having a rectangular profile, as shown in FIG. 23D), when the tractor rolls over the distal end opening of the catheter, particularly where the strand (e.g., ribbon) is at an angle relative to the distal end opening (and the distal-facing inverting portion of the tractor), as shown in FIG. 23E, the edge of the strand projects upwards and away from the tractor, out of the plane of the tractor. This is schematically shown in FIG. 23E, showing a rectangular strand or ribbon that may be woven, e.g., in a helical weave, and the edge 11505 of the woven strand twists up and out of the plane of the tractor as it inverts over the catheter to form a projection 11507 as shown in FIG. 23E. This projection may act as a scoop or shovel-like element that may help grab the clot, even if the tractor is lubricated and/or lubricious.

Figure 24A:
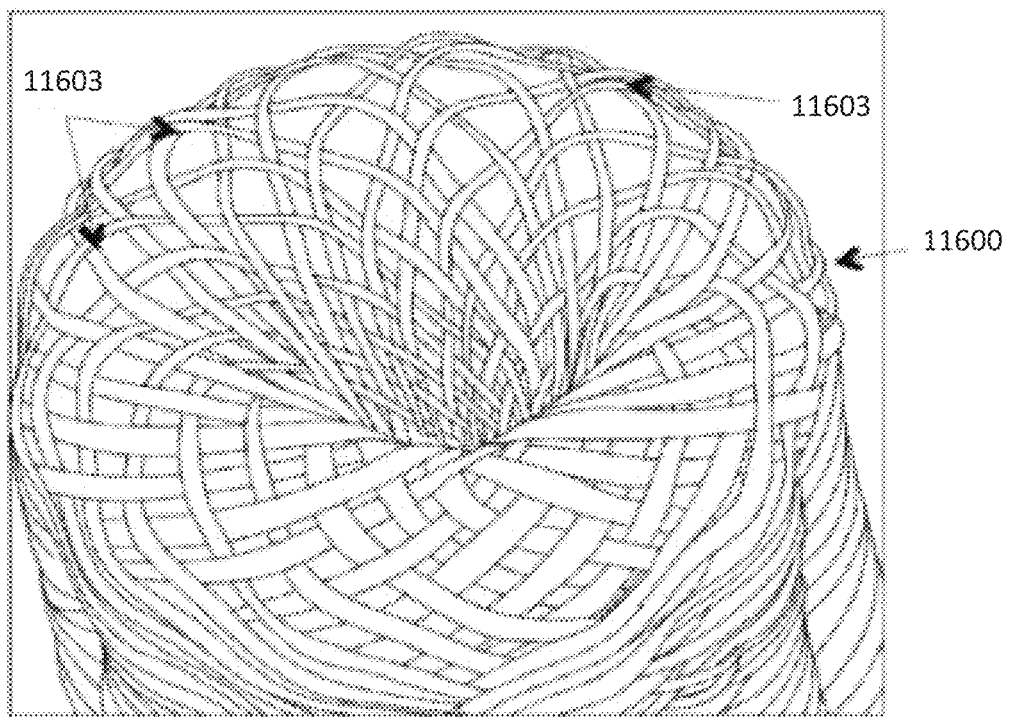
FIGS. 24A and 24B illustrate an example of a tractor having a plurality of projections formed by rectangular filaments (e.g., ribbon filaments) as schematically illustrated in FIGS. 23D-23E.
Figure 24B:
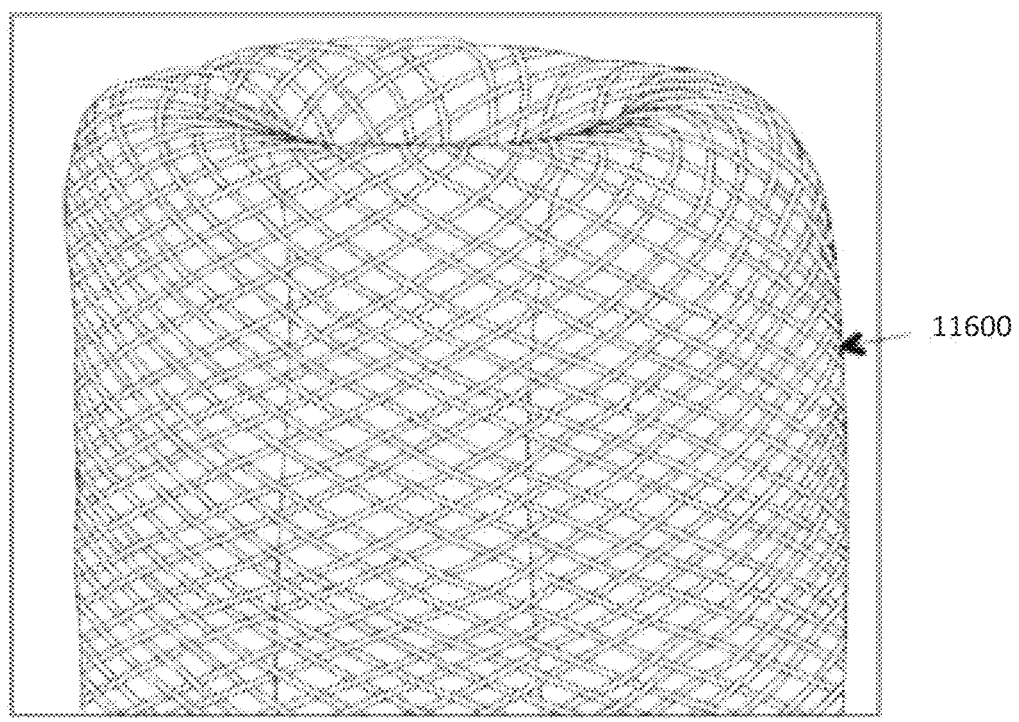

FIGS. 24A-24B illustrate an example of a tractor formed from a plurality of strands having an edge; shown here as strands that are ribbons having an edge (forming a rectangular profile).

In FIGS. 24A and 24B, the apparatus includes a catheter having a distal end and a distal end opening (not visible beneath the distal end-face of the tractor shown), and a tractor 11600 that includes a flexible tube that extends within the catheter, inverts over the distal end opening of the catheter and extends over the distal end of the catheter. The tractor forms a tubular wall and is configured to invert by rolling over the distal end opening of the catheter, as shown in FIG. 24A, when a first end of the tractor is pulled proximally within the catheter. The tractor includes a plurality of projections 11603 (in this example, formed by the edges of the ribbon-shaped strands, that extend from the distal-facing portion of the tractor as it is inverted over the distal end opening of the catheter. As the tractor rolls over the distal end opening of the catheter, the ribbon-shaped strands twist up and out 11603 of the tractor. These twisting edges form projections that can help grab a clot. Thus, FIG. 24A shows a distal end-face of the tractor inverting region as it rolls over the distal end opening of the catheter from the outer diameter to the inner diameter of the catheter. The plurality of projection regions 11603 are formed as the strands (ribbons) twist so that the edges of the strands extend up out of the plane of the tractor. As shown in FIG. 24B, when the tractor is over the outer diameter of the catheter, including the catheter distal end and more proximal regions, these strands do not project out of the tractor, but remain flush against the outer diameter, even when the catheter, and therefore the tractor, are bent and positioned in a tortious vessel; only when inverting do they project outward. Thus, the projections are not extended from the tractor in the portion of the tractor that extends over the distal end of the catheter. The center of this apparatus forms a guidewire lumen extending through the catheter and the tractor and may pass a guidewire. When the tractor is extended along the outer diameter of the catheter proximal to the inverting region, the strands, which are helically woven to form the tractor, remain flat, in the flat cylindrical surface ("plane") of the tractor.

As will be described in greater detail below, in some variations, including knitted tractor variations, the cells of the tractor may extend up and out of the inverting distal-facing region as it rolls around the catheter. These projections may also act as scoops, shovels, etc. and may help grab onto a clot.

Some variations of the tractors described herein may be formed of a non-woven, non-braided and non-knitted material. The tractor may be formed of a sheet and/or tube of material that may be directly fabricated (e.g., extrusion, etc.). This tractor may be cut, including laser cut, to form slots. In some variations these cuts may form projections. For example, the tractor may be formed of a solid (including porous) material into which a pattern is formed (e.g., slots, cut-out regions, etc.) including patterns that produce projections as described above. A tractor region may be formed of a tube of material into which slots or cut-out regions are formed. Such apparatuses may include a tractor formed from a tube of material such as ePTFE (which may be relatively soft, strong in tension and radial compression), NiTi (a super elastic and/or thermally settable material), a fabric (which may be a soft, thin walled material having a reasonably high radial/axial strength), or the like. The tractor may have material frictional properties and material surface hardness that are appropriate to grabbing a clot. In general, materials that are softer may be easier to track the apparatus in the anatomy. As mentioned, the tractor may have pores and may therefore have a tube porosity. The pores may be formed by removing material (or shaping into the openings) and may be oriented to aid in flexibility, rolling and/or tissue grabbing. A tube forming a tractor may be laser cut at an angle relative to axial length, or it may be laser cut (e.g., perpendicular versus angled relative to the tube thickness). Angled cuts may create a cutting surface to mince or macerate a clot, whereas perpendicular or rounded cuts through the thickness of the tractor may enhance grabbing of clot. Any of the tractors described herein may have a final shaped cross-section that is heat-set and/or formed on a mandrel (e.g., formed shape as set on heat treatment mandrel). The tractor regions described herein may be self-expanding. For example, in particular, the tractor may be set (e.g., as a shape-memory material) to expand outwards when inverted (e.g., within the catheter) and may therefore collapse inward slightly when inverted over the outside of the catheter. As discussed above in reference to FIGS. 10C and 11A-11C, this may aid in forming a trumpet shaped distal-facing region of the tractor, where the tractor is inverted over itself. Some variations of tractors may not be self-expanding. As mentioned, the tractor may be formed of a polymeric material (e.g., ePTFE, PET, PP, Nylon), metals (including alloys) or combinations of these. The tractor may have a low profile (e.g., minimum thickness), may be highly flexible and able to navigate through tortuous vessels, may be able to invert around the catheter tip, may have clot grabbing properties (including projections and/or surface roughness) and may provide a column strength in compression (e.g., strut stiffness), and may be partially or completely radiopaque. The tractors described herein may scale from 1 mm OD fully formed to 15 mm. Any of these tractors may include a lubricious surface on one or both sides (particularly the side that faces outwards when extending over the outer diameter.

Examples of slotted laser cut tubes forming a tractor are provided herein, including those shown in FIGS. 25A-33B. The starting tubes may be flexible or rigid. For example, a soft flexible tube, strip, or roll of material such as ePTFE or a dense fabric (e.g., knit or weave or braid) may be used. Flexible tubes may provide tractors and/or combinations of tractors and catheters that allow tracking of the apparatus to the treatment site even in tortious vessels. Tracking allows pushing of the apparatus through tortuous vessels of small caliber over long distances from their introduction site to the human body, over length that can exceed 1 meter in some uses. A flexible tube (pre-laser cutting to form the tractor) may have a softness resulting in a low radial crush force, such as a micro-porous, polymer-based tube. The tube may be processed (e.g., by cutting or any of the other techniques mentioned herein) to provide flexibility (e.g., the ability to pull the tractor into catheter, invert, and expand over catheter outer diameter) and/or to create a textured/porous surface that may aid in grabbing a clot (e.g., emboli) and may provide free spaces (voids) that may help store and/or masticate emboli, making them easier to store within the apparatus and transport. Prior to forming into the tractors the sheets or tubes (e.g., films, rolls, etc.) may have a smooth surface. Patterns may be formed into the sheet or tube to form the tractor. For example, laser slot patterns may be formed in the material to increase macro-surface roughness. Holes, slots, edges, divots, and bumps may be formed on the material. In addition to helping grab and hold emboli, such holes or slots may create free space in the tube wall to cut the clot and/or carry it away. The patterns used to form any of the tractors described herein may have a shorter strut length to strut width ratios. Short, wider struts may create tractors that are stiffer and may grab clot better. In combination with strut length to width, in some variations, thicker walls may be preferred. Thicker slotted walls may create stiffer struts and more aggressive surface texture to grab clots. Furthermore, thicker walls may enhance clot storage capacity within the slot gaps.

In some variations, it may be beneficial to provide slot designs which do not foreshorten. For example, if the slotted tube design is pulled axial (e.g., down its length), the tube diameter may not decrease. A decreasing diameter slotted tube may grab the outside of the catheter and cleat, increasing drag force when the tube is pulled.

In variations in which the initial tube or sheet of material used to form the tractor tube is relatively rigid (e.g., formed of a material such as Steel, Nitinol, Polyester, PTFE, Nylon, etc.), the initial tube stiffness/hardness may enhance the clot-grabbing ability when the tractor is slotted properly, to allow both increased flexibility, expansion and rolling. For example, a rigid tube may include slot designs that focuses in catheter tracking and creates a flexibly bending tractor with minimal foreshortening, that is able to be pulled into a catheter (inverting) structure. As with the more flexible starting tubes discussed above, tractors formed of more rigid starting materials may grab and transfer a clot, and the number of slots and/or voids may be increased to increase clot grabbing and/or carrying capacity. A slotted tube forming a tractor may include surface grabbing features, such as channels/corrugations (e.g. any of the microstructures such as those shown in FIGS. 20A-20I above. More rigid tubes may create harder or stiffer slotted tractors. For example, when struts are formed into the tractor (e.g., by cutting, etc.), the slot strut length to strut width may be greater than with less rigid starting materials, and may be a function of the rigid tubes elastic modulus. Higher elasticity materials (e.g., NiTi, PET, PTFE) may have strut length to width ratios from 10 to 100. Stiffer materials (e.g., steel, MP35N) may have a length to width ratio greater than 50. The wall thickness to strut width for elastic materials may be, for example, between 0.5 to 10; for stiffer materials it may be between 0.25 to 5.

As mentioned, any of the apparatuses described herein may include a tractor region that is non-foreshortening. The foreshortening of the tractor may depend at least in part on the slot designs for non-woven, non-braided, non-knitted designs (e.g., tractors that are not formed of a strand or strands of material). FIGS. 25A-25D illustrate an example of non-foreshortening design. Also, for both flexible and rigid starting tubes forming a non-woven tractor, the tube inner diameter can be slightly bigger than catheter tube outer diameter pre-slotting. Slotted tube designs which foreshorten may reach their smallest diameter limit when tensioned axially. If the tube is sized to be slightly larger than the catheter outer diameter, then it may jam (preventing any foreshortening) before it cleats to the catheter outer diameter. Tractor regions formed of an initially rigid material may grab clot more efficiently than tractors having an equivalent thickness but formed of a more flexible material. More flexible materials may deform as a function of stiffness.

Figure 25A:
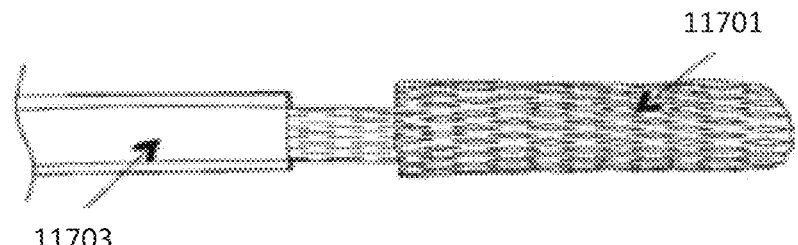
FIGS. 25A-25D illustrate exemplary tractors formed by cutting (e.g., laser cutting) a tubular material.

FIGS. 25A-25D illustrate an example of tractors that are formed by cutting slots and/or windows into tubes of material. In FIGS. 25A-25D, an initially soft material (e.g., ePTFE) was formed by a subtractive manufacturing technique to from, slots, pores and textures in the soft flexible tube. In FIGS. 25A-25D, a 3 mm ID ePTFE tube (configured to be used with a 2.9 mm OD catheter) was made to be highly flexible and have some level of column stiffness and radial/hoop stiffness by laser-cutting slot patterns into the tube wall to create textures and bend zones which impart clot grabbing and rolling. The ePTFE itself is highly lubricous. Addition of a lubricant (e.g., hydrophilic coating) may improve tracking and rolling. Lubricant can be applied to ID and OD or to either separately. FIG. 25A shows a first pattern 11701, having minimal cuts to create a smooth rolling of the tractor around the catheter 11703 portion of the apparatus.

Figure 25B:
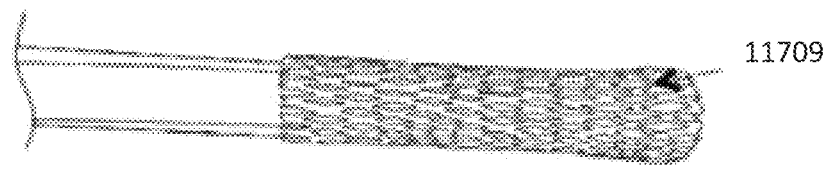

A second exemplary pattern is shown in FIG. 25B. In this example, the apparatus slightly larger cut-out regions 1709 (removed by laser cutting in this example), which may create better clot grabbing properties and more clot holding capacity. In FIG. 25B, the ePTFE tube forming the tractor region is slotted on the outside of the catheter. Note that the porosity (14 holes around the circumference) may help grab and hold colt. In both FIGS. 25A and 25B, the laser pattern may foreshorten, but may jam before it grips/cleats the catheter outer surface.

Another example of a tractor was made from a 2.9 mm OD ePTFE tube (configured for use with a 3 mm ID catheter). This example was made to be highly flexible and have some level of column stiffness and radial/hoop stiffness by laser-cutting slot patterns into the tube wall in a pattern to create textures and configured to include bend zones which impart clot grabbing and rolling. Similarly, a tractor may be made of, e.g., a 2.9 mm OD PET woven fabric tube (for use with a 3 mm ID catheter). The tractor may be formed of 30 Denier PET multi-filaments, 0.003" thickness. The resulting tractor may be configured to be soft and have some level of column stiffness and radial/hoop stiffness by laser cutting slot patterns into the tube wall in a patterns providing texture and bend zones which may impart clot grabbing and rolling. As with ePTFE, the PET material may itself be lubricous although additional lubricant may be added to improve tracking and rolling. Lubricant can be applied to ID and OD or to either separately.

An example of a tractor made from a somewhat rigid starting material was formed from a nickel titanium (NiTi) tube having a 3 mm OD (which may be used with, e.g., a 2.9 mm ID catheter). The wall thickness in these examples was between 0.001" and 0.002". Laser slot patterns were cut into the tube wall in various patterns to create textures and purpose-designed bend zones which may help impart clot grabbing and rolling. A lubricant may be applied, e.g., as a coating, to the ID and OD or to either separately. A first pattern similar to that shown in FIG. 25A was made by minimal laser cutting to create a smooth rolling tractor. The strut length to width ratio was between 25-50. A second pattern having larger slots/openings (similar to that shown in FIG. 25B) was formed by laser cutting. These patterns may foreshorten, but typically minimize or stop foreshortening before the tractor grips/cleats the catheter outer surface (which may result in jamming). The NiTi design has the additional benefits of radiopacity, thermal shaping and super elasticity.

Any of these designs or patterns may for projections that may extend from the rolling distal-facing and inverting portion of the tractor, as discussed above. Such projection may be cut out as "teeth" or elongate members. The regions forming the projections may be sharp, e.g., pointy and/or cutting. Sharp projections may be chew and cut a mature clot. These projections regions may be short or long, may extend in one or more directions (e.g., forward or backward or bidirectional), and may be scoop-shaped (e.g., paddle-shaped). The number of projections may be selected based on the desired coarseness, e.g., the number of projections, the size (length/width/thickness), etc. The projections may change density down their length. For example, the laser pattern can be designed to allow tractor rolling (e.g., long struts) more easily initially, then have grabbing teeth at higher density; alternatively the tractor may be configured for greater initially grabbing, having a pattern with more and/or larger projections initially (distally) then transitioning to more slits (and flexibility) toward the proximal end, which may make it easier to pull. Further, the distribution of projections can be uniform around the tube perimeter and/or non-uniform (e.g., forming a spiral pattern, distributed in patches, having open areas, etc.).

Any of the tractors described herein may include a marker or makers (e.g., radiopaque markers, such as gold, Pt, etc.). When forming the tractor from a tube or sheet, the tubes may be cut, then shaped to have any profile, such as straight, rolled over the tip, flaring at the proximal end, etc. Any of the microstructure described herein may be included or formed, as mentioned above, e.g., wells on the struts may help carry and grab clot. Tractors formed of tubes from which material was removed (or sheets formed into tubes) may be configured to have less cleating of the tractor onto the outer diameter of the clot, preventing jamming, particularly compared to woven or braided or knitted materials. However, any of the slotted tube tractor configurations described herein may be used with, e.g., in combination with, a braid or knit or polymer sleeve, including either in parallel or in series. In general, any of these tractors may be formed as multi-layers, particular these slotted tube tractors.

For example, a tractor portion of an apparatus may be formed by removing material from a NiTi tube that is slightly smaller than the inner diameter of the catheter that it will be used with, or it may be made from a tube that is slightly larger than the outer diameter of the catheters. The tube may be cut with a pattern that increase the coarseness of the outer surface (e.g., to include projections such as struts/scoops/teeth). For example, a 0.001" tube wall thickness or smaller may be used.

Figure 25C:
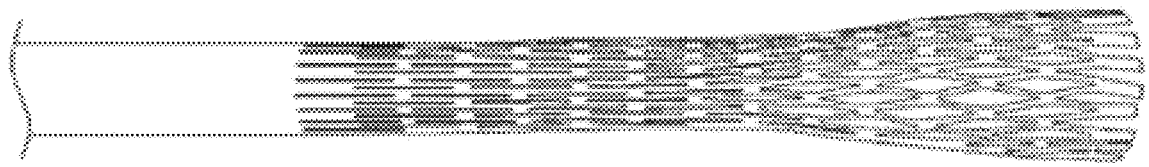
Figure 25D:
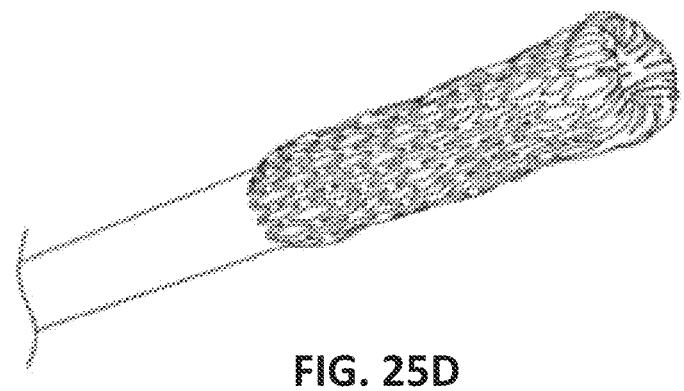

FIGS. 25C and 25D illustrate an example of a tractor region cut from paper. In FIG. 25C a rigid paper tube was cut to include slots and the distal end expanded, a shown. It may be inverted over itself and used as a tractor region. This paper prototype was prepared to illustrate the effectiveness of this pattern. Similarly, FIG. 25D is an example of a prototype tractor region.

Figure 26A:
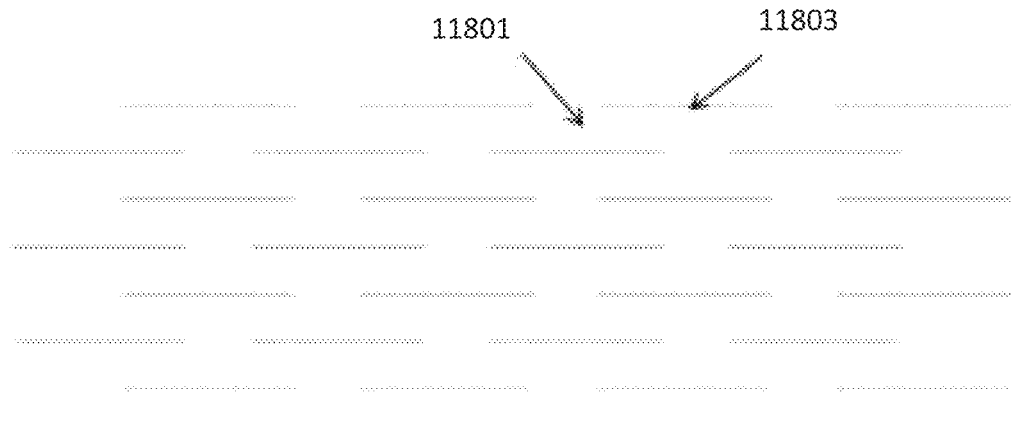
FIGS. 26A-26C illustrate different slotted patterns that may be cut into a tube (or sheet) to form a tractor region.
Figure 26B:
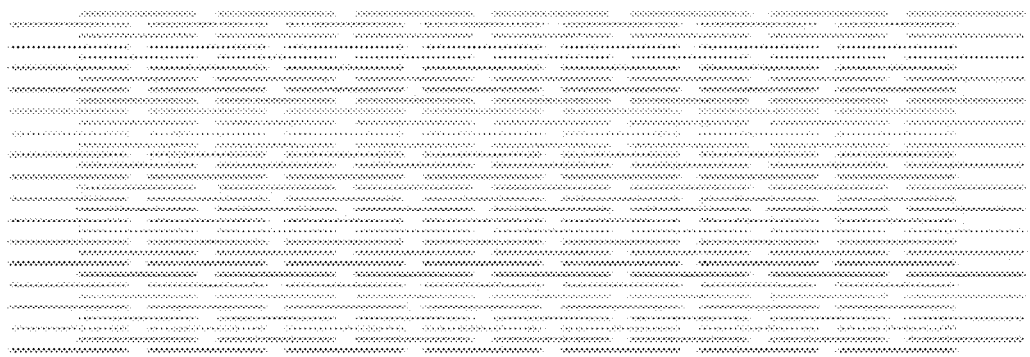
Figure 26C:
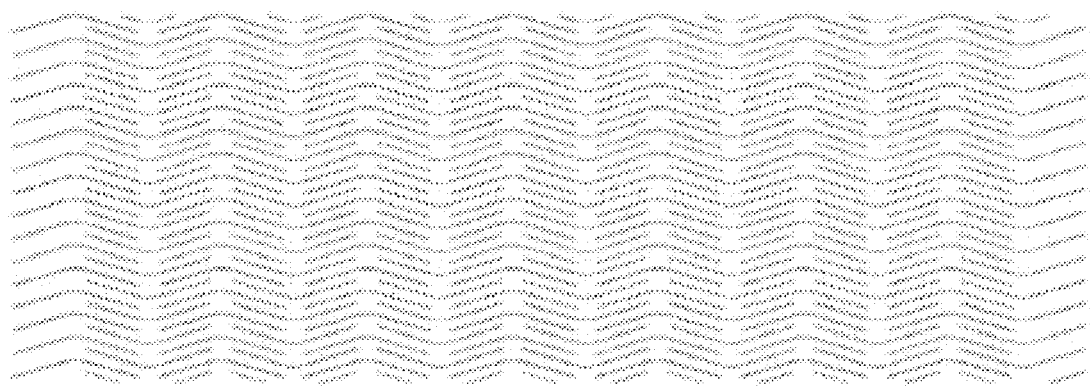

FIGS. 26A-26C illustrate examples of patterns that may be formed into a flat sheet or tubular member to form a tractor (e.g., slotted tractor). Similar to those shown in FIGS. 25A-25D. In FIG. 26A, the pattern may be cut to form the tractor. White regions 11801 may represent or form struts, while the lines indicate slots 11803 from which material is removed. This pattern is one of many resulting in a flexible tube having stout struts. FIG. 26B shows a similar example having a higher density of slots forming thinner struts and potentially higher porosity, which may result in a larger clot-carrying capacity. FIG. 26C illustrates an example of a pattern having curves that may produce a slightly more bendable (flexible in bending stiffness) slotted tractor. In FIGS. 26A-26C, the pattern is oriented so that the distal direction of the tractor formed by the pattern is at the right or left of the pattern shown (e.g., the tube is oriented right and left, relative to the figures, so that the tube is formed by rolling up from the bottom of the figure).

Figure 27:
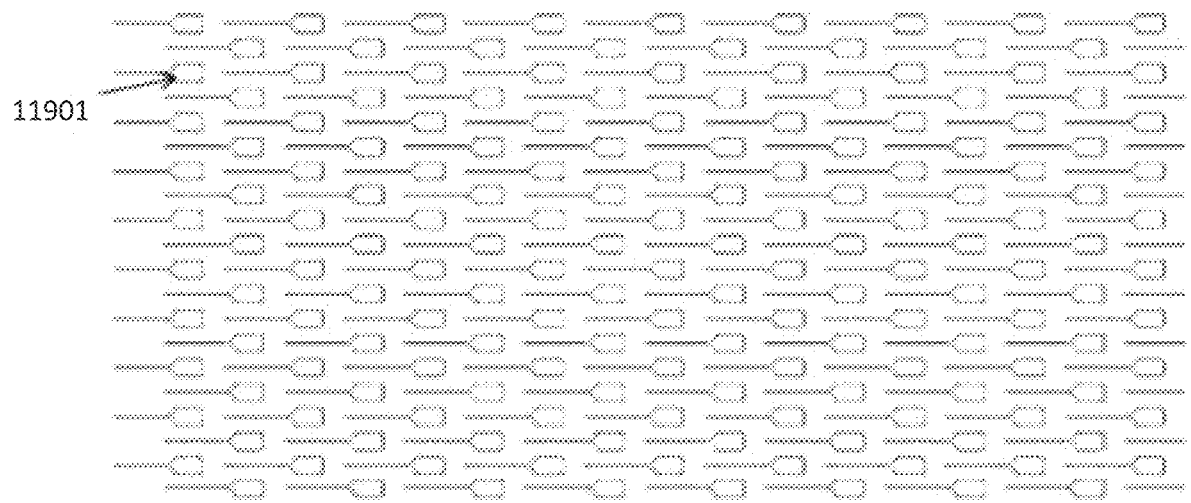
FIG. 27 is another example of a pattern that may be used to form a tractor region.
Figure 28A:
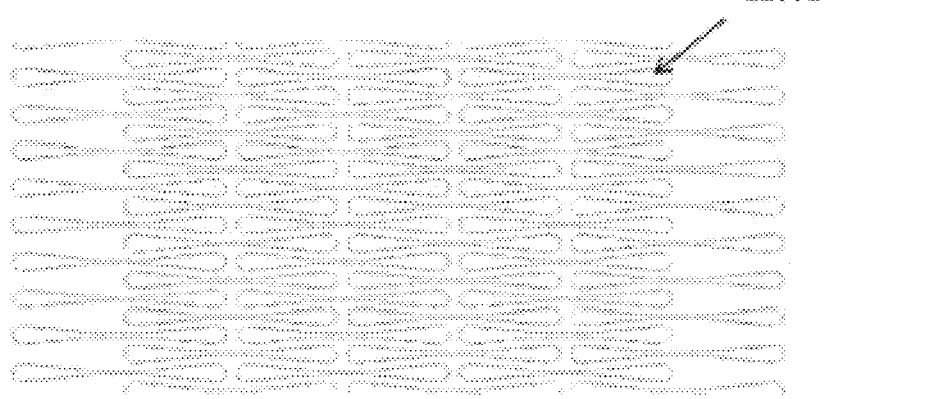
FIGS. 28A-28B show an example of a pattern that may be used to form a tractor region.
Figure 28B:
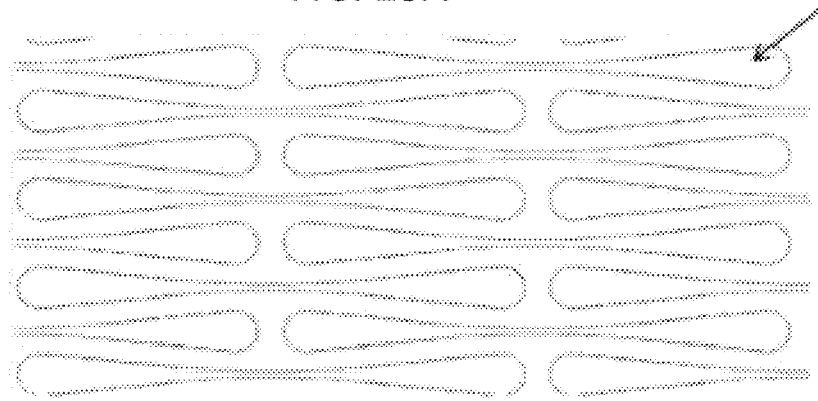

FIG. 27 is an example of a pattern that may be formed into a tube as part of a tractor having a plurality of both slots 11903 and cut-out regions 11901 (holes). Another example of a pattern having a plurality of cut-out holes 12001 formed into it is shown in FIGS. 28A and 28B. FIG. 28B shows an enlarged view.

An example of a pattern having a plurality of projections is shown in FIGS. 29A-32B. For example in FIGS. 29A and 29B, the pattern includes a plurality of slots 12101 and cut-out regions that leave a projecting strut or tooth 12105 behind. In these examples, the tooth 12105 is pointed and oriented to the left of the page, which may be the distal end direction of the tractor. (e.g., the left side of the image may correspond to the distal end of the tractor); thus when the pattern is formed into a tubular body to form the tractor, and the tractor is inverted over itself (e.g., rolling over the distal end opening of a catheter) the plurality of pointed projections 12105 may extend out of the tractor, and may help grab and draw clot into the catheter.

Figure 29A:
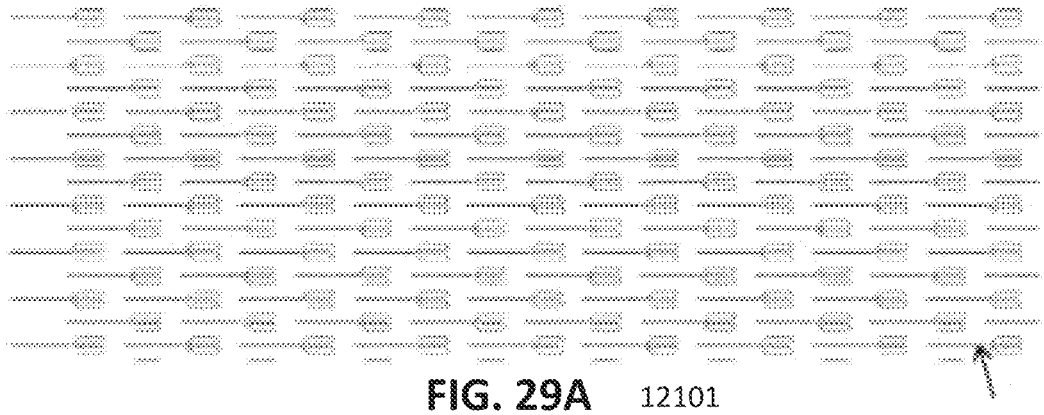
FIGS. 29A-29B show an example of a pattern that may be used to form a tractor region.
Figure 29B:
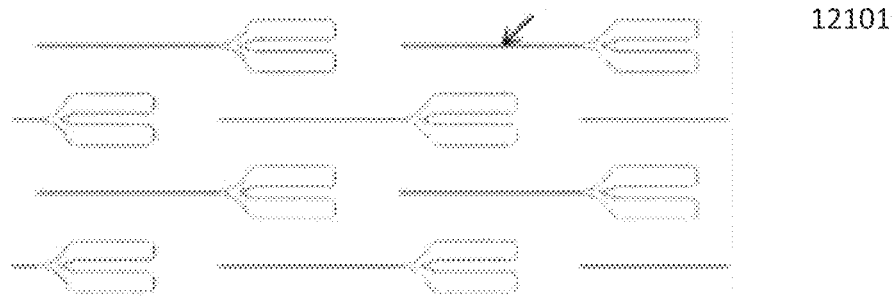
Figure 30A:
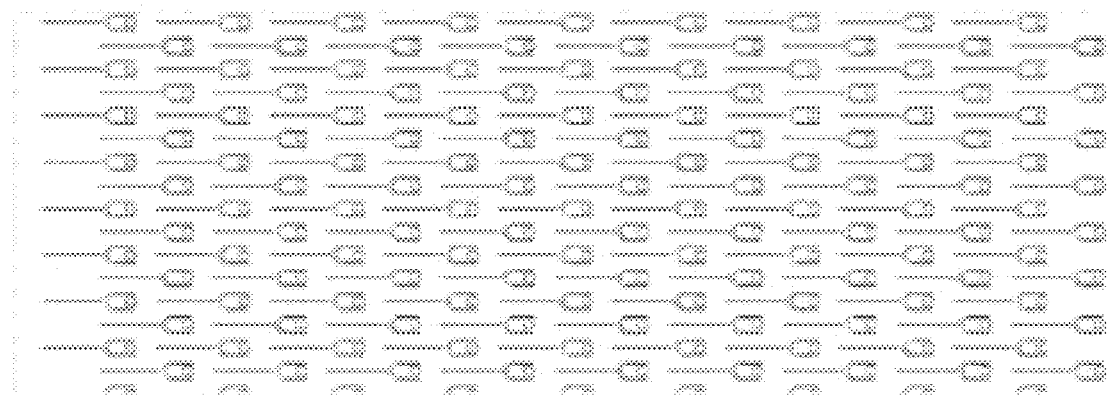
FIGS. 30A-30B show an example of a pattern that may be used to form a tractor region.
Figure 30B:
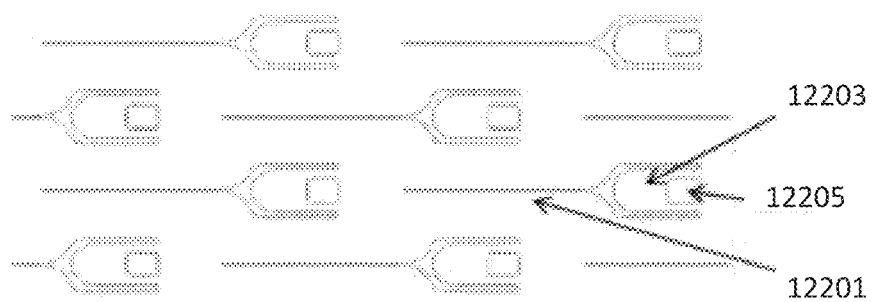
Figure 31A:
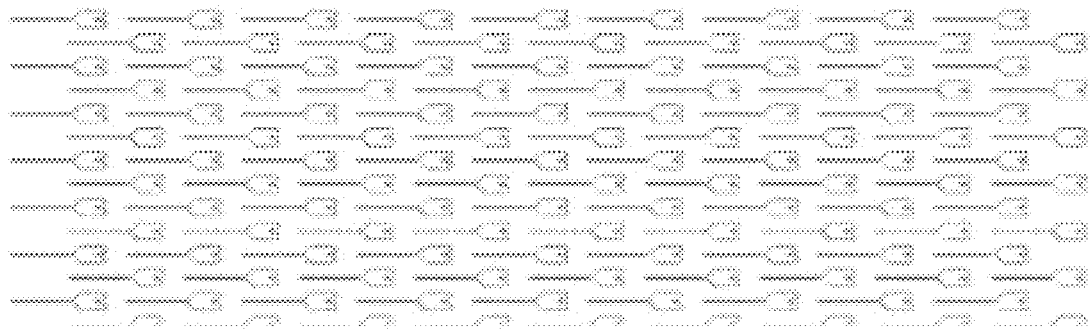
FIGS. 31A-31B show an example of a pattern that may be used to form a tractor region.
Figure 31B:
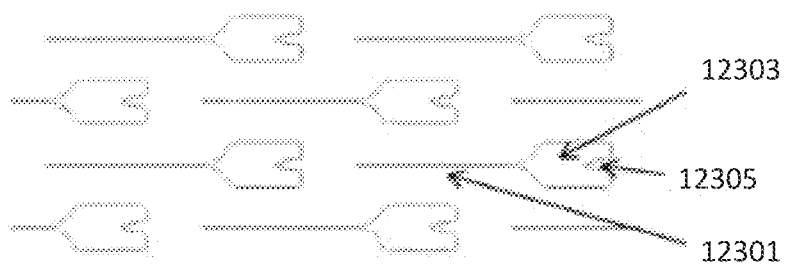
Figure 32A:
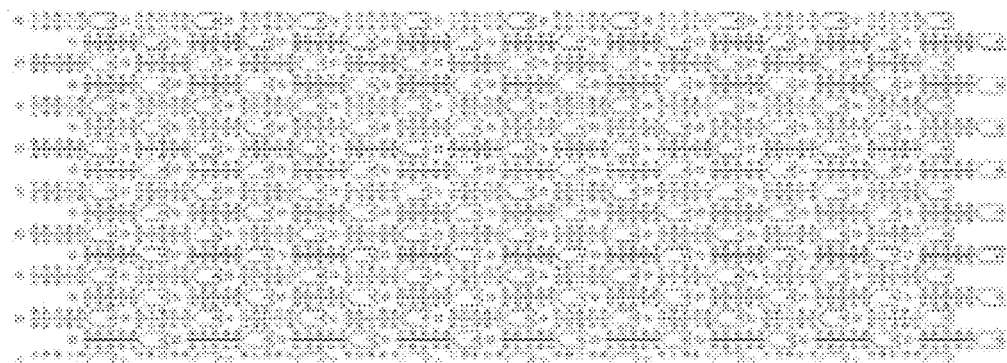
FIGS. 32A-32B show an example of a pattern that may be used to form a tractor region.
Figure 32B:
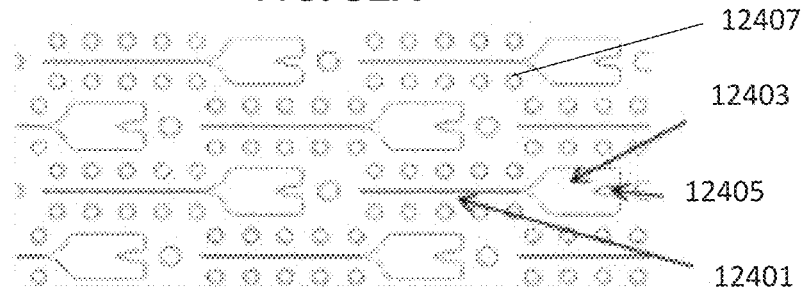

Similarly, the pattern shown in FIGS. 30A-30B illustrate another example include a slot 12201, a projection 12203 and a cut-out portion 12205. As in FIGS. 29A and 29B, the projection may extend out of the plane of the tubular tractor (shown here as the plane of the paper, even when rolled up to form the tractor region). FIG. 31A, and enlarged view of FIG. 32B, shows another example of a pattern for a tractor that is similar to that shown in FIG. 29A-29B, but with smaller projecting regions. In this example, the projections 12305 are sharp, and open into an opening 12303 connected to a slot 12301. The pattern shown in FIGS. 32A-32B is similar to that shown in FIG. 31A-31B but with additional openings (cut out regions 12407) which may increase the carrying capacity (e.g., clot carrying capacity) of the tractor region.

Figure 33A:
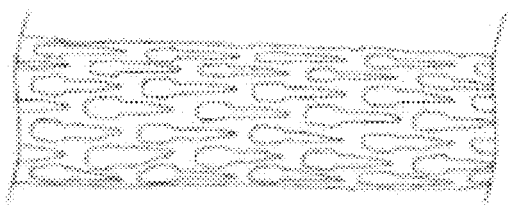
FIGS. 33A-33C illustrate tractor regions having different patterns of slots and openings.
Figure 33C:
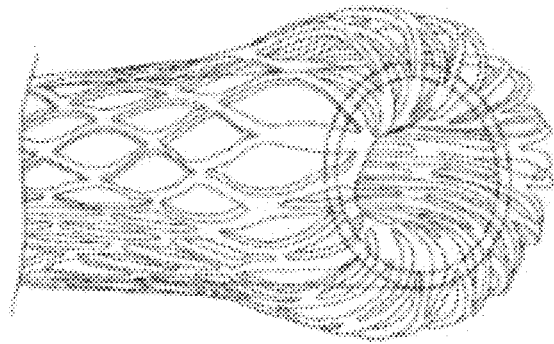
Figure 33B:
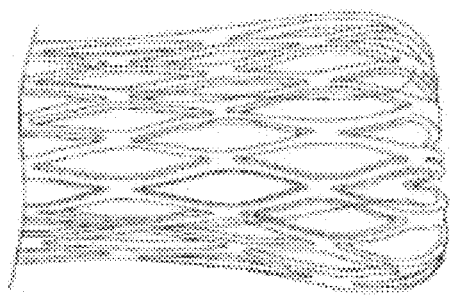

FIGS. 33A-33C are examples of laser-cut tube prototypes of tractor regions. In FIGS. 33B and 33C the tractor region is inverted over the distal end opening of the catheter.

In any of the tractor regions described herein, the tractor may have sufficient coarseness to grab the clot, yet still roll easily around catheter tip. Coarseness may relate to the thickness profile of the tractor region. For example, knitted tractors may be more course than braided tractors, due to the macro structure (e.g., cells, wire cross overs, shape of cells). The ability of the tractor to capture and transfer (like a conveyor) clot material through the catheter may be aided by coarser macro structures. In addition, as mentioned above, projections may both increase the coarseness and may help aid in grabbing clot. However, projections that extend only when inverting the tractor may be desirable; e.g., the tractor may feel smooth to the touch unless the dozer is rolled around a corner. The act of rolling the tractor may expose or activate the passive grabbing elements (projections). As mentioned, any of these apparatuses may include pores. For example, any of these apparatuses may include pores having a size that is greater than ⅕oth of the catheter circumference. For example, the pore size may be 200 μm or greater (e.g., 300 μm or greater, 400 μm or greater, 500 μm or greater, etc.). In some variations the number pores (openings) per circumference may be between 5-20, 5-10, 10-15, 15-20, etc. pores on per catheter circumference on the tractor. As mentioned, the projections may be sharp, or dull, or may have an enlarged surface area (e.g., paddle-shaped). Sharp strut edges may grab and/or cut clots, while projections may also help grab clot. For example, a tractor may have a texture/roughness of at 0.0005" or greater (e.g., 0.0001"-0.0010"). The tractor may be formed of an inherently lubricious material, and/or may be lubricated through the use of hydrophilic coating on the tractor and/or OD of aspiration catheter or construction of lubricious hydrophobic materials such as Polyethylene, Polypropylene, fluoropolymers, FEP, PTFE.

Tractors Having Alternating Stiffness

Also described herein are tractors having alternating stiffness along their length. For example, a mechanical thrombectomy apparatus for removing a clot from a vessel may include a elongate inversion support including a catheter and having a distal end and a distal end opening and a tractor that is configured as a flexible tube that extends longitudinally within the catheter and doubles back over the distal end of the catheter to extend over the distal end of the catheter. The tractor may be formed of longitudinally alternating regions of higher and lower stiffness, wherein the regions of higher stiffness have a stiffness that is greater than the regions of lower stiffness. In some variations this may allow the lower stiffness regions to act as hinge-regions relative to the stiffer regions, when the tractor is pulled into the catheter. These variations may result in a seesawing motion at the distal end opening of the catheter, as the tractor is inverted and pulled into the catheter. This is illustrated schematically in FIGS. 38A-38D. For example, a portion of a length of tractor may include more stiff regions 13001 and less stiff regions 13003 that are alternating along the long axis of the tractor, as shown schematically in FIG. 38A. As the tractor region is inverted over the distal opening of the catheter (shown in FIG. 38B, in which a portion of the catheter wall is shown 13009), pulling the tractor over the wall 13009 causes the more flexible portions to bend over the wall, while the less flexible regions 13001 bend less or not at all. FIGS. 38B-38D illustrate progression of a tractor portion over the distal end opening, showing the bending of the less stiff/more flexible regions 13003 over the wall, while the more stiff/less flexible regions 13001 do not bend. The result is that, as shown by the arrows on the bottom, the diameter of the distal-facing region changes, and oscillates, as the tractor is pulled into the catheter.

Thus, the tractor may be configured so that it rolls around the catheter tip opening an inverts in a ratcheting fashion, in which parts of the tractor that are stiffer than other sections alternate with more stiff regions. These differently-stiff sections may cause the tractor rolling around the catheter tip to move in a semi-rigid manor and/or a pivoting/seesawing motion around the distal face of the catheter opening and the regions adjacent to the distal opening.

Tractors having alternating stiff/less stiff regions down the length of the catheter (including arranged in a helical manner spiraling down the length) may be formed in a variety of different manners, including constructing braids, laser cut tubes, knits, weaves, and laminates. For example, FIGS. 39A-39D illustrate an example of a knitted tractor region having this configuration. As the variable stiffness tractor rolls around the catheter, sections of the tractor may temporarily dive to towards the center of the catheter ID, which may also aid in grabbing clot or a foreign body to pull into the catheter. The apparatus may be configured so that the tractor includes sections that sea-saw around the catheter tip so the dozer protrudes into the catheter ID by a distal equivalent to 5%, 10,%, 15%, 20%, 25%, 30%, 40%, 50%, 70%, 80%, 90% of the catheter's inner radius length, or any range of the numbers.

The tractor shown in FIG. 39A is a knit construct which has sections that are stiffer alternating with others sections that are less stiff. A first region 12401 of FIG. 39A, is stiffer than the adjacent second region 12403, which is also adjacent to another stiffer region 12401'; the stiffer/less stiff regions alternate and spiral in a helix along the length of the tractor. As the knit tractor shown in FIG. 39A rolls around the catheter, the less stiff section 12403 of the knit shown may temporarily bend, diving the stiffer region 12401 towards the center of the catheter inner diameter in a seesawing motion. FIG. 29B shows a side view of an apparatus including a knit tractor such as shown in FIG. 39A, having alternating stiff/less stiff regions extending down the length of the tractor. FIG. 39C illustrates the distal-facing and inverting tractor that is rolling (in a seesawing manner) over the distal end opening in the catheter. FIGS. 39D and 39E show alternative side and end views, respectively, of a mechanical thrombectomy apparatus including a tractor region such as is shown in FIG. 39A.

In this example, when the tractor rolls over the distal end opening of the catheter, the alternating stiff/less stiff construction causes the stiffer region to moves towards the center of the catheter, which may aid in grabbing clot or a foreign body to pull into the catheter. The tractor may therefore seesaw around the catheter tip opening so that the tractor protrudes into the catheter ID by a distal equivalent to 5%, 10,%, 15%, 20%, 25%, 30%, 40%, 50%, etc. of the catheter's inner radius length, before withdrawing, and then repeating the cycle.

The alternating stiff and less stiff regions may have a distance (e.g., axial distance, along the long axis of the tractor) that is related to the inner diameter of the catheter.

In particular, if the stiff regions are too large relative to the catheter inner diameter, then the tractor may jam in the catheter, as illustrated in FIGS. 40A and 40B. In FIGS. 40A and 40B, for example, the stiff regions are greater than half the diameter of the inner diameter of the catheter. As shown in FIG. 40B, pulling the tractor into the catheter results in locking or jamming the tractor in the end of the catheter. In some variations the stiff region may be slightly larger than half the diameter without jamming, for example, if the adjacent stiff and less stiff regions wind around the tractor at a sufficiently large angle (e.g., greater than 10 degrees, 15 degrees, 20 degrees, etc.) so that only a subset of the stiff regions moving into the inner diameter of the catheter at the same time. Thus, the length of the stiffer regions may be 0.7 times the diameter of the catheter ID or less (e.g., 0.65 times, 0.6 times, 0.55 times, 0.5 time, 0.45 times, 0.4 times, etc., the diameter of the catheter ID or less). This may also be expressed the length of the stiff region being 1.3 times the radius of the catheter ID or less (e.g., 1.2 times, 1.1 times, 1.0 times, 0.9 times, 0.8 times, etc. the radius of the catheter ID or less).

Similarly, if the length of the stiff regions is too small, it will not see-saw in any appreciable amount and may, in some variations, jam onto the end of the catheter, as illustrated in FIGS. 40C and 40D. In FIGS. 40C and 40D, the length of the stiffer alternating regions is not substantially larger than the thickness of the catheter (e.g., the distance between the ID and OD of the catheter), so that no seesawing motion will occur. For example, the length of the stiff region may be 1.1 times or more than the thickness of the catheter (e.g., 1.2 times, 1.3 times, 1.4 times, 1.5 times, 1.6 times, 1.7 times, 1.8 times, 1.9 times, 2 times, etc. or more than the thickness of the catheter). Alternatively the length of the stiff regions maybe 0.1 times the radius of the catheter or greater (e.g., 0.2 times the radius of the catheter, 0.3 times the radius of the catheter, etc.).

In FIG. 40A-40B, the tractors formed of knit materials having different sizes post-heat treatment (e.g., 0.002" knit 26 needle (SN5923) heat treated on a 0.085" mandrel) than those shown in FIGS. 40C and 40D. In FIGS. 40A-40B, the knit material locked on and could not be rolled over the catheter. Relative to the size of the knit, the ID of the catheter (0.045" ID/0.055" OD) was too small. In contrast, in FIGS. 40C and 40D, the catheter dimensions were too large for the knit (e.g., 0.085" ID 72D PEBAX, 0.95" OD); the knit material could not pull around and invert on the tubing of this size.

Figure 42:
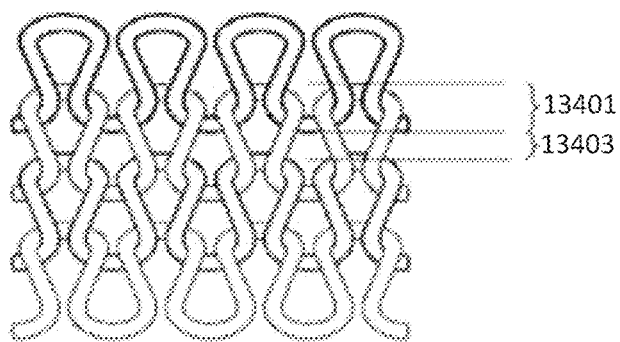
FIG. 42 is a schematic of a knitted tractor.
Figure 43A:
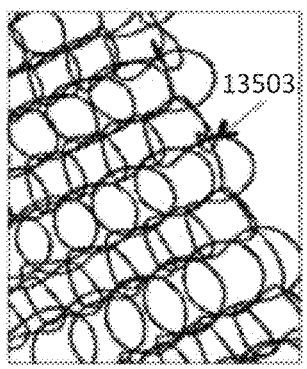
FIGS. 43A-43C illustrate movement of the loops of a knitted tractor having loops of a nickel titanium filament forming alternating stiff/less stiff regions (arranged down the long axis of the tractor).
Figure 43B:
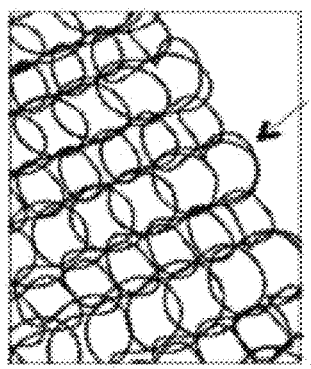
Figure 43C:
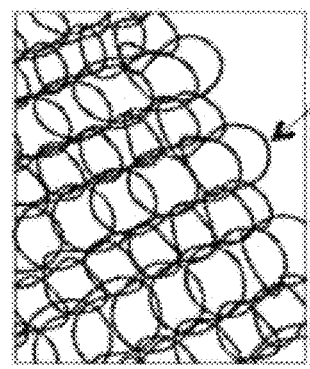
Figure 44A:
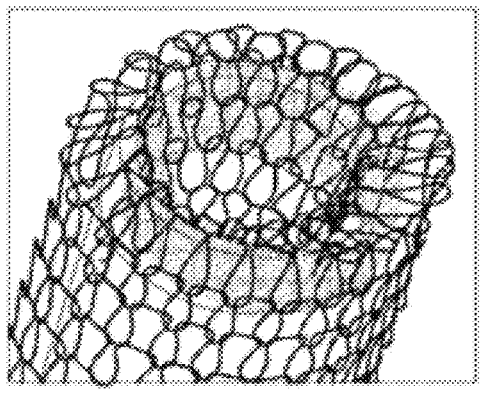
FIGS. 44A-44B illustrate end perspective and side perspective views, respectively, or an apparatus having a knitted tractor.
Figure 44B:
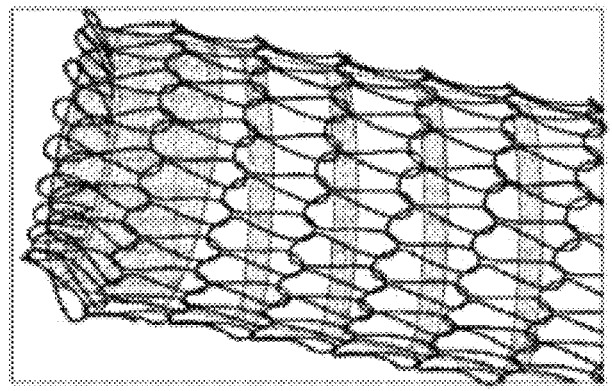
Figure 45A:
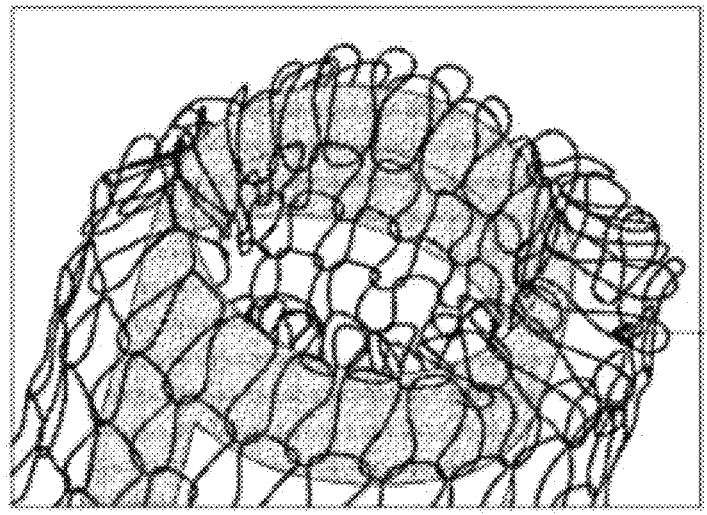
FIGS. 45A-45C illustrate seesawing operation of the apparatus of FIGS. 44A-44B.
Figure 45B:
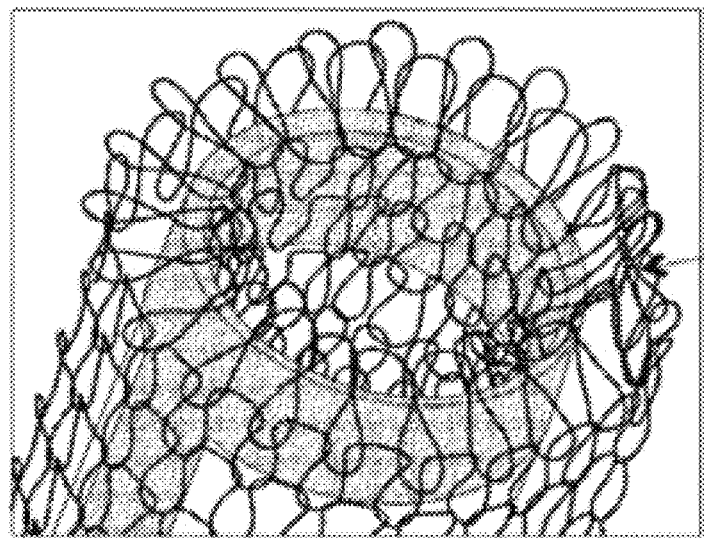
Figure 45C:
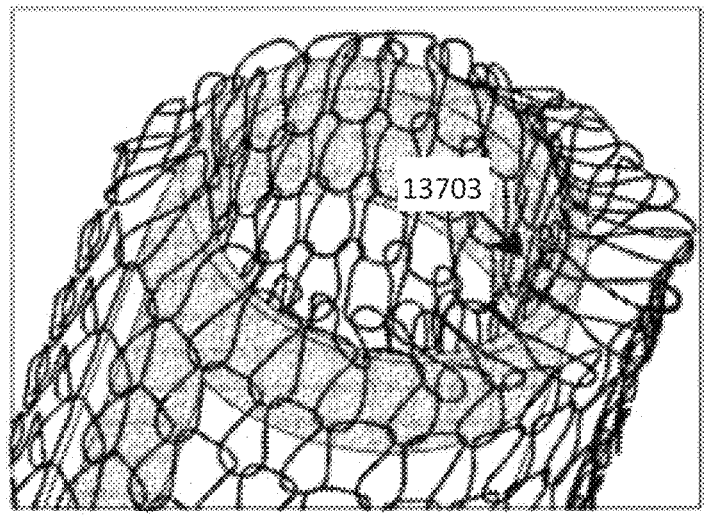

FIGS. 41A and 41B illustrate another example of a seesawing tractor formed from a knitted material. FIG. 42 shows an enlarged view of a portion of knitted material forming a tractor. The knitted tractor is formed from a filament (a monofilament or group of fibers collected into a filament) that is knitted to itself. The knit may be a tubular knitted material formed from a filament (monofilament or group of filaments) forming interlocking loops as shown in FIG. 42. In this example, the regions of overlap 13401 between the loops form the stiffer region, while the non-overlapping regions form the less stiff regions 13403. In any of the variations described herein, the loops formed by the knit may also act as protrusions as discussed above and may aid in drawing the clot into the catheter and/or macerating the clot. For example, the sequence of illustrations in FIGS. 43A-43C show a portion of a knitted tractor having loops of nickel titanium forming alternating stiff/less stiff regions (arranged down the long axis of the tractor) as they roll in a seesawing manner over the distal end opening of the catheter. In this example, a single loop 13501 has been indicated showing it's progression from flush against the wall of the outer diameter of the catheter as the tractor is pulled into the catheter, until, as it approaches the distal opening of the catheter, it inverts by swinging the loop portion 13501 out of the plane of the tractor and up, where it may help grab clot material, as shown in FIGS. 43B-43C. The seesawing motion of a knitted tractor may also be seen in FIGS. 44A-44B and 45A-45C. An example of a mechanical thrombectomy apparatus is shown in FIGS. 44A-44B from end and side perspective views. FIGS. 45A-45C illustrate a method (e.g., that may be used for grabbing and removing a clot from a vessel) including pulling the distal end of the tractor (in this example, a knitted, seesawing tractor) proximally into the catheter. As shown in FIG. 45A the tractor may initially pull a stiff region 13703 towards the catheter opening. Because it is sufficiently stiff that it does not bend over the edge of the catheter, but is 'hinged to an adjacent stiff region, as the tractor is pulled proximally, the stiff region eventually tilts over the edge (in a seesawing motion), so that one end flips up away from the opening, as shown in FIG. 45B (stiff segment 13703 is indicated); finally it slides forward into the inner diameter of the catheter, as shown in FIG. 45C.

As discussed above, it may be desirable to have a tractor region that is sufficiently and/or selectively coarse so that it may grab a clot. In some variations a rougher tractor may grab clot despite the lubriciousness of the tractor. Knits may be generally more course than braids due to their macro structure (e.g., cells, wire cross overs, shape of cells). Knits may also have the desired porosity discussed above (e.g., having a porosity that permits the tractor to grab and store clot/clot carrying capacity). The size of the pores may be, e.g., between 5-20, 5-10, 10-15 or 15-20 pores on the tractor per circumference. The knit may be formed of any appropriate material, including, e.g., Nickle titanium (NiTi) wire. For example, a knit may be formed of a PET monofilament, a PTFE monofilament, etc. A knitted tractor may also have a surface lubricity based on either material properties (e.g., metal, polymer, etc.) or added lubricant (inside, outside, both), and may be radiopaque (e.g., including an inter weave in Pt., DFT, over braid wires with Pt., etc.)

Patterned Tractors

Also described herein are tractors having a pattern of lubricious and/or non-lubricious regions on their outward-facing surfaces. These patterned regions may be coatings and/or surface modification, they may be formed by the material properties of the tractor, and/or they may be due to the application of a lubricious material (e.g., lubricant) in the pattern. A pattern of lubrication and/or non-lubricous material may assist in reducing friction while enhancing clot grabbing. A uniform lubricant (e.g., hydrophilic surface) on the outer-facing surface of the tractor has been found to reduce the ability of the tractor to grab a clot, particularly in the absence of other clot-grabbing features, such as the protrusions and edges discussed and illustrated above. Thus, described herein are patterns of lubricious and/or non-lubricous (including less lubricious, and tacky or adhesive) materials that may be included on the outward-facing surface of the tractor that may enhance pulling the tractor proximally into the device (e.g., the catheter of the elongate inversion support) and inverting the tractor, while still permitting or even enhancing clot grabbing.

Figure 48A:
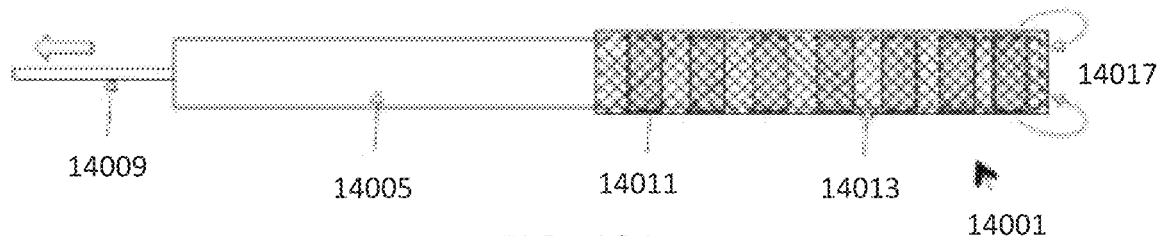
FIGS. 48A-48C illustrate apparatuses as described herein including patterned coatings (e.g., hydrophilic and/or hydrophobic coatings).
Figure 48B:
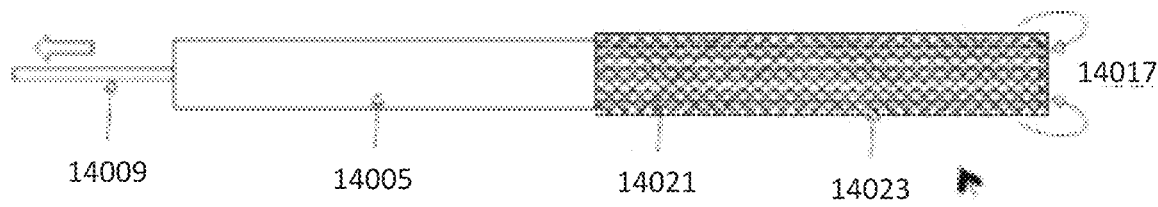
Figure 48C:
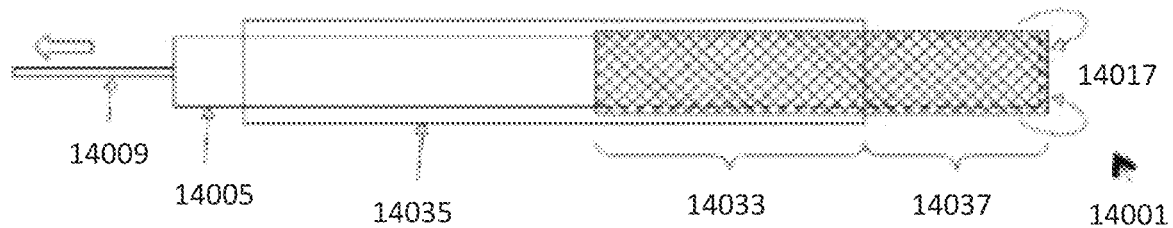

For example, any of the methods and apparatuses described herein may also include a pattern of non-uniform hydrophilic and/or hydrophobic coating (e.g., a patterned lubricious coating) that may assist with the positioning of the apparatus within the tortuous vessels before or during grabbing a clot. Even a partial hydrophilic coating (e.g., lubricious coating) on the outer-facing surface of the tractor element may reduce friction within the vessel ID. These lubricious regions (e.g., coatings) may be arranged in a pattern such as alternating regions (e.g., bands, stripes, checkerboard pattern, grid, spots, etc.). For example, it may be preferred to partially coat the tractor (e.g., braid) with a hydrophilic material such as using, e.g., a 5 mm coated length of braid followed by a 5 mm non-coated section. This coating may be in other patterns, as mentioned, including strips (longitudinal strips), a spiral pattern coating, a random pattern coating, etc. FIGS. 48A-48C illustrate examples of hydrophilic coating options.

For example, FIG. 48A shows an example of an apparatus including a tractor region and 14001 a catheter of an elongate inversion support 14005 into which the tractor is inverted and drawn proximally at the distal end of the tractor. The tractor 14001 may be attached to a puller 14009 (e.g., pull wire or pull catheter) to pull, or in any of these variations, push and pull, the tractor within the catheter from the distal end of the tractor. The proximal end of the tractor is attached over the outer surface (OD) of the outer catheter 14005. In FIGS. 48A-48C the tractor is shown as a braided tractor, but any of the tractor types (braided, woven, knitted, solid/cut-out, etc.) described herein may be configured to include a pattern of more/less lubricious regions.

The tractor shown in FIG. 49A includes a pattern of lubricious regions arranged in bands along the distal-to-proximal elongate length of the tractor. For example, regions coated with a lubricious material 14011 and uncoated (less lubricious or even sticky) regions 14013 alternate down the length of the tractor. Alternatively, the pattern may be formed of a grid or checkered pattern, a spiral/helical pattern along the length of the tractor, etc. As the tractor is drawn into the catheter and inverted 14017, the alternating lubricious/non-lubricious regions may help grab clot, which is particularly or only important when initially pulling the clot material into the inverting tractor and therefore the catheter.

FIG. 48B illustrates another example of a tractor 14001 in which elongate (in the long axis of the tractor) lengths of lubricious 14021 and non-lubricious 14023 regions alternate to form a stripe pattern down the length of the tractor. These "stripes" may be varying in size (e.g., diameter) and may be curved, zigzag, wavy, etc.

In some variations, lubricious regions may be separated by non-lubricious regions by a minimum and/or maximum distance. For example the lubricous regions may be alternated with non-lubricous regions (including less lubricious and/or sticky/adhesive regions) by between 0.05 mm and 15 mm (e.g., by greater than at least: 0.005 mm, 0.01 mm, 0.02 mm, 0.03 mm, 0.04 mm, 0.05 mm, 0.06 mm, 0.07 mm, 0.08 mm, 0.09 mm, 0.1 mm 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, etc.). Similarly the maximum separation between lubricious regions may be less than about: 20 mm, 15 mm, 10 mm, 9 mm, 8 mm, 7 mm, 6 mm, 5 mm, etc.). The minimum and maximum distance may be determined based on the size of the tractor (e.g., diameter), and/or the rate at which the tractor is to be pulled. The minimum distance may also or alternatively be based on the lubriciousness of the coating. More highly lubricious materials may be separated by a greater minimum distance.

In some variations only a portion of the tractor is coated, either completely or in a pattern, and the proximal end portion (e.g., the last portion be drawn into the catheter) is not lubricious (e.g., uncoated or coated in a tacky/sticky material); the region distal to that (e.g., the region near the initial distal-facing inverting portion of the tractor is lubricious. Alternatively, the proximal end portion is lubricious (e.g., coated with a lubricious material) but the region distal to that (e.g., the region near the initial distal-facing inverting portion of the tractor) is uncoated or is tacky/sticky to help initially grab the clot.

For example, FIG. 48C shows an example of an apparatus including a sleeve 14035 or cover over the most proximal end of the tractor 14001. This sleeve may itself be lubricious on the outer-facing surface and may protect or hold the tractor in position until it is drawn distally over the catheter, exposed, and inverted to grab/pull clot 14017. The proximal end of the tractor under the sleeve may be lubricious and/or non-lubricious (e.g., patterned) 14033. The region proximal to the inverting portion, and distal to the sleeve, 14037 may be lubricious or (preferably) non-lubricious and/or a pattern of non-lubricious and lubricous regions.

Elongate Inversion Supports

In general, the elongate inversion supports described herein may be or may include catheters that are operated with the tractor and are configured so that the tractor may invert over the distal end opening (aperture) of the elongate inversion support. Any appropriate elongate inversion support may be used and may be configured as a catheter (or micro catheter). Since the tractor region is pulled against the catheter to invert it, the catheter may be configured to have high compression resistance while maintaining superior tip bending (e.g., flexible tip) which may allow it to reach distal vessel segments within the human vasculature.

Small bore catheters including those for use herein may have braid reinforced segments combined with coil reinforcement. A braid may be used on the proximal end of the catheter to provide column stiffness and medium shaft flexibility, and coils are typically used distally to enhance flexibility while sacrificing column strength. The apparatuses described herein may use a catheter having a slotted tube distal segment element that, when activated, can create a significant axial column compression through the entire catheter shaft. Typically, this column compression may result in some catheter foreshortening and catheter bending (e.g., cork screwing). Described herein are catheters that may reduce this foreshortening and corkscrewing by leveraging slotted tube elements into the catheter distal segment (e.g., the last 8 cm or less).

Figures 34A, 34B, 34C:
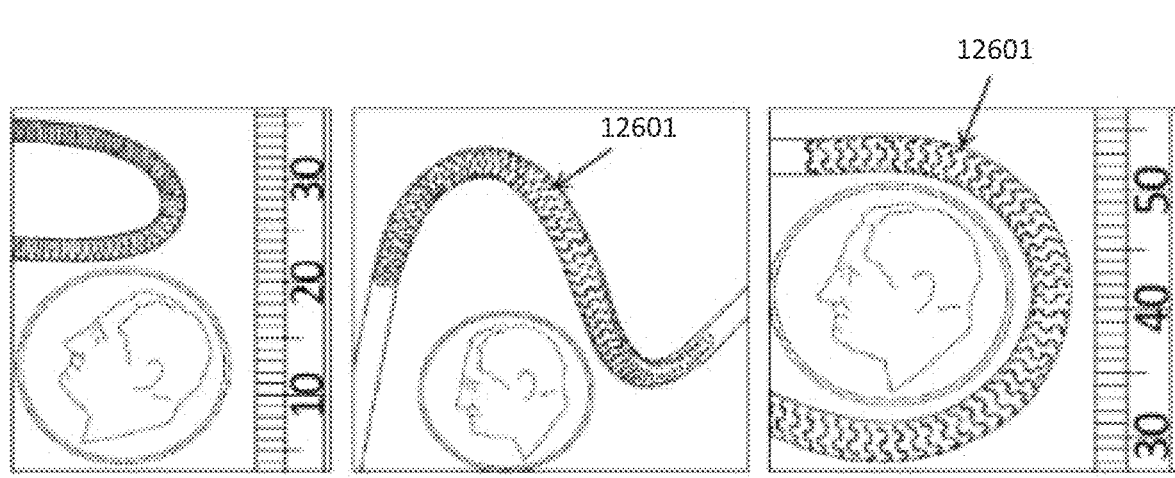
FIG. 34A illustrates bending of a typical small-bore catheter distal tip.
FIGS. 34B-34C show examples of a catheter comprising a keyed slotted tube extending along the entire length of the catheter.

FIG. 34A illustrates bending of a typical small-bore catheter distal tip. As seen in FIG. 29A, the catheter may bend around a small radius (as compared to the reference dime). The distal segment of this catheter may include a coil, and a low-durometer thin-walled polymer that is relatively soft, flexible and stretchy.

FIGS. 34B-34C illustrate, for comparison, a catheter comprising a keyed slotted tube extending along the entire length of the catheter. In this variation, the interlocking key segment 12601 of the design provides an axial stiffness when the structure sees compressive loads in the axial direction through the interlocking segments stacking or contacting a one or more point about its circumference. This structure still allows for adequate conformability around a tight radius allowing it to be push-able through a tortuous anatomy (i.e. neuro tortuous vessel). In order to increase bending flexibility and therefore the ability to make tighter turns, the keys may be shorter or longer and/or nested.

Figure 35:
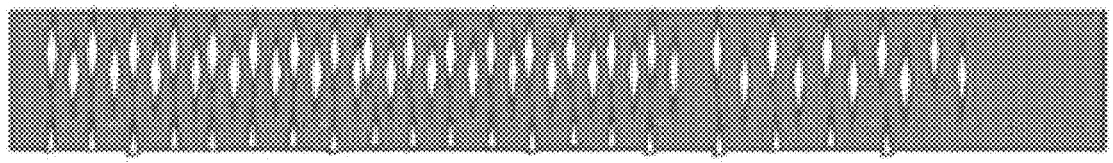
FIG. 35 shows an example of a catheter design formed as a slotted tube.

In general, the bending stiffness of the catheter is a function of the material, material composite structure, wall thickness, strut length, strut width, cell angle, strut shape, and cell length. FIG. 35 shows an example of a catheter design formed as a slotted tube. The tube includes cut-out regions that provide flexibility while leaving column strength.

Figure 36A:
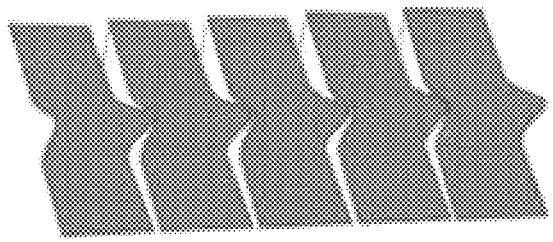
FIGS. 36A-36B is an example of a catheter design.
Figure 36B:
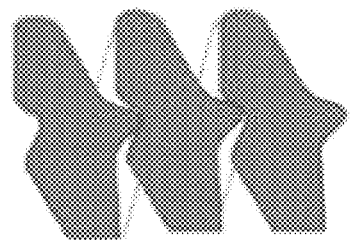

Another example of a catheter configured to have a high column strength and stiffness along its entire length is shown in FIGS. 36A-36B. In FIG. 36A, a hybrid laser-formed coil (spiral) has compaction-resistant features, along the entire continuous length of the catheter. The coil bending stiffness in this design is a function of the material, wall thickness, coil width, helix angle, hinge shape, hinge height, hinge location (e.g., linear axial or out of phase/helix), shape of coil surface and the catheter material stiffness.

Figure 37A:
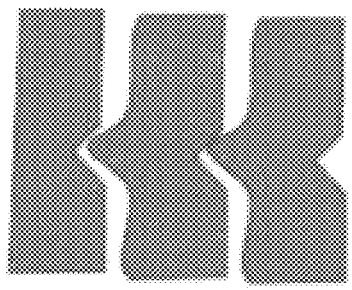
Figure 37B:
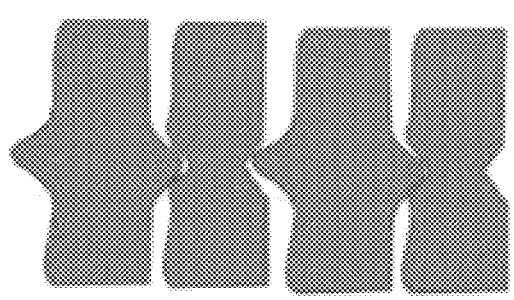

The catheter configuration shown in FIGS. 37A-37B illustrate variations in which individual hoop/ring segments are linked by a polymer wall of the catheter only. The ring bending stiffness is a function of the material, wall thickness, ring width, hinge shape, hinge height, hinge location (linear axial or out of phase/helix), shape of ring surface and the catheter material stiffness.

Any of the apparatuses described herein may include a catheter having a hard distal tip (e.g., formed of a PTFE, PEEK, stainless steel, etc.) and may be radiused to enhance rolling. The tip opening may be radiused from a middle of catheter wall, without an outer radius. Any of these catheters may include a lubricious coating. Finally, any of these catheters may also be configured to permit aspiration (e.g., drawing suction) through them, which may be helpful.

FIGS. 50A-51D, described in greater detail below, including examples of elongate inversion supports that may be used in any of the apparatuses described.

For example, any of the apparatuses described herein may include or be configure for use with a vacuum. The vacuum may aid in initially gasping or grabbing the thrombus. The vacuum may be applied from the distal end of the apparatus and/or of an intermediate or outer catheter or sleeve that is used with the apparatuses (e.g., elongate inversion support and inverting tractor) described herein. Also described herein are apparatuses that are adapted for use with a vacuum, including for use with an intermediate or outer catheter through which the apparatus may be delivered to the clot. The apparatus may grab clot from within the outer catheter, or it may be extended distally out of the intermediate or outer catheter.

FIG. 49A shows an example of a configuration in which an outer/intermediate catheter or sleeve that is highly flexible may be maneuvered, for example with a guidewire, to a distal end of the device. Thus, the intermediate catheter may be maneuvered near, or adjacent to, the thrombus. As in any of these methods of use described herein, imaging (such as fluoroscopy, contrast imaging, etc.) may be used. Once in positioned, the guidewire may be removed or left in place, and the apparatus including the elongate inversion support and inverting tractor may be extended within the intermediate catheter/sleeve. In FIG. 49A, the intermediate catheter 14104 is shown positioned within the vessel 14109 distally. As with any of the illustrations here, in the vessel maybe highly tortious and branching, although for convenience it is shown as straight in the figures. The apparatus 14100 is extended distally through the intermediate catheter and extends out of the distal opening of the intermediate catheter to grab the clot 14111, as shown. The puller 14105 may thus be drawn proximally (to the left in the figure) to pull the tractor 14103 from over the catheter portion of the elongate inversion support 14113, so that it inverts and rolls into the lumen of the elongate inversion support, capturing and drawing the clot in with it. The clot may be compressed.

Thus, this configuration may be referred to as a vessel cleaner. In addition to the rolling of the tractor to grab and pull the clot, the clot may be pulled by a vacuum applied from one or both of the intermediate catheter 14121 and/or the elongate inversion support 14123. Vacuum may be applied, e.g., within the intermediate catheter, before the apparatus is positioned distally (or even within the intermediate catheter at all) or after it has been extended distally from the intermediate catheter. This configuration shown in FIG. 49A may introduce the tractor through outer catheter to the face of clot. As mentioned, the mechanical thrombectomy apparatus may be extended distally from the intermediate catheter either by pushing it out distally and/or by pulling back the intermediate catheter to deploy all or part of the tractor into vessel, as shown. If vacuum is applied through the catheter, the catheter forming the elongate inversion support may be jacketed or sealed to allow aspiration through this catheter.

Optionally pull vacuum through outer and/or inner and/or puller. As mentioned, thereafter the tractor may be pulled proximally relative to the elongate inversion support to pull the clot. The intermediate catheter may then be advanced distally and/or the mechanical thrombectomy apparatus may be withdrawn proximally to remove the apparatus once the clot has been removed. Thereafter an angiogram may be taken to confirm that the clot has been removed.

Alternatively, in FIG. 49B, a clot may be removed using the intermediate catheter to draw a vacuum with the mechanical thrombectomy apparatus within the lumen (e.g., near the distal end, but not extending fully from the distal end) of the intermediate catheter. As described for FIG. 49A, in FIG. 49B the intermediate catheter may be inserted into the vessel (e.g., using a guidewire) so that the distal end is positioned near the clot. Suction may be used to draw the clot into the intermediate catheter either before the mechanical thrombectomy device is inserted or after it has been inserted.

In FIG. 49B, the elongate inversion support 14113' is particularly well suited for use with a vacuum applied through the intermediate catheter 14104 surrounding the apparatus. For example, in FIG. 49B, the elongate inversion support 14113' include a distal catheter region 14125 that extends just a few cm from the distal end opening in which the clot is drawn. The elongate inversion support then tapers down to an elongate support, which may be formed by a wire, hypotube or skived region. This configuration may prevent the catheter from blocking the lumen of the intermediate catheter and therefore increasing the resistance of the vacuum before it can reach the open distal end and apply suction to draw the clot. Alternatively or additionally, the outer diameter of the catheter portion of the elongate inversion support may be sized to allow more of the vacuum to pass. For example, the apparatus may be sized such that there is at least about 0.002 inches or greater (e.g., 0.003, 0.004, 0.005, 0.006, etc., inches) between the outer diameter of the catheter and the inner diameter of the intermediate catheter ("outer catheter"). This may also permit unimpeded rolling of the tractor over the distal end opening of the elongate inversion support.

In operation, the method of removing clot such as shown in FIG. 49B may include pulling at least the tip of a clot into the intermediate catheter through the use of a vacuum 14121. Typically the clot may clog within the intermediate catheter; the mechanical thrombectomy apparatuses described herein may be used to remove the clot from within the intermediate catheter. For example, while maintaining vacuum, the mechanical thrombectomy apparatus may be inserted (or it may be preloaded in intermediate catheter as mentioned) and the tractor puller 14105 may be pulled to pull the clot out of the intermediate catheter and the vessel, compress and/or macerate it and pull it into the apparatus and therefore the intermediate catheter, where it can be withdrawn proximally, e.g., by removing the mechanical thrombectomy apparatus. As mentioned, an angiogram may be taken through intermediate catheter (e.g., leaving it in place in case the mechanical thrombectomy apparatus needs to be re-inserted and used to remove more clot) to confirm clot has been removed.

Figure 50A:
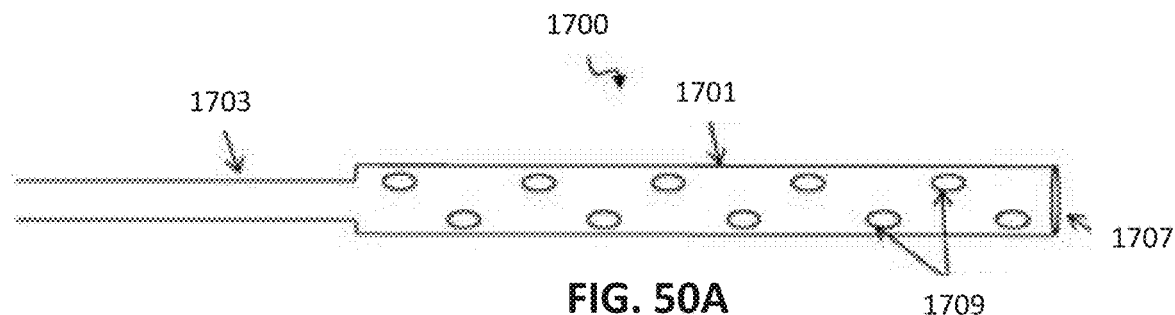
FIGS. 50A-50B illustrate a variation of a catheter of an elongate inversion support having both different diameters (e.g., a larger-diameter distal catheter connected to a smaller-diameter proximal region extending longitudinally in the proximal-to-distal axis), and a plurality of openings (e.g., cut-out regions, holes, etc.).
Figure 50B:
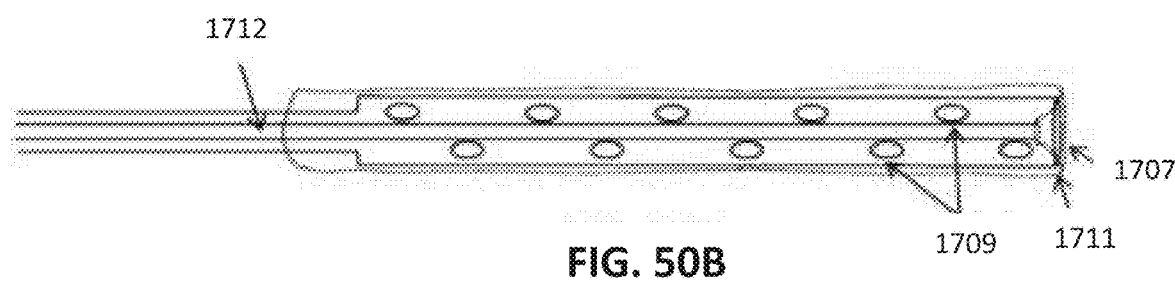

As mentioned, a full catheter such as shown in FIG. 49A may block or prevent the vacuum from reaching the distal end of the intermediate vessel. Therefore it may be beneficial to adapt the mechanical thrombectomy apparatus so that it can be used with vacuum within an intermediate catheter or sleeve, as shown in FIG. 49B. This may be achieved as mentioned above, by minimizing the larger-diameter catheter portion of the elongate inversion support forming the distal end opening over which the tractor inverts. In FIG. 50A for example, the elongate inversion support 1700 has a distal catheter portion 1701 having a larger diameter than the more proximal region 1703, and also includes a plurality of openings, holes, gaps, cut-out regions, slots, etc. 1709 that may allow the flow of vacuum through the elongate inversion support more easily. The elongate inversion support shown also includes a distal end 1707 into which a tractor 1711 inverts, as shown in FIG. 50B. In FIG. 50B, the elongate inversion support is shown transparent so that the puller 713 and tractor within the elongate inversion support is visible.

Figure 50C:
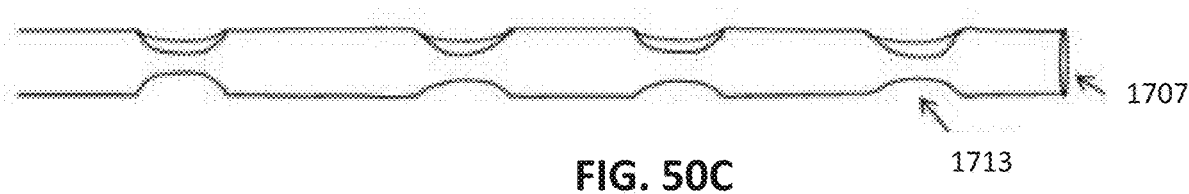
FIGS. 50C-50D illustrate another variation of a catheter of an elongate inversion support having a plurality of opening formed therethrough.
Figure 50D:
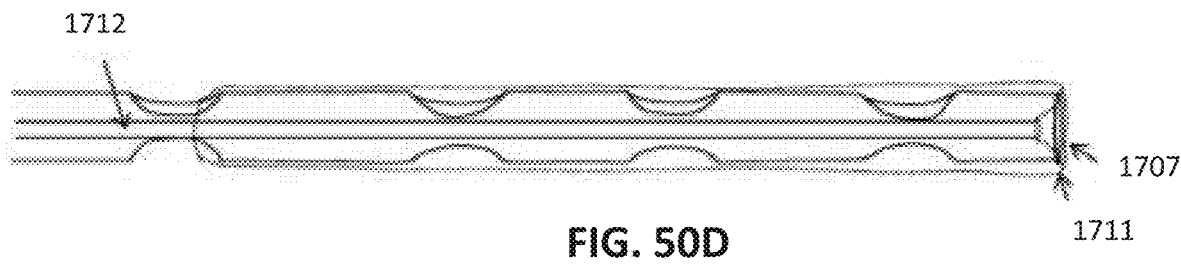
Figure 50E:
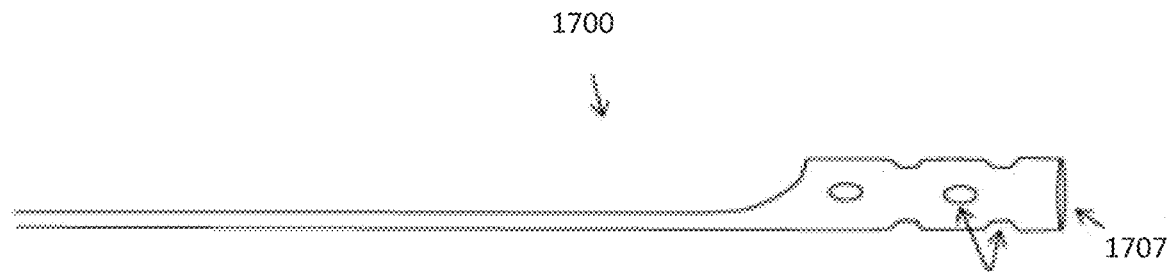
FIGS. 50E-50F illustrate another variation of a catheter of an elongate inversion support having a distal catheter region and an elongate support member formed by skive cutting the catheter.
Figure 50F:
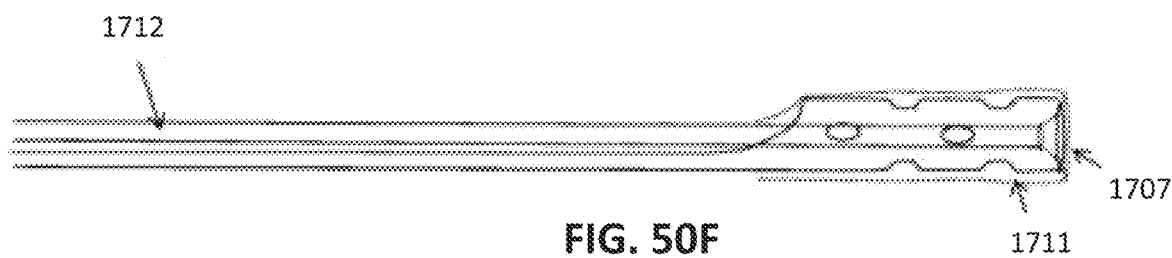
Figure 50G:
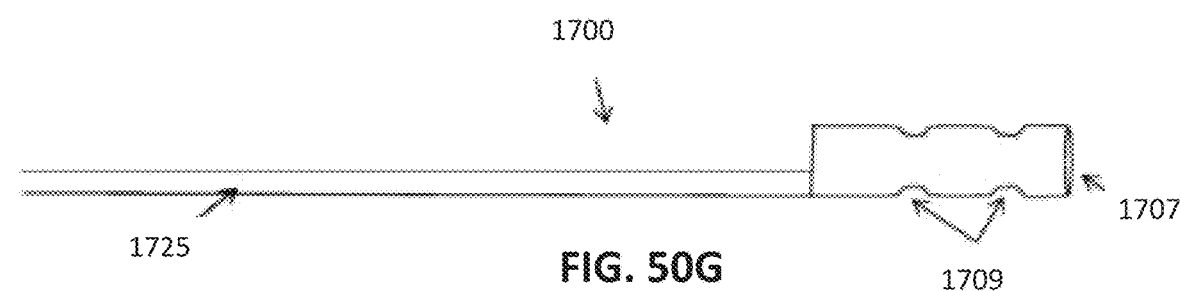
FIGS. 50G-50H illustrate another variation of an elongate inversion support having a distal catheter region and an elongate support member extending from the catheter region.
Figure 50H:
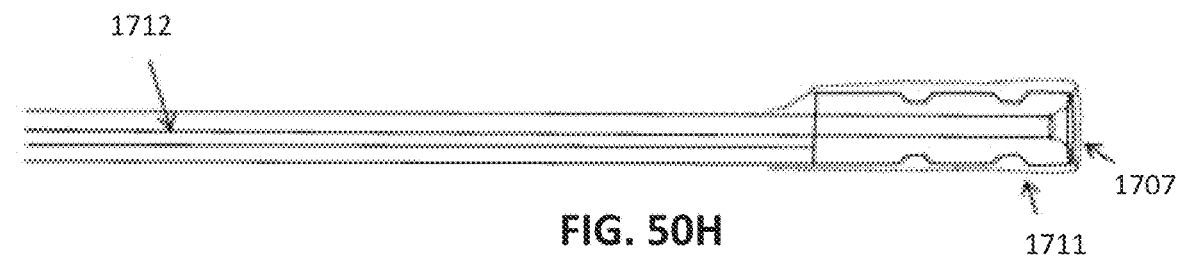
Figure 50I:
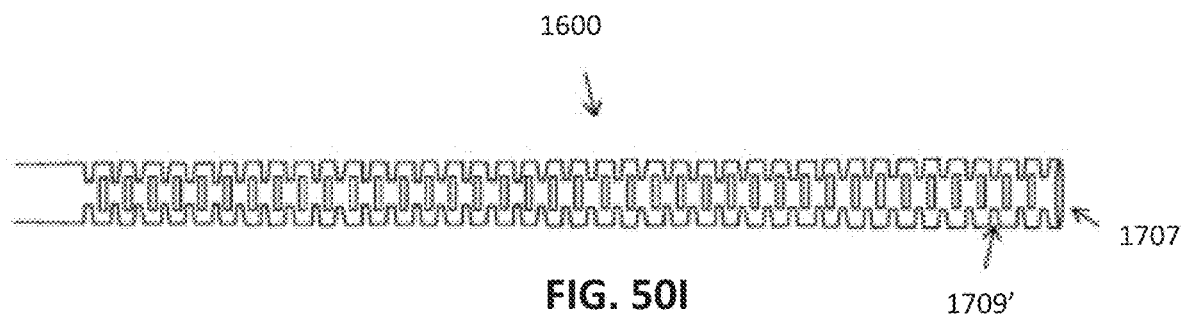
FIGS. 50I-50J illustrate another variation of an elongate inversion support having a plurality or openings along the distal-to-proximal length.
Figure 50J:
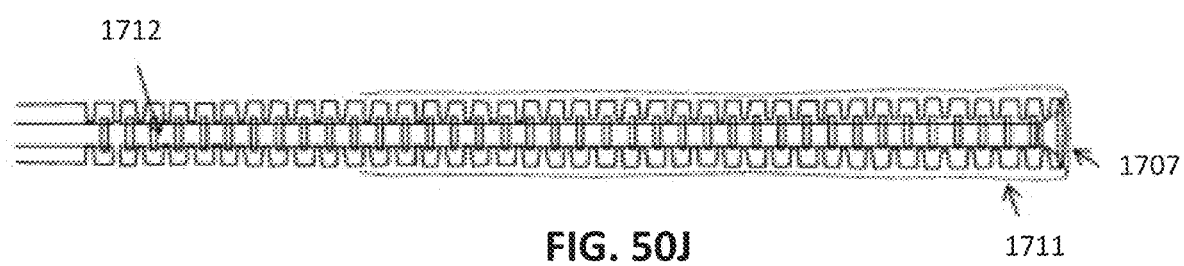

Similarly, in FIGS. 50B and 50C, the entire length of the elongate inversion support includes a plurality of cut-out regions 1713 which may increase the ability to allow the flow of a vacuum or other fluid within the apparatus, but may still allow the elongate inversion support to provide column strength to resist collapsing up to at least 500 g of compressive longitudinal force applied by, e.g., pulling on the tractor. Similarly, the elongate inversion support of FIGS. 50E and 50F show a skived catheter that also includes openings 1709 along its length. The puller and tractor 1412 are shown within the elongate inversion support in FIG. 20F. FIGS. 50G and 50H illustrate an example in which rather than a skived portion of the catheter, the distal catheter region of the elongate inversion support is formed by a wire, bar, tube, 1721 etc., that is attached to the catheter at the distal end. The catheter may also optionally include openings 1709. The elongate inversion support of FIGS. 50I and 50J includes openings 1709' along all or much of its length (particularly near the distal end region) as shown.

Figure 50K:
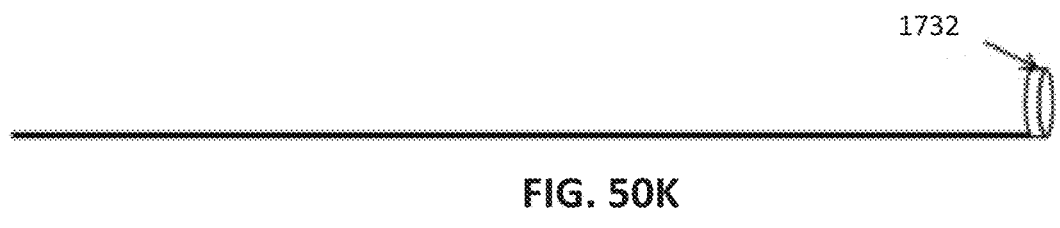
FIGS. 50K-50L illustrate another variation of an elongate inversion support having a minimal catheter region at the distal end forming a distal end opening that is connected to an elongate support (e.g., wire, tube, bar, rod, etc.).
Figure 50L:
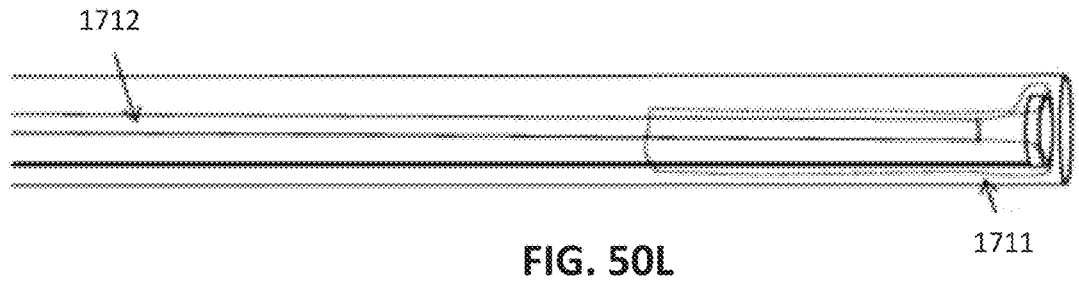

Finally, the variation of the elongate inversion support shown in FIG. 50K includes a minimal catheter portion 1732 that is connected to a wire, bar, tube, hypotube, skived region, etc.

Figure 51A:
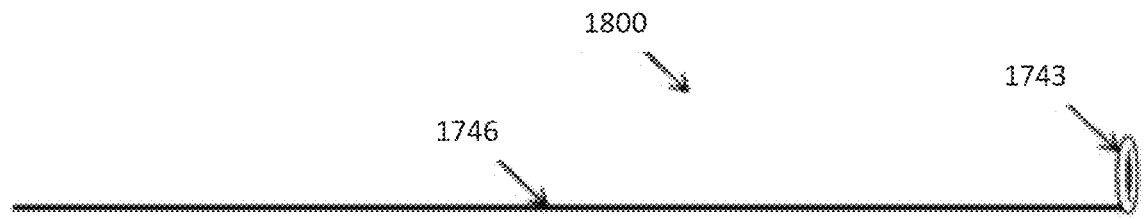
FIG. 51A is another variation of an elongate inversion support having a minimal catheter region at the distal end.
Figure 51B:
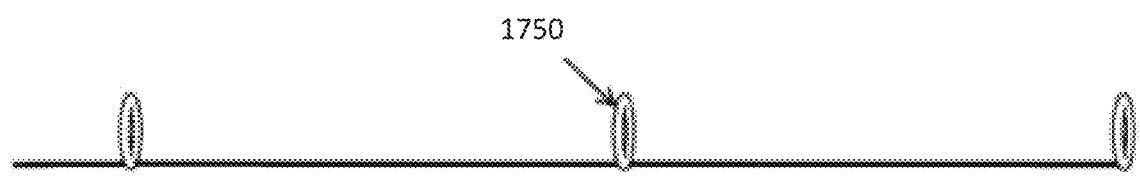
FIGS. 51B-51D illustrate an elongate inversion support such as the one shown in FIG. 51A having additional supports (FIG. 51B) and used as part of a mechanical thrombectomy apparatus (FIGS. 51C and 51D).
Figure 51C:
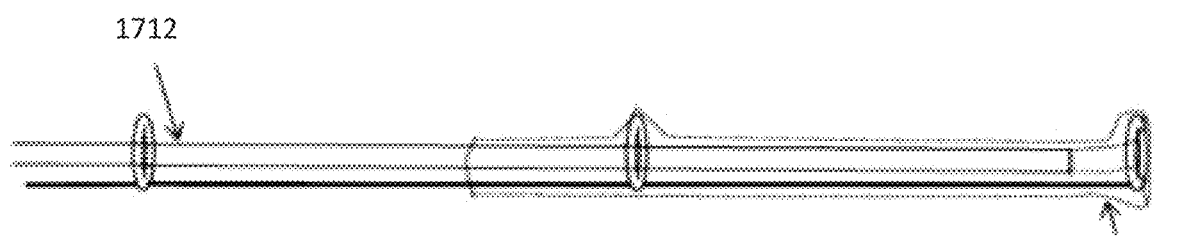
Figure 51D:
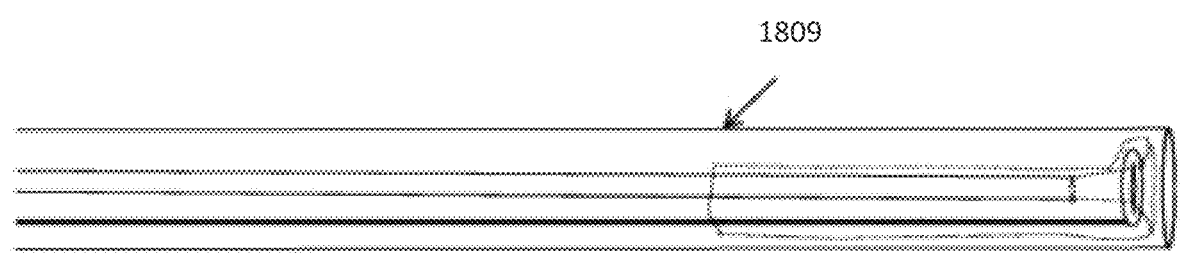

FIGS. 51A-51D illustrate the operation of a similar minimal elongate inversion support 800. In this example, the apparatus includes a distal aperture 1743 bonded securely to a wire, bar, tube, hypotube, skived region, etc. 1746 forming an elongate support. The elongate support may be hollow (e.g., may include a lumen for a guidewire) or solid. The elongate support may also include one or more additional support guides 1750 as shown in FIG. 51B. These supports may help contain the puller and/or tractor within the elongate inversion support. Any of the elongate inversion supports described herein may include additional support guides. The elongate inversion support of FIG. 16B is shown with a tractor 1711 and puller 1712 in FIG. 51C. As mentioned, this variation may be particularly well suited for use with an intermediate (e.g., "outer") catheter, sleeve, or the like 1809, as shown in FIG. 51D.

Power Driven Tractors

Figure 46A:
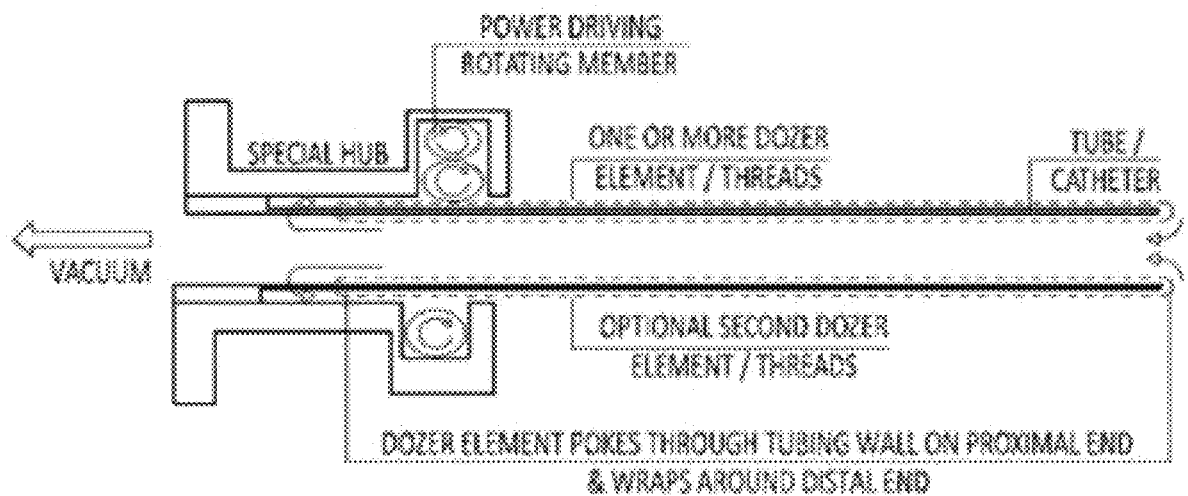
FIGS. 46A-46B show an example of an apparatus having a motor-driven tractor.
Figure 46B:
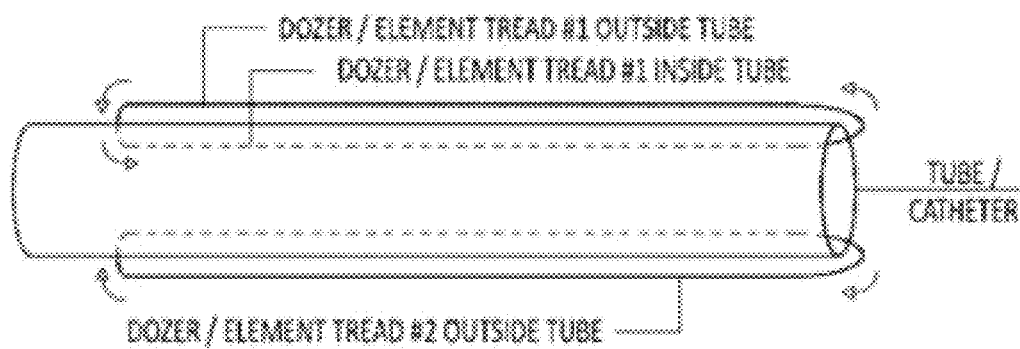
Figure 47A:
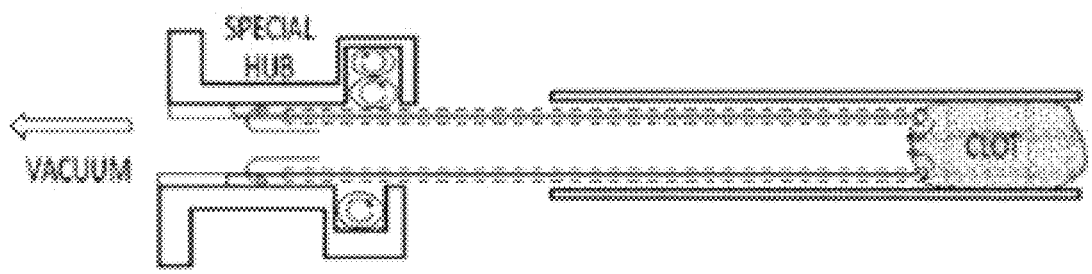
FIGS. 47A-47C illustrate operation of the apparatus of FIGS. 46A-46B.
Figure 47B:
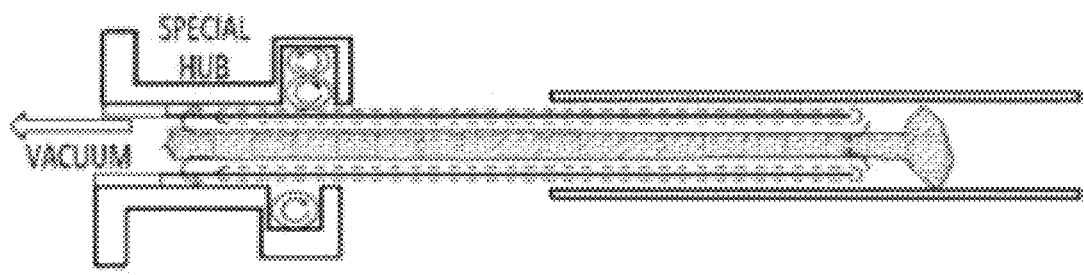
Figure 47C:
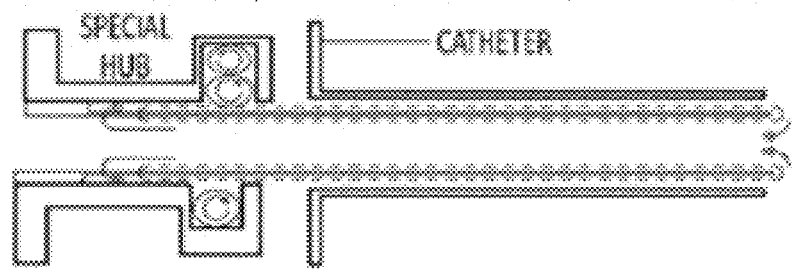

Also described herein are mechanical thrombectomy apparatuses in which the tractor is power driven. Any of the tractors described herein may also be driven by a motor, instead of or in addition to the manual driven tractor described. For example, a power-driven tractor is shown in FIGS. 46A-46B and 47A-47C. In FIG. 46A the tractor is a continuous tractor. FIG. 46B illustrates the catheter and tractor region, without the motor shown in FIG. 46A. The tractor comprises a plurality of belts, chains, lengths, etc. that run longitudinally and may act like a conveyor to pull clot into the apparatus. The loops of material may therefore be run as a power-driven tractor. FIGS. 47A-47C illustrate the operation of the apparatus of FIGS. 46A-46B, shown grabbing a clot.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Expandable Distal Ends

Figure 52A:
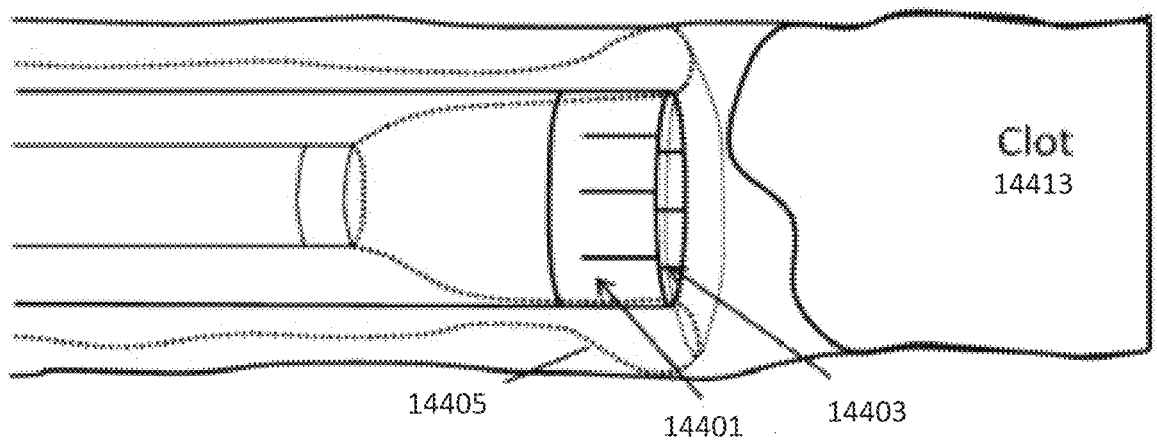
FIGS. 52A-52C illustrates an example of the operation of a mechanical thrombectomy apparatus with an expandable distal end region.
Figure 52B:
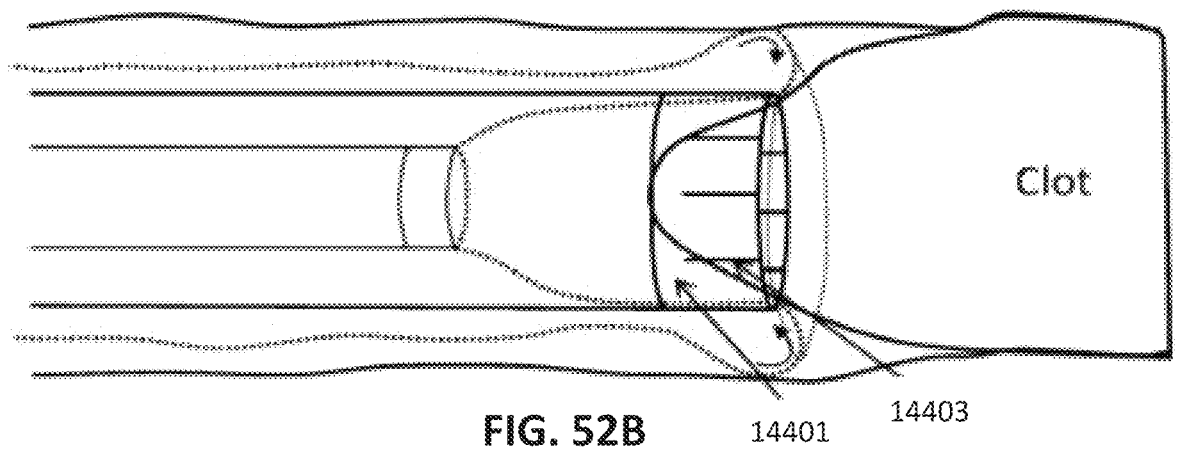
Figure 52C:
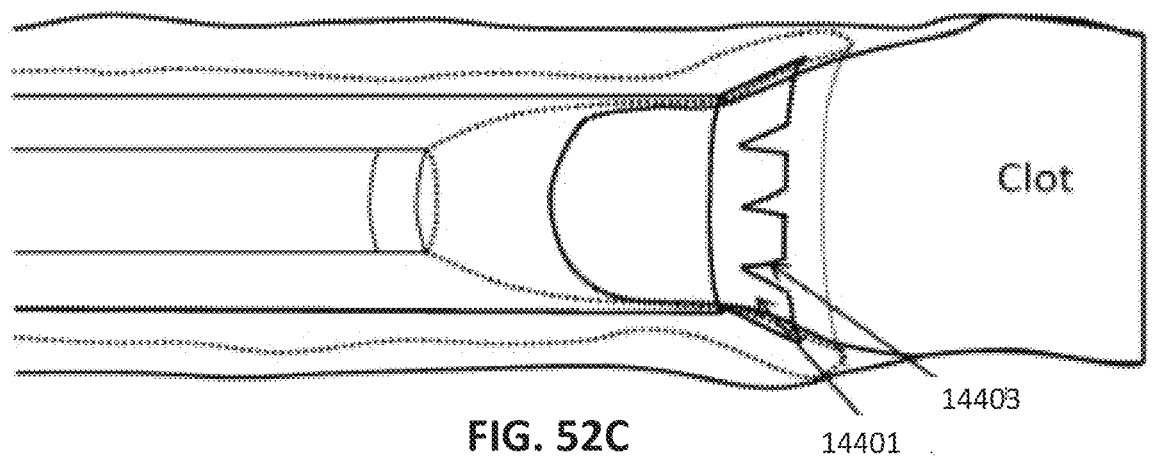

Any of the mechanical thrombectomy apparatuses described herein may include an elongate inversion support having a distal end that is expandable from a smaller diameter aperture (e.g., distal end opening) to a larger-diameter aperture. This expansion may be performed by pulling the clot within the catheter. For example, FIGS. 52A-52C illustrates the operation of an example of an elongate inversion support configured as a catheter having an expandable distal end. In this variation the catheter distal end 14401 may include slots or slits 14403 formed or cut, e.g., by laser-cutting, in the distal end of the catheter of the elongate inversion support. The apparatus may be operated as described above, positioning near (e.g., against or adjacent to) a clot, and pulling proximally on the puller to draw the tractor 14405 into the catheter, as shown in FIG. 52B. Although the apparatuses described herein may generally compress a clot greatly, compression may be made easier and/or more efficient by providing a more gradual decrease in radial diameter. As shown in FIG. 52B, when the tractor is rolled over the distal end opening and inverted, the clot maybe drawn in along with the tractor. As the large clot 14413 is brought into the distal end opening, the distal end opening may expand and open along the slots or slits 4403, as shown in FIG. 52C, so that the distal end opening flares out. In some variations an elastic sleeve, gasket, ring or cover (not shown in FIG. 52A-52C) may be included at least partially covering the distal end to prevent the edge from catching the tractor. For example, and elastic or stretchable layer may cover the cut distal end so that the distal end may be opened to form an outward flare. In FIG. 52C the outward-flared distal end is shown forming a funnel-shape into which the clot may be pulled. This funnel-shaped opening may help compress the clot so that it may be drawn into the mechanical thrombectomy apparatus.

In some variations the elongate inversion support may be configured to have, or to assume, a funnel-shape at the distal-facing end. The distal-facing end may always have a funnel-shaped mouth at the distal end opening, or the distal end opening may be configured to assume a funnel shape, as shown in FIGS. 52A-52C. In some variations the distal end of the elongate inversion support is configured to be elastic in a radial directly but maintain stiffness along the proximal-to-distal axis (in compressive load). For example, the distal end of the elongate inversion support may be configured with strands or rods extending in the proximal-to-distal axis that have a high compressive load strength, but which may separate from each other to enlarge the distal end opening; for example they may be connected by rings in which more distal rings are more elastic/stretchable than more proximal rings.

Figure 53A:
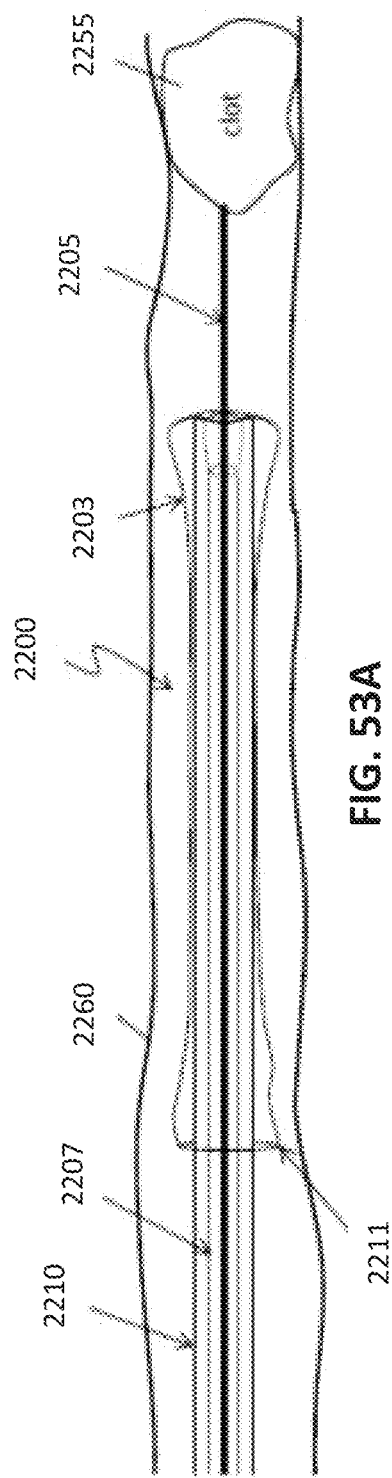
FIGS. 53A-53C illustrate a mechanical thrombectomy apparatus deploying prematurely within a vessel.
Figure 53B:
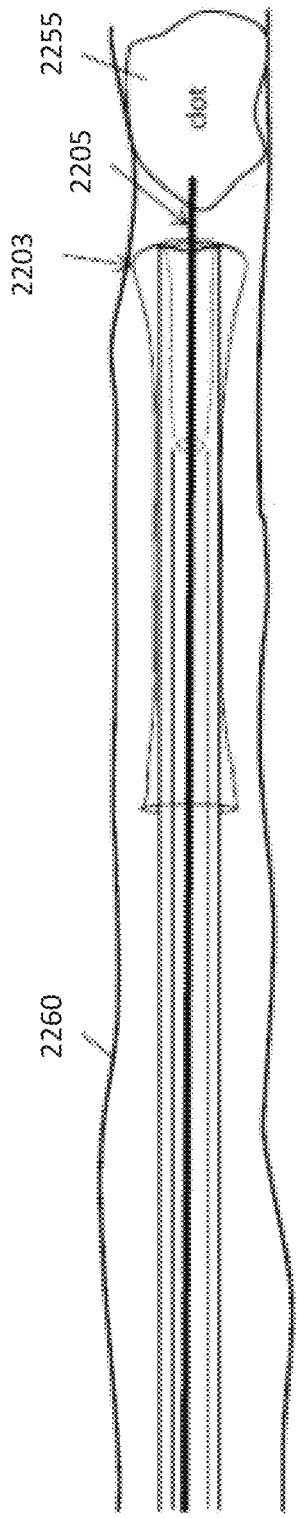
Figure 53C:
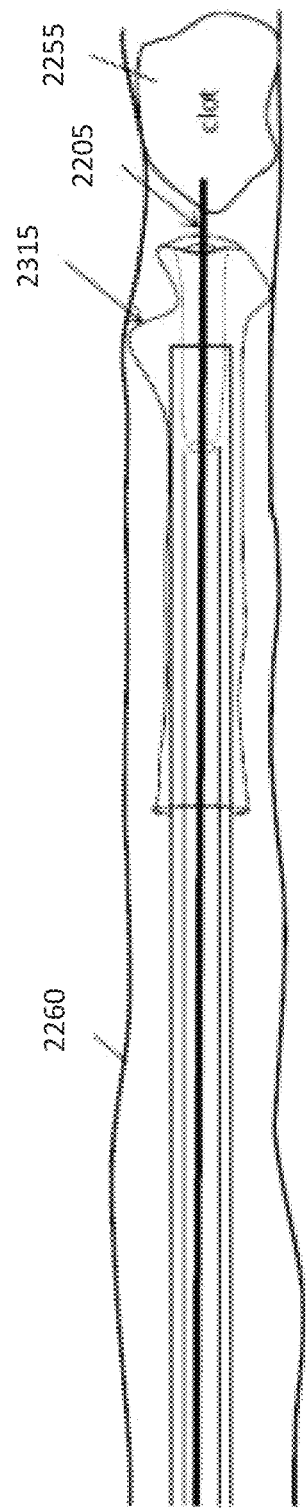

An example of premature deployment is shown in FIGS. 53A-53C. For example, in FIG. 53A, the tractor 2200 is guided over a guidewire 2205 to a clot 2255 (alternatively, the apparatus may be delivered without using a guidewire). In this example, the apparatus includes a tractor 2203 that extends over and into a catheter 2210. The inner end of the tractor is connected to a puller 2207 (shown in this example as an inner catheter). The outer end 2211 of the catheter is loose and is shown slightly expanded over the catheter outer diameter. As the apparatus is advanced distally towards the clot, shown in FIG. 53B, the tractor is, by virtue of being deployed, driven into the catheter prematurely, shortening the length of the tractor that is outside of the catheter and available to roll for capture of the clot. Further, the loose outer end of the tractor may interfere with accurate positioning of the apparatus. FIG. 53C illustrates the premature deployment compromising the rolling of the tractor 2315. Once the tractor is prematurely deployed, moving it back and forth in the vessel to position it may result in the tractor, which may contact the vessel wall when deployed, folding or tangling, as shown in FIG. 53C.

In general, the apparatuses described herein are configured to prevent premature movement of the tractor on an outside, e.g., outer diameter, of the catheter during catheter access to a target location.

Any of the variations described herein may include a tractor hold that includes a sticky, tacky, gummy, or adhesive material on the tractor or between the tractor and the catheter over a portion of the tractor that is held against the outer diameter of the catheter. For example, as illustrated in FIGS. 55A-55C, the apparatus may include a sticky substance, like silicone, impregnated on the end of the tractor that is wrapped over the catheter (e.g., the outer end of the tractor, which may be referred to as the proximal-most most end of tractor). The sticky material may impregnated over a small portion of the tractor (e.g., local regions at or near the proximal end and/or discrete regions, or patterns including spots, bands, etc. along the length of the outer portion of the tractor. The presence of the sticky regions may prevent premature slipping of the tractor (e.g., braid, woven, etc.) with respect to the catheter. For example, a silicone impregnated braid may sit on or over a section of the catheter that is not coated with a hydrophilic coating before the tractor is pulled around distal end opening of the catheter, which may help prevent the tractor from prematurely slipping off or over the catheter. As mentioned, a sticky (e.g., tacky, adhesive, gummy, etc.) region may be present on the entire tractor, on just an inside surface of the tractor (e.g., the surface that faces the catheter when applied over the outer diameter of the catheter), on both inner and outer surface of the tractor, and/or in discrete locations (including patterns) of the portion of the tractor outside of the catheter. For example, the apparatus may include a plurality of regions of sticky material arranged over the length of the proximal end of the tractor. In some variations the sticky material is arranged in a pattern. The material applied may be referred to as sticky with respect to the catheter (e.g., causing temporary and/or releasable attachment between the catheter and the tractor). In some variations, the sticky material may be coated or applied to the outer diameter of the catheter. When arranged in a pattern (e.g., on the tractor and/or OD of the catheter), the pattern of sticky material locations on the tractor (and/or catheter) may be arranged in multiple, non-contiguous locations along the length or the tractor. Patterns may include stripes, spirals, rings, spots, etc.

Alternatively or additionally, the tractor may be temporarily secured to the outside of the catheter through other methods to provide a temporary attachment of the tractor to the catheter outer diameter (OD). For example, a temporary attachment may be presented between the tractor and the catheter OD such that, when axial tension if applied to the tractor, e.g., by the user pulling the tractor to pull the tractor around catheter tip, the temporary attachment (e.g., a temporary bond, temporary securement, etc.) between the tractor and the catheter OD may be released, allowing the braid to slide relative to the catheter. Alternatively or in addition to the use of a sticky material between the tractor and the catheter, temporary attachments between the tractor and the OD of catheter may include: hydrophilic coatings on the tractor and/or catheter, and/or spot (including micro-spot) boding between the catheter and the tractor.

For example a hydrophilic surface on the tractor (e.g., inner face of the tractor) and/or catheter OD may be applied as a coating. The tractor may be pre-assembled onto the catheter and a hydrophilic/hydrophobic surface may provide a temporary attachment between the catheter and the tractor. A layer of hydrophilic coating (or two adjacent layers) may secure the tractor to the catheter OD, and may help the apparatus track through a body vessel/lumen to the target location, after which the tractor may be deployed by pulling to separate the surfaces of the tractor and catheter OD, and to allow the tractor to roll over the distal end opening freely so that it may engage with a clot and draw it into the apparatus. In some variations, a hydrophilic coating may be separately applied to the tractor and/or the catheter. For example, the catheter OD and tractor may be separately coated with a hydrophilic coating and then assembled. When the apparatus is assembled (e.g., with the tractor over catheter distal end region, inverted and within the catheter), the coating on both subassemblies (e.g., tractor and catheter) may cold flow together. When the assembly is wetted in the body during catheter access and when approaching the target clot to be removed, the user may pull the tractor proximally (by pulling on the puller attached to the inner end of the tractor) which may slide the tractor with respect to the catheter OD, disengaging the tractor hold.

Alternatively the tractor hold can be formed by spot- or selectively bonding the tractor to the catheter OD. A spot or micro-bond may be adequate to prevent premature sliding of the tractor relative to the catheter OD during catheter access. For example, a spot bond or a plurality of micro-bonds can be created, e.g., by heat bonding (melting) or applying adhesive to attach the tractor to the catheter OD. The micro bonds can be placed circumferentially at several locations along the length of the braid, continuously along the braid/catheter contact length or in any other pattern, as discussed above.

FIG. 55A illustrates an example of a thermoplastic polyurethane (TPU) 2404 that may be used to temporarily secure the tractor 2406 to the outer diameter of the catheter; once in position, the distal end of the catheter (internal to the catheter) may be pulled proximally to break the material (in this example, pellathane) and release the tractor so that it may be rolled distally over the catheter to draw a clot into the catheter. In this example, the frangible (e.g., breakable) material is coated over a region on the catheter and/or tractor (shown here as a braided tractor) that does not include a hydrophilic coating). For example, the frangible material may be applied over a region that is masked (uncoated) from hydrophilic coating.

In FIGS. 55B and 55C, examples of mechanical thrombectomy apparatuses 2400, 2400' are shown, each having an outer catheter 2409, and a tractor that extends over the distal end region of the catheter, and inverts over the distal end opening (annulus 2411) of the catheter, and into the catheter where it connects to a puller 2407. In FIG. 55B, the tractor is releasably adhered to the outer diameter of the catheter by a sticky (e.g., hydrophilic) region 2414 that engages the outer end of the tractor to a region on the outer diameter of the catheter. Thus, in order to pull the tractor proximally within the catheter and therefore roll the tractor over and into the distal end opening as described above (and shown, e.g., in FIG. 54C), an initial deployment force threshold (e.g., between 0.5 N and 50 N) may be required. Once the force is applied and the tractor is deployed to axially move distally over the outer surface, roll, invert and into the catheter, the force required to continue rolling may be substantially (e.g., the deployment force threshold may be 1.1×, 1.2×, 1.5×, 1.7×, 2×, 3×, 4×, 5×, 10×, or more the force required to roll the apparatus).

Similarly, in FIG. 55C, the apparatus may include a plurality of spot attachments 2424 at the outer end of the tractor. As mentioned, there spots may be an adhesive attached into (e.g., into the mesh, etc.) of the tractor, or between the tractor and the outer diameter of the catheter. In both FIGS. 55B and 55C, the tractor may be held slightly in tension over the distal end region of the catheter, preventing the tractor from deploying and expanding, including expanding at the distal tip region (forming the trumpet-shaped opening such as shown in FIGS. 53A-53B).

Figure 54A:
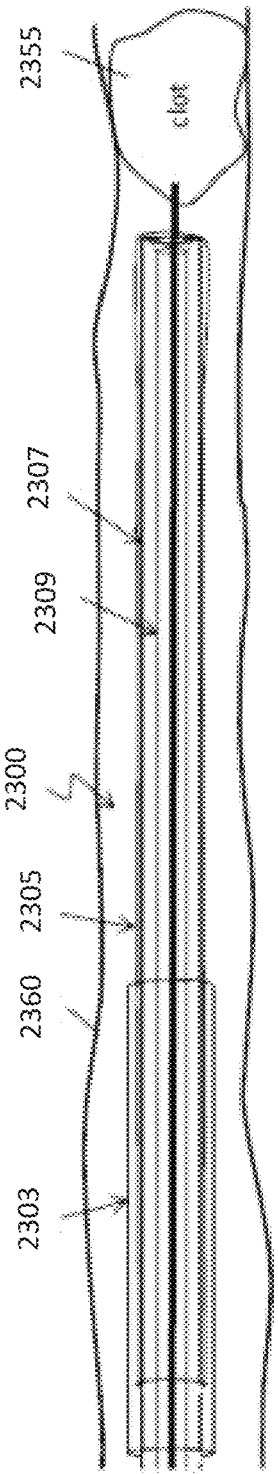
FIGS. 54A-54C illustrate a method of operating a mechanical thrombectomy apparatus that includes a tractor hold to prevent premature deployment.
Figure 54B:
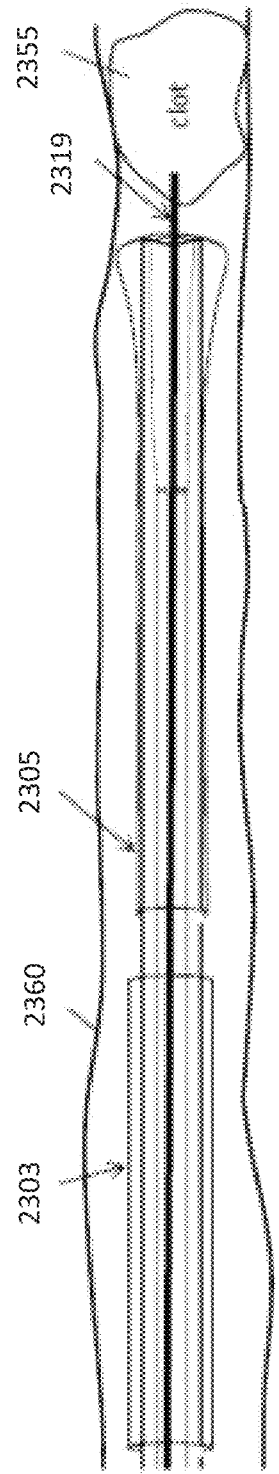
Figure 54C:
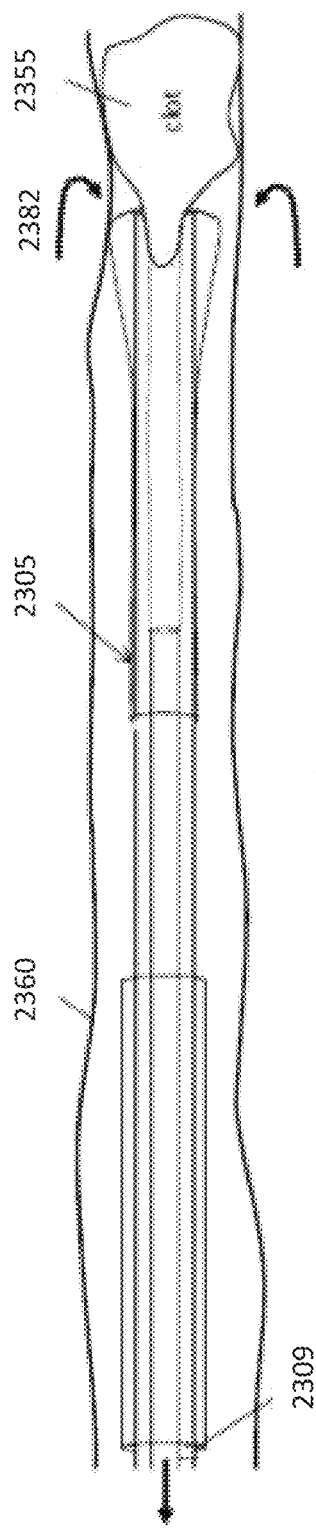

Alternatively or additionally, any of the apparatuses described herein may include a tractor hold that is configured as a housing or garage for holding the outer end of the tractor, as shown in FIGS. 54A-54C and FIGS. 56A-56C. In these examples the tractor hold extends only partially down the catheter, which may prevent the hold from increasing the flexibility and maneuverability of the apparatus in the lumen. FIGS. 54A-54C illustrate the method of use of a variation of a mechanical thrombectomy apparatus 2300 including a tractor hold 2303. In this example, the tractor hold is positioned over the catheter, as shown in FIG. 54A, and holds the outer end of the tractor 2305 against the outer diameter of the catheter 2307. The tractor is connected to the puller 2309. The tractor hold may be attached to the catheter (e.g., at a proximal end of the hold) or it may be applied over the catheter (e.g., shrink-wrapped over the catheter and the outer end of the tractor. The apparatus 2300 may be guided over a guidewire 2319, as shown, or it may be directed to the clot 2355 within the vessel 2360 without the use of a guidewire.

Once the distal end of the apparatus is near the clot, as shown in FIG. 54A, a force greater than a deployment threshold force (e.g., the force required to pull the tractor out of the tractor hold 2303, leaving the tractor hold behind, and allowing the tractor to roll 2382 over the distal end opening of the catheter, as illustrated in FIG. 54C. The apparatus may be advanced distally while pulling the inner end of the tractor proximally with the puller to invert and roll the tractor into the catheter. The tractor may then grab a clot and pull it into the catheter, as shown.

Figure 56A:
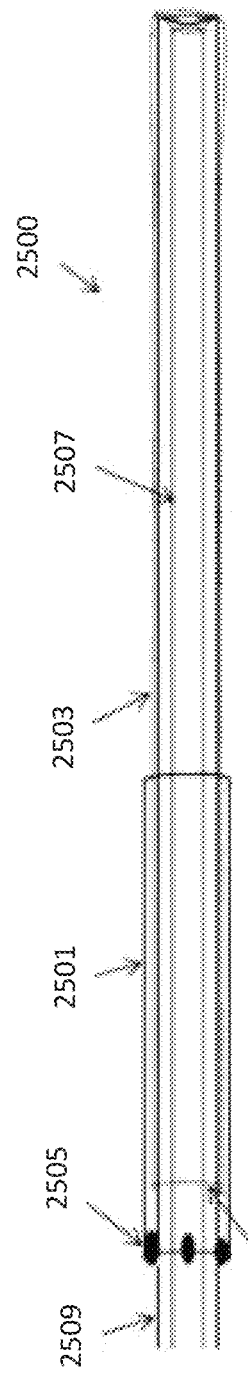
FIGS. 56A-56C illustrate examples of mechanical thrombectomy apparatus including a tractor hold as described herein.
Figure 56B:
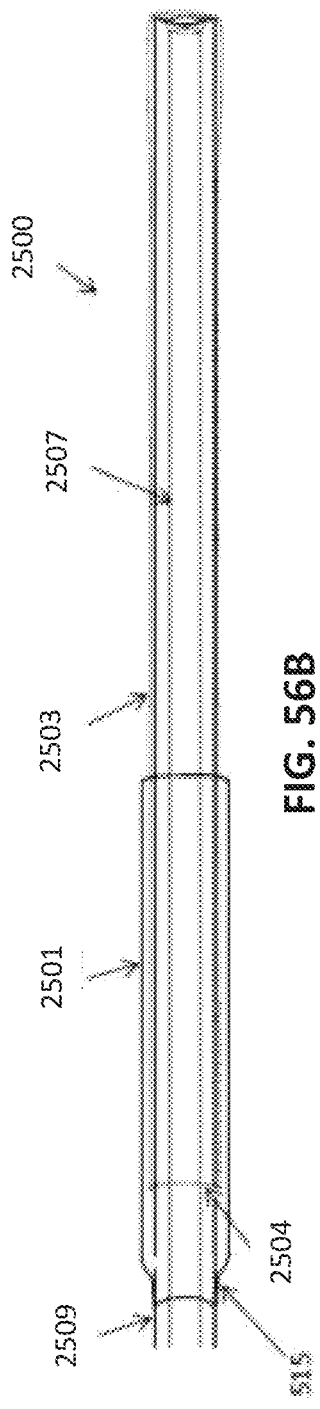
Figure 56C:
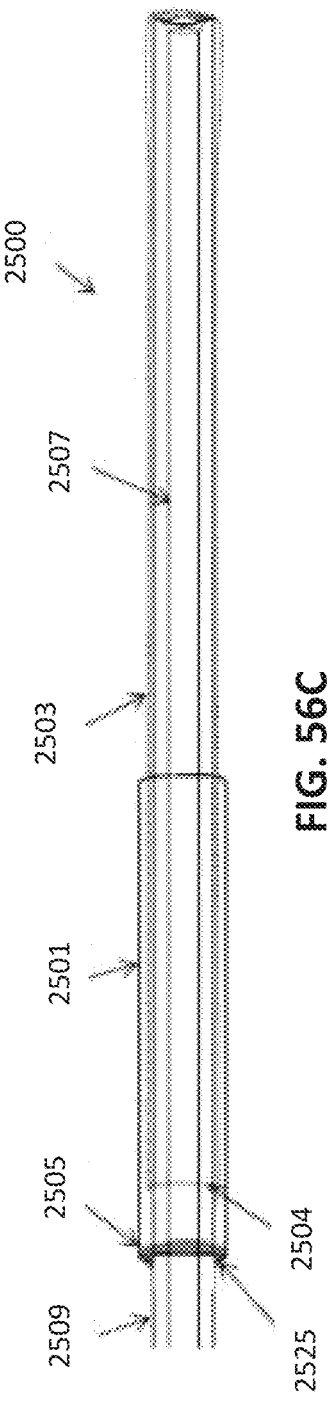

Similarly, in FIGS. 56A-56C, the apparatus 500 includes a tractor 2503 coupled to a puller 2507 at an inner end that is within a catheter 509. In this example, the outer end 2504 of the tractor is pinned against the outer diameter of the catheter by a tractor hold 2501 configured as a garage or housing. The housing may hold the end of the tractor lightly or it may secure it against the catheter more tightly, depending on the desired deployment threshold. In FIG. 56A, the tractor hold is secured to the outer diameter of the catheter by a weld or welds 505. Similarly in FIGS. 56B and 56C the tractor hold is secured by either being shrunk-fit to the outer diameter at the proximal end 2515, or by an adhesive or glue 2525, respectively.

In all of the examples shown in FIGS. 54A-54C and 56A-56C, the tractor hold extends only slightly down the length of the catheter, e.g., a few cm (e.g., less than 10 cm, less than 9 cm, less than 8 cm, less than 7 cm, less than 6 cm, less than 5 cm, less than 4 cm, less than 3 cm, etc.).

Figure 57A:
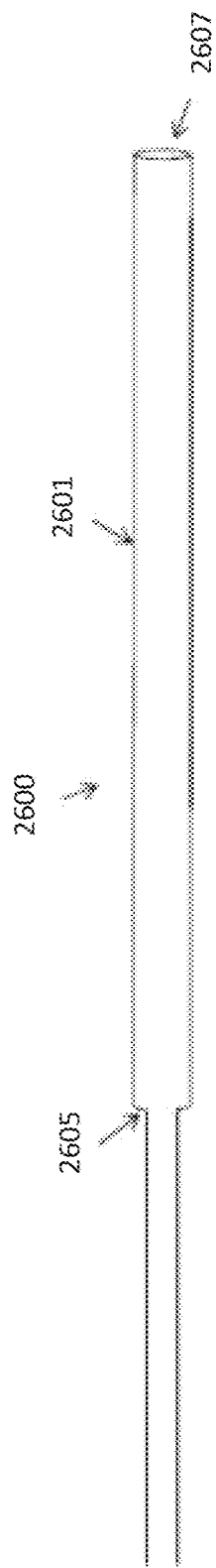
FIG. 57A illustrates a catheter for a mechanical thrombectomy apparatus with an outer diameter that steps up from a first proximal outer diameter to a second, larger distal outer diameter.
Figure 57B:
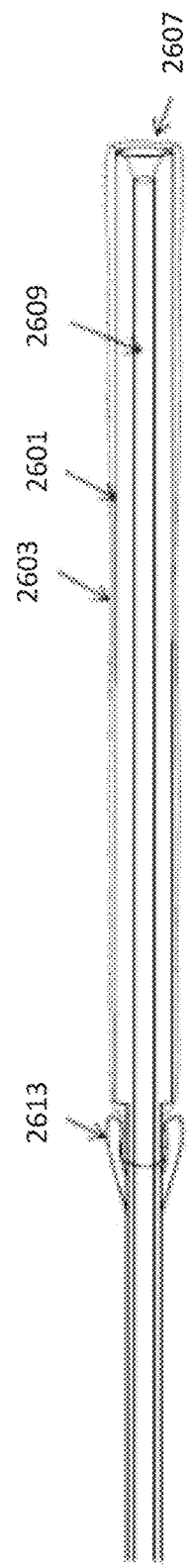
FIGS. 57B-57D illustrate the catheter of FIG. 57A as part of different mechanical thrombectomy apparatuses having tractor holds that secure the tractor to the catheter.
Figure 57C:
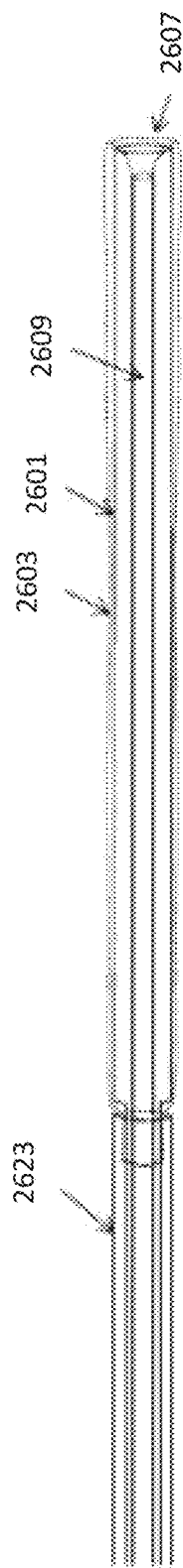

In any of the variations described herein, the elongate inversion support may have a different outer diameter along its axial (longitudinal) length. For example, although the catheter shown in FIG. 1A has a uniform diameter along its length, other apparatuses may include a catheter having a larger diameter at the distal end region than at more proximal regions, as shown in FIGS. 57A-59C. For example, in FIG. 57A, the elongate inversion support is a catheter having a larger outer diameter at the distal end than at the proximal end. The transition between the two regions is a step 2605. The annular region (distal end opening 2607) therefore has the same, larger, outer diameter as the distal end region. FIGS. 57B-57C, illustrates examples in which a tractor is held over the outer diameter and may be secured by a tractor hold. In general, particularly where the tractor is configured to contract down onto the tractor, simply having the transition, and particularly a rapid (including step) transition between a region of larger diameter and a region of smaller diameter, as shown in FIG. 57A, may help secure the tractor over the catheter. In FIG. 57B, the same catheter shown in FIG. 57A has had a tractor 2603 attached so that it extends along the distal outer diameter region, inverts over the distal end opening 2607, and into the catheter inner lumen, where it is connected to or integral with a puller 2609. In FIG. 57B, the outer end of the tractor is held in place with a tractor hold 2613; in this example, the tractor hold 2613 is one or more arms that hold the tractor against the smaller inner diameter immediately adjacent to the step up to the larger diameter region of the catheter.

In FIG. 57B, the tractor hold is a narrower catheter that extends proximally; the tractor is held between the distal opening of the tractor hold and the step up to the larger diameter catheter 2601. The outer surfaces of the tractor hold and the catheter 2601 may be flush, e.g., having the same height. In FIG. 57B, if the tractor hold extends proximally far enough (e.g., to or beyond the end of the catheter) it may be actively disengaged, reducing or eliminating the deployment threshold force.

Figure 57D:
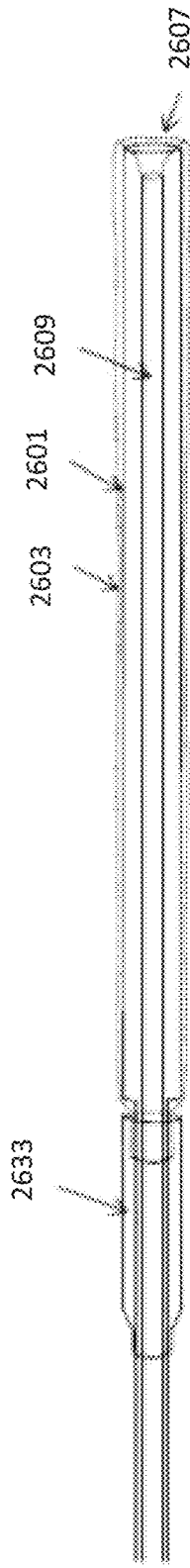

FIG. 57D shows another example of a tractor lock 2633, similar to that shown in FIG. 57C, only extending partially proximally down the catheter. In any of these variations the tractor hold may be fixed to the outer diameter or it may be movable (e.g., slideable) relative to the outer diameter of the catheter.

Figure 58A:
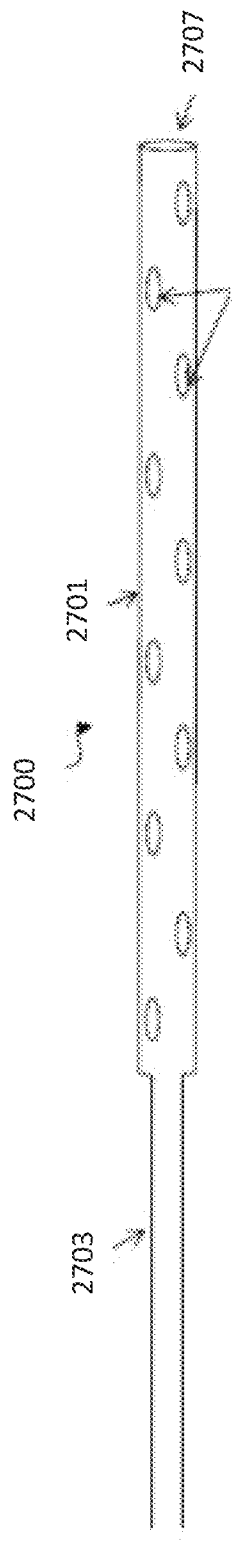
Figure 58B:
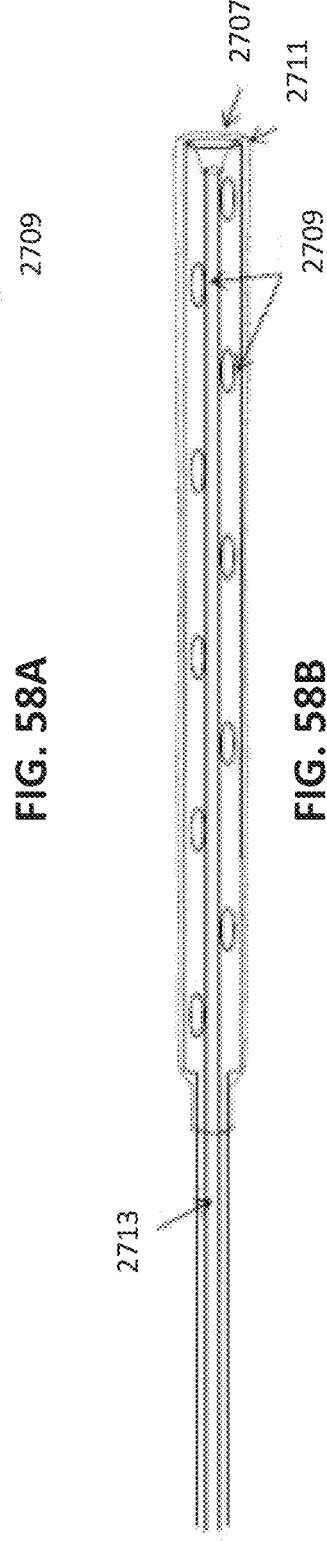

FIGS. 58A-58L illustrate different variations of catheters that may be used as part of any of the apparatuses described herein. For example, FIG. 58A shows an example of a catheter 2700 having a larger-diameter distal end region that also includes a plurality of openings, slots, holes, windows, slits, etc. 2709. These openings may provide for delivery of fluid (including drugs) to the site of use, and/or removal of material, e.g., the application of vacuum through the apparatus, particularly useful when used with an intermediate catheter into which the apparatus (e.g., an elongate inversion support, a puller and tractor) is inserted, as will be described in greater detail below. FIG. 58B shows the apparatus of FIG. 58A with an attached puller and tractor.

Figure 58C:
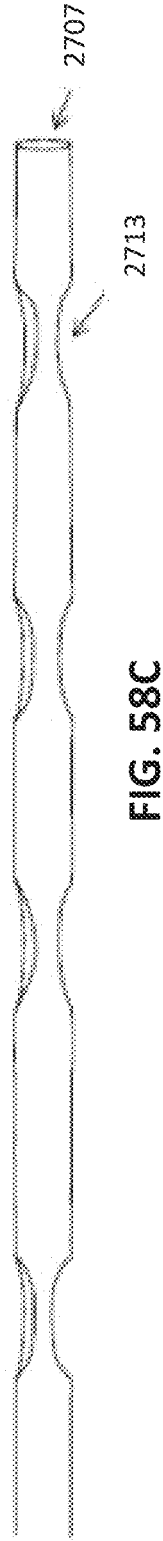
Figure 58D:
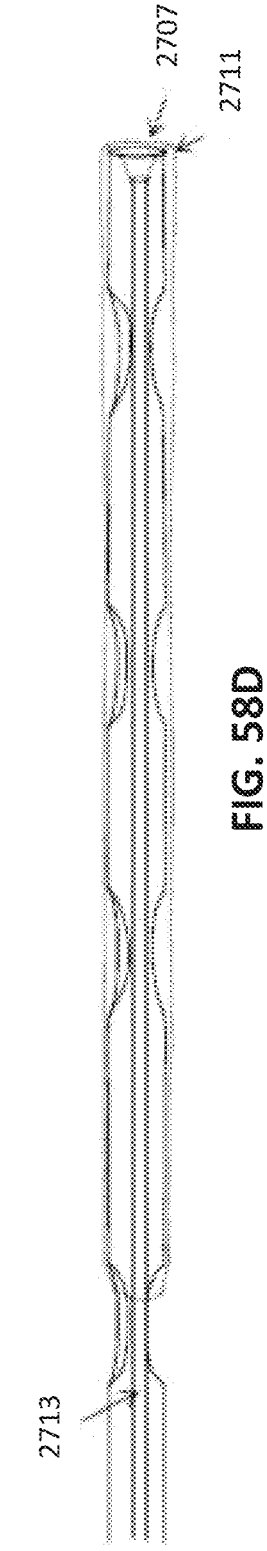

FIGS. 58C and 58D illustrate another variation of a catheter that may be used as part of any of the apparatuses described herein, including, as here, catheters that have a plurality of cut-out regions. Similarly, FIGS. 58E and 58F show an example including a catheter having a large proximal skive region, leaving the majority of the outer diameter much smaller than at the distal end region, as shown. In addition, the distal end of the catheter may include openings, slots, cut-out regions, etc. 2725. FIG. 58F shows the catheter of FIG. 58E with a tractor 2714 coupled on an inner end to a puller 2713. The puller is still pulled within the lumen of the catheter. A similar example is shown in FIGS. 58G and 58H, however instead of being skived, the elongate inversion support includes a distal portion formed of a catheter having cut-out regions 2725 that is coupled to a rod, pole, wire or (as shown) a hypotube. This hypotube may be used as a guidewire lumen and/or as a channel for a stiffening or support member that may, once the device is positioned, enhance the column strength to allow pulling of the tractor proximally when inverting the tractor to roll.

Figure 58I:
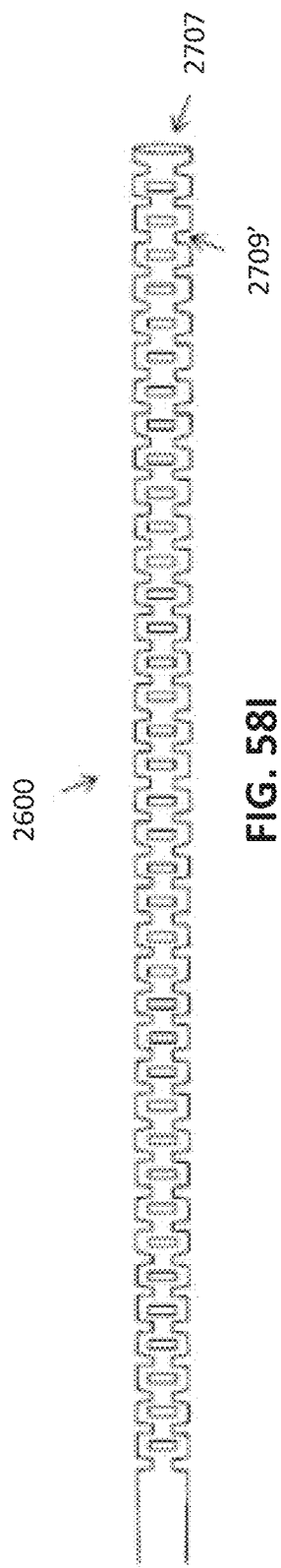
Figure 58J:
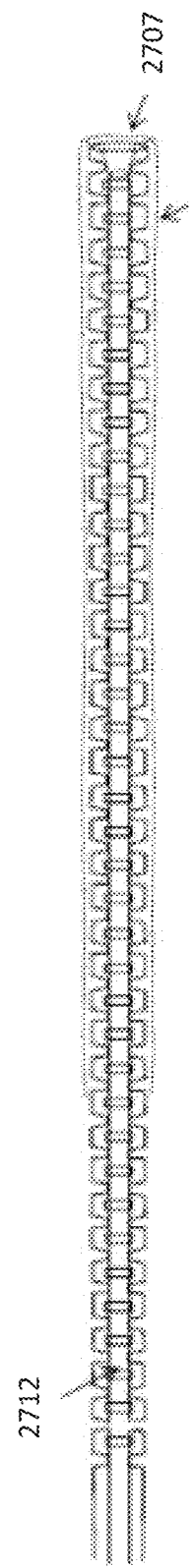

FIGS. 58I and 58J illustrate an example of a catheter (FIG. 58I) and an apparatus including the catheter (FIG. 58J) in which the sides of the catheter have been slotted, which may provide enhanced flexibility while maintaining column strength. An apparatus including the catheter of FIG. 58I is shown in FIG. 58J, also including a tractor and puller.

Figure 58K:
Figure 58L:
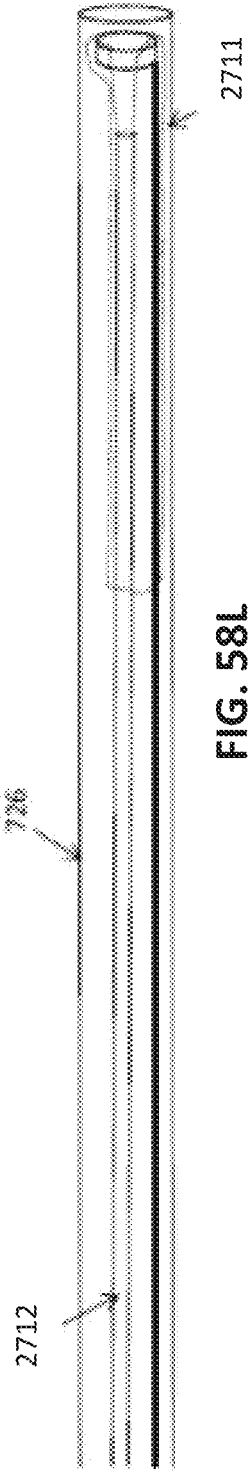

FIG. 58K is an example of an elongate inversion support in which the distal end is a cylinder 2716, formed, for example, from a very small portion of a catheter. The distal end opening (annulus 2707) may be used to invert the tractor, as shown in FIG. 58L. The elongate shaft 2717 of the elongate inversion support may be a rod, tube, wire, etc. as described above. An additional outer catheter 2726 may be included in any of these apparatuses, as shown in the exemplary apparatus shown in FIG. 58L, which includes the elongate inversion support of FIG. 58K.

Figure 59A:
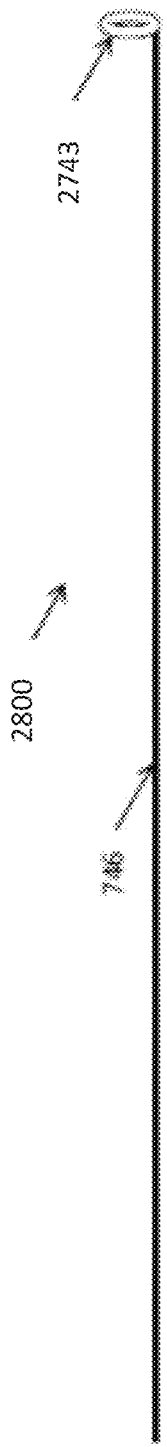
FIGS. 59A-59D illustrate another example of an elongate inversion support that may be used as part of a mechanical thrombectomy apparatus.
Figure 59B:
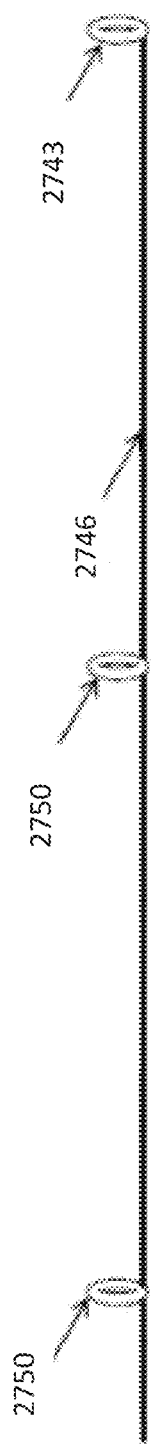
Figure 59C:
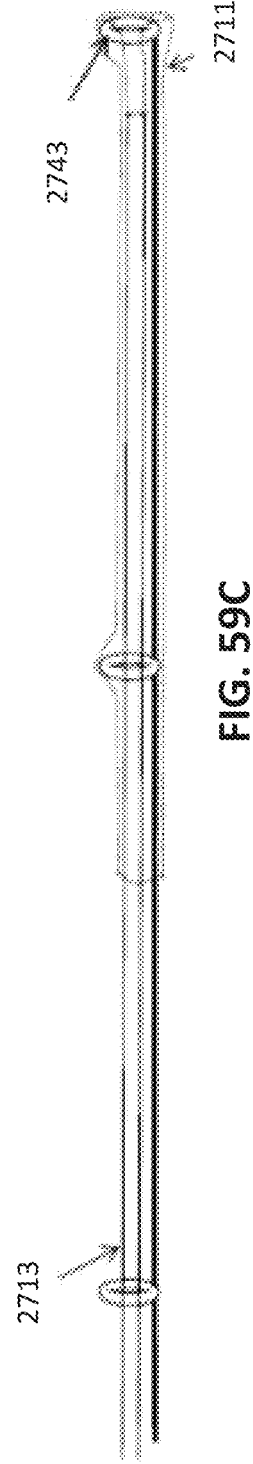
Figure 59D:
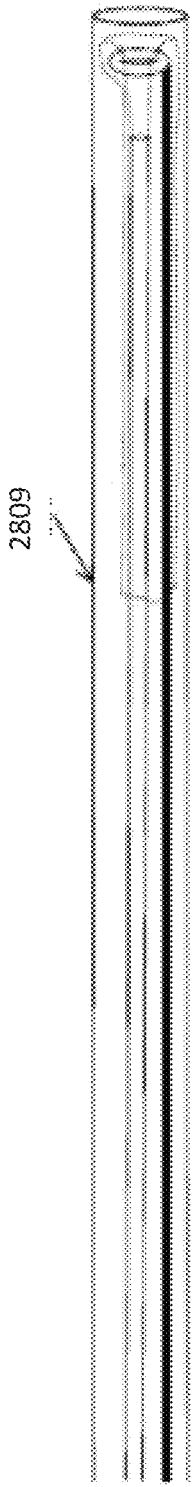

FIGS. 59A-59D also illustrate another example of an elongate inversion support having a distal annulus or aperture 2743, shown in this example a ring (e.g., toroid ring) bonded to a hypotube 2746 (which may alternatively be a rod, wire, small-diameter catheter, etc.); as mentioned above, a stiffening member may be inserted into the elongate body of the elongate inversion support prior to or during pulling of the tractor proximally through the distal annulus. FIG. 59B shows a similar variations of the elongate inversion support of FIG. 59A, only with a plurality of guides 2750 extending down the length of the support into which the tractor puller and/or tractor may be held, as illustrated in FIG. 59C. In this example, the tractor 2810 extends over the elongate inversion support and can be pulled proximally by the tractor puller 2812. Although the tractor puller is shown as a catheter, in any of the apparatuses described herein, the tractor puller may instead be a wire, hypotube, etc. as mentioned above. FIG. 59D is an apparatus similar to that shown in FIG. 59C with the addition of an outer catheter 2809.

Releasable Lock

Figure 61A:
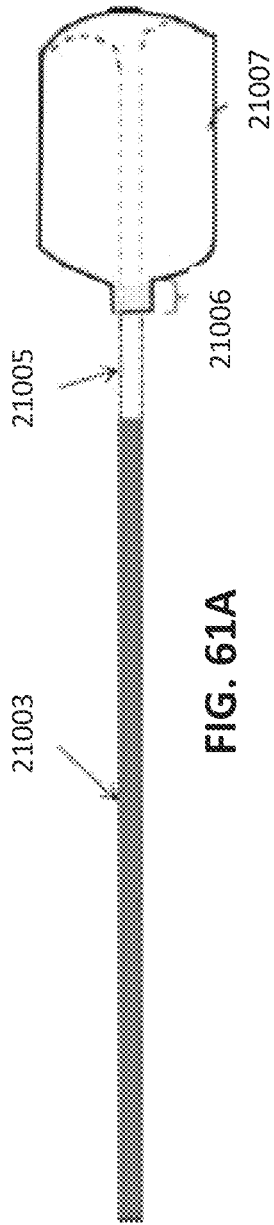
FIGS. 61A-61C illustrate an example of a mechanical thrombectomy apparatuses having a tractor hold configured to engage a tractor lock on the tractor.
Figure 61B:
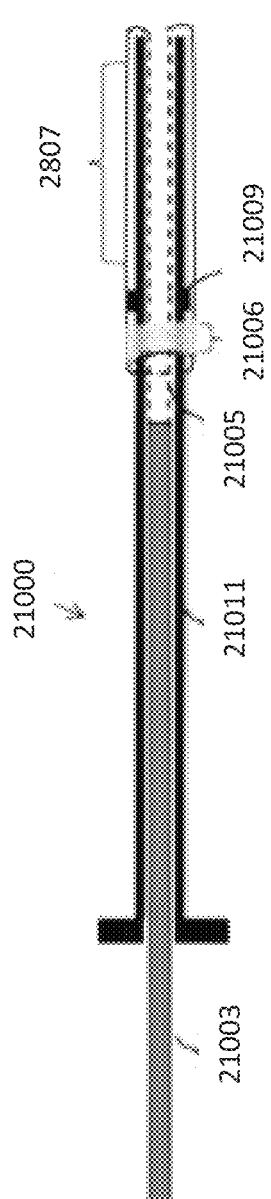
Figure 61C:
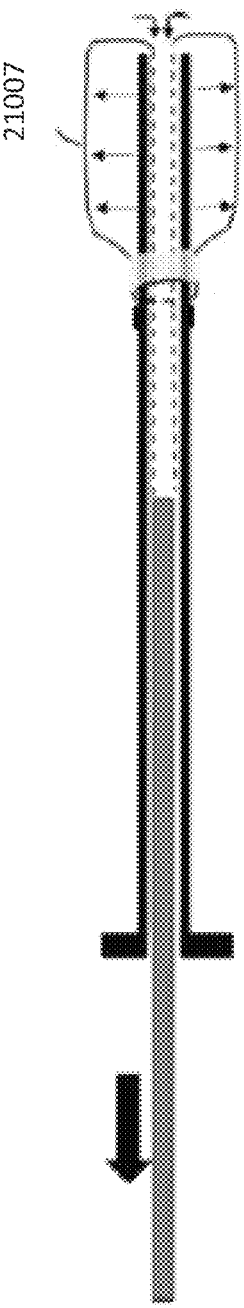

In some variations, the tractor hold and distal end region of the catheter to which it is applied over may be configured as (or may include) a releasable lock, in addition to or instead of the tractor holds described above (e.g., a sticky materials, frangible release, housing, etc.). For example, the catheter may include a tractor hold comprising a friction lock (e.g., bump, protrusion, enlarged diameter, region, O-ring, etc.) on the outer diameter of the catheter that engages with a locking region (e.g., construction, inward-pointing bump, sticky coating, etc.) on the outer (e.g., proximal) end region of the tractor. The locking region on the outer end portion of the tractor may be proximally beyond the locking region (e.g., friction bump) on the catheter, so that the catheter locking region may be initially held beneath the tractor. When force is applied (e.g., deployment force applied by the user) to pull the tractor region proximally from the inside of the tractor, the force may overcome the locking engagement between the tractor locking region (e.g., constriction, inwardly-facing protrusion, etc.) and the locking catheter locking region (e.g., friction bump, radial enlargement, O-ring, etc.) and the tractor may be released roll distally over the catheter. See FIGS. 61A-61C for an example of this arrangement. Note that this releasable lock may be used in combination with any of the features described above. In FIG. 61A-61C, the tractor 21007 includes a tractor lock 21006 at the outer end of the tractor. FIG. 61A shows just the tractor and puller 21003. The mechanical thrombectomy apparatus 21000 shown in FIG. 61B also includes a catheter 21011, and the catheter includes a tractor hold 21009. The tractor hold engages with the tractor lock; in FIG. 61B, the tractor hold is a protrusion that holds the tractor lock on the tractor on a proximal side of the tractor hold, until sufficient force is applied above the deployment threshold to deploy the tractor by pulling the tractor lock distally over the tractor hold, allowing the tractor 21007 to deploy and/or expanded, and be rolled over the distal end opening of the catheter, to capture a clot.

In any of these variations, but particularly the locking variations described herein, the tractor region may be held in tension, although tension is not necessary. Alternatively or additionally, a second outer cover or catheter may be used, or may be absent.

Apparatuses Having Distal-Extending Pullers

In any of the variations described herein, the puller may extend more distally than the tractor in the apparatus. For example, a pre-assembled apparatus having the distal end of a tractor puller (e.g., catheter, hypotube, wire, etc.) that extends more distally beyond the catheter(s) or the rest of the apparatus may be used to help capture the clot. As mentioned above, any of these variations may include the use of a vacuum, e.g., for aspirating the clot. The vacuum may be applied through the puller. It may be easier to grab onto a clot when using aspiration to initiate the grabbing.

Figure 60A:
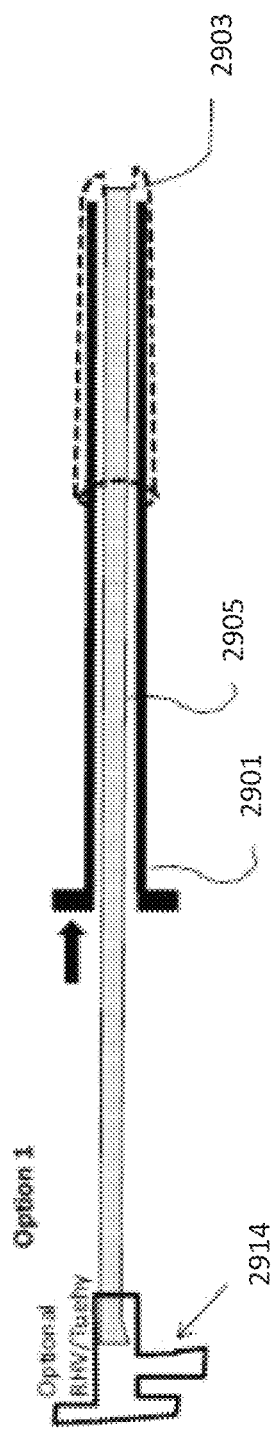
FIGS. 60A-60C illustrate mechanical thrombectomy apparatuses, including apparatuses having pullers that may extend distally of the catheter (FIGS. 60B and 60C).

For example, FIG. 60A illustrates an example of a mechanical thrombectomy apparatus similar to that described above. The tractor 2903 is connected to a puller 2905 and the tractor extends along the outer diameter 2901 of the catheter. In some variations, the tractor may be infused, bonded or laminated with a stiffening element in part to make it less likely that the tractor collapses in diameter when the dozer catheter is pulled and allows for vacuum applied to the applied to the proximal end of the tractor puller 2905 to exert force/vacuum on the clot via the distal end of the assembly, as shown in FIGS. 60B and 60C.

Figure 60B:
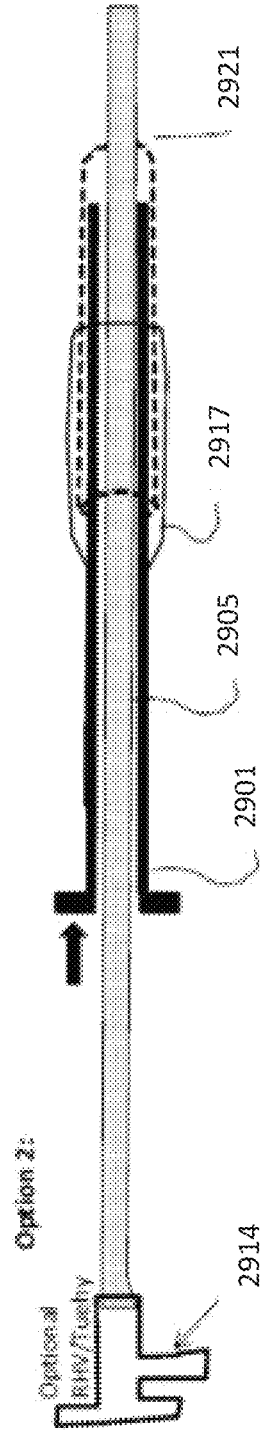

In FIG. 60B, the tractor is coupled to a portion of the tractor puller 2905 that is proximal 2921 to a distal end of the puller. Thus, as the puller is extended distally, the tip may extend past the distal end of the catheter, prior to inverting the tractor. FIG. 60B also shows an (optional) tractor hold 2917

Figure 60C:
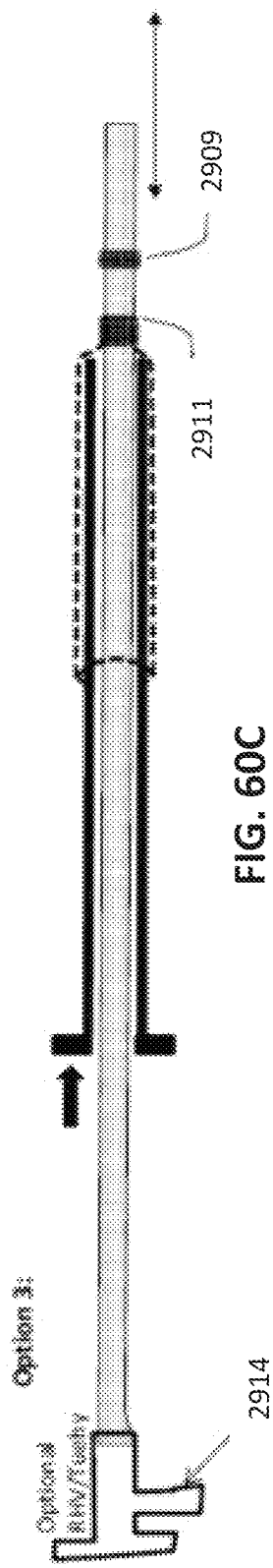

In FIG. 60C, the apparatus includes a stop element attached at or near the distal end of the puller 2905. A sliding ring 2911 on the tractor may be used to allow the puller to slide distally without pulling on the tractor; only when the puller is withdrawn proximally far enough that the stop 2909 engages with the sliding ring 2911 does the puller pull the tractor proximally, and invert the tractor over the distal end opening of the catheter, rolling the tractor an pulling in any clot material, which may be aided by the application of vacuum 2914 through the puller. Thus, this arrangement may allow the user to extend the tractor puller distally at lengths beyond the distal end of the catheter without pulling the tractor distally.

In any of the variations described herein, including those shown in FIGS. 60A-60C, the apparatus may be coupled to a valve 2923 for connection to a vacuum source 2914. The vacuum may be connected to the elongate inversion support (e.g., catheter) and/or to the puller, as shown in FIGS. 60A-60C.

Any of the apparatus variations described herein may include a lubricous coatings such as hydrophilic coatings applied on the OD &/or ID of the tractor, on any and all sections, and/or on the outer or inner diameter of the elongate inversion support (e.g., catheter).

In general, the apparatuses described herein may allow delivery of a guidewire and/or a smaller catheter through the outer catheter and tractor, which may be useful for both guidewire operation (for clot access) and also for applying optional vacuum. In addition, the tractors described herein may have minimal to no collapsing when they are inverted inside the outer catheter when under axial tension, which may prevent jamming on the catheter distal tip and may reduce the amount and/or volume of clot that can be extracted. Further, any of the tractors described herein may have adequate coarseness to grab the clot, yet still roll smoothly around the distal annulus. Typically, the tractor does not adversely affect catheter tracking, as it may be extremely flexible and slippery.

As just discussed above, the pre-loaded tractors described herein may not slide with respect to the OD of catheter during vessel access. The tractor may only slide on the OD of catheter when the user pulls the tractor puller.

In general, the user may advance the elongate inversion support (e.g., catheter) forward while holding the tractor puller fixed, thereby enveloping clot in place rather than pulling clot to catheter. Further, the tractor may be biased (e.g., heat-shaped) to a preferred configuration to help grab clot effectively and roll nicely around the catheter tip. In general, the distal end of the catheter (tip) may be stiffer than the catheter section just proximal to the tip (to allow rolling of dozer around tip). The tip may include a lubricious coating. The catheter tip may have a radius of >0.00025", >0.00035", >0.0004", >0.0004", >0.00025", or <0.0005" to allow rolling of tractor more easily. For example, the catheter tip hardness may be greater than >72D, and/or may be formed of a polymeric material such as PTFE, nylon, PEEK, stainless steel, etc.

In some variations, the distal region (e.g., distal 5 cm, 10 cm, etc.) of the catheter allows for tracking through ⅛" diameter radius and also has a limited axial compress to <10% of the distal catheter length during axial compression loads of, e.g., 100 g, 200 g, and 300 g, etc. when pulling in the dozer and grabbing clot.

As mentioned above, any of these apparatuses may allow for the delivery of guidewire and/or smaller catheter through aspiration catheter. In general, the tractor may be configured to have a Poisson ratio <1.5 (e.g., <1.2, <1.1, etc.) when under tension (this helps prevent the tractor from jamming on catheter tip).

In any of the variations described herein, the tractor and/or catheter may be radiopaque. For example, a band or region may be radiopaque. The entire tractor may be radiopaque, e.g., NiTi wire filled with PT or Tantalum (DFT wire) may be used to form the tractor. Alternatively, the proximal and/or distal end of the tractor may have radiopaque markers.

The apparatuses described herein may be used to remove materials such as clots, including to prevent or treat stroke. For example, the apparatuses described herein may be used to track up through the siphon of the carotid artery, which is typically highly tortious. When pulled, the tractor may roll around the catheter distal end without locking up, while still grabbing clot. As mentioned, any of these apparatuses may also work in combination with a vacuum. The use of a vacuum may be unnecessary, but may be beneficial, particularly when initially engaging the clot with the tractor region and/or the distal end of the catheter. Any of the apparatuses described herein may also be configured to grab a clot in a large variety of vessels, including those ranging from 1.5 mm to 3.5 mm, even when the catheter has approximately the same outer diameter as the inner diameter of the vessel, or where the catheter is otherwise corked in the vessel.

Apparatuses Adapted for Use with Aspiration

As mentioned, any of the apparatuses described herein may be adapted for use with a vacuum to apply suction (e.g. aspiration) to assist in clot removal. Although the device may be used without the use of aspiration, in some instances clot removal may be aided by the use of the mechanical atherectomy apparatuses described herein. Furthermore, traditional techniques for removing a clot using aspiration (e.g., using a simple flexible catheter, commonly referred to as an intermediate catheter) may be improved by the use of the mechanical atherectomy apparatuses described herein. Use of aspiration alone often results in clogging of the intermediate (aspiration) catheter and may therefore have trouble removing the entire clot, particularly in the tortious vessels. Any of the apparatuses described herein may be used with an intermediate catheter, and may be adapted for use with vacuum clot removal technique, including being adapted to permit vacuum to be applied while the apparatus is within the lumen of the intermediate catheter, so that aspiration may still be applied from the distal end of the intermediate catheter and/or the apparatus, as well as permitting aspiration to be applied while the apparatus is extended distally from the intermediate catheter. The applied vacuum may aid in initially gasping or grabbing the thrombus. The vacuum may be applied from the distal end of the apparatus and/or of an intermediate or outer catheter or sleeve that is used with the apparatuses (e.g., elongate inversion support and inverting tractor). Also described herein are apparatuses that are adapted for use with a vacuum, including for use with an intermediate or outer catheter through which the apparatus may be delivered to the clot. The apparatus may grab clot from within the outer catheter, or it may be extended distally out of the intermediate or outer catheter. For example, FIGS. 7A-8D, described above and in additional detail below, are examples of elongate inversion supports that may be used in any of the apparatuses described; these elongate inversion supports may be particularly well suited to applying aspiration from the intermediate catheter.

Figure 62A:
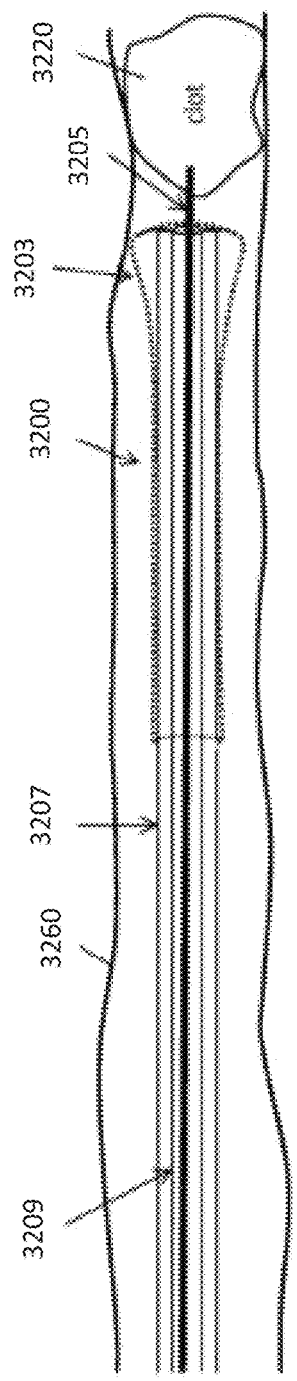
FIGS. 62A-62G illustrate a method of capturing a clot with a rolling mechanical thrombectomy apparatus after it has jammed or clogged the catheter of the rolling mechanical thrombectomy apparatus.
Figure 62B:
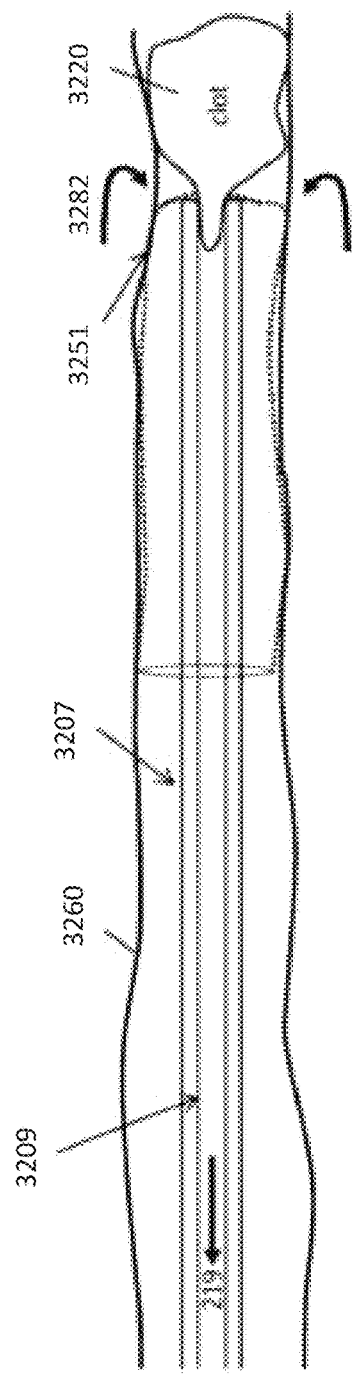

As mentioned, a full catheter such as shown in FIG. 62A may block or prevent the vacuum from reaching the distal end of the intermediate vessel. Therefore it may be beneficial to adapt the mechanical thrombectomy apparatus so that it can be used with vacuum within an intermediate catheter or sleeve, as shown in FIG. 62B. This may be achieved as mentioned above, by minimizing the larger-diameter catheter portion of the elongate inversion support forming the distal end opening over which the tractor inverts. Returning now to FIGS. 58A-59D, in FIG. 58A, the elongate inversion support 2700 has a distal catheter portion 2701 having a larger diameter than the more proximal region 2703, and also includes a plurality of openings, holes, gaps, cut-out regions, slots, etc. 2709 that may allow the flow of vacuum through the elongate inversion support more easily. The elongate inversion support shown also includes a distal end 2707 into which a tractor 2711 inverts, as shown in FIG. 58B. In FIG. 58B, the elongate inversion support is shown transparent so that the puller 2713 and tractor within the elongate inversion support is visible.

Similarly, in FIGS. 58B and 58C, the entire length of the elongate inversion support includes a plurality of cut-out regions 2713 which may increase the ability to allow the flow of a vacuum or other fluid within the apparatus, but may still allow the elongate inversion support to provide column strength to resist collapsing up to at least 500 g of compressive longitudinal force applied by, e.g., pulling on the tractor. Similarly, the elongate inversion support of FIGS. 58E and 58F show a skived catheter that also includes openings 2709 along its length. The puller and tractor 2412 are shown within the elongate inversion support in FIG. 58F. FIGS. 58G and 58H illustrate an example in which rather than a skived portion of the catheter, the distal catheter region of the elongate inversion support is formed by a wire, bar, tube, 2721 etc., that is attached to the catheter at the distal end. The catheter may also optionally include openings 2709. The elongate inversion support of FIGS. 58I and 58J includes openings 2709' along all or much of its length (particularly near the distal end region) as shown.

Finally, the variation of the elongate inversion support shown in FIG. 58K includes a minimal catheter portion (cylinder 2716) that is connected to a wire, bar, tube, hypotube, skived region, etc. 2717.

FIGS. 59A-59D illustrate the operation of a similar minimal elongate inversion support 2800. In this example, the apparatus includes a distal aperture 2743 bonded securely to a wire, bar, tube, hypotube, skived region, etc. 2746 forming an elongate support. The elongate support may be hollow (e.g., may include a lumen for a guidewire) or solid. The elongate support may also include one or more additional support guides 2750 as shown in FIG. 59B. These supports may help contain the puller and/or tractor within the elongate inversion support. Any of the elongate inversion supports described herein may include additional support guides. The elongate inversion support of FIG. 59B is shown with a tractor 2711 and puller 2713 in FIG. 59C. As mentioned, this variation may be particularly well suited for use with an intermediate (e.g., "outer") catheter, sleeve, or the like 2809, as shown in FIG. 59D.

Any of the apparatuses described herein may be used to withdraw a clot and/or a clot engaging member. For example, FIGS. 62A-62G illustrate removal of a clot using a rolling thrombectomy apparatus. The apparatus may also be referred to as an inverting thrombectomy apparatus. In any of the variations described herein a vacuum may be used to help secure the clot to the tractor.

In FIG. 62A, the rolling mechanical thrombectomy apparatus 3200 is brought near to the clot 3220. In this example, a guidewire 3205 may be used to help position the apparatus adjacent to the clot. The guidewire may be left in place or removed. Alternatively, as described in variations in which a clot engaging member on the distal end of an elongate manipulator is used, the apparatus 3200 may be directed over the elongate manipulator. In FIG. 62A, the rolling thrombectomy apparatus includes a tractor 3203 that is configured to roll over the distal end opening of a catheter 3207. In FIG. 62A, the tractor is held in tension by holding in a fixed position relative to the catheter at a second (outer) end of the tractor; a tractor hold (not shown in FIG. 62A) may be used to releasably hold an end of the tractor fixed relative to the catheter. When a force sufficient to overcome the deployment force (e.g., 100 g of force or greater, 200 g of force or greater, etc.) is applied by pulling 3219 the first end of the tractor, as shown in FIG. 62B. In FIG. 62B, the puller 3209, coupled to the first end of the tractor within the catheter, is pulled to deploy the tractor. When deployed the tractor may expand away from the catheter and towards the wall(s) of the vessel 3260.

As shown in FIG. 62B, the tractor may be rolled and inverted 3282 into the catheter by pulling the first end of the tractor from within the catheter (e.g., by pulling 3219 the puller proximally). The puller in FIGS. 62A-62G is shows as a hollow member (e.g., catheter, tube, etc.) but it may be a wire, cable, etc.

Figure 62C:
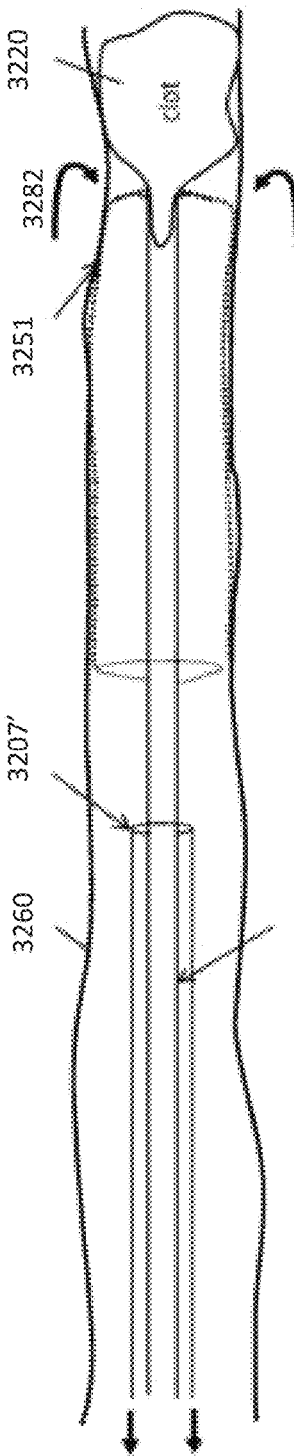

Occasionally, if the clot diameter is too large compared to the diameter of the distal end opening of the catheter, and/or if the clot is too stiff and difficult to compress, the clot 3220 may jam in the distal end opening of the catheter after at least a portion of the clot has been grabbed by the tractor. This is illustrated in FIGS. 62B and 62C. In this example the force required to pull the clot into the catheter may be too high (e.g., greater than the longitudinal compression strength of the catheter, such as greater than 500 g of force, greater than 600 g of force, greater than 700 g of force, greater than 800 g of force, greater than 900 g of force, greater than 1000 g of force, greater than 1100 g of force, greater than 1200 g of force, greater than 1300 g of force, greater than 1400 g of force, greater than 1500 g of force, etc. the threshold may depend on the catheter type and structure.

When the clot is jammed within the catheter distal end opening, as shown in FIG. 62B (and in FIG. 63A), the method may then proceed to engulf and remove the clot with the tractor by withdrawing the catheter and continuing to pull the first end of the tractor proximally by pulling the puller proximally. In FIG. 62C, the catheter distal end opening 3207' is shown withdrawn a substantial distance, e.g., beyond the second (outer) end of the tractor; alternatively the catheter may be withdrawn just slightly relatively to the tractor and/or may be withdrawn with the puller as the puller is withdrawn proximally.

Figure 62D:
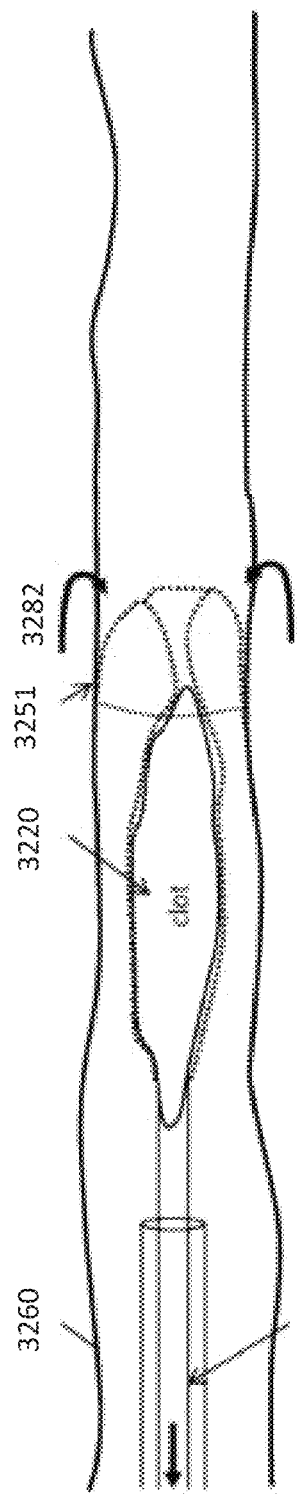
Figure 62E:
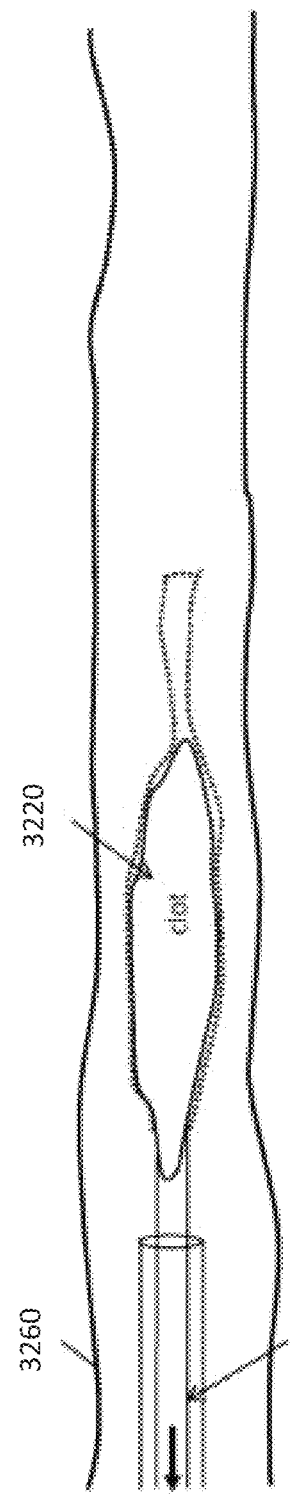

As shown in FIG. 62D, when the puller is pulled proximally either with the catheter or with the catheter withdrawn proximally (as shown) so that the tractor cannot roll over the distal end opening of the tractor, the interference between the wall of the vessel 3260 and the expanded tractor 3251 may hold the tractor in place as the clot, which is still secured to the tractor either by the force of interaction between the tractor and the clot, and/or by suction (e.g., through the puller or other lumen connected to the tractor), is pulled proximally with the tractor. Thus, as shown in FIGS. 62D and 62E, the clot may be engulfed by the tractor and pulled proximally into the expanded tractor.

Figure 62F:
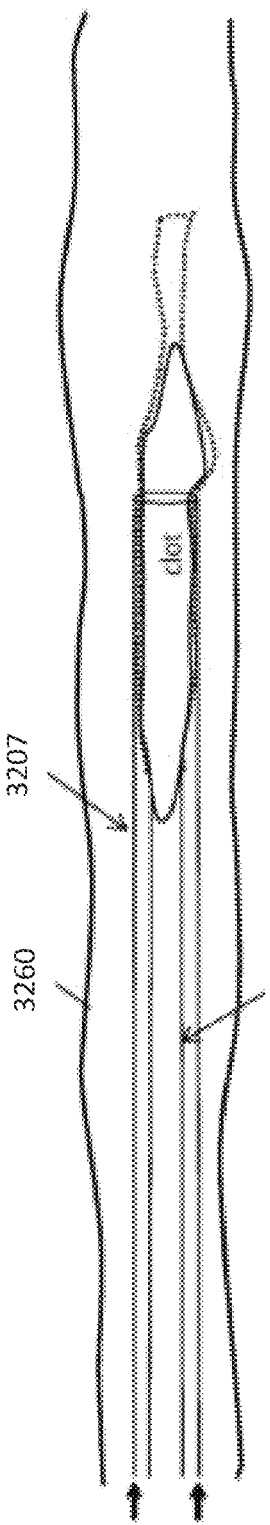
Figure 62G:
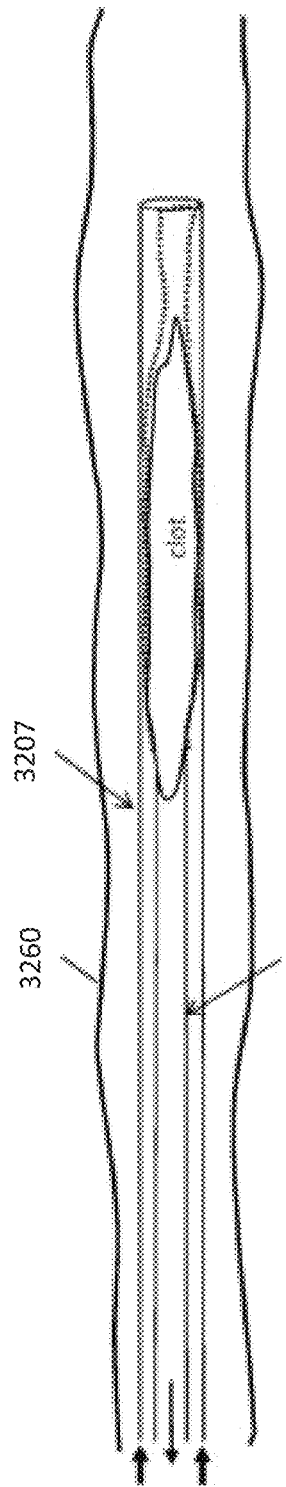
Figure 63A:
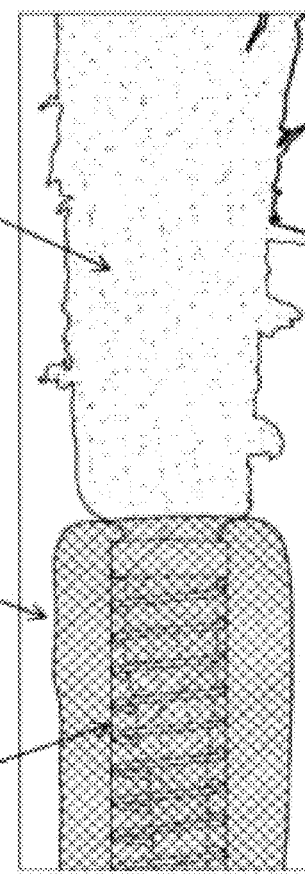
FIG. 63A illustrates an example of a rolling mechanical thrombectomy apparatus in which the clot has jammed while rolling the tractor into the distal end opening of the catheter portion of the rolling mechanical thrombectomy apparatus, similar to that shown in FIG. 62B.
Figure 63B:
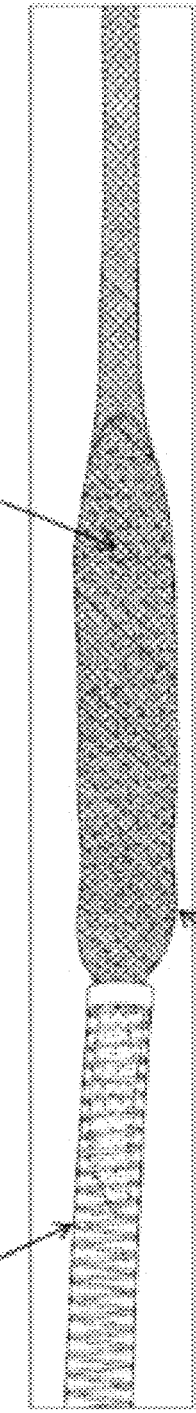
FIG. 63B illustrates an example of the clot engulfed by the tractor as illustrated in FIGS. 62C-62F.

Ultimately, the tractor, clot and catheter may be removed proximally from the vessel. In some variations, as shown in FIGS. 62F and 62G, the clot may be pulled with the tractor into the catheter once it has been fully engulfed by the tractor. As illustrated in FIG. 63A, the clot may be jammed so that it is unable to be pulled into catheter by rolling the tractor so that it inverts into the catheter, similar to what was described above for FIG. 62B. In FIG. 63B, the clot has been pulled proximally with the tractor but not rolled over the catheter distal end opening; instead, the catheter has been withdrawn and the clot pulled into the tractor to invert itself round and engulf the clot within the tractor. Thus, pulling back the catheter proximally, even without pulling the tractor proximally or while pulling both the tractor and the catheter proximally, may drag the clot proximally and inert the tractor over the clot, as shown. As mentioned above, it may be helpful to have the tractor expand radially within the vessel to contact the wall of the vessel. This may help lock the tractor in position as the catheter and/or tractor is pulled proximally. The tractor may include at least a portion of its length that has an element that expands to the vessel wall. Inverting the tractor over the clot in this manner may reduce the risk of creating emboli compared to other techniques, including aspiration-only techniques, and also may not require the additional cost and risk of delivering a secondary device, such as a clot engaging member prior to or with the rolling mechanical thrombectomy apparatuses described herein (see below with regard to FIGS. 65A-67B for examples in which a clot engaging member is used in addition to the rolling mechanical thrombectomy apparatuses described herein.

Figure 64G:
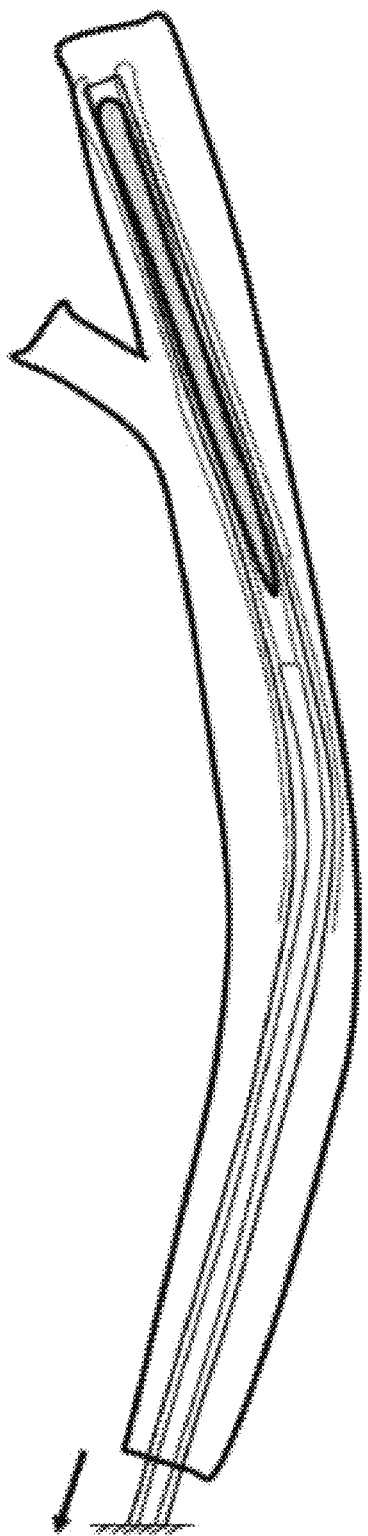

FIGS. 64A-64G illustrate another example of a method of capturing and/or removing a clot from a vessel using a rolling mechanical thrombectomy apparatus. In this example, rather than pulling the clot proximally into the tractor, the tractor (and catheter) may be advanced distally forward over the clot. For example, in FIG. 64A, a guide wire 3405 (or other guide member) may be steered or driven distally to the clot 3420. The guidewire may extend just to the clot or may pass at least partially though the clot. In some variations it may be beneficial to stop the guidewire prior to entering the clot, in order to avoid disrupting the clot. Once the guidewire is positioned, a rolling mechanical thrombectomy apparatus 3400 may be positioned over the guidewire so that it is adjacent to the clot. The apparatus may include the catheter 3401 and a tractor 3403 that is coupled at a first end within the catheter to a puller (shown as a puller inner catheter 3407). Optionally, the guidewire may be removed (as shown in FIG. 64C), leaving the rolling mechanical thrombectomy apparatus 3400 behind.

The tractor may then be rolled into the catheter and inverted by either pulling proximally on the puller (coupled within the catheter to the first end of the tractor), or alternatively and/or additionally by moving the catheter distally against the tractor, as shown in FIGS. 64C and 64D. In this example, the tractor puller is held in a relatively fixed position and the catheter is slowly advanced distally, towards the clot. The tractor therefore rolls and inverts 451 into the advancing catheter distal end, which may then travel up and into the clot 3420, as shown in FIG. 64E. As the catheter advances, rolling the tractor so that it grabs and pulls the clot into the catheter distal end with the tractor, the tractor also envelops the clot and compresses it into the catheter inner lumen 3460. Once the clot is engulfed and/or completely enveloped by the apparatus, the catheter forward (distal) motion may stop, as shown in FIG. 64F. Thereafter the catheter and tractor may be fixed in relative position (e.g., no motion relative to each other) and the apparatus slowly removed from out of the vessel, as shown in FIG. 64G, with the clot within the tractor and the tractor and clot within the lumen of the catheter.

As mentioned above, any of the methods and apparatuses described herein may be used with (and/or may integrate into them) a clot engaging member on the distal end of an elongate manipulator. Any type of clot engaging member may be used, and particularly those on the distal end of an elongate manipulator. For example, FIGS. 65A-65C illustrate different schematic variations of clot engaging member on the distal end of an elongate manipulator. In FIG. 65A the clot engaging member 501 is a coil that is on the distal end of an elongate manipulator 3503. The coil may be expandable, e.g., may be compressed so that when released at or near the clot it may expand. The clot engaging member may be secured into the clot or through the clot so that, once expanded, it may help mechanically capture the clot.

FIG. 65B shows another example of a clot engaging member 3501' on the distal end of an elongate manipulator 3503'. In FIG. 65B, the clot engaging member includes a plurality of wires that may expand outward within the clot. Similarly, FIG. 65C illustrates another example of a clot engaging member 3501" on the distal end of an elongate manipulator 3503".

Any of the apparatuses described herein may be used in conjunction with a clot engaging member, and particularly a clot engaging member on the distal end of an elongate manipulator.

Figure 66F:
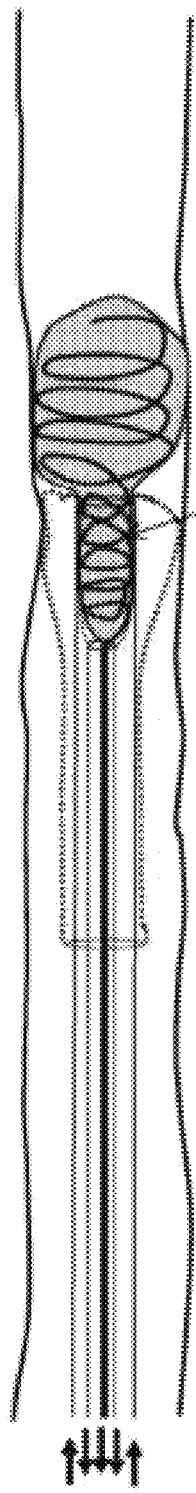
Figure 66G:
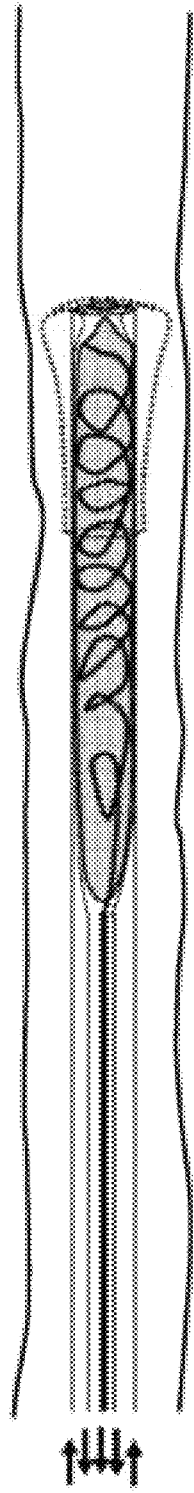
Figure 66H:
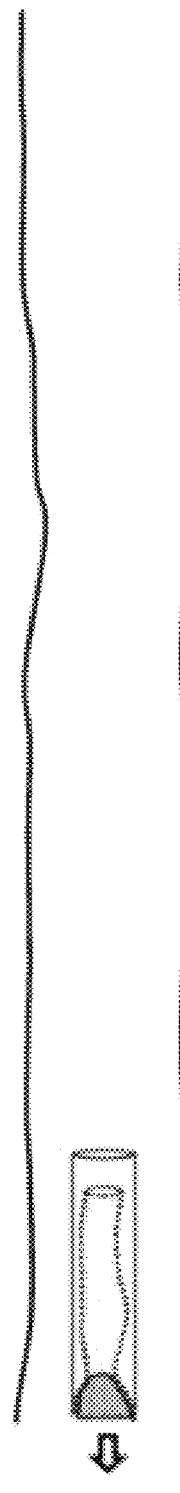
Figure 66I:
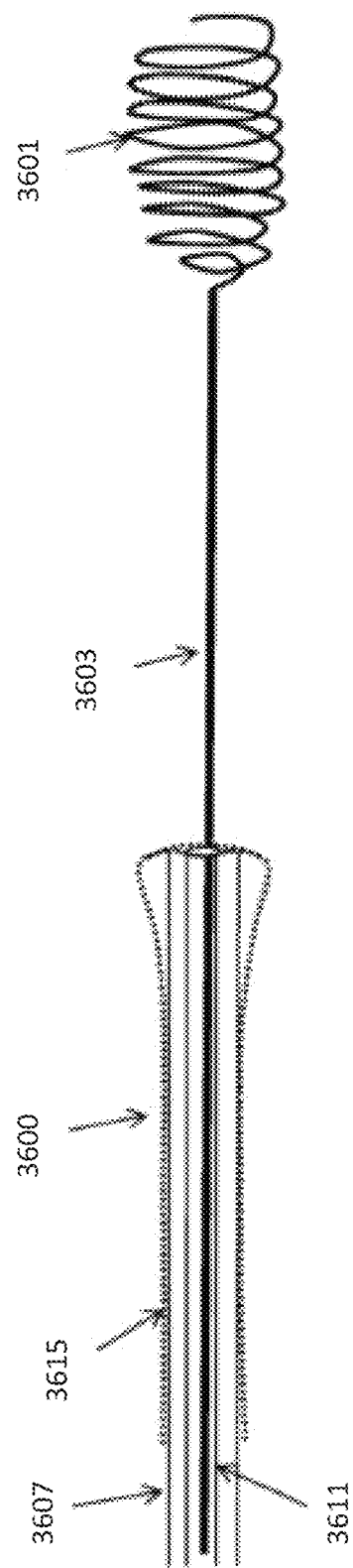
FIG. 66I illustrates an example of a mechanical thrombectomy system for removing a clot from within a vessel.

FIG. 66I illustrates an example of a mechanical thrombectomy system for removing a clot from within a vessel. In FIG. 66I, the apparatus (e.g., system) includes an elongate inversion support comprising a catheter 3607 having a distal end and a distal end opening, a tractor 3615 comprising a flexible tube that extends distally in an un-inverted configuration within the catheter, inverts over the distal end opening of the catheter and extends proximally in an inverted configuration along the distal end of the catheter, wherein the tractor is configured to invert by rolling over the distal end opening of the catheter when a first end of the tractor is pulled proximally within the catheter. The system also includes a puller 3611 connected to the first end of the tractor that extends proximally within the catheter. The system also includes a clot engaging member 3601 on the distal end of an elongate manipulator 603. The elongate member is shown passing through a lumen extending continuously through the puller and the tractor and configured to pass the expandable elongate manipulator. This system may be used to remove a clot.

For example, a clot engaging member on the distal end of an elongate manipulator may be advanced through a clot; the expansive/expandable clot engaging member on the distal end of the elongate manipulator may engage with a clot and lock the clot in place in the vessel. The rolling mechanical thrombectomy apparatus may then be delivered, e.g., over the elongate manipulator to the clot and the clot engaging member. Once near the clot, the tractor may be rolled into the distal end of the catheter by pulling the first end of the tractor (e.g., by pulling a puller) proximally and advancing the catheter distally and/or by holding the puller in a relatively fixe position and driving the catheter distally to roll the tractor and invert it into the catheter. Preferably, as illustrated in FIGS. 64A-64G above, the catheter may be advanced forward in the vessel and the proximal end of the tractor may be held and/or fixed (in a fixed longitudinal position). For example, the proximal end of the tractor may be a puller/catheter that is slid over the elongate manipulator and, once positioned adjacent to the clot, held in a fixed position relative to the elongate manipulator. Holding the proximal puller fixed to the elongate manipulator while advancing the catheter forward distally relative to the elongate manipulator may therefore invert the tractor over the clot and clot engaging member similar. This action may force the tractor to roll into the distal end opening of the catheter and grab and engulf the clot along with the clot engaging member. In this example, the clot engaging member may be in the clot and/or distal to the clot, and the elongate manipulator acts as a guide rail for the rolling mechanical thrombectomy apparatus as the catheter is advanced forward. This example is illustrated in FIGS. 66A-66I.

For example, in FIG. 66A, the clot engaging member 3601 on the distal end of an elongate manipulator 3603 is advanced distally into and through the clot 3620. Thus, the clot engaging member engages the clot from the distal side of the clot and may pull against the clot when drawn proximally. Alternatively, FIG. 66B shows an example in which the engaging member 3601 on the distal end of an elongate manipulator 3603 is deployed within the clot 3620. The engaging member may engage the clot by expanding within the clot.

Once deployed, the engaging member and clot may be captured by a rolling mechanical thrombectomy apparatus, as shown in FIG. 66C. Once adjacent to the clot, the apparatus may be advanced distally by driving the catheter 3607 distally 3609, as shown in FIG. 66D. The elongate manipulator 3603 and the puller 3611 coupled to the first end of the tractor may be held fixed relative to one another (and/or may be jointly pulled proximally) while the catheter 3607 is pushed distally 3609, as shown in FIG. 66E. This may therefore roll the tractor over the distal end of the catheter and capture the clot and clot engaging member, pulling it into the catheter 3613 as shown in FIG. 66F. This process may be continued until the entire clot and clot engaging member is engulfed and held within the catheter, as shown in FIG. 66G. Once complete, the apparatus, clot and clot engagement member may be withdrawn proximally out of the vessel, as shown in FIG. 66H.

Alternatively, a clot engagement member may be deployed through a rolling mechanical thrombosis apparatus in order the engage with the clot before removing with the rolling mechanical thrombosis apparatus. In any of the variations described herein, the tractor may be actuated by advancing the catheter portion distally over the clot and clot engagement member either with or without pulling the tractor (e.g., puller) proximally within the catheter. The tractor may grab the clot and clot engagement member and may be advanced forward distally over both the clot and the clot engagement mechanism. This technique may avoid dragging the clot engagement apparatus within the vessel and may provide active capturing. This may reduce the risk of any distal emboli on embolization of new territories. As mentioned above, in any of these variations suction/aspiration can be used in combination with any of these steps. In any of these variations, the clot engaging mechanism may be pulled proximally into the pre-loaded dozer catheter, rather than advancing the apparatus over the clot engaging mechanism; as the clot engagement mechanism pulls into the pre-loaded tractor and catheter, the tractor may grab and encapsulate the clot as the clot and clot engagement mechanism is pulled proximally.

FIGS. 67A and 67B illustrate an example in which the clot engagement apparatus 3703 is linked to the puller 3705, so that the two may be moved or held motionless together, relative to the catheter 3707, and/or the vessel. For example, in FIG. 67B, the apparatus is inserted into the vessel and adjacent to clot engagement mechanism and held motionless while the catheter is driven forward, allowing the tractor 3713 to roll distally and into the catheter and capture the clot without requiring the clot and/or clot engagement mechanism to move within the vessel. This may reduce the risk for further embolization.

As mentioned above, any of the apparatuses and methods described herein may be used with aspiration (e.g., vacuum). For example, any of these methods described herein may be may use a combination of aspiration and a tractor pull mechanism. For example, to initiate the grabbing of the clot by the tractor, the tractor may be rolled around a catheter wall and may make physical (e.g., direct) contact with the clot. A user may apply vacuum through the catheter (e.g., via a syringe or pump, etc.) prior to or at the same time as pulling tractor into the catheter. Alternatively or additionally, vacuum may be applied through the puller (e.g., a pulling catheter). If vacuum is applied prior to pulling the tractor the vacuum may be applied 1 sec to 5 min prior to ensure that the clot is in good contact with the distal end of the catheter. Preferred range of 5-60 sec vacuum prior to activating/pulling dozer. The application of vacuum prior to pulling the braid will ensure the proximal most end of the clot is in contact with the catheter tip and some amount of the clot (>0.5 mm) is extruded into the lumen of the catheter tip. Next when the dozer is pulled there will be clot at the tip of the catheter for the braid/dozer to grab and pull in. Also, when the dozer is pulled there are resultant forces from the braid/dozer that put compression forces on the catheter tip encouraging the catheter tip to buckle and/or move proximally away from the proximal edge of the clot. The application of vacuum ensures that even if the catheter tip wants to move proximally when pulling the tractor that the clot will stay in contact with the clot and/or prevent the catheter tip from pulling back away from the clot. Once the tractor engages (e.g., grabs) a few mm of clot, the vacuum may be kept on or turned off.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus for removing a material from a lumen, the apparatus comprising:
an inversion support catheter having a distal end and a distal end opening;
a puller within the inversion support catheter;
a flexible tube that is coupled at a first end region to the puller, wherein a second end region of the flexible tube and at least a first portion of the flexible tube extends over an outer surface of the inversion support catheter, wherein the first portion of the flexible tube is held in a compressed configuration on the outer surface of the inversion support catheter by a releasable attachment that is configured to secure the second end region of the flexible tube to a longitudinal position on the inversion support catheter; and
wherein the puller is configured to be withdrawn proximally through the inversion support catheter to pull the flexible tube proximally within the inversion support catheter so that the flexible tube inverts over the distal end opening.

2. The apparatus of claim 1, wherein the flexible tube is a knitted material.

3. The apparatus of claim 1, wherein the flexible tube is a woven material.

4. The apparatus of claim 1, wherein the flexible tube is formed of one or more strands of a steel, a nickel titanium, a polyester, a nylon, or an expanded Polytetrafluorethylene (ePTFE).

5. The apparatus of claim 1, wherein the tractor comprises one or more coatings from the group of: a lubricious coating, a metal coating, a heparin coating, an adhesive coating, and a drug coating.

6. The apparatus of claim 1, wherein the flexible tube includes a first end, the first end of the flexible tube is coupled proximal to a distal end of the puller.

7. The apparatus of claim 1, wherein the apparatus is configured so that the flexible tube may be retracted into the inversion support catheter by applying less than 300 grams of force to a distal end of the flexible tube.

8. The apparatus of claim 1, wherein the puller comprises an elongate microcatheter.

9. An apparatus for removing a material from a lumen, the apparatus comprising:
an inversion support catheter having a distal end and a distal end opening;
a puller within the inversion support catheter;
a flexible tube that is coupled at a first end region of the flexible tube to a distal end region of the puller that is proximal to the distal end of the puller, wherein a second end region of the flexible tube and at least a first portion of the flexible tube extends over an outer surface of the inversion support catheter, wherein the first portion of the flexible tube is held in a compressed configuration on the outer surface of the inversion support catheter by a releasable attachment securing the second end region of the flexible tube relative to the inversion support catheter; and
wherein the puller is configured to be withdrawn proximally through the inversion support catheter to pull the flexible tube proximally within the inversion support catheter so that the flexible tube inverts over the distal end opening.

10. A method of removing a material from a lumen, the method comprising:
positioning a distal end of an apparatus adjacent to the material within the lumen, wherein the apparatus includes a flexible tube that extends along an outer surface of an inversion support catheter and inverts over a distal end of the inversion support catheter, wherein the flexible tube is held in a longitudinally compressed configuration over the outer surface of the inversion support catheter by a releasable attachment;
pulling a first end of the flexible tube proximally within the inversion support catheter to roll the flexible tube over the distal end of the inversion support catheter so that the flexible tube inverts into the inversion support catheter and draws the material into the inversion support catheter.

11. The method of claim 10, wherein pulling comprises applying less than 300 grams of force to the first end of the flexible tube to invert the flexible tube into the inversion support catheter and draw the material into the inversion support catheter.

12. The method of claim 10, further comprising securing a second end of the flexible tube relative to the inversion support catheter to maintain the flexible tube longitudinally compressed over the outer surface of the inversion support catheter.

13. The method of claim 10, further comprising releasing a releasable attachment holding the flexible tube in the longitudinally compressed configuration over the outer surface of the inversion support catheter.

14. The method of claim 10, wherein positioning the distal end of the apparatus comprises advancing the apparatus through a body lumen until a distal end of a puller that is coupled to the first end of the flexible tube is positioned adjacent or into the material within the lumen.

15. The method of claim 10, wherein positioning comprises sliding the apparatus over a guidewire.

16. The method of claim 10, wherein the flexible tube is a knitted material.

17. The method of claim 10, wherein the flexible tube is a woven material.

18. The method of claim 10, wherein pulling comprises pulling a puller proximally within the inversion support catheter, wherein the first end of the flexible tube is coupled to the puller.

* * * * *